US012604660B2

(12) United States Patent
Voges et al.

(10) Patent No.: US 12,604,660 B2
(45) Date of Patent: Apr. 14, 2026

(54) ELECTRONIC DEVICE

(71) Applicant: Merck Patent GmbH, Darmstadt (DE)

(72) Inventors: Frank Voges, Darmstadt (DE); Teresa Mujica-Fernaud, Darmstadt (DE); Elvira Montenegro, Darmstadt (DE); Thomas Eberle, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 18/217,636

(22) Filed: Jul. 3, 2023

(65) Prior Publication Data

US 2024/0008359 A1 Jan. 4, 2024

Related U.S. Application Data

(63) Continuation of application No. 16/339,594, filed as application No. PCT/EP2017/075437 on Oct. 6, 2017.

(30) Foreign Application Priority Data

Oct. 10, 2016 (EP) .................................... 16193116

(51) Int. Cl.

| | |
|---|---|
| ***H10K 85/60*** | (2023.01) |
| ***C07D 311/96*** | (2006.01) |
| ***C07D 335/04*** | (2006.01) |
| ***C07D 405/04*** | (2006.01) |
| ***C07D 407/12*** | (2006.01) |
| ***C07D 409/12*** | (2006.01) |
| ***C09K 11/06*** | (2006.01) |
| *H10K 50/15* | (2023.01) |

(52) U.S. Cl.

CPC ......... *H10K 85/636* (2023.02); *C07D 311/96* (2013.01); *C07D 335/04* (2013.01); *C07D 405/04* (2013.01); *C07D 407/12* (2013.01); *C07D 409/12* (2013.01); *C09K 11/06* (2013.01); *H10K 85/633* (2023.02); *H10K 85/6572* (2023.02); *H10K 85/6574* (2023.02); *C09K 2211/1018* (2013.01); *H10K 50/15* (2023.02); *H10K 50/156* (2023.02); *H10K 85/615* (2023.02); *H10K 85/626* (2023.02); *H10K 85/6576* (2023.02)

(58) Field of Classification Search

None

See application file for complete search history.

(56) References Cited

U.S. PATENT DOCUMENTS

| | | | |
|---|---|---|---|
| 7,318,966 | B2 | 1/2008 | Tominaga et al. |
| 9,978,949 | B2 | 5/2018 | Mujica-Fernaud et al. |
| 2004/0219386 | A1 | 11/2004 | Thoms |
| 2012/0217449 | A1 | 8/2012 | Spreitzer et al. |
| 2015/0295181 | A1 | 10/2015 | Mujica-Fernaud et al. |
| 2015/0322198 | A1 | 11/2015 | Hayer et al. |
| 2015/0333277 | A1 | 11/2015 | Kim et al. |
| 2016/0141508 | A1 | 5/2016 | Jatsch et al. |
| 2017/0331053 | A1* | 11/2017 | Voges .................... H10K 85/30 |
| 2018/0287068 | A1 | 10/2018 | Ha et al. |
| 2018/0337341 | A1 | 11/2018 | Heo et al. |

FOREIGN PATENT DOCUMENTS

| | | | |
|---|---|---|---|
| CN | 103664860 | A | 3/2014 |
| CN | 103666454 | A | 3/2014 |
| CN | 103666455 | A | 3/2014 |
| CN | 104263351 | A | 1/2015 |
| CN | 104781247 | A | 7/2015 |
| CN | 105924395 | A | 9/2016 |
| EP | 3348552 | A1 | 7/2018 |
| JP | 2003-096072 | A | 4/2003 |
| JP | 2009-191232 | A | 8/2009 |
| JP | 2016-500917 | A | 1/2016 |
| JP | 2016-505518 | A | 2/2016 |
| KR | 10-2013-0140303 | A | 12/2013 |
| KR | 10-2014-0135117 | A | 11/2014 |
| KR | 10-2015-0106501 | A | 9/2015 |
| KR | 10-2015-0144487 | A | 12/2015 |
| KR | 10-2017-0013799 | A | 2/2017 |
| WO | 02/43449 | A1 | 5/2002 |
| WO | 2014/000860 | A1 | 1/2014 |
| WO | 2014/072017 | A1 | 5/2014 |
| WO | 2015/000549 | A1 | 1/2015 |
| WO | WO-2016/062368 | A1 * | 4/2016 |

OTHER PUBLICATIONS

Chu, Z., et al., "Synthesis of spiro[fluorene-9,9'-xanthene] derivatives and their application as hole-transporting materials for organic light-emitting devices", Synthetic Metals, vol. 162, No. 7, (2012), pp. 614-620.

International Preliminary Report on Patentability received for PCT Patent Application No. PCT/EP2017/075437, mailed on Apr. 25, 2019, 17 pages (8 pages of English Translation and 9 pages of Original Document).

International Search Report and Written Opinion received for PCT Patent Application No. PCT/EP2017/075437, mailed on Jan. 26, 2018, 21 pages (9 pages of English Translation and 12 pages of Original Document).

Machine English translation of Yu et al. (CN 105924395 A). Jul. 26, 2021.

* cited by examiner

*Primary Examiner* — Jay Yang

(74) *Attorney, Agent, or Firm* — Faegre Drinker Biddle & Reath LLP

(57) ABSTRACT

The present application relates to an electronic device comprising a xanthene or thioxanthene compound of a particular formula. The electronic device is preferably an organic electroluminescent device (OLED). The application further relates to particular xanthene or thioxanthene compounds as such, and to the use thereof in the abovementioned devices, and to processes for preparation thereof.

6 Claims, No Drawings

ELECTRONIC DEVICE

CROSS-REFERENCE TO RELATED APPLICATIONS

This application is a continuation application of U.S. Ser. No. 16/339,594 filed Apr. 4, 2019, which is a national stage application (under 35 U.S.C. § 371) of PCT/EP2017/075437, filed Oct. 6, 2017, which claims benefit of European Application No. 16193116.7, filed Oct. 10, 2016, all of which are incorporated herein by reference in their entirety.

The present application relates to an electronic device comprising a xanthene or thioxanthene compound of a formula defined further down. The electronic device is preferably an organic electroluminescent device (OLED). The application further relates to particular xanthene or thioxanthene compounds as such, to the use thereof in the abovementioned devices, and to processes for preparation thereof.

Electronic devices in the context of this application are understood to mean organic electronic devices, i.e. devices which contain organic semiconductor materials as functional materials. More particularly, these are understood to mean OLEDs. The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by layers having a hole-transporting function. These layers include hole-injecting layers, hole transport layers and electron blocker layers. For use in these layers, new materials having hole-transporting properties are still being sought.

In addition, there is a need for new device constructions, and for new combinations of functional materials in different layers of the OLEDs. What are of significance here are especially the layers having a hole-transporting function, the composition thereof and the sequence thereof, in order to improve the performance data of OLEDs.

The prior art, for example in published specifications WO 2014/072017 and CN 103666454, describes xanthene and thioxanthene compounds that bear an arylamino group as OLED functional materials.

Compared to the OLED constructions comprising the compounds mentioned that are described therein, however, there is still a need for improvement with regard to the performance data of the OLEDs, especially operating voltage, lifetime and efficiency.

In addition, there is still a need for improvement with regard to the specific compounds disclosed therein.

In the context of the present invention, it has been found that OLEDs containing particular xanthene or thioxanthene compounds in a layer adjoining the anode, or comprising these compounds in a layer having at least two further layers between this layer and the emitting layer closest to the anode, have excellent performance data.

It has additionally been found that particular novel xanthene or thioxanthene compounds have excellent performance data.

The present invention therefore provides an electronic device comprising, in this sequence, an anode, a hole-transporting layer, an emitting layer and a cathode, wherein said hole-transporting layer comprises a compound of a formula (I)

Formula (I)

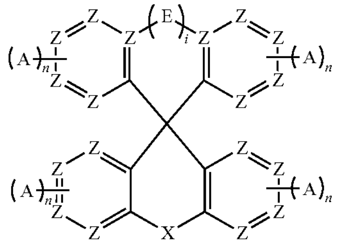

where:

A is an arylamino group optionally substituted by one or more $R^1$ radicals, or a carbazole-containing group optionally substituted by one or more $R^1$ radicals;

E is a single bond;

X is O or S,

Z is the same or different at each instance and is $CR^2$ or N or C, where a Z group is C in the specific case when an A or E group is bonded to the Z group in question;

$R^1$ is the same or different at each instance and is selected from H, D, F, $C(=O)R^3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by $-R^3C{\equiv}CR^3-$, $-C{\equiv}C-$, $Si(R^3)_2$, C=O, $C=NR^3$, $-C(=O)O-$, $C(=O)NR^3-$, $NR^3$, $P(=O)(R^3)$, —O—, —S—, SO or $SO_2$, $R^2$ is the same or different at each instance and is selected from H, D, F, $C(=O)R^3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by $-R^3C=CR^3-$, $-C{\equiv}C-$, $Si(R^3)_2$, C=O, $C=NR^3$, $-C(=O)O-$, $C(=O)NR^3-$, $NR^3$, $P(=O)(R^3)$, —O—, —S—, SO or $SO_2$, $R^3$ is the same or different at each instance and is selected from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $—R^4C{=}CR^4—$, —C≡C—, $Si(R^4)_2$, C═O, $C{=}NR^4$, —C(═O)O—, $C({=}O)NR^4—$, $NR^4$, $P({=}O)(R^4)$, —O—, —S—, SO or $SO_2$, $R^4$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^4$ radicals may be joined to one another and may form a ring; and where the alkyl, alkoxy, alkenyl and alkynyl groups, aromatic ring systems and heteroaromatic ring systems mentioned may be substituted by F or CN;

i is 0 or 1;

n is the same or different at each instance and is 0 or 1, where the sum total of all the indices n is 1, 2, 3 or 4;

where at least one condition selected from conditions a) and b) is met:

a) the hole-transporting layer directly adjoins the anode;

b) there are at least two further layers arranged between the hole-transporting layer and the emitting layer, and there are no further emitting layers arranged between the emitting layer and the anode.

The application further provides xanthene and thioxanthene compounds of a particular formula (S) as such, which are defined and described further down.

An arylamino group as A group is understood to mean a group comprising at least one unit in which at least one aryl group or heteroaryl group is bonded to a trivalent nitrogen atom. The further structure of the group and whether it comprises further units and, if so, which units are immaterial to the definition.

A carbazole-containing group as A group is also understood to mean groups containing derivatives of carbazole, for example carbazole groups having fused-on benzene rings, or azacarbazole compounds. The further structure of the group and whether it comprises further units and, if so, which units are immaterial to the definition.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the nonaromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

In the compound of the formula (I), X is preferably O.

In addition, i is preferably 1.

In addition, the sum total of the indices n in formula (I) is preferably 1 or 2, more preferably 1.

In addition, preferably not more than 2 Z groups per ring are N. In addition, preferably not more than 4 Z groups per compound of the formula (I), most preferably not more than 2 Z groups per compound of the formula (I), are Z.

More preferably, Z is $CR^2$, where, in the case that an A or E group is bonded to the Z group in question, this Z group is C.

Preferably, $R^1$ is the same or different at each instance and is selected from H, D, F, CN, $Si(R^3)_3$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms, where the alkyl and alkoxy groups mentioned, the aromatic ring systems mentioned and the heteroaromatic ring systems mentioned may each be substituted by one or more $R^3$ radicals; and where one or more $CH_2$ groups in the alkyl or alkoxy groups mentioned may be replaced by —C≡C—, $—R^3C{=}CR^3—$, $Si(R^3)_2$, C═O, $C{=}NR^3$, $—NR^3—$, —O—, —S—, —C(═O)O— or $—C({=}O)NR^3—$.

More preferably, $R^1$ is the same or different at each instance and is selected from H, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^3$ radicals.

Preferably, $R^2$ is the same or different at each instance and is selected from H, D, F, CN, $Si(R^3)_3$, straight-chain alkyl or alkoxy groups having 1 to carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms, where the alkyl and alkoxy groups mentioned, the aromatic ring systems mentioned and the heteroaromatic ring systems mentioned may each be substituted by one or more $R^3$ radicals; and where one or more $CH_2$ groups in the alkyl or alkoxy groups mentioned may be replaced by —C≡C—, $—R^3C{=}CR^3—$, $Si(R^3)_2$, C═O, $C{=}NR^3$, $—NR^3—$, —O—, —S—, —C(═O)O— or $—C({=}O)NR^3—$.

More preferably, $R^2$ is the same or different at each instance and is selected from H, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^3$ radicals.

Most preferably, $R^2$ is H.

Preferably, $R^3$ is the same or different at each instance and is selected from H, D, F, CN, $Si(R^4)_3$, straight-chain alkyl or alkoxy groups having 1 to carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms, where the alkyl and alkoxy groups mentioned, the aromatic ring systems mentioned and the heteroaromatic ring systems mentioned may each be substituted by one or more $R^4$ radicals; and where one or more $CH_2$ groups in the alkyl or alkoxy groups mentioned may be replaced by —C≡C—, $—R^4C{=}CR^4—$, $Si(R^4)_2$, C═O, $C{=}NR^4$, $—NR^4—$, —O—, —S—, C(═O)O— or $—C({=}O)NR^4—$.

More preferably, $R^3$ is the same or different at each instance and is selected from H, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more $R^4$ radicals.

Preferably, the A group is an arylamino group which may be substituted by one or more $R^1$ radicals.

The arylamino group as A group preferably corresponds to a formula (A)

Formula (A)

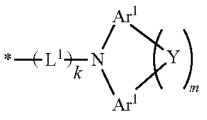

where:

$L^1$ is the same or different at each instance and is C═O, $Si(R^1)_2$, $PR^1$, $P(═O)(R^1)$, O, S, SO, $SO_2$, an alkylene group having 1 to 20 carbon atoms or an alkenylene or alkynylene group having 2 to 20 carbon atoms, where one or more $CH_2$ groups in the groups mentioned may be replaced by C═O, $C═NR^1$, C═O—O, C═O—$NR^1$, $Si(R^1)_2$, $NR^1$, $P(═O)(R^1)$, O, S, SO or $SO_2$ and where one or more hydrogen atoms in the abovementioned groups may be replaced by D, F or CN, or an aromatic or heteroaromatic ring system which has 6 to 24 aromatic ring atoms and may be substituted by one or more $R^1$ radicals;

$Ar^1$ is the same or different at each instance and is an aromatic or heteroaromatic ring system which has 6 to 30 aromatic ring atoms and may be substituted by one or more $R^1$ radicals;

Y is selected from a single bond, $BR^1$, $C(R^1)_2$, $C(R^1)_2$—$C(R^1)_2$, $Si(R^1)_2$, $Si(R^1)_2$—$Si(R^1)_2$, C═O, $C═NR^1$, $C═C(R^1)_2$, $C(═O)N(R^1)$, O, S, S═O, $SO_2$ and $NR^1$;

k is 0, 1, 2 or 3;

m is 0 or 1;

where the A group is bonded to the rest of the compound of the formula (I) via the bond marked with *.

Preferably, in formula (A), $L^1$ is the same or different at each instance and is $Si(R^1)_2$, O, S, an alkylene group having 1 to 10 carbon atoms or an alkenylene or alkynylene group having 2 to 10 carbon atoms, where one or more $CH_2$ groups in the groups mentioned may be replaced by $Si(R^1)_2$, O or S and where one or more hydrogen atoms in the abovementioned groups may be replaced by D, F or CN, or an aromatic or heteroaromatic ring system which has 6 to 24 aromatic ring atoms and may be substituted by one or more $R^1$ radicals.

More preferably, $L^1$ is the same or different at each instance and is an aromatic or heteroaromatic ring system which has 6 to 18 aromatic ring atoms and may be substituted by one or more $R^1$ radicals. Most preferably, $L^1$ is the same or different at each instance and is phenyl, biphenyl, naphthyl, terphenyl, fluorenyl, spirobifluorene, indenofluorenyl, carbazole, dibenzofuran or dibenzothiophene, each of which may be substituted by one or more $R^1$ radicals.

Particularly preferred $L^1$ groups are the following groups:

($Ar^L$-1)

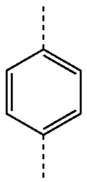

-continued ($Ar^L$-2)

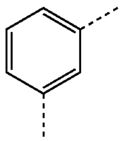

($Ar^L$-3)

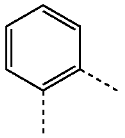

($Ar^L$-4)

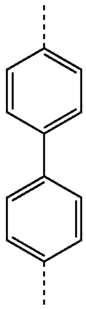

($Ar^L$-5)

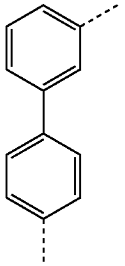

($Ar^L$-6)

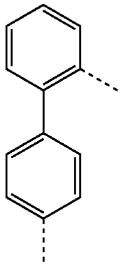

($Ar^L$-7)

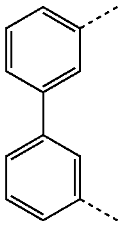

-continued
(Ar$^L$-8)
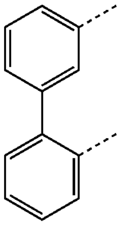
(Ar$^L$-9)
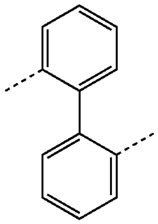
(Ar$^L$-10)
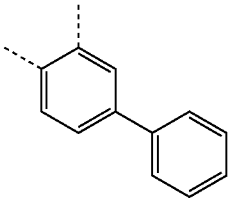
(Ar$^L$-11)
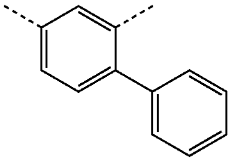
(Ar$^L$-12)
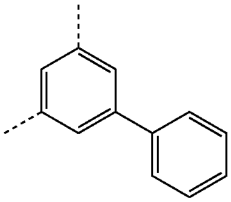
(Ar$^L$-13)
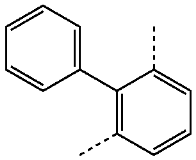
(Ar$^L$-14)
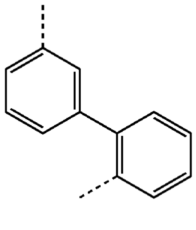
-continued
(Ar$^L$-15)
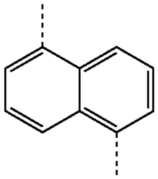
(Ar$^L$-16)
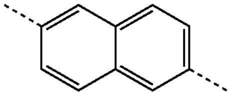
(Ar$^L$-17)
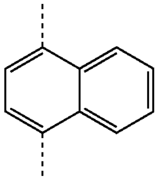
(Ar$^L$-18)
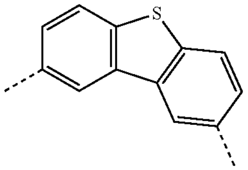
(Ar$^L$-19)
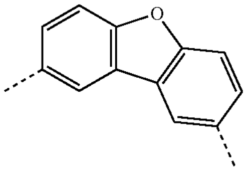
(Ar$^L$-20)
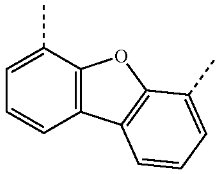
(Ar$^L$-21)
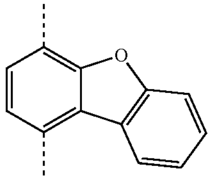
(Ar$^L$-22)
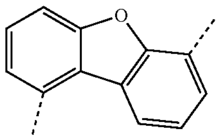
(Ar$^L$-23)
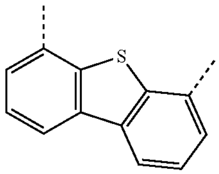

-continued (Ar$^L$-24)

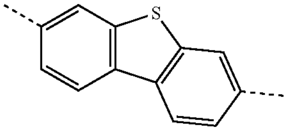

(Ar$^L$-25)

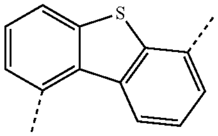

(Ar$^L$-26)

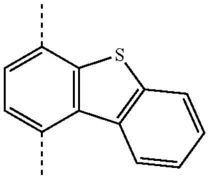

(Ar$^L$-27)

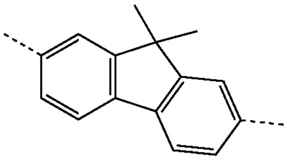

(Ar$^L$-28)

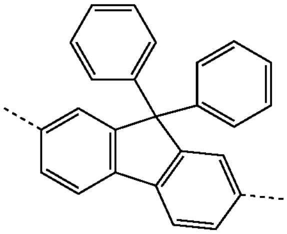

(Ar$^L$-29)

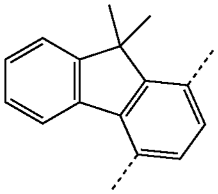

(Ar$^L$-30)

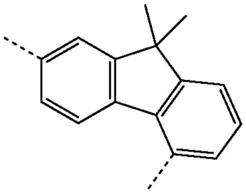

(Ar$^L$-31)

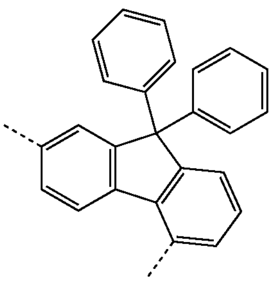

-continued (Ar$^L$-32)

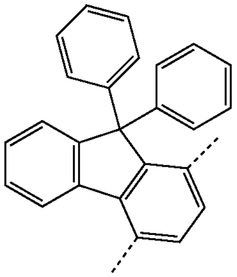

(Ar$^L$-33)

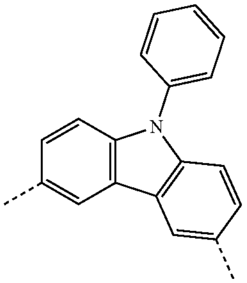

(Ar$^L$-34)

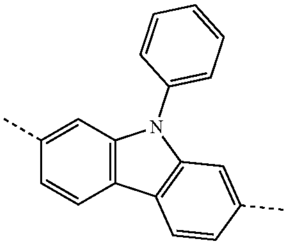

(Ar$^L$-35)

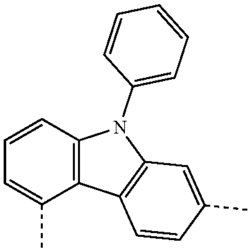

(Ar$^L$-36)

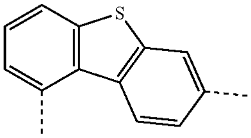

(Ar$^L$-37)

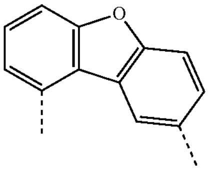

where the dotted bonds indicate the bonds from $L^1$ to the rest of the compound, and where the groups may each be substituted by $R^1$ radicals at the positions shown as unsubstituted, and where the groups are preferably not substituted by $R^1$ radicals at the positions shown as unsubstituted.

In addition, k in formula (A) is preferably 0 or 1, more preferably 0.

In addition, m in formula (A) is preferably 0, meaning that the two $Ar^1$ groups are not bonded to one another.

In addition, $Ar^1$ in formula (A) is the same or different at each instance and is an aromatic or heteroaromatic ring system which has 6 to 24 aromatic ring atoms and may be substituted by one or more $R^1$ radicals. Among these, very particular preference is given to phenyl, biphenyl, naphthyl, terphenyl, fluorenyl, spirobifluorene, indenofluorenyl, carbazolyl, dibenzofuranyl and dibenzothiophenyl, which may be substituted by one or more $R^1$ radicals.

Preferred $Ar^1$ groups are depicted in the following table:

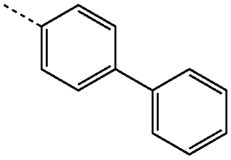

$Ar^1$-1

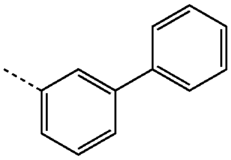

$Ar^1$-3

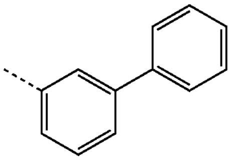

$Ar^1$-3

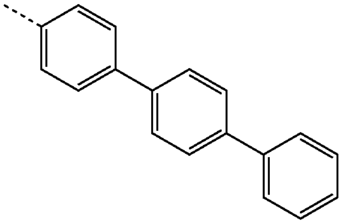

$Ar^1$-4

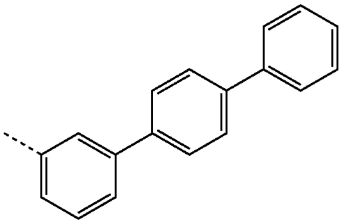

$Ar^1$-5

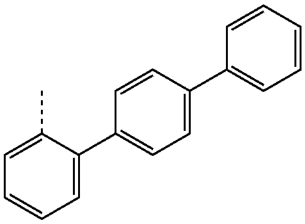

$Ar^1$-6

-continued

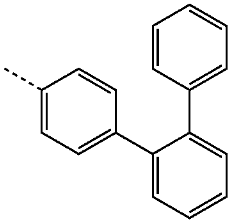

$Ar^1$-7

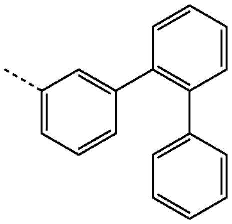

$Ar^1$-8

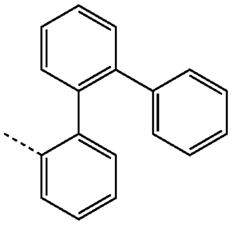

$Ar^1$-9

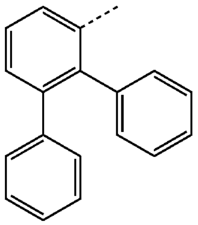

$Ar^1$-10

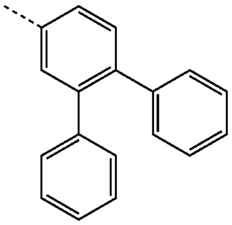

$Ar^1$-11

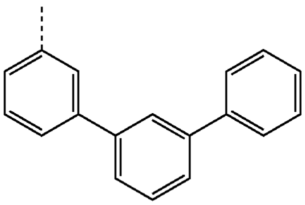

$Ar^1$-12

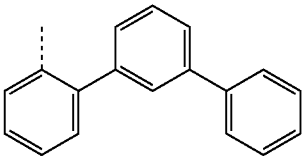

$Ar^1$-13

-continued
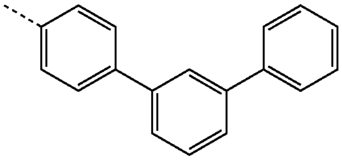
Ar[1]-14
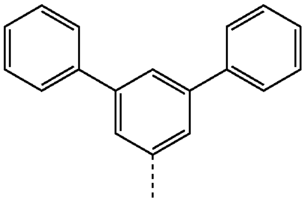
Ar[1]-15
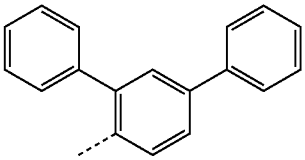
Ar[1]-16
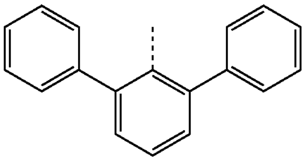
Ar[1]-17
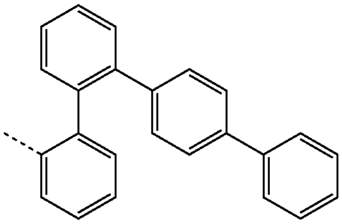
Ar[1]-18
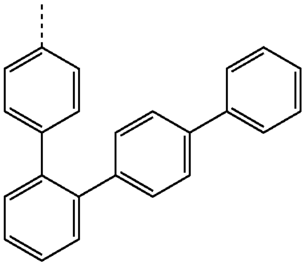
Ar[1]-19
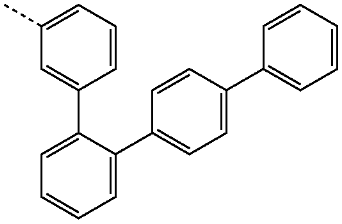
Ar[1]-20
-continued
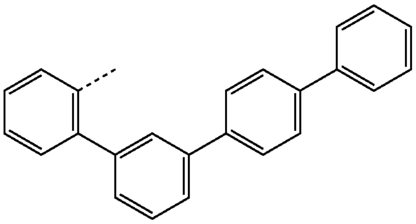
Ar[1]-21
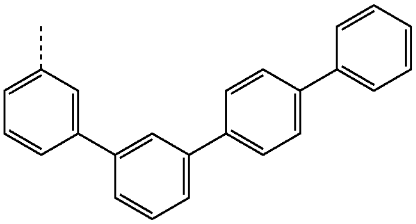
Ar[1]-22
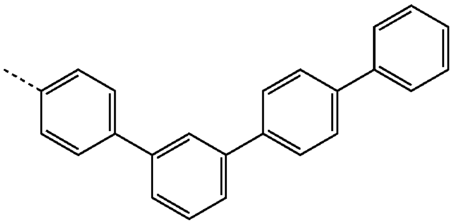
Ar[1]-23
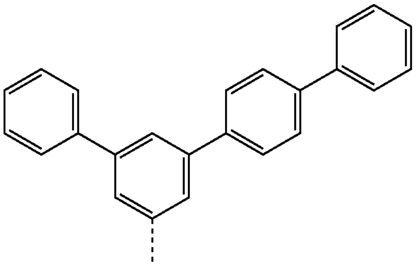
Ar[1]-24
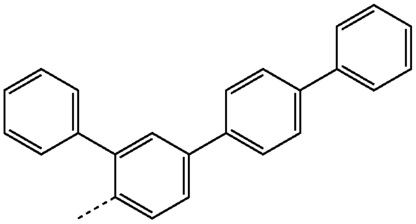
Ar[1]-25
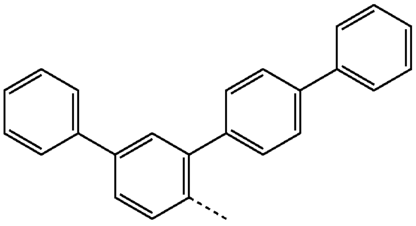
Ar[1]-26

-continued
Ar1-27
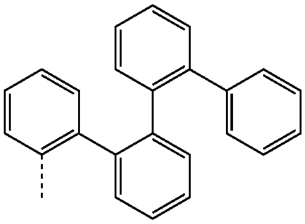
Ar1-28
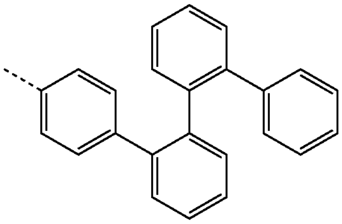
Ar1-29
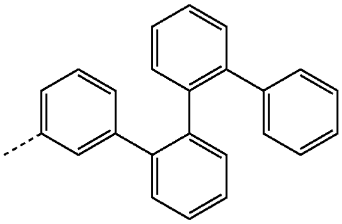
Ar1-30
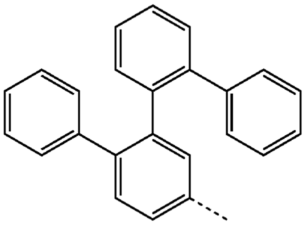
Ar1-31
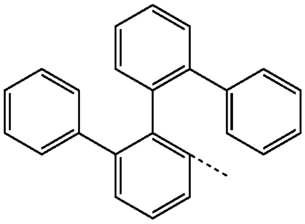
Ar1-32
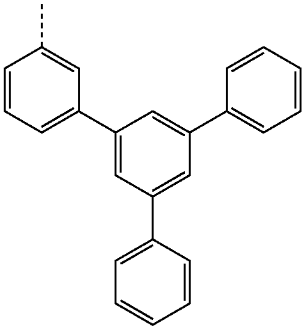
-continued
Ar1-33
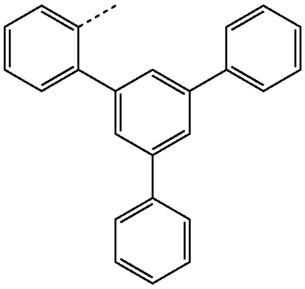
Ar1-34
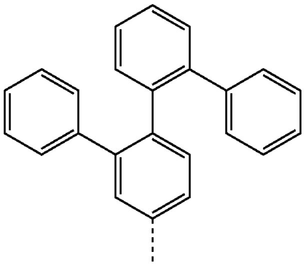
Ar1-35
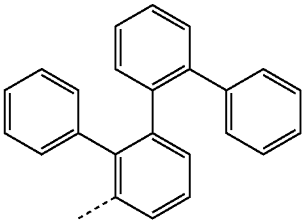
Ar1-36
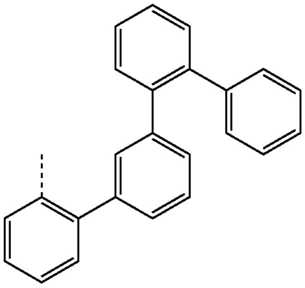
Ar1-37
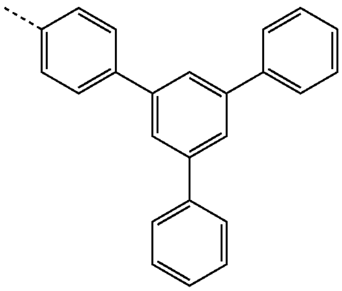
Ar1-38
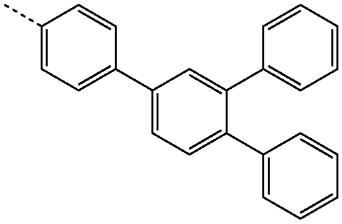

-continued
$Ar^1$-39
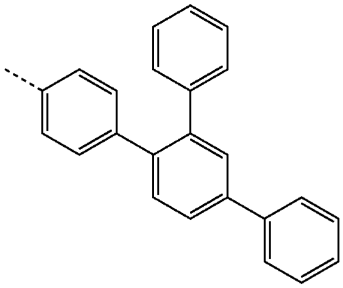
$Ar^1$-40
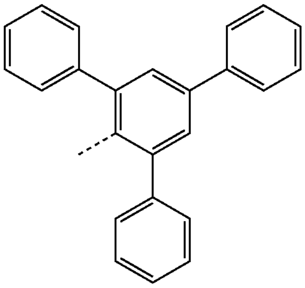
$Ar^1$-41
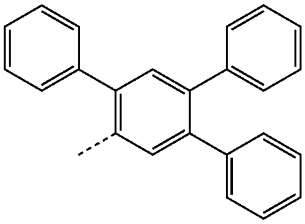
$Ar^1$-42
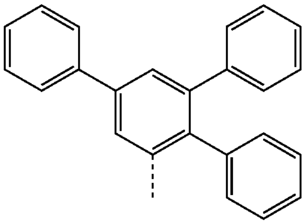
$Ar^1$-43
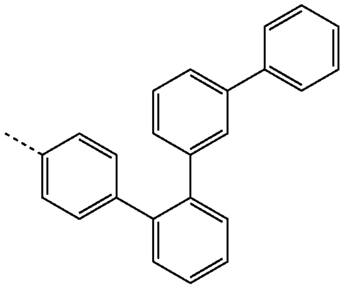
-continued
$Ar^1$-44
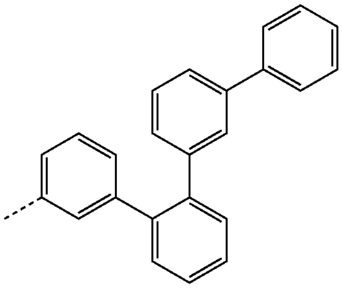
$Ar^1$-45
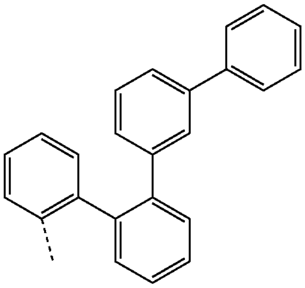
$Ar^1$-46
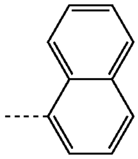
$Ar^1$-47
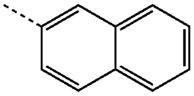
$Ar^1$-48
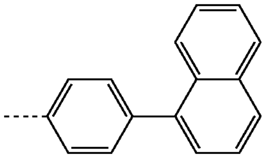
$Ar^1$-49
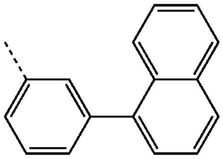
$Ar^1$-50
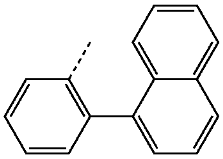
$Ar^1$-51
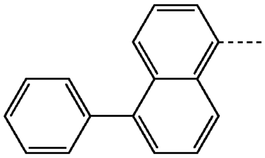

-continued
$Ar^1$-52
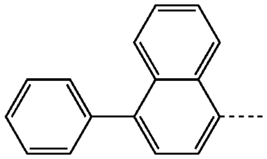
$Ar^1$-53
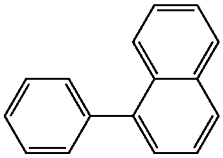 [SMILES: c1ccc(-c2cccc3ccccc23)cc1]
$Ar^1$-54
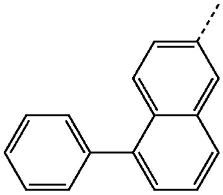
$Ar^1$-55
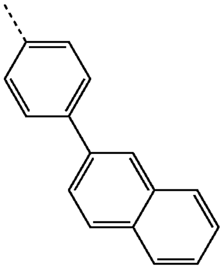
$Ar^1$-56
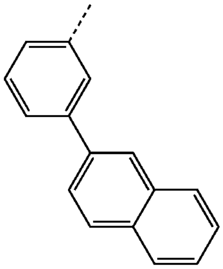
$Ar^1$-57
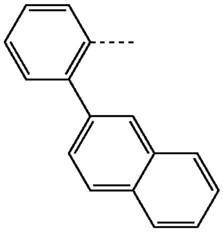
$Ar^1$-58
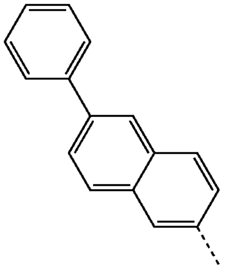
-continued
$Ar^1$-59
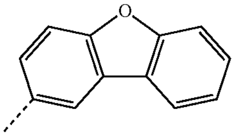
$Ar^1$-60
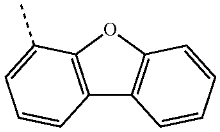
$Ar^1$-61
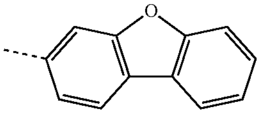
$Ar^1$-62
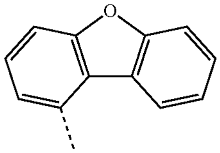
$Ar^1$-63
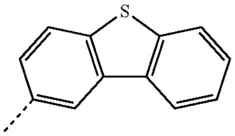
$Ar^1$-64
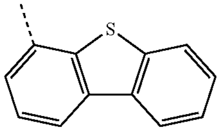
$Ar^1$-65
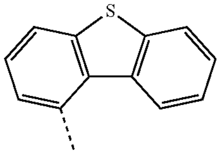
$Ar^1$-66
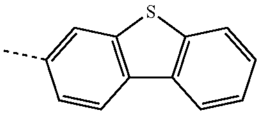
$Ar^1$-67
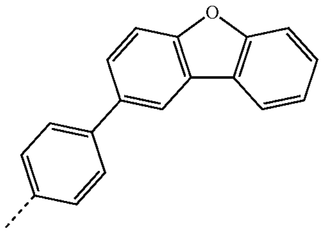
$Ar^1$-68
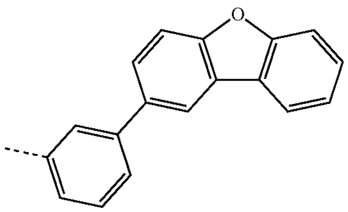

-continued
Ar$^1$-69
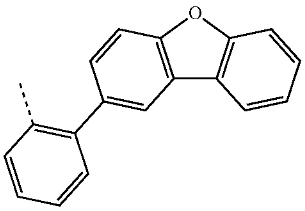
Ar$^1$-70
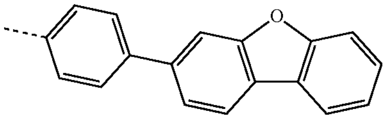
Ar$^1$-71
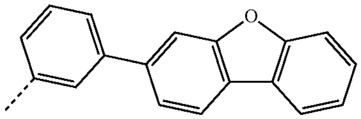
Ar$^1$-72
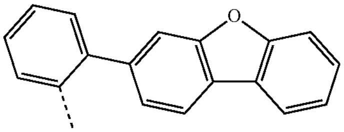
Ar$^1$-73
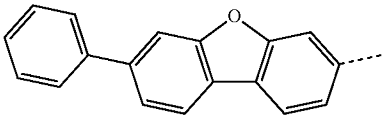
Ar$^1$-74
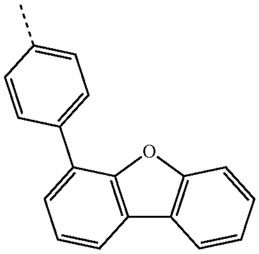
Ar$^1$-75
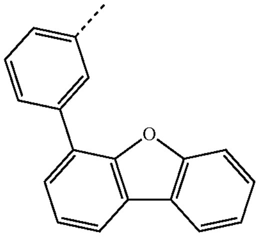
Ar$^1$-76
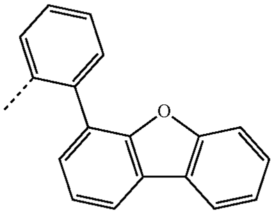
-continued
Ar$^1$-77
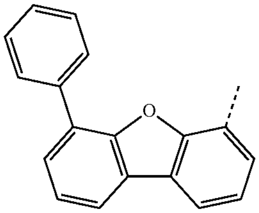
Ar$^1$-78
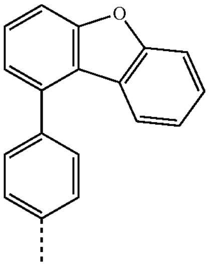
Ar$^1$-79
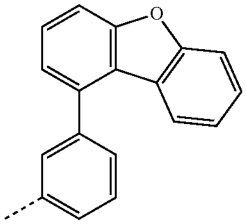
Ar$^1$-80
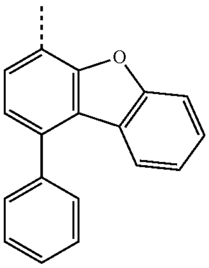
Ar$^1$-81
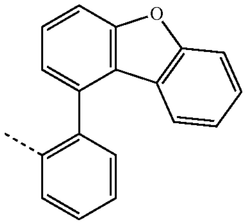
Ar$^1$-82
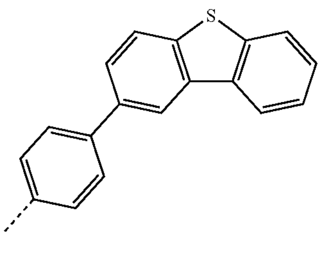

-continued
Ar$^1$-83
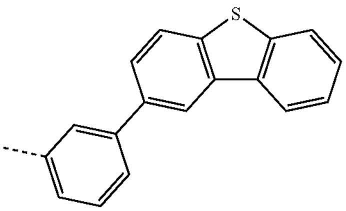
Ar$^1$-84
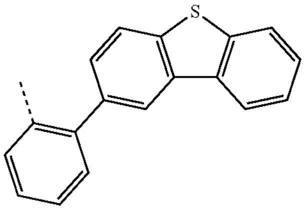
Ar$^1$-85
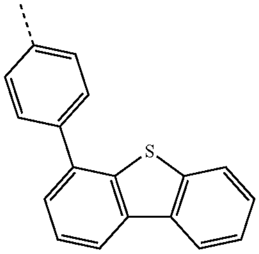
Ar$^1$-86
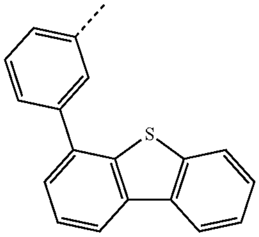
Ar$^1$-87
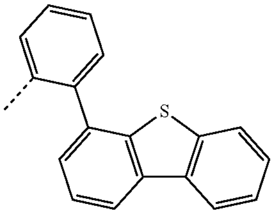
Ar$^1$-88
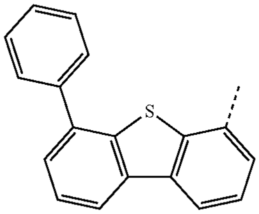
Ar$^1$-89
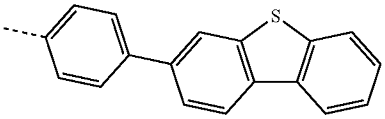
-continued
Ar$^1$-90
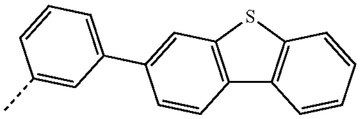
Ar$^1$-91
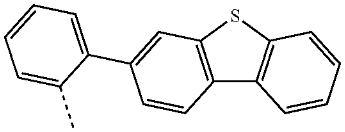
Ar$^1$-92
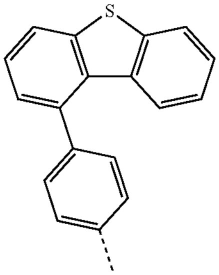
Ar$^1$-93
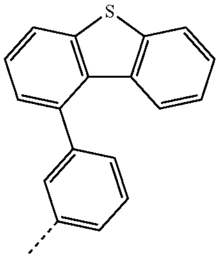
Ar$^1$-94
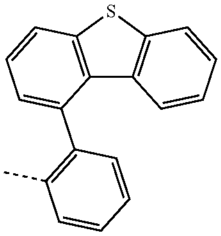
Ar$^1$-95
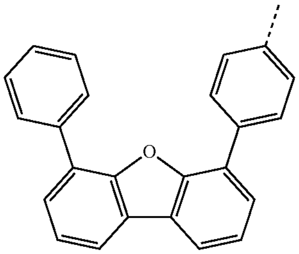
Ar$^1$-96
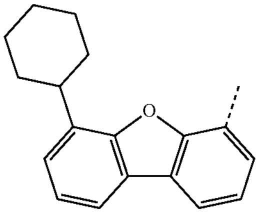

-continued
$Ar^1$-94
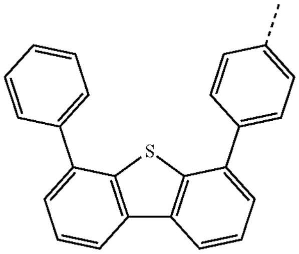
$Ar^1$-95
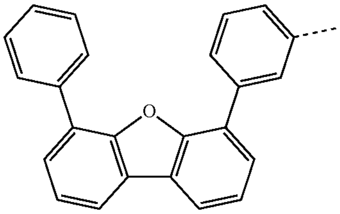
$Ar^1$-96
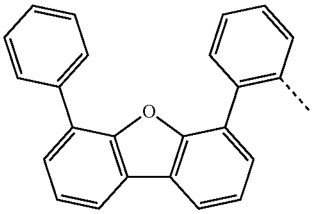
$Ar^1$-97
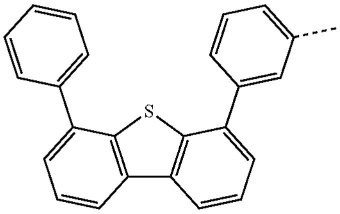
$Ar^1$-98
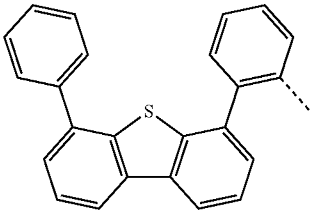
$Ar^1$-99
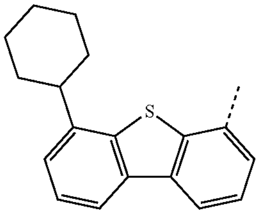
-continued
$Ar^1$-100
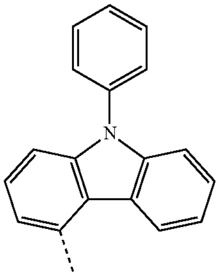
$Ar^1$-101
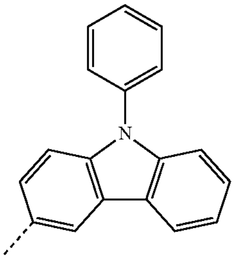
$Ar^1$-102
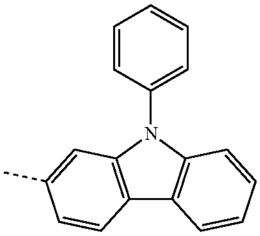
$Ar^1$-103
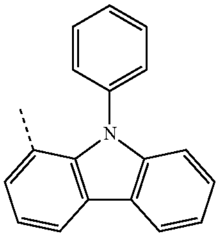
$Ar^1$-104
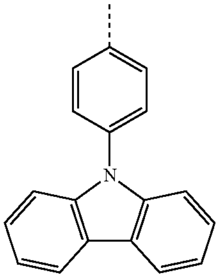
$Ar^1$-105
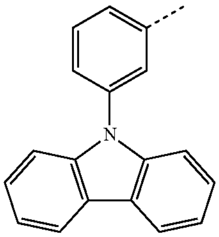

-continued
Ar[1]-106
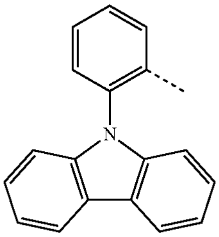
Ar[1]-107
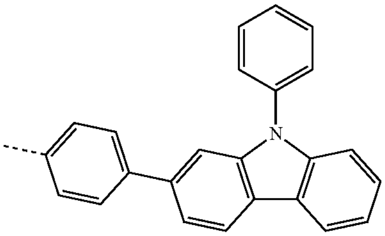
Ar[1]-108
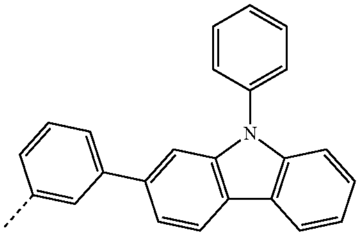
Ar[1]-109
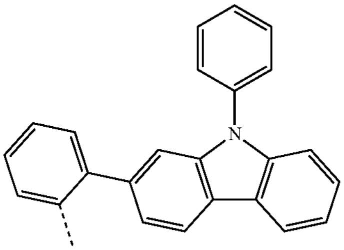
Ar[1]-110
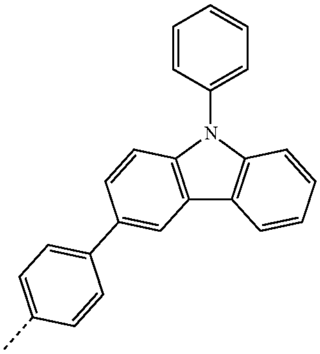
-continued
Ar[1]-111
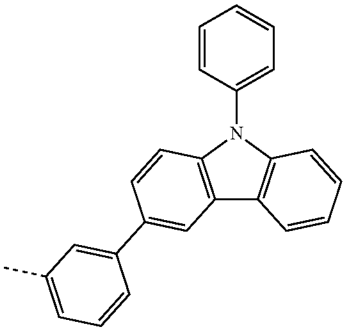
Ar[1]-112
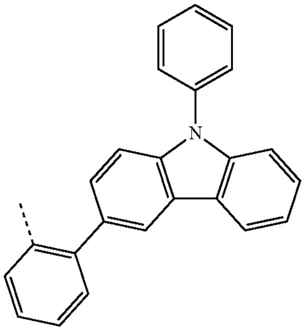
Ar[1]-113
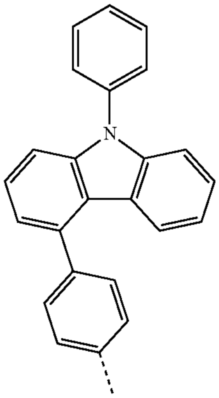
Ar[1]-114
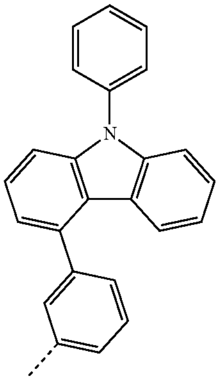

-continued
Ar$^1$-115
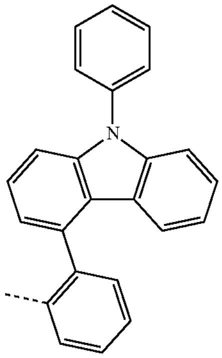
Ar$^1$-116
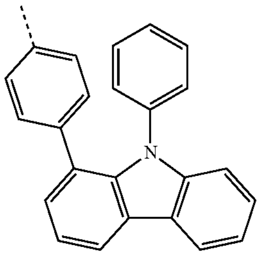
Ar$^1$-117
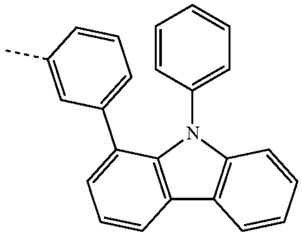
Ar$^1$-118
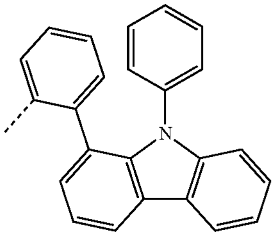
Ar$^1$-119
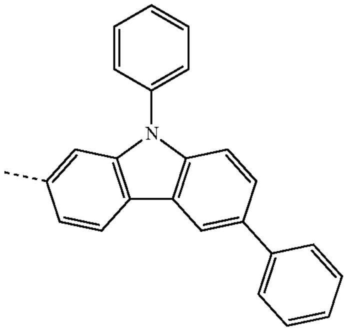
-continued
Ar$^1$-120
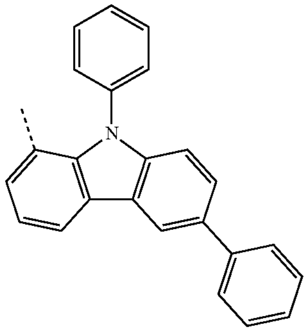
Ar$^1$-121
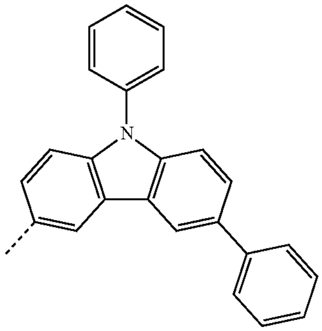
Ar$^1$-122
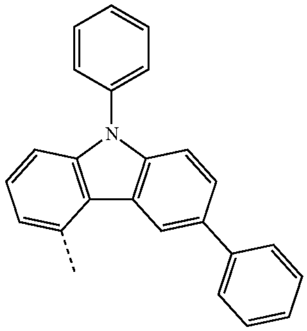
Ar$^1$-123
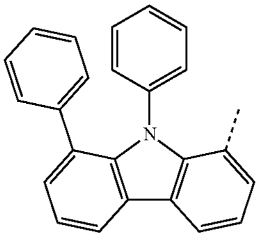
Ar$^1$-124
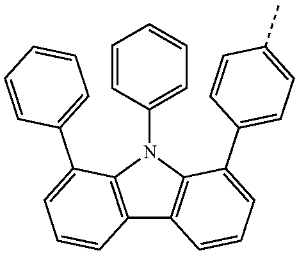

-continued
Ar1-125
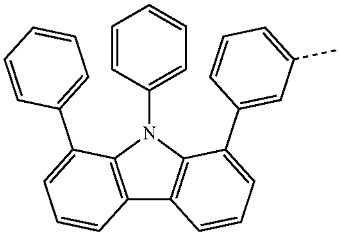
Ar1-126
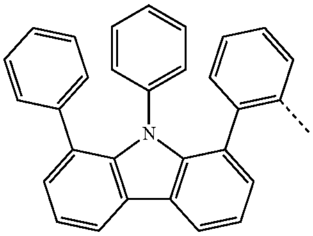
Ar1-127
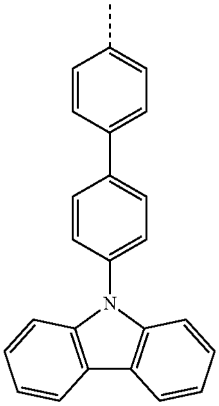
Ar1-128
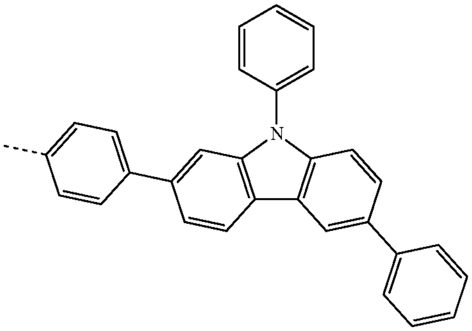
Ar1-129
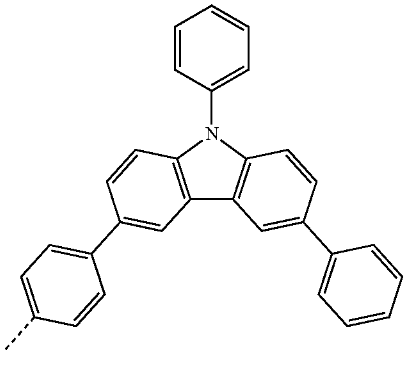
-continued
Ar1-130
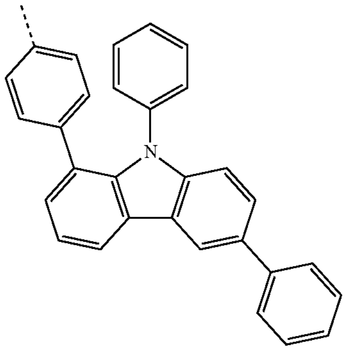
Ar1-131
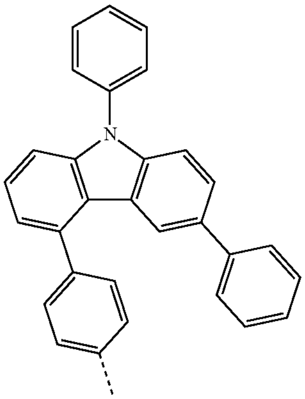
Ar1-132
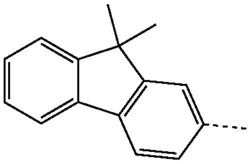
Ar1-133
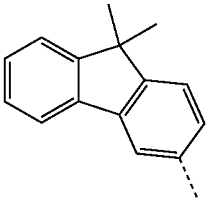
Ar1-134
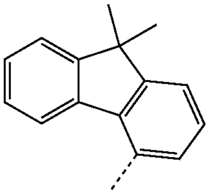
Ar1-135
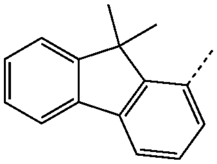

-continued
Ar1-136
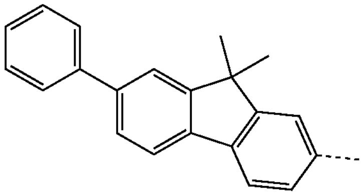
Ar1-137
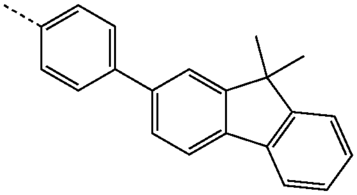
Ar1-138
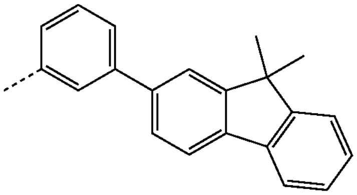
Ar1-139
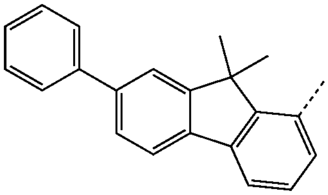
Ar1-140
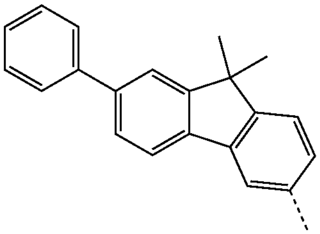
Ar1-141
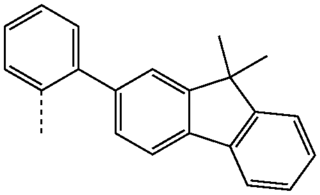
Ar1-142
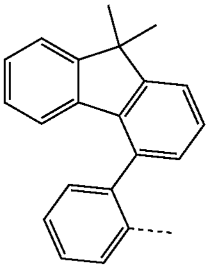
-continued
Ar1-143
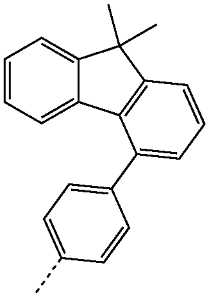
Ar1-144
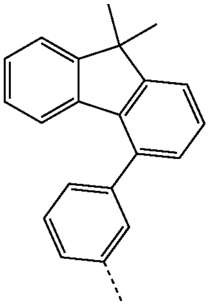
Ar1-145
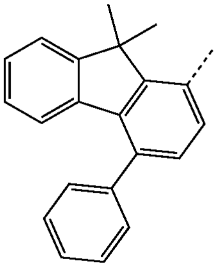
Ar1-146
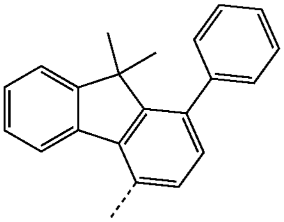
Ar1-147
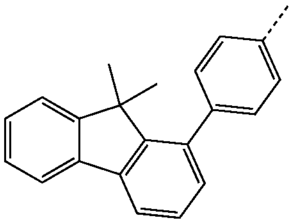
Ar1-148
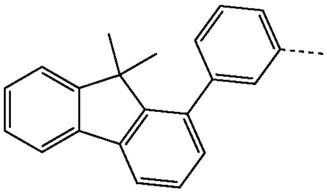

-continued
Ar1-149
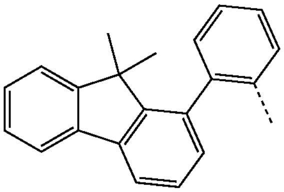
Ar1-150
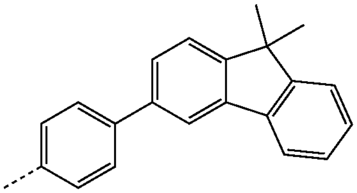
Ar1-151
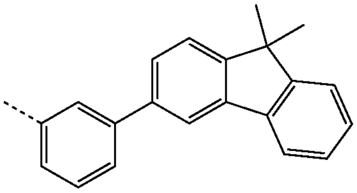
Ar1-152
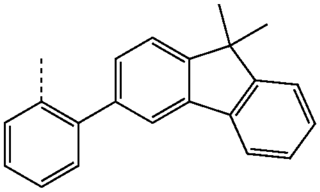
Ar1-153
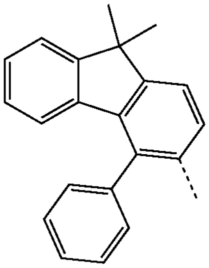
Ar1-154
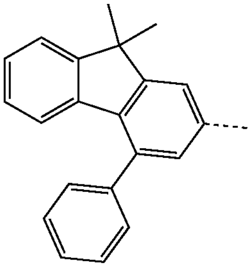
Ar1-155
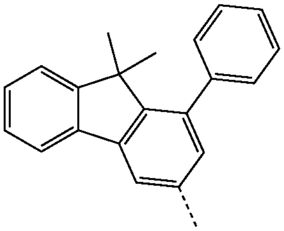
-continued
Ar1-156
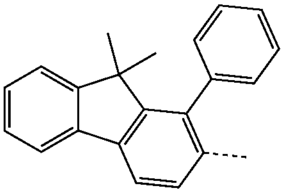
Ar1-157
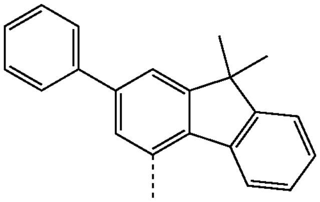
Ar1-158
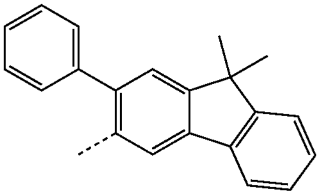
Ar1-159
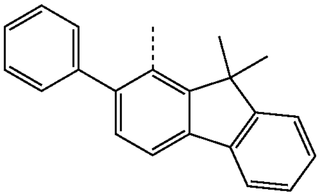
Ar1-160
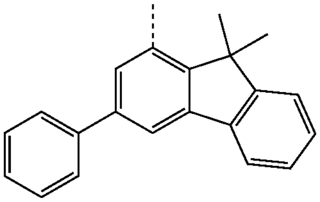
Ar1-161
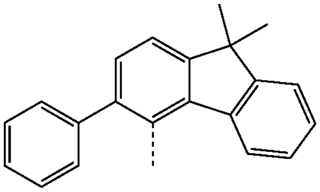
Ar1-162
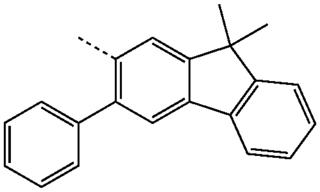

-continued
$Ar^1$-163
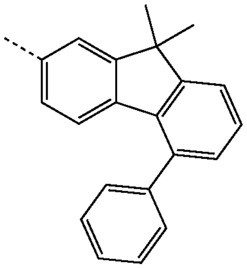
$Ar^1$-164
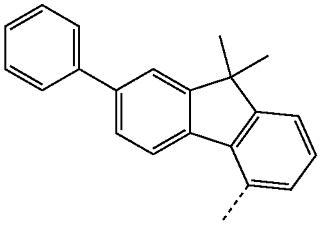
$Ar^1$-165
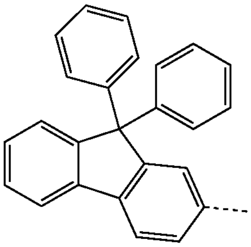
$Ar^1$-166
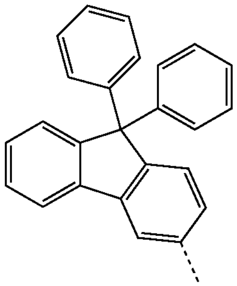
$Ar^1$-167
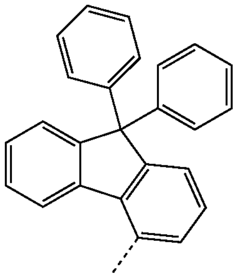
$Ar^1$-168
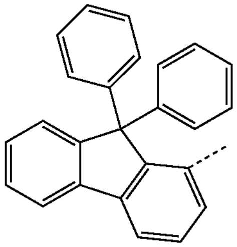
-continued
$Ar^1$-169
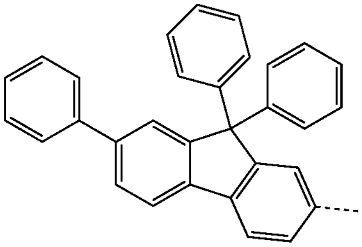
$Ar^1$-170
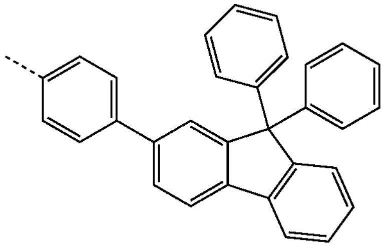
$Ar^1$-171
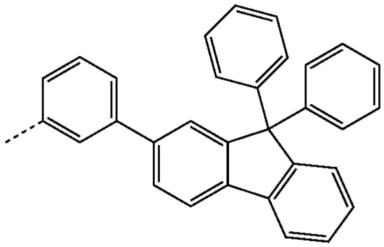
$Ar^1$-172
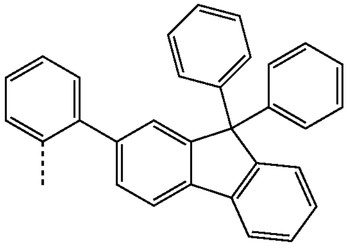
$Ar^1$-173
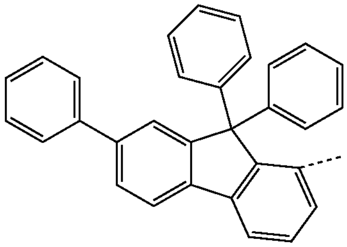
$Ar^1$-174
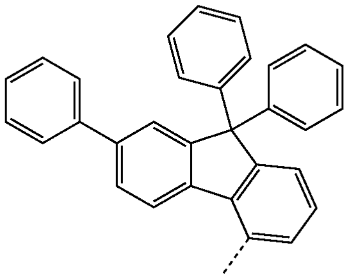

-continued
Ar1-175
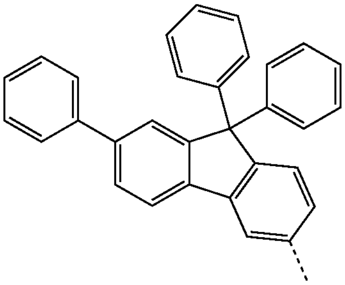
Ar1-176
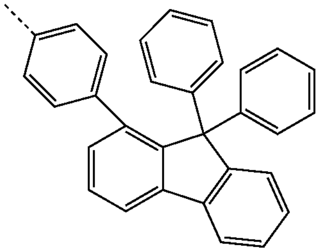
Ar1-177
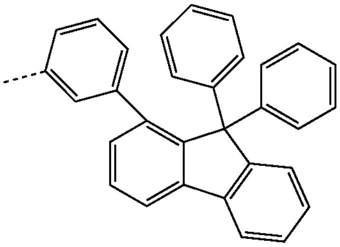
Ar1-178
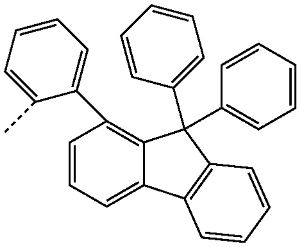
Ar1-179
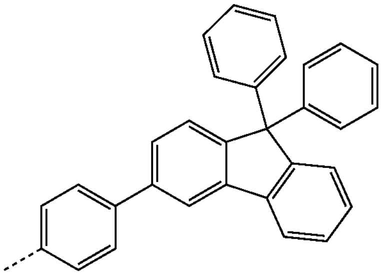
-continued
Ar1-180
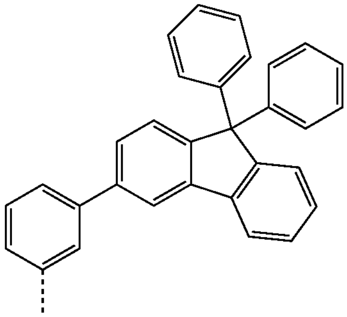
Ar1-181
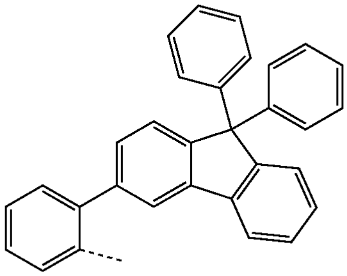
Ar1-182
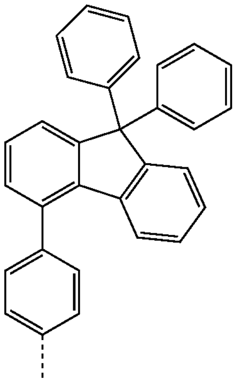
Ar1-183
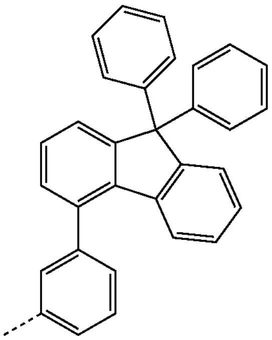

-continued
Ar$^{1}$-184
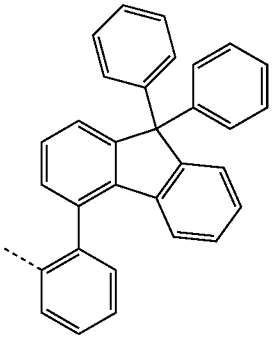
Ar$^{1}$-185
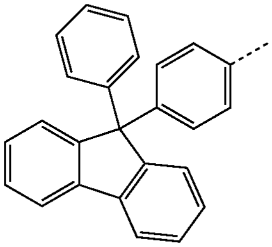
Ar$^{1}$-186
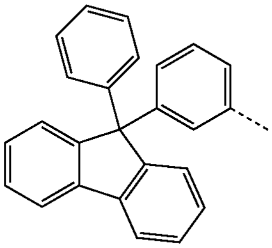
Ar$^{1}$-187
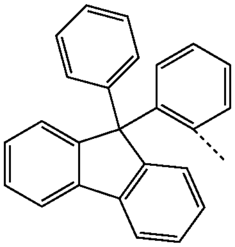
Ar$^{1}$-188
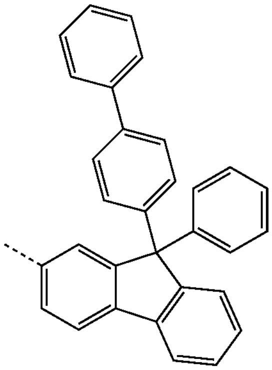
-continued
Ar$^{1}$-189
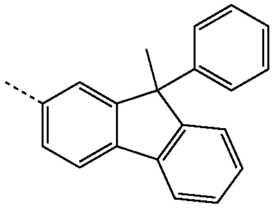
Ar$^{1}$-190
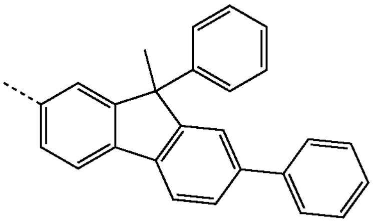
Ar$^{1}$-191
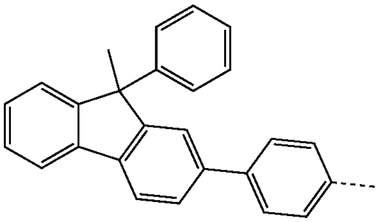
Ar$^{1}$-192
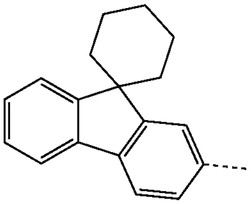
Ar$^{1}$-193
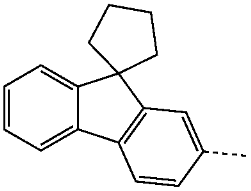
Ar$^{1}$-194
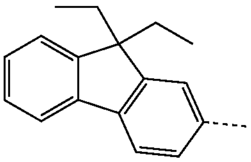
Ar$^{1}$-195
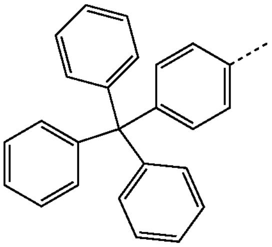

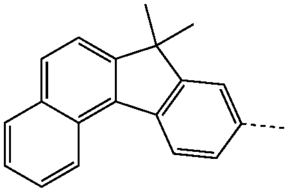
Ar1-196
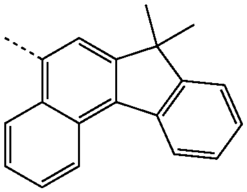
Ar1-197
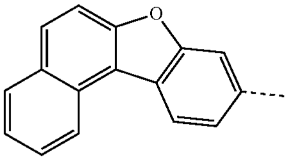
Ar1-198
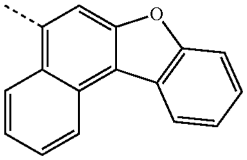
Ar1-199
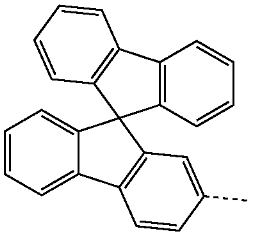
Ar1-200
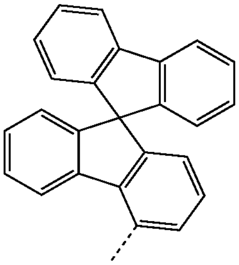
Ar1-201
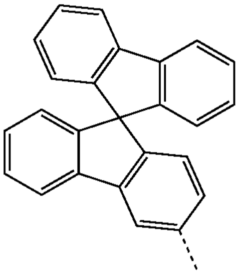
Ar1-202
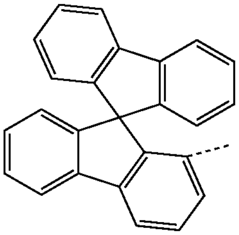
Ar1-203
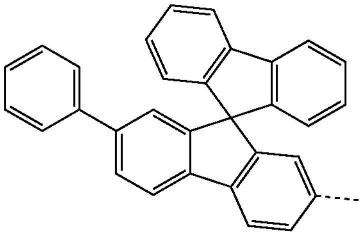
Ar1-204
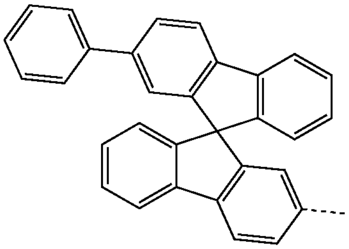
Ar1-205
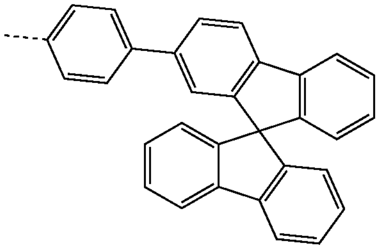
Ar1-206
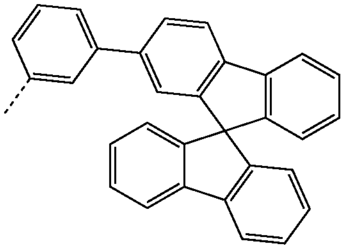
Ar1-207
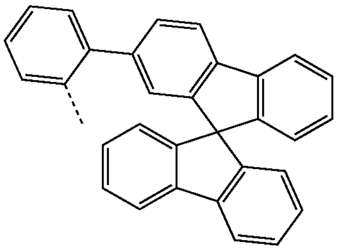
Ar1-208

-continued
Ar[1]-209
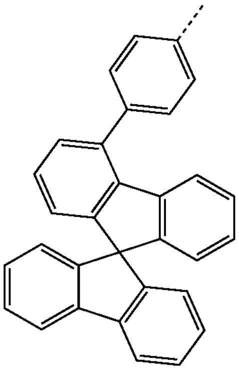
Ar[1]-210
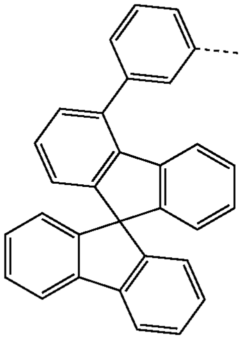
Ar[1]-211
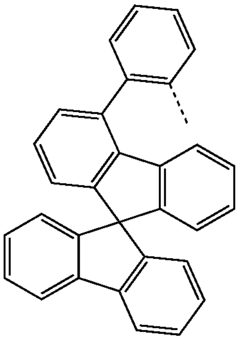
Ar[1]-212
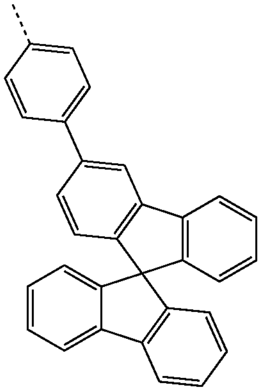
-continued
Ar[1]-213
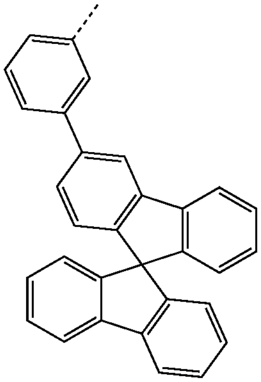
Ar[1]-214
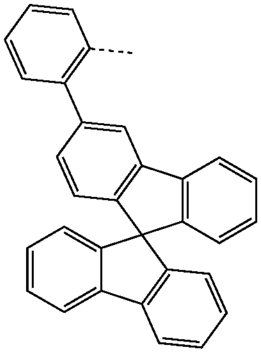
Ar[1]-215
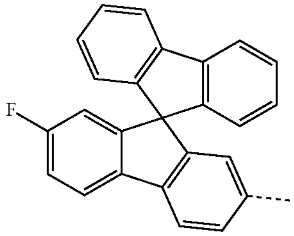
Ar[1]-216
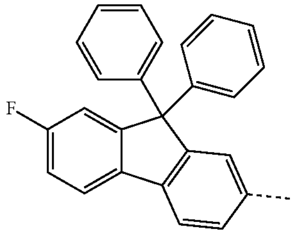
Ar[1]-217
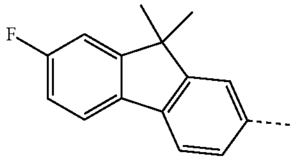
Ar[1]-218
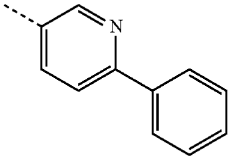

-continued
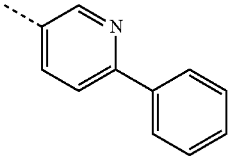
Ar$^1$-219
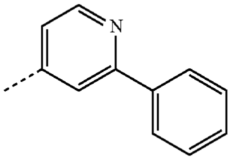
Ar$^1$-220
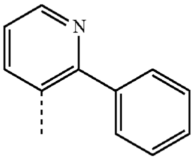
Ar$^1$-221
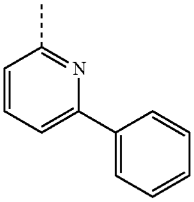
Ar$^1$-222
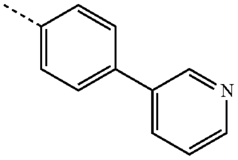
Ar$^1$-223
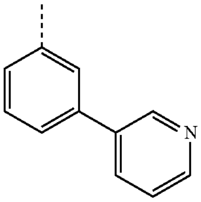
Ar$^1$-224
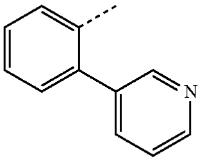
Ar$^1$-225
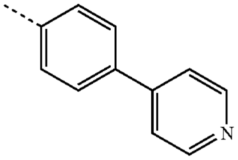
Ar$^1$-226
-continued
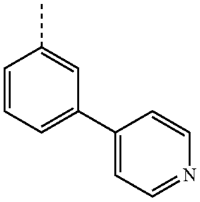
Ar$^1$-227
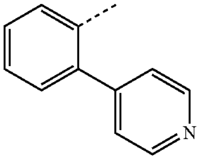
Ar$^1$-228
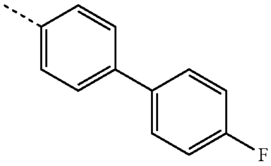
Ar$^1$-229
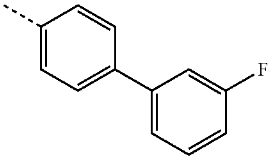
Ar$^1$-230
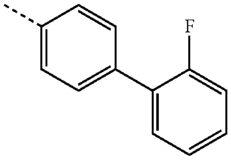
Ar$^1$-231
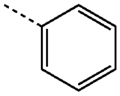
Ar$^1$-232
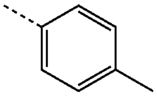
Ar$^1$-233
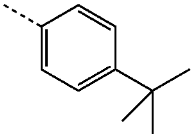
Ar$^1$-234
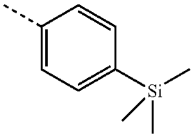
Ar$^1$-235
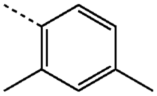
Ar$^1$-236

-continued

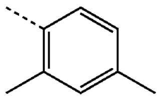

$Ar^1$-237

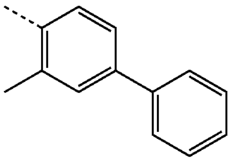

$Ar^1$-238

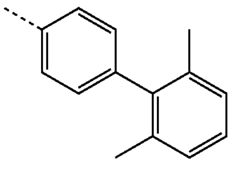

$Ar^1$-239

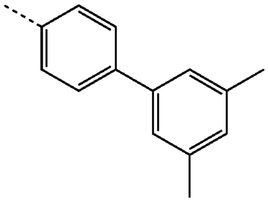

$Ar^1$-240

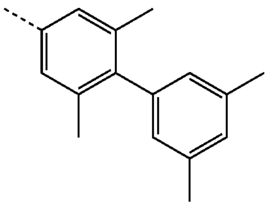

$Ar^1$-241

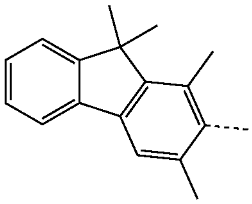

$Ar^1$-242

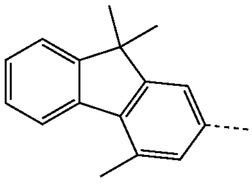

$Ar^1$-243

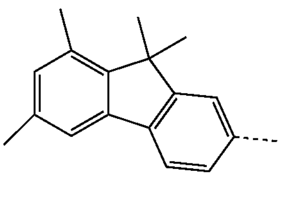

$Ar^1$-244

-continued

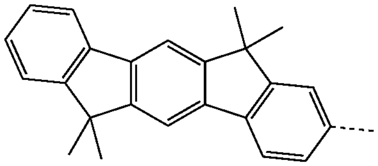

$Ar^1$-245

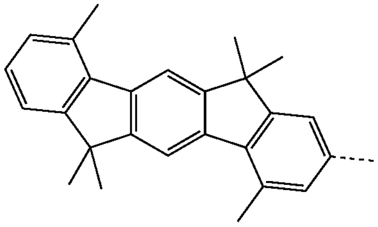

$Ar^1$-246

The groups shown above may each be substituted by $R^1$ radicals at their positions shown as unsubstituted.

Among the $Ar^1$ groups mentioned, particular preference is given to the $Ar^1$-1, $Ar^1$-2, $Ar^1$-3, $Ar^1$-4, $Ar^1$-5, $Ar^1$-6, $Ar^1$-15, $Ar^1$-16, $Ar^1$-46, $Ar^1$-47, $Ar^1$-48, $Ar^1$-55, $Ar^1$-59, $Ar^1$-60, $Ar^1$-61, $Ar^1$-62, $Ar^1$-63, $Ar^1$-64, $Ar^1$-65, $Ar^1$-66, $Ar^1$-67, $Ar^1$-70, $Ar^1$-74, $Ar^1$-78, $Ar^1$-82, $Ar^1$-89, $Ar^1$-92, $Ar^1$-100, $Ar^1$-101, $Ar^1$-102, $Ar^1$-104, $Ar^1$-107, $Ar^1$-110, $Ar^1$-113, $Ar^1$-127, $Ar^1$-132, $Ar^1$-133, $Ar^1$-134, $Ar^1$-135, $Ar^1$-136, $Ar^1$-137, $Ar^1$-143, $Ar^1$-145, $Ar^1$-147, $Ar^1$-163, $Ar^1$-164, $Ar^1$-165, $Ar^1$-166, $Ar^1$-167, $Ar^1$-168, $Ar^1$-188, $Ar^1$-189, $Ar^1$-200, $Ar^1$-201, $Ar^1$-202, $Ar^1$-203 and $Ar^1$-232 groups. Among the above-mentioned $Ar^1$ groups, very particular preference is given to the $Ar^1$-1, $Ar^1$-74, $Ar^1$-132, $Ar^1$-134, $Ar^1$-136, $Ar^1$-137, $Ar^1$-165, $Ar^1$-200 and $Ar^1$-201 groups.

In addition, the Y group in formula (A) is preferably selected from a single bond, $C(R^1)_2$, O, S and $NR^1$. More preferably, Y is a single bond.

When the A group is a carbazole-containing group, it is preferably a carbazole group as such and in the narrower sense, or an indenocarbazole group as such and in the narrower sense. The carbazole group may be bonded to the rest of the compound via its nitrogen atom, or via one of its benzene rings.

Particularly preferred A groups correspond to the following formulae:

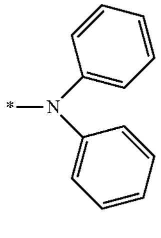

Formula (A-1)

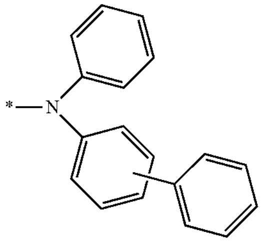

Formula (A-2)

-continued
Formula (A-3)
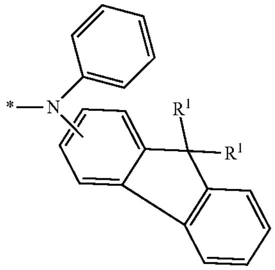
Formula (A-4)
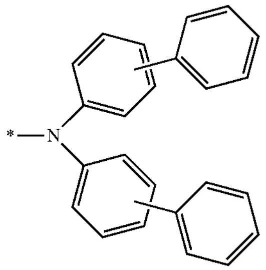
Formula (A-5)
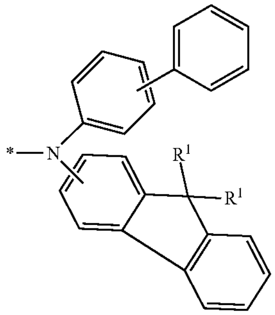
Formula (A-6)
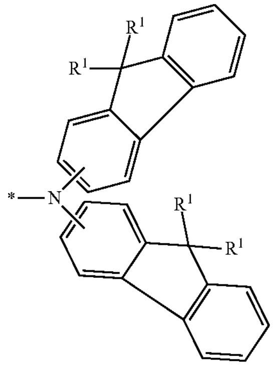
Formula (A-7)
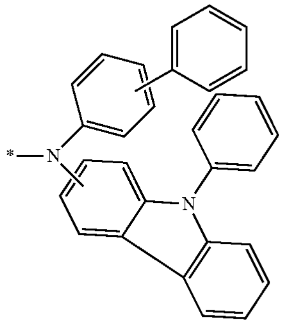
-continued
Formula (A-8)
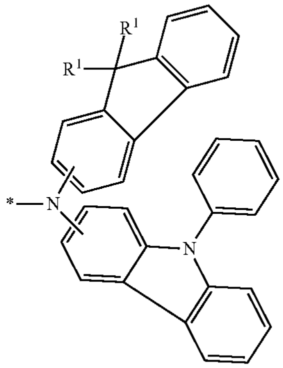
Formula (A-9)
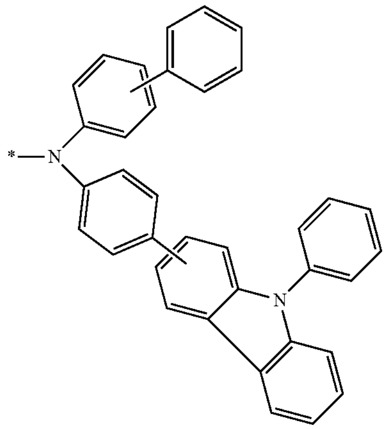
Formula (A-10)
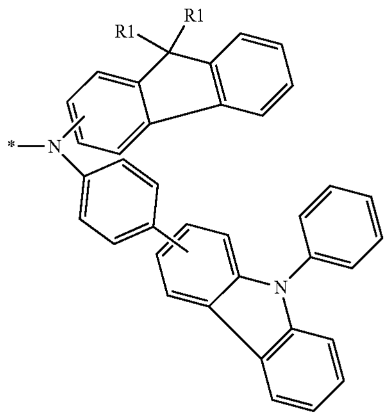
Formula (A-11)
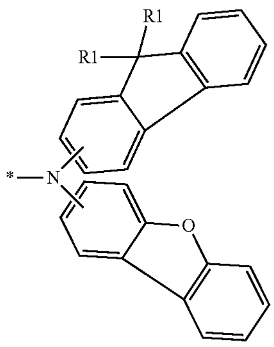

-continued
Formula (A-12)
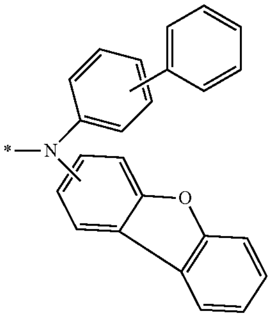
Formula (A-13)
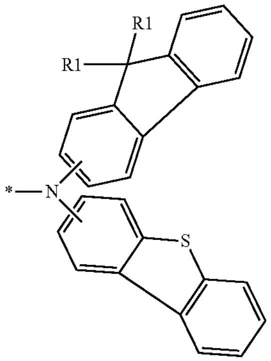
Formula (A-14)
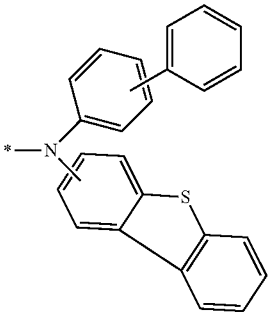
Formula (A-15)
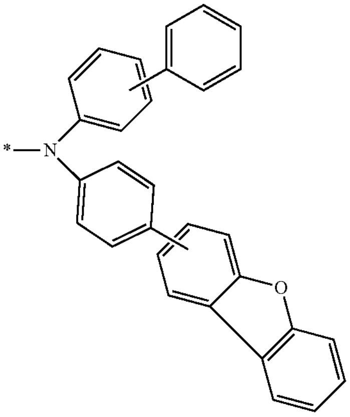
-continued
Formula (A-16)
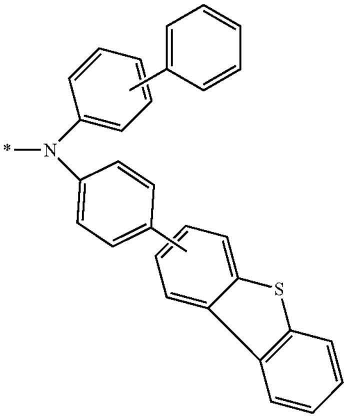
Formula (A-17)
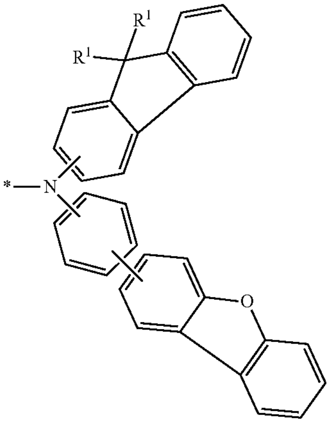
Formula (A-18)
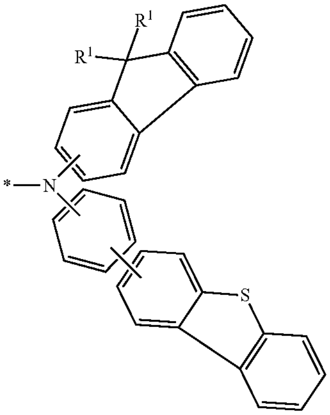
Formula (A-19)
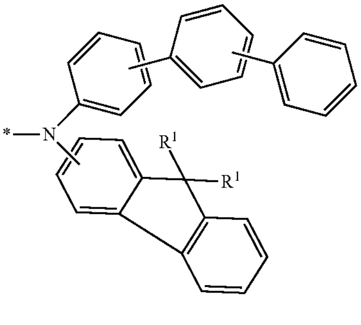

-continued
Formula (A-20)
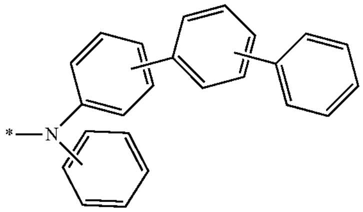
Formula (A-21)
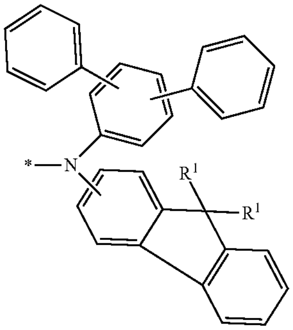
Formula (A-22)
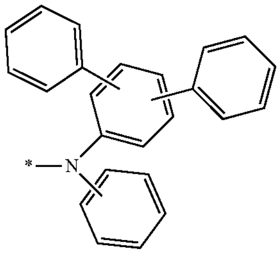
Formula (A-23)
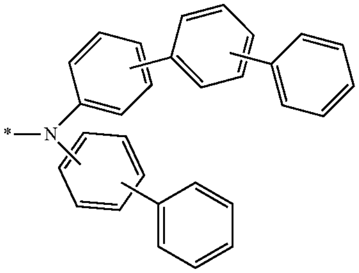
Formula (A-24)
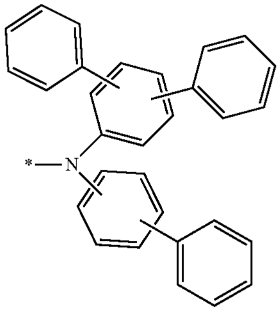
Formula (A-24)
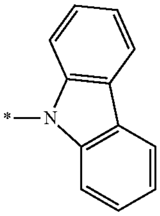
-continued
Formula (A-25)
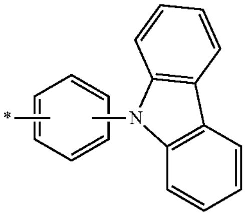
Formula (A-26)
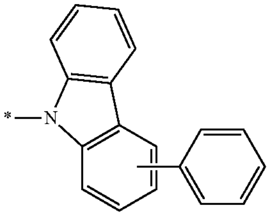
Formula (A-27)
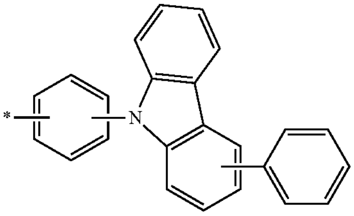
Formula (A-28)
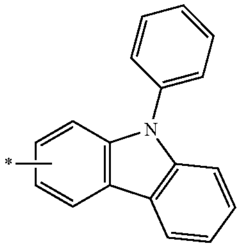
Formula (A-29)
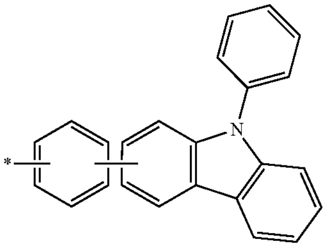
Formula (A-30)
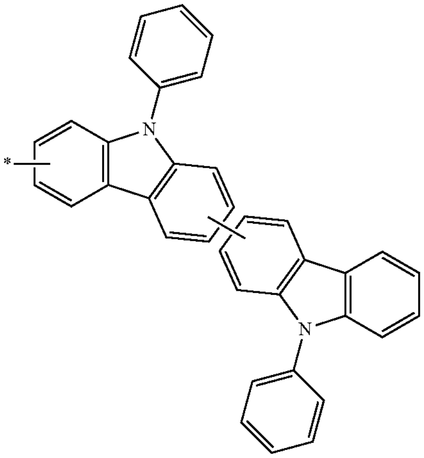

-continued
Formula (A-31)
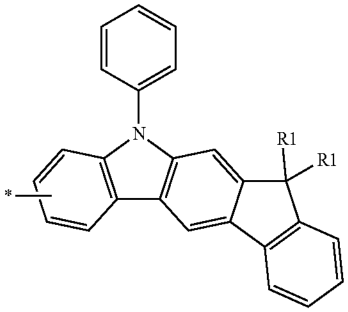
Formula (A-32)
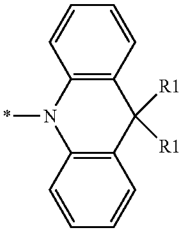
Formula (A-33)
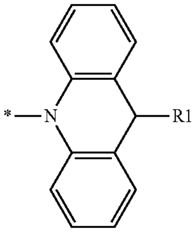
Formula (A-34)
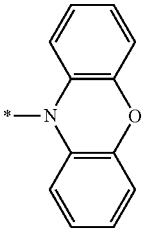
Formula (A-35)
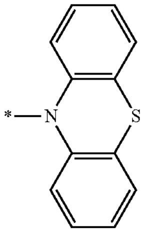
Formula (A-36)
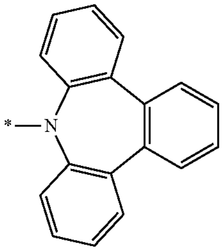
-continued
Formula (A-37)
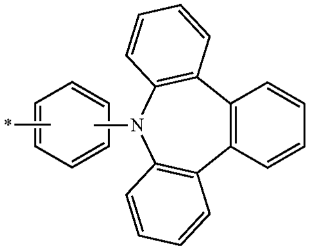
Formula (A-38)
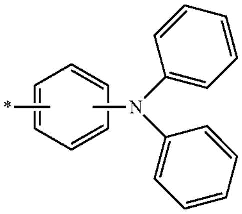
Formula (A-39)
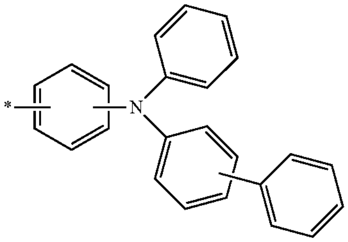
Formula (A-40)
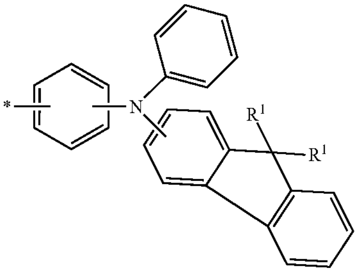
Formula (A-41)
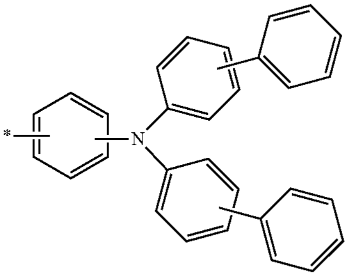
Formula (A-42)
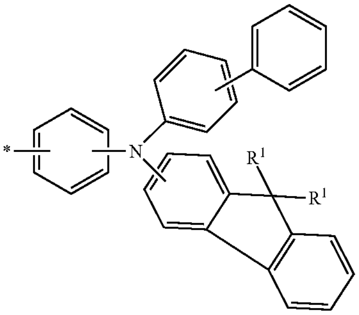

-continued
Formula (A-43)
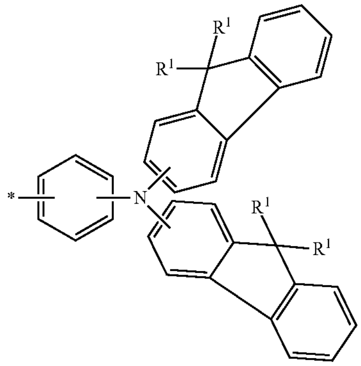
Formula (A-44)
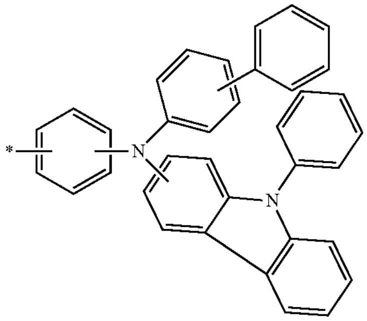
Formula (A-45)
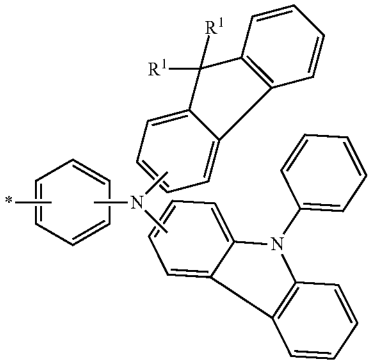
Formula (A-46)
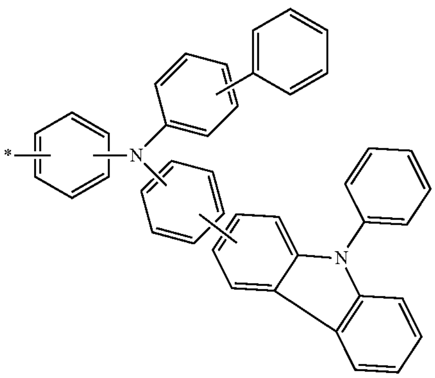
-continued
Formula (A-47)
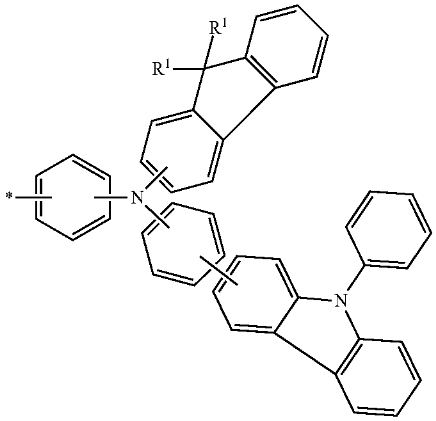
Formula (A-48)
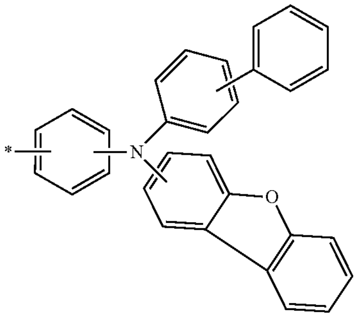
Formula (A-49)
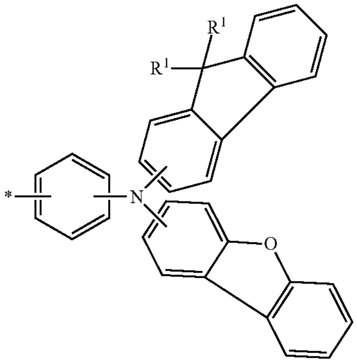
Formula (A-50)
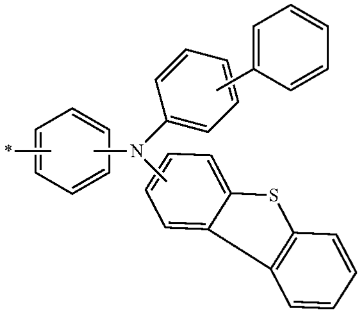

-continued
Formula (A-51)
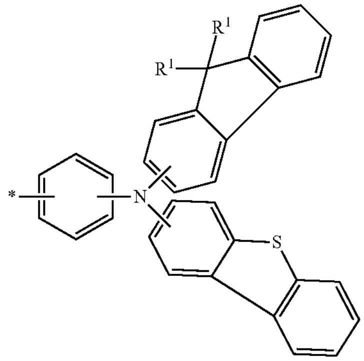
Formula (A-52)
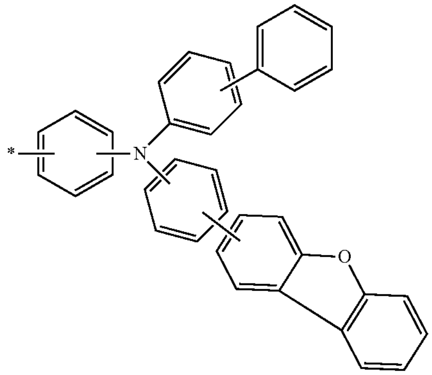
Formula (A-53)
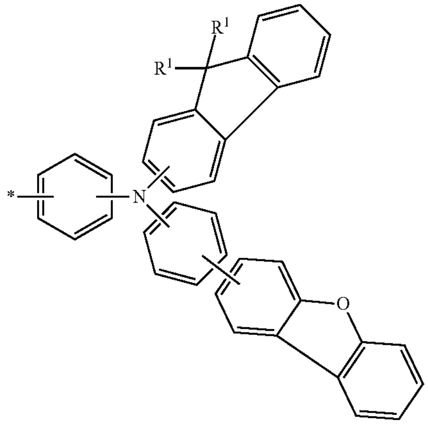
Formula (A-54)
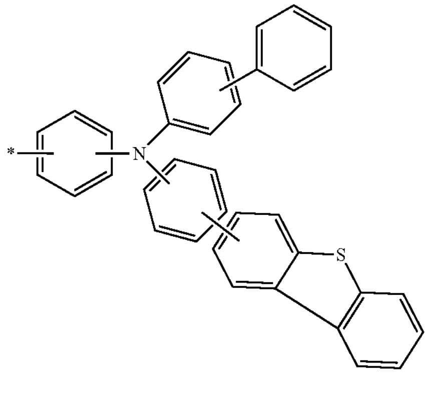
-continued
Formula (A-55)
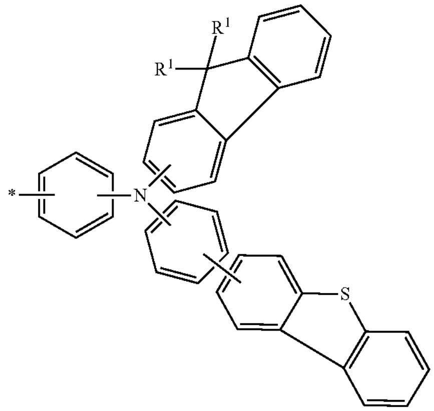
Formula (A-56)
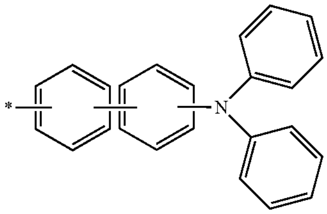
Formula (A-57)
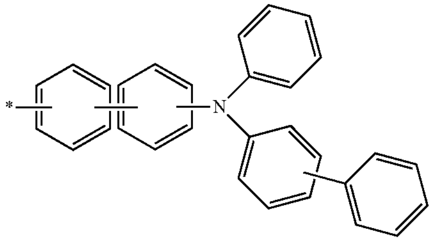
Formula (A-58)
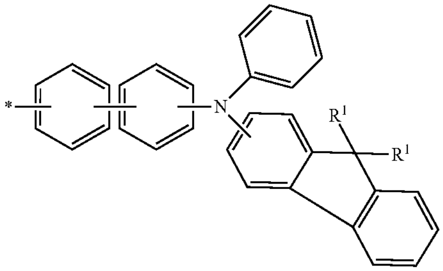
Formula (A-59)
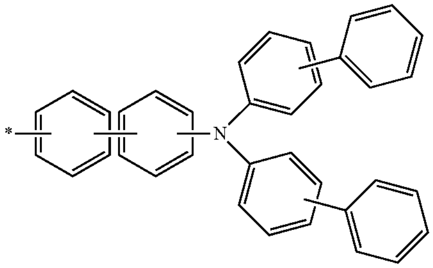

-continued

Formula (A-60)

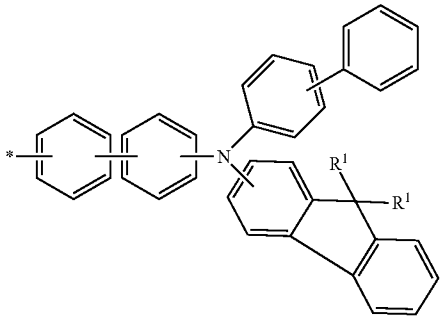

Formula (A-61)

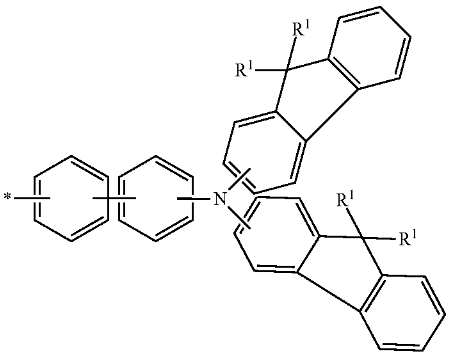

Formula (A-62)

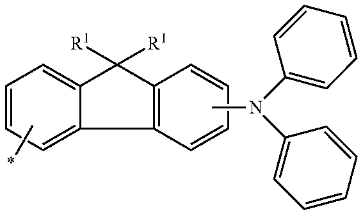

Formula (A-63)

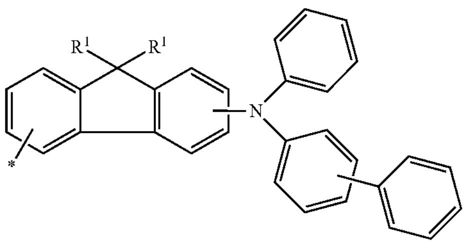

Formula (A-64)

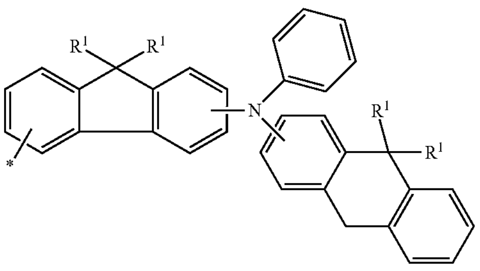

-continued

Formula (A-65)

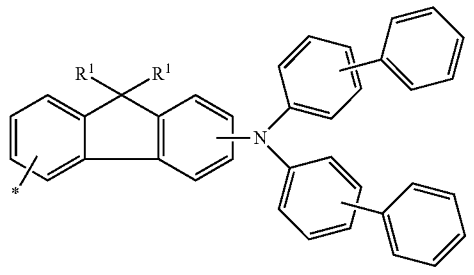

Formula (A-66)

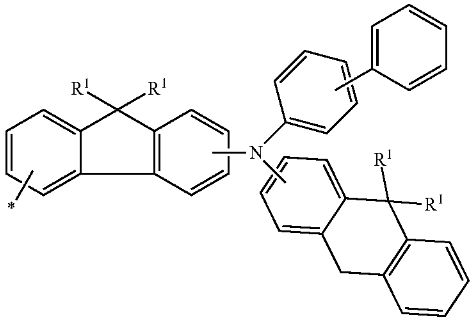

Formula (A-67)

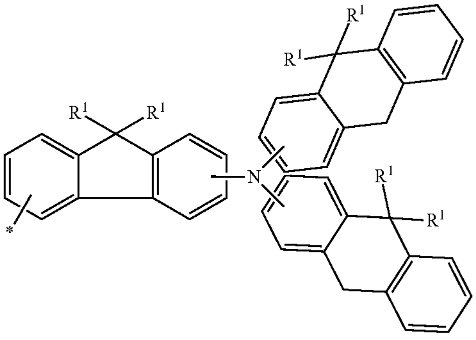

where the groups may be substituted at all unoccupied positions by one or more $R^1$ radicals as defined above. It is preferable that $R^1$ radicals here are defined as per their preferred embodiments. Preferably, the compounds are unsubstituted at their unoccupied positions.

A preferred embodiment of the compound of the formula (I) corresponds to the following formula (I-1):

Formula (I-1)

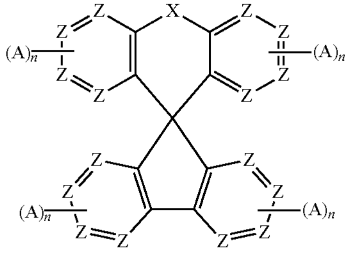

where the variables that occur are as defined above. Preferably, the variables that occur correspond to their above-mentioned preferred embodiments.

Particularly preferred embodiments of the compounds of the formula (I) correspond to the following formulae:

Formula (I-1-1)
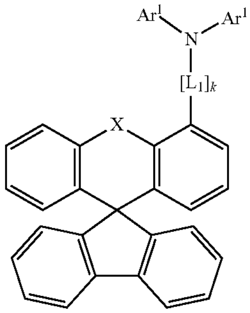
Formula (I-1-2)
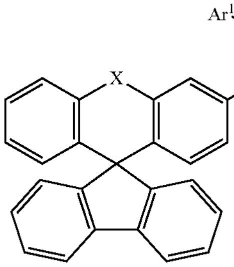
Formula (I-1-3)
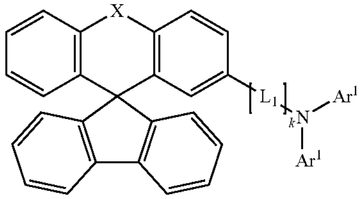
Formula (I-1-4)
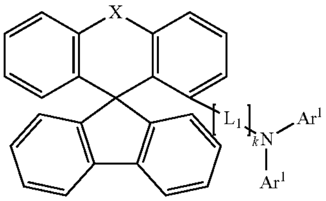
Formula (I-1-5)
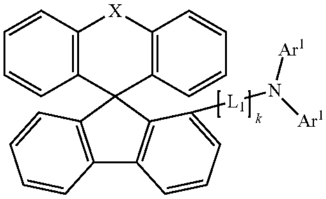
Formula (I-1-6)
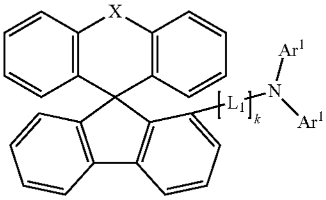
-continued
Formula (I-1-7)
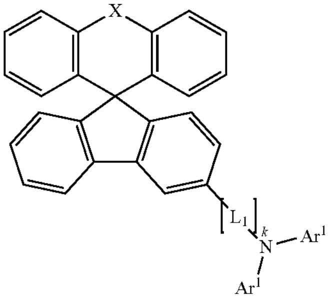
Formula (I-1-8)
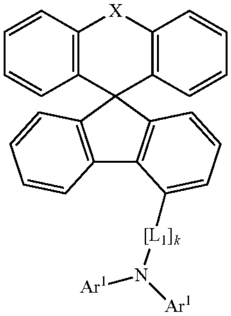
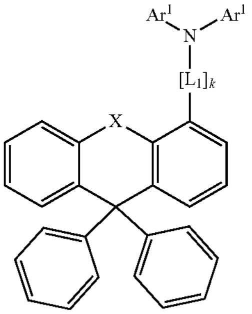
Formula (I-2-2)
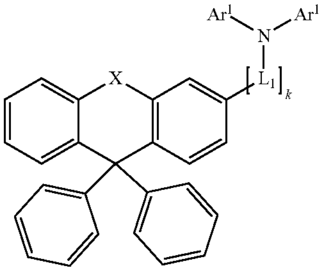
Formula (I-2-3)
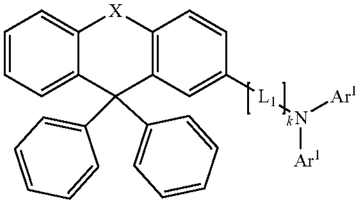
Formula (I-2-4)
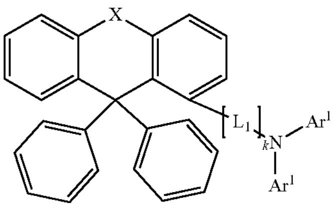

-continued
Formula (I-2-5)
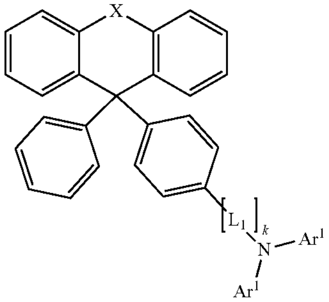
Formula (I-2-6)
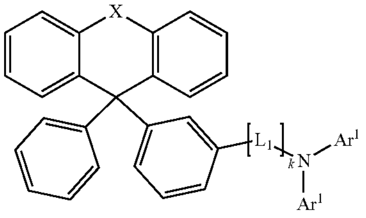
Formula (I-2-7)
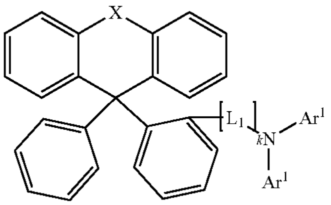
Formula (I-1-9)
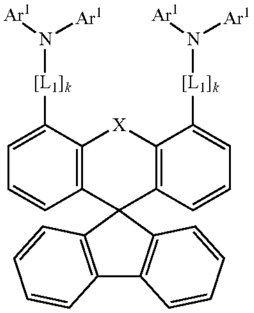
Formula (I-1-10)
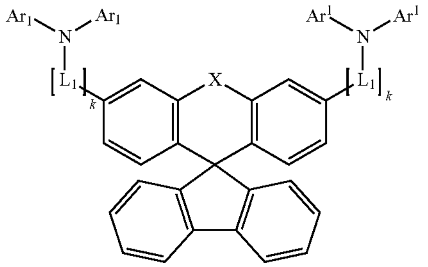
Formula (I-1-11)
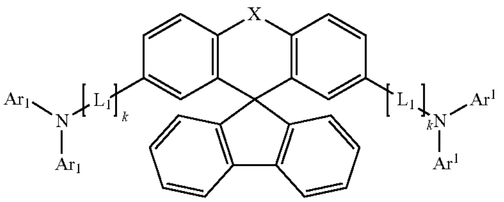
-continued
Formula (I-1-12)
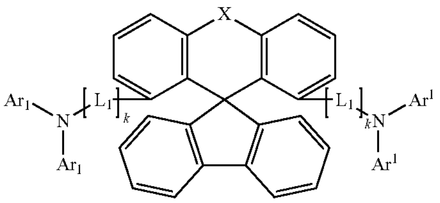
Formula (I-1-13)
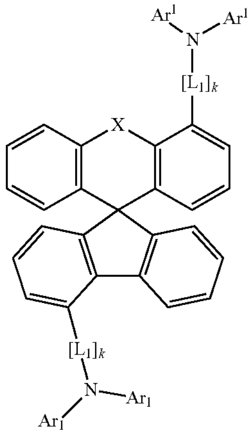
Formula (I-1-14)
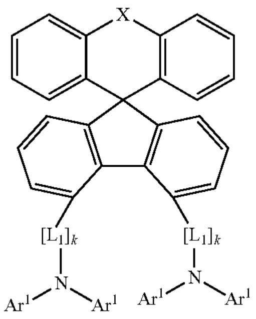
Formula (I-1-15)
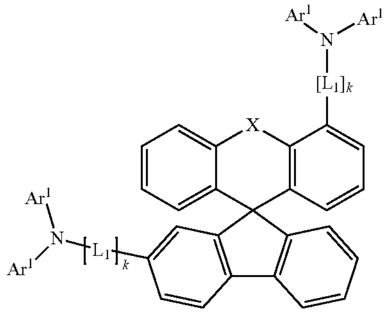

-continued

Formula (I-1-16)

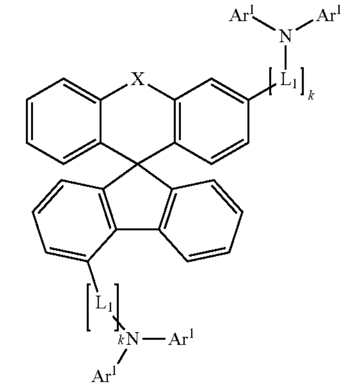

Formula (I-1-17)

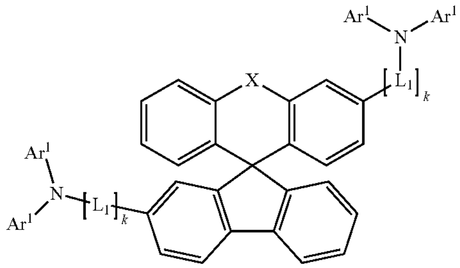

Formula (I-1-18)

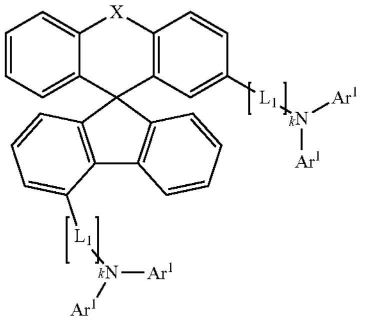

Formula (I-1-19)

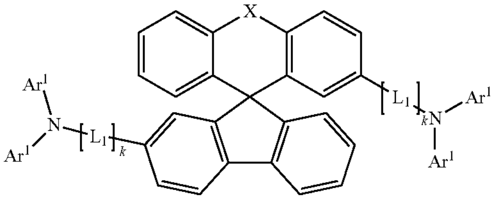

Formula (I-1-20)

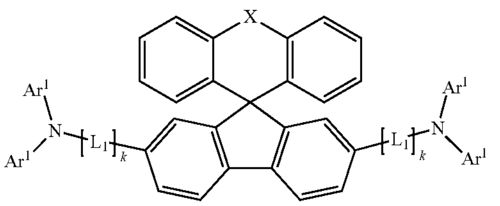

where the variables that occur are as defined above, and where the compounds may each be substituted on the benzene rings at the positions shown as unsubstituted by $R^2$ radicals. Preferably, the compounds are each unsubstituted on the benzene rings at the positions shown as unsubstituted.

Most preferably, the compound corresponds to one of the formulae (I-1-1) to (I-1-8), most preferably to one of the formulae (I-1-1) to (I-1-3). For compounds of this kind, particularly good performance data have been found in the case of use in the device of the invention.

Preferably, in the above formulae, $L_1$ is selected from aromatic and heteroaromatic ring systems which have 6 to 24 aromatic ring atoms and may be substituted by one or more $R^1$ radicals.

Preferably, in the above formulae, k is 0 or 1.

Particular preference is given to the combination of the formulae (I-1-1) to (I-1-20) and (I-2-1) to (I-2-7) with the preferred embodiments of $Ar^1$.

Particularly preferred definitions of the compounds of the formula (I) are shown in the following table, where the variables are as defined above and there are preferably no further substituents other than those mentioned:

| | Base skeleton | $L^1$ or k = 0 | $Ar^1$ | $Ar^1$ |
|---|---|---|---|---|
| 1 | I-1-2-O | k = 0 | $Ar^1$-1 | $Ar^1$-1 |
| 2 | " | " | " | $Ar^1$-74 |
| 3 | " | " | " | $Ar^1$-132 |
| 4 | " | " | " | $Ar^1$-134 |
| 5 | " | " | " | $Ar^1$-136 |
| 6 | " | " | " | $Ar^1$-137 |
| 7 | " | " | " | $Ar^1$-165 |
| 8 | " | " | " | $Ar^1$-200 |
| 9 | " | " | " | $Ar^1$-201 |
| 10 | " | " | $Ar^1$-74 | $Ar^1$-74 |
| 11 | " | " | " | $Ar^1$-132 |
| 12 | " | " | " | $Ar^1$-134 |
| 13 | " | " | " | $Ar^1$-136 |
| 14 | " | " | " | $Ar^1$-137 |
| 15 | " | " | " | $Ar^1$-136 |
| 16 | " | " | " | $Ar^1$-200 |
| 17 | " | " | " | $Ar^1$-201 |
| 18 | " | " | $Ar^1$-132 | $Ar^1$-132 |
| 19 | " | " | " | $Ar^1$-134 |
| 20 | " | " | " | $Ar^1$-136 |
| 21 | " | " | " | $Ar^1$-137 |
| 22 | " | " | " | $Ar^1$-165 |
| 23 | " | " | " | $Ar^1$-200 |
| 24 | " | " | " | $Ar^1$-201 |
| 25 | " | " | $Ar^1$-134 | $Ar^1$-134 |
| 26 | " | " | " | $Ar^1$-136 |
| 27 | " | " | " | $Ar^1$-137 |
| 28 | " | " | " | $Ar^1$-165 |
| 29 | " | " | " | $Ar^1$-200 |
| 30 | " | " | " | $Ar^1$-201 |
| 31 | " | " | $Ar^1$-136 | $Ar^1$-136 |
| 32 | " | " | " | $Ar^1$-137 |
| 33 | " | " | " | $Ar^1$-165 |
| 34 | " | " | " | $Ar^1$-200 |
| 35 | " | " | " | $Ar^1$-201 |
| 36 | " | " | $Ar^1$-137 | $Ar^1$-137 |
| 37 | " | " | " | $Ar^1$-165 |
| 38 | " | " | " | $Ar^1$-200 |
| 39 | " | " | " | $Ar^1$-201 |
| 40 | " | " | $Ar^1$-165 | $Ar^1$-165 |
| 41 | " | " | " | $Ar^1$-200 |
| 42 | " | " | " | $Ar^1$-201 |
| 43 | " | " | $Ar^1$-200 | $Ar^1$-200 |
| 44 | " | " | " | $Ar^1$-201 |
| 45 | " | " | $Ar^1$-201 | $Ar^1$-201 |
| 46 | " | $Ar^1$-1 | $Ar^1$-1 | $Ar^1$-1 |
| 47 | " | " | " | $Ar^1$-74 |
| 48 | " | " | " | $Ar^1$-132 |
| 49 | " | " | " | $Ar^1$-134 |
| 50 | " | " | " | $Ar^1$-136 |
| 51 | " | " | " | $Ar^1$-137 |
| 52 | " | " | " | $Ar^1$-165 |
| 53 | " | " | " | $Ar^1$-200 |
| 54 | " | " | " | $Ar^1$-201 |
| 55 | " | " | $Ar^1$-74 | $Ar^1$-74 |
| 56 | " | " | " | $Ar^1$-132 |
| 57 | " | " | " | $Ar^1$-134 |
| 58 | " | " | " | $Ar^1$-136 |

-continued

| | Base skeleton | $L^1$ or k = 0 | $Ar^1$ | $Ar^1$ |
|---|---|---|---|---|
| 59 | " | " | " | $Ar^1$-137 |
| 60 | " | " | " | $Ar^1$-165 |
| 61 | " | " | " | $Ar^1$-200 |
| 62 | " | " | " | $Ar^1$-201 |
| 63 | " | " | $Ar^1$-132 | $Ar^1$-132 |
| 64 | " | " | " | $Ar^1$-134 |
| 65 | " | " | " | $Ar^1$-136 |
| 66 | " | " | " | $Ar^1$-137 |
| 67 | " | " | " | $Ar^1$-165 |
| 68 | " | " | " | $Ar^1$-200 |
| 69 | " | " | " | $Ar^1$-201 |
| 70 | " | " | $Ar^1$-134 | $Ar^1$-134 |
| 71 | " | " | " | $Ar^1$-136 |
| 72 | " | " | " | $Ar^1$-137 |
| 73 | " | " | " | $Ar^1$-165 |
| 74 | " | " | " | $Ar^1$-200 |
| 75 | " | " | " | $Ar^1$-201 |
| 76 | " | " | $Ar^1$-136 | $Ar^1$-136 |
| 77 | " | " | " | $Ar^1$-137 |
| 78 | " | " | " | $Ar^1$-165 |
| 79 | " | " | " | $Ar^1$-200 |
| 80 | " | " | " | $Ar^1$-201 |
| 81 | " | " | $Ar^1$-137 | $Ar^1$-137 |
| 82 | " | " | " | $Ar^1$-165 |
| 83 | " | " | " | $Ar^1$-200 |
| 84 | " | " | " | $Ar^1$-201 |
| 85 | " | " | $Ar^1$-165 | $Ar^1$-165 |
| 86 | " | " | " | $Ar^1$-200 |
| 87 | " | " | " | $Ar^1$-201 |
| 88 | " | " | $Ar^1$-200 | $Ar^1$-200 |
| 89 | " | " | " | $Ar^1$-201 |
| 90 | " | " | $Ar^1$-201 | $Ar^1$-201 |
| 91 | " | $Ar^1$-2 | $Ar^1$-1 | $Ar^1$-1 |
| 92 | " | " | " | $Ar^1$-74 |
| 93 | " | " | " | $Ar^1$-132 |
| 94 | " | " | " | $Ar^1$-134 |
| 95 | " | " | " | $Ar^1$-136 |
| 96 | " | " | " | $Ar^1$-137 |
| 97 | " | " | " | $Ar^1$-165 |
| 98 | " | " | " | $Ar^1$-200 |
| 99 | " | " | " | $Ar^1$-201 |
| 100 | " | " | $Ar^1$-74 | $Ar^1$-74 |
| 101 | " | " | " | $Ar^1$-132 |
| 102 | " | " | " | $Ar^1$-134 |
| 103 | " | " | " | $Ar^1$-136 |
| 104 | " | " | " | $Ar^1$-137 |
| 105 | " | " | " | $Ar^1$-165 |
| 106 | " | " | " | $Ar^1$-200 |
| 107 | " | " | " | $Ar^1$-201 |
| 108 | " | " | $Ar^1$-132 | $Ar^1$-132 |
| 109 | " | " | " | $Ar^1$-134 |
| 110 | " | " | " | $Ar^1$-136 |
| 111 | " | " | " | $Ar^1$-137 |
| 112 | " | " | " | $Ar^1$-165 |
| 113 | " | " | " | $Ar^1$-200 |
| 114 | " | " | " | $Ar^1$-201 |
| 115 | " | " | $Ar^1$-134 | $Ar^1$-134 |
| 116 | " | " | " | $Ar^1$-136 |
| 117 | " | " | " | $Ar^1$-137 |
| 118 | " | " | " | $Ar^1$-165 |
| 119 | " | " | " | $Ar^1$-200 |
| 120 | " | " | " | $Ar^1$-201 |
| 121 | " | " | $Ar^1$-136 | $Ar^1$-136 |
| 122 | " | " | " | $Ar^1$-137 |
| 123 | " | " | " | $Ar^1$-165 |
| 124 | " | " | " | $Ar^1$-200 |
| 125 | " | " | " | $Ar^1$-201 |
| 126 | " | " | $Ar^1$-137 | $Ar^1$-137 |
| 127 | " | " | " | $Ar^1$-165 |
| 128 | " | " | " | $Ar^1$-200 |
| 129 | " | " | " | $Ar^1$-201 |
| 130 | " | " | $Ar^1$-165 | $Ar^1$-165 |
| 131 | " | " | " | $Ar^1$-200 |
| 132 | " | " | " | $Ar^1$-201 |
| 133 | " | " | $Ar^1$-200 | $Ar^1$-200 |
| 134 | " | " | " | $Ar^1$-201 |
| 135 | " | " | $Ar^1$-201 | $Ar^1$-201 |
| 136 | " | $Ar^1$-3 | $Ar^1$-1 | $Ar^1$-1 |
| 137 | " | " | " | $Ar^1$-74 |
| 138 | " | " | " | $Ar^1$-132 |
| 139 | " | " | " | $Ar^1$-134 |
| 140 | " | " | " | $Ar^1$-136 |
| 141 | " | " | " | $Ar^1$-137 |
| 142 | " | " | " | $Ar^1$-165 |
| 143 | " | " | " | $Ar^1$-200 |
| 144 | " | " | " | $Ar^1$-201 |
| 145 | " | " | " | $Ar^1$-74 |
| 146 | " | " | " | $Ar^1$-132 |
| 147 | " | " | " | $Ar^1$-134 |
| 148 | " | " | " | $Ar^1$-136 |
| 149 | " | " | " | $Ar^1$-137 |
| 150 | " | " | " | $Ar^1$-165 |
| 151 | " | " | " | $Ar^1$-200 |
| 152 | " | " | " | $Ar^1$-201 |
| 153 | " | " | $Ar^1$-132 | $Ar^1$-132 |
| 154 | " | " | " | $Ar^1$-134 |
| 155 | " | " | " | $Ar^1$-136 |
| 156 | " | " | " | $Ar^1$-137 |
| 157 | " | " | " | $Ar^1$-165 |
| 158 | " | " | " | $Ar^1$-200 |
| 159 | " | " | " | $Ar^1$-201 |
| 160 | " | " | $Ar^1$-134 | $Ar^1$-134 |
| 161 | " | " | " | $Ar^1$-136 |
| 162 | " | " | " | $Ar^1$-137 |
| 163 | " | " | " | $Ar^1$-165 |
| 164 | " | " | " | $Ar^1$-200 |
| 165 | " | " | " | $Ar^1$-201 |
| 166 | " | " | $Ar^1$-136 | $Ar^1$-136 |
| 167 | " | " | " | $Ar^1$-137 |
| 168 | " | " | " | $Ar^1$-165 |
| 169 | " | " | " | $Ar^1$-200 |
| 170 | " | " | " | $Ar^1$-201 |
| 171 | " | " | $Ar^1$-137 | $Ar^1$-137 |
| 172 | " | " | " | $Ar^1$-165 |
| 173 | " | " | " | $Ar^1$-200 |
| 174 | " | " | " | $Ar^1$-201 |
| 175 | " | " | $Ar^1$-165 | $Ar^1$-165 |
| 176 | " | " | " | $Ar^1$-200 |
| 177 | " | " | " | $Ar^1$-201 |
| 178 | " | " | $Ar^1$-200 | $Ar^1$-200 |
| 179 | " | " | " | $Ar^1$-201 |
| 180 | " | " | $Ar^1$-201 | $Ar^1$-201 |
| 181 | I-1-4-O | k = 0 | $Ar^1$-1 | $Ar^1$-1 |
| 182 | " | " | " | $Ar^1$-74 |
| 183 | " | " | " | $Ar^1$-132 |
| 184 | " | " | " | $Ar^1$-134 |
| 185 | " | " | " | $Ar^1$-136 |
| 186 | " | " | " | $Ar^1$-137 |
| 187 | " | " | " | $Ar^1$-165 |
| 188 | " | " | " | $Ar^1$-200 |
| 189 | " | " | " | $Ar^1$-201 |
| 190 | " | " | $Ar^1$-74 | $Ar^1$-74 |
| 191 | " | " | " | $Ar^1$-132 |
| 192 | " | " | " | $Ar^1$-134 |
| 193 | " | " | " | $Ar^1$-136 |
| 194 | " | " | " | $Ar^1$-137 |
| 195 | " | " | " | $Ar^1$-165 |
| 196 | " | " | " | $Ar^1$-200 |
| 197 | " | " | " | $Ar^1$-201 |
| 198 | " | " | $Ar^1$-132 | $Ar^1$-132 |
| 199 | " | " | " | $Ar^1$-134 |
| 200 | " | " | " | $Ar^1$-136 |
| 201 | " | " | " | $Ar^1$-137 |
| 202 | " | " | " | $Ar^1$-165 |
| 203 | " | " | " | $Ar^1$-200 |
| 204 | " | " | " | $Ar^1$-201 |
| 205 | " | " | $Ar^1$-134 | $Ar^1$-134 |
| 206 | " | " | " | $Ar^1$-136 |
| 207 | " | " | " | $Ar^1$-137 |
| 208 | " | " | " | $Ar^1$-165 |
| 209 | " | " | " | $Ar^1$-200 |
| 210 | " | " | " | $Ar^1$-201 |

-continued

| | Base skeleton | $L^1$ or k = 0 | $Ar^1$ | $Ar^1$ |
|---|---|---|---|---|
| 211 | " | " | $Ar^1$-136 | $Ar^1$-136 |
| 212 | " | " | " | $Ar^1$-137 |
| 213 | " | " | " | $Ar^1$-165 |
| 214 | " | " | " | $Ar^1$-200 |
| 215 | " | " | " | $Ar^1$-201 |
| 216 | " | " | $Ar^1$-137 | $Ar^1$-137 |
| 217 | " | " | " | $Ar^1$-165 |
| 218 | " | " | " | $Ar^1$-200 |
| 219 | " | " | " | $Ar^1$-201 |
| 220 | " | " | $Ar^1$-165 | $Ar^1$-165 |
| 221 | " | " | " | $Ar^1$-200 |
| 222 | " | " | " | $Ar^1$-201 |
| 223 | " | " | $Ar^1$-200 | $Ar^1$-200 |
| 224 | " | " | " | $Ar^1$-201 |
| 225 | " | " | $Ar^1$-201 | $Ar^1$-201 |
| 226 | " | $Ar^1$-1 | $Ar^1$-1 | $Ar^1$-1 |
| 227 | " | " | " | $Ar^1$-74 |
| 228 | " | " | " | $Ar^1$-132 |
| 229 | " | " | " | $Ar^1$-134 |
| 230 | " | " | " | $Ar^1$-136 |
| 231 | " | " | " | $Ar^1$-137 |
| 232 | " | " | " | $Ar^1$-165 |
| 233 | " | " | " | $Ar^1$-200 |
| 234 | " | " | " | $Ar^1$-201 |
| 235 | " | " | $Ar^1$-74 | $Ar^1$-74 |
| 236 | " | " | " | $Ar^1$-132 |
| 237 | " | " | " | $Ar^1$-134 |
| 238 | " | " | " | $Ar^1$-136 |
| 239 | " | " | " | $Ar^1$-137 |
| 240 | " | " | " | $Ar^1$-165 |
| 241 | " | " | " | $Ar^1$-200 |
| 242 | " | " | " | $Ar^1$-201 |
| 243 | " | " | $Ar^1$-132 | $Ar^1$-132 |
| 244 | " | " | " | $Ar^1$-134 |
| 245 | " | " | " | $Ar^1$-136 |
| 246 | " | " | " | $Ar^1$-137 |
| 247 | " | " | " | $Ar^1$-165 |
| 248 | " | " | " | $Ar^1$-200 |
| 249 | " | " | " | $Ar^1$-201 |
| 250 | " | " | $Ar^1$-134 | $Ar^1$-134 |
| 251 | " | " | " | $Ar^1$-136 |
| 252 | " | " | " | $Ar^1$-137 |
| 253 | " | " | " | $Ar^1$-165 |
| 254 | " | " | " | $Ar^1$-200 |
| 255 | " | " | " | $Ar^1$-201 |
| 256 | " | " | $Ar^1$-136 | $Ar^1$-136 |
| 257 | " | " | " | $Ar^1$-137 |
| 258 | " | " | " | $Ar^1$-165 |
| 259 | " | " | " | $Ar^1$-200 |
| 260 | " | " | " | $Ar^1$-201 |
| 261 | " | " | $Ar^1$-137 | $Ar^1$-137 |
| 262 | " | " | " | $Ar^1$-165 |
| 263 | " | " | " | $Ar^1$-200 |
| 264 | " | " | " | $Ar^1$-201 |
| 265 | " | " | $Ar^1$-165 | $Ar^1$-165 |
| 266 | " | " | " | $Ar^1$-200 |
| 267 | " | " | " | $Ar^1$-201 |
| 268 | " | " | $Ar^1$-200 | $Ar^1$-200 |
| 269 | " | " | " | $Ar^1$-201 |
| 270 | " | " | $Ar^1$-201 | $Ar^1$-201 |
| 271 | " | $Ar^1$-2 | $Ar^1$-1 | $Ar^1$-1 |
| 272 | " | " | " | $Ar^1$-74 |
| 273 | " | " | " | $Ar^1$-132 |
| 274 | " | " | " | $Ar^1$-134 |
| 275 | " | " | " | $Ar^1$-136 |
| 276 | " | " | " | $Ar^1$-137 |
| 277 | " | " | " | $Ar^1$-165 |
| 278 | " | " | " | $Ar^1$-200 |
| 279 | " | " | " | $Ar^1$-201 |
| 280 | " | " | $Ar^1$-74 | $Ar^1$-74 |
| 281 | " | " | " | $Ar^1$-132 |
| 282 | " | " | " | $Ar^1$-134 |
| 283 | " | " | " | $Ar^1$-136 |
| 284 | " | " | " | $Ar^1$-137 |
| 285 | " | " | " | $Ar^1$-165 |
| 286 | " | " | " | $Ar^1$-200 |
| 287 | " | " | " | $Ar^1$-201 |
| 288 | " | " | $Ar^1$-132 | $Ar^1$-132 |
| 289 | " | " | " | $Ar^1$-134 |
| 290 | " | " | " | $Ar^1$-136 |
| 291 | " | " | " | $Ar^1$-137 |
| 292 | " | " | " | $Ar^1$-165 |
| 293 | " | " | " | $Ar^1$-200 |
| 294 | " | " | " | $Ar^1$-201 |
| 295 | " | " | $Ar^1$-134 | $Ar^1$-134 |
| 296 | " | " | " | $Ar^1$-136 |
| 297 | " | " | " | $Ar^1$-137 |
| 298 | " | " | " | $Ar^1$-165 |
| 299 | " | " | " | $Ar^1$-200 |
| 300 | " | " | " | $Ar^1$-201 |
| 301 | " | " | $Ar^1$-136 | $Ar^1$-136 |
| 302 | " | " | " | $Ar^1$-137 |
| 303 | " | " | " | $Ar^1$-165 |
| 304 | " | " | " | $Ar^1$-200 |
| 305 | " | " | " | $Ar^1$-201 |
| 306 | " | " | $Ar^1$-137 | $Ar^1$-137 |
| 307 | " | " | " | $Ar^1$-165 |
| 308 | " | " | " | $Ar^1$-200 |
| 309 | " | " | " | $Ar^1$-201 |
| 310 | " | " | " | $Ar^1$-165 |
| 311 | " | " | " | $Ar^1$-200 |
| 312 | " | " | " | $Ar^1$-201 |
| 313 | " | " | $Ar^1$-200 | $Ar^1$-200 |
| 314 | " | " | " | $Ar^1$-201 |
| 315 | " | " | $Ar^1$-201 | $Ar^1$-201 |
| 316 | " | $Ar^1$-3 | $Ar^1$-1 | $Ar^1$-1 |
| 317 | " | " | " | $Ar^1$-74 |
| 318 | " | " | " | $Ar^1$-132 |
| 319 | " | " | " | $Ar^1$-134 |
| 320 | " | " | " | $Ar^1$-136 |
| 321 | " | " | " | $Ar^1$-137 |
| 322 | " | " | " | $Ar^1$-165 |
| 323 | " | " | " | $Ar^1$-200 |
| 324 | " | " | " | $Ar^1$-201 |
| 325 | " | " | $Ar^1$-74 | $Ar^1$-74 |
| 326 | " | " | " | $Ar^1$-132 |
| 327 | " | " | " | $Ar^1$-134 |
| 328 | " | " | " | $Ar^1$-136 |
| 329 | " | " | " | $Ar^1$-137 |
| 330 | " | " | " | $Ar^1$-165 |
| 331 | " | " | " | $Ar^1$-200 |
| 332 | " | " | " | $Ar^1$-201 |
| 333 | " | " | $Ar^1$-132 | $Ar^1$-132 |
| 334 | " | " | " | $Ar^1$-134 |
| 335 | " | " | " | $Ar^1$-136 |
| 336 | " | " | " | $Ar^1$-137 |
| 337 | " | " | " | $Ar^1$-165 |
| 338 | " | " | " | $Ar^1$-200 |
| 339 | " | " | " | $Ar^1$-201 |
| 340 | " | " | $Ar^1$-134 | $Ar^1$-134 |
| 341 | " | " | " | $Ar^1$-136 |
| 342 | " | " | " | $Ar^1$-137 |
| 343 | " | " | " | $Ar^1$-165 |
| 344 | " | " | " | $Ar^1$-200 |
| 345 | " | " | " | $Ar^1$-201 |
| 346 | " | " | $Ar^1$-136 | $Ar^1$-136 |
| 347 | " | " | " | $Ar^1$-137 |
| 348 | " | " | " | $Ar^1$-165 |
| 349 | " | " | " | $Ar^1$-200 |
| 350 | " | " | " | $Ar^1$-201 |
| 351 | " | " | $Ar^1$-137 | $Ar^1$-137 |
| 352 | " | " | " | $Ar^1$-165 |
| 353 | " | " | " | $Ar^1$-200 |
| 354 | " | " | " | $Ar^1$-201 |
| 355 | " | " | $Ar^1$-165 | $Ar^1$-165 |
| 356 | " | " | " | $Ar^1$-200 |
| 357 | " | " | " | $Ar^1$-201 |
| 358 | " | " | $Ar^1$-200 | $Ar^1$-200 |
| 359 | " | " | " | $Ar^1$-201 |
| 360 | " | " | $Ar^1$-201 | $Ar^1$-201 |
| 361 | I-1-5-O | k = 0 | $Ar^1$-1 | $Ar^1$-1 |
| 362 | " | " | " | $Ar^1$-74 |

-continued

| | Base skeleton | $L^1$ or k = 0 | $Ar^1$ | $Ar^1$ |
|---|---|---|---|---|
| 363 | " | " | " | $Ar^1$-132 |
| 364 | " | " | " | $Ar^1$-134 |
| 365 | " | " | " | $Ar^1$-136 |
| 366 | " | " | " | $Ar^1$-137 |
| 367 | " | " | " | $Ar^1$-165 |
| 368 | " | " | " | $Ar^1$-200 |
| 369 | " | " | " | $Ar^1$-201 |
| 370 | " | " | $Ar^1$-74 | $Ar^1$-74 |
| 371 | " | " | " | $Ar^1$-132 |
| 372 | " | " | " | $Ar^1$-134 |
| 373 | " | " | " | $Ar^1$-136 |
| 374 | " | " | " | $Ar^1$-137 |
| 375 | " | " | " | $Ar^1$-165 |
| 376 | " | " | " | $Ar^1$-200 |
| 377 | " | " | " | $Ar^1$-201 |
| 378 | " | " | $Ar^1$-32 | $Ar^1$-132 |
| 379 | " | " | " | $Ar^1$-134 |
| 380 | " | " | " | $Ar^1$-136 |
| 381 | " | " | " | $Ar^1$-137 |
| 382 | " | " | " | $Ar^1$-165 |
| 383 | " | " | " | $Ar^1$-200 |
| 384 | " | " | " | $Ar^1$-201 |
| 385 | " | " | $Ar^1$-134 | $Ar^1$-134 |
| 386 | " | " | " | $Ar^1$-136 |
| 387 | " | " | " | $Ar^1$-137 |
| 388 | " | " | " | $Ar^1$-165 |
| 389 | " | " | " | $Ar^1$-200 |
| 390 | " | " | " | $Ar^1$-201 |
| 391 | " | " | $Ar^1$-136 | $Ar^1$-136 |
| 392 | " | " | " | $Ar^1$-137 |
| 393 | " | " | " | $Ar^1$-165 |
| 394 | " | " | " | $Ar^1$-200 |
| 395 | " | " | " | $Ar^1$-201 |
| 396 | " | " | $Ar^1$-137 | $Ar^1$-137 |
| 397 | " | " | " | $Ar^1$-165 |
| 398 | " | " | " | $Ar^1$-200 |
| 399 | " | " | " | $Ar^1$-201 |
| 400 | " | " | $Ar^1$-165 | $Ar^1$-165 |
| 401 | " | " | " | $Ar^1$-200 |
| 402 | " | " | " | $Ar^1$-201 |
| 403 | " | " | $Ar^1$-200 | $Ar^1$-200 |
| 404 | " | " | " | $Ar^1$-201 |
| 405 | " | " | $Ar^1$-201 | $Ar^1$-201 |
| 406 | " | $Ar^1$-1 | $Ar^1$-1 | $Ar^1$-1 |
| 407 | " | " | " | $Ar^1$-74 |
| 408 | " | " | " | $Ar^1$-132 |
| 409 | " | " | " | $Ar^1$-134 |
| 410 | " | " | " | $Ar^1$-136 |
| 411 | " | " | " | $Ar^1$-137 |
| 412 | " | " | " | $Ar^1$-165 |
| 413 | " | " | " | $Ar^1$-200 |
| 414 | " | " | " | $Ar^1$-201 |
| 415 | " | " | $Ar^1$-74 | $Ar^1$-74 |
| 416 | " | " | " | $Ar^1$-132 |
| 417 | " | " | " | $Ar^1$-134 |
| 418 | " | " | " | $Ar^1$-136 |
| 419 | " | " | " | $Ar^1$-137 |
| 420 | " | " | " | $Ar^1$-165 |
| 421 | " | " | " | $Ar^1$-200 |
| 422 | " | " | " | $Ar^1$-201 |
| 423 | " | " | $Ar^1$-132 | $Ar^1$-132 |
| 424 | " | " | " | $Ar^1$-134 |
| 425 | " | " | " | $Ar^1$-136 |
| 426 | " | " | " | $Ar^1$-137 |
| 427 | " | " | " | $Ar^1$-165 |
| 428 | " | " | " | $Ar^1$-200 |
| 429 | " | " | " | $Ar^1$-201 |
| 430 | " | " | $Ar^1$-134 | $Ar^1$-134 |
| 431 | " | " | " | $Ar^1$-136 |
| 432 | " | " | " | $Ar^1$-137 |
| 433 | " | " | " | $Ar^1$-165 |
| 434 | " | " | " | $Ar^1$-200 |
| 435 | " | " | " | $Ar^1$-201 |
| 436 | " | " | $Ar^1$-136 | $Ar^1$-136 |
| 437 | " | " | " | $Ar^1$-137 |
| 438 | " | " | " | $Ar^1$-165 |

-continued

| | Base skeleton | $L^1$ or k = 0 | $Ar^1$ | $Ar^1$ |
|---|---|---|---|---|
| 439 | " | " | " | $Ar^1$-200 |
| 440 | " | " | " | $Ar^1$-201 |
| 441 | " | " | $Ar^1$-137 | $Ar^1$-137 |
| 442 | " | " | " | $Ar^1$-165 |
| 443 | " | " | " | $Ar^1$-200 |
| 444 | " | " | " | $Ar^1$-201 |
| 445 | " | " | $Ar^1$-165 | $Ar^1$-165 |
| 446 | " | " | " | $Ar^1$-200 |
| 447 | " | " | " | $Ar^1$-201 |
| 448 | " | " | $Ar^1$-200 | $Ar^1$-200 |
| 449 | " | " | " | $Ar^1$-201 |
| 450 | " | " | $Ar^1$-201 | $Ar^1$-201 |
| 451 | " | $Ar^1$-2 | $Ar^1$-1 | $Ar^1$-1 |
| 452 | " | " | " | $Ar^1$-74 |
| 453 | " | " | " | $Ar^1$-132 |
| 454 | " | " | " | $Ar^1$-134 |
| 455 | " | " | " | $Ar^1$-136 |
| 456 | " | " | " | $Ar^1$-137 |
| 457 | " | " | " | $Ar^1$-165 |
| 458 | " | " | " | $Ar^1$-200 |
| 459 | " | " | " | $Ar^1$-201 |
| 460 | " | " | $Ar^1$-74 | $Ar^1$-74 |
| 461 | " | " | " | $Ar^1$-132 |
| 462 | " | " | " | $Ar^1$-134 |
| 463 | " | " | " | $Ar^1$-136 |
| 464 | " | " | " | $Ar^1$-137 |
| 465 | " | " | " | $Ar^1$-165 |
| 466 | " | " | " | $Ar^1$-200 |
| 467 | " | " | " | $Ar^1$-201 |
| 468 | " | " | $Ar^1$-132 | $Ar^1$-132 |
| 469 | " | " | " | $Ar^1$-134 |
| 470 | " | " | " | $Ar^1$-136 |
| 471 | " | " | " | $Ar^1$-137 |
| 472 | " | " | " | $Ar^1$-165 |
| 473 | " | " | " | $Ar^1$-200 |
| 474 | " | " | " | $Ar^1$-201 |
| 475 | " | " | $Ar^1$-134 | $Ar^1$-134 |
| 476 | " | " | " | $Ar^1$-136 |
| 477 | " | " | " | $Ar^1$-137 |
| 478 | " | " | " | $Ar^1$-165 |
| 479 | " | " | " | $Ar^1$-200 |
| 480 | " | " | " | $Ar^1$-201 |
| 481 | " | " | $Ar^1$-136 | $Ar^1$-136 |
| 482 | " | " | " | $Ar^1$-137 |
| 483 | " | " | " | $Ar^1$-165 |
| 484 | " | " | " | $Ar^1$-200 |
| 485 | " | " | " | $Ar^1$-201 |
| 486 | " | " | $Ar^1$-137 | $Ar^1$-137 |
| 487 | " | " | " | $Ar^1$-165 |
| 488 | " | " | " | $Ar^1$-200 |
| 489 | " | " | " | $Ar^1$-201 |
| 490 | " | " | $Ar^1$-165 | $Ar^1$-165 |
| 491 | " | " | " | $Ar^1$-200 |
| 492 | " | " | " | $Ar^1$-201 |
| 493 | " | " | $Ar^1$-200 | $Ar^1$-200 |
| 494 | " | " | " | $Ar^1$-201 |
| 495 | " | " | $Ar^1$-201 | $Ar^1$-201 |
| 496 | " | $Ar^1$-3 | $Ar^1$-1 | $Ar^1$-1 |
| 497 | " | " | " | $Ar^1$-74 |
| 498 | " | " | " | $Ar^1$-132 |
| 499 | " | " | " | $Ar^1$-134 |
| 500 | " | " | " | $Ar^1$-136 |
| 501 | " | " | " | $Ar^1$-137 |
| 502 | " | " | " | $Ar^1$-165 |
| 503 | " | " | " | $Ar^1$-200 |
| 504 | " | " | " | $Ar^1$-201 |
| 505 | " | " | $Ar^1$-74 | $Ar^1$-74 |
| 506 | " | " | " | $Ar^1$-132 |
| 507 | " | " | " | $Ar^1$-134 |
| 508 | " | " | " | $Ar^1$-136 |
| 509 | " | " | " | $Ar^1$-137 |
| 510 | " | " | " | $Ar^1$-165 |
| 511 | " | " | " | $Ar^1$-200 |
| 512 | " | " | " | $Ar^1$-201 |
| 513 | " | " | $Ar^1$-132 | $Ar^1$-132 |
| 514 | " | " | " | $Ar^1$-134 |

-continued

| | Base skeleton | $L^1$ or k = 0 | $Ar^1$ | $Ar^1$ |
|---|---|---|---|---|
| 515 | " | " | " | $Ar^1$-136 |
| 516 | " | " | " | $Ar^1$-137 |
| 517 | " | " | " | $Ar^1$-165 |
| 518 | " | " | " | $Ar^1$-200 |
| 519 | " | " | " | $Ar^1$-201 |
| 520 | " | " | $Ar^1$-134 | $Ar^1$-134 |
| 521 | " | " | " | $Ar^1$-136 |
| 522 | " | " | " | $Ar^1$-137 |
| 523 | " | " | " | $Ar^1$-165 |
| 524 | " | " | " | $Ar^1$-200 |
| 525 | " | " | " | $Ar^1$-201 |
| 526 | " | " | $Ar^1$-136 | $Ar^1$-136 |
| 527 | " | " | " | $Ar^1$-137 |
| 528 | " | " | " | $Ar^1$-165 |
| 529 | " | " | " | $Ar^1$-200 |
| 530 | " | " | " | $Ar^1$-201 |
| 531 | " | " | $Ar^1$-137 | $Ar^1$-137 |
| 532 | " | " | " | $Ar^1$-165 |
| 533 | " | " | " | $Ar^1$-200 |
| 534 | " | " | " | $Ar^1$-201 |
| 535 | " | " | $Ar^1$-165 | $Ar^1$-165 |
| 536 | " | " | " | $Ar^1$-200 |
| 537 | " | " | " | $Ar^1$-201 |
| 538 | " | " | $Ar^1$-200 | $Ar^1$-200 |
| 539 | " | " | " | $Ar^1$-201 |
| 540 | " | " | $Ar^1$-201 | $Ar^1$-201 |
| 541 | I-1-7-O | k = 0 | $Ar^1$-1 | $Ar^1$-1 |
| 542 | " | " | " | $Ar^1$-74 |
| 543 | " | " | " | $Ar^1$-132 |
| 544 | " | " | " | $Ar^1$-134 |
| 545 | " | " | " | $Ar^1$-136 |
| 546 | " | " | " | $Ar^1$-137 |
| 547 | " | " | " | $Ar^1$-165 |
| 548 | " | " | " | $Ar^1$-200 |
| 549 | " | " | " | $Ar^1$-201 |
| 550 | " | " | $Ar^1$-74 | $Ar^1$-74 |
| 551 | " | " | " | $Ar^1$-132 |
| 552 | " | " | " | $Ar^1$-134 |
| 553 | " | " | " | $Ar^1$-136 |
| 554 | " | " | " | $Ar^1$-137 |
| 555 | " | " | " | $Ar^1$-165 |
| 556 | " | " | " | $Ar^1$-200 |
| 557 | " | " | " | $Ar^1$-201 |
| 558 | " | " | $Ar^1$-132 | $Ar^1$-132 |
| 559 | " | " | " | $Ar^1$-134 |
| 560 | " | " | " | $Ar^1$-136 |
| 561 | " | " | " | $Ar^1$-137 |
| 562 | " | " | " | $Ar^1$-165 |
| 563 | " | " | " | $Ar^1$-200 |
| 564 | " | " | " | $Ar^1$-201 |
| 565 | " | " | $Ar^1$-134 | $Ar^1$-134 |
| 566 | " | " | " | $Ar^1$-136 |
| 567 | " | " | " | $Ar^1$-137 |
| 568 | " | " | " | $Ar^1$-165 |
| 569 | " | " | " | $Ar^1$-200 |
| 570 | " | " | " | $Ar^1$-201 |
| 571 | " | " | $Ar^1$-136 | $Ar^1$-136 |
| 572 | " | " | " | $Ar^1$-137 |
| 573 | " | " | " | $Ar^1$-165 |
| 574 | " | " | " | $Ar^1$-200 |
| 575 | " | " | " | $Ar^1$-201 |
| 576 | " | " | $Ar^1$-137 | $Ar^1$-137 |
| 577 | " | " | " | $Ar^1$-165 |
| 578 | " | " | " | $Ar^1$-200 |
| 579 | " | " | " | $Ar^1$-201 |
| 580 | " | " | $Ar^1$-165 | $Ar^1$-165 |
| 581 | " | " | " | $Ar^1$-200 |
| 582 | " | " | " | $Ar^1$-201 |
| 583 | " | " | $Ar^1$-200 | $Ar^1$-200 |
| 584 | " | " | " | $Ar^1$-201 |
| 585 | " | " | $Ar^1$-201 | $Ar^1$-201 |
| 586 | " | $Ar^1$-1 | $Ar^1$-1 | $Ar^1$-1 |
| 587 | " | " | " | $Ar^1$-74 |
| 588 | " | " | " | $Ar^1$-132 |
| 589 | " | " | " | $Ar^1$-134 |
| 590 | " | " | " | $Ar^1$-136 |

-continued

| | Base skeleton | $L^1$ or k = 0 | $Ar^1$ | $Ar^1$ |
|---|---|---|---|---|
| 591 | " | " | " | $Ar^1$-137 |
| 592 | " | " | " | $Ar^1$-165 |
| 593 | " | " | " | $Ar^1$-200 |
| 594 | " | " | " | $Ar^1$-201 |
| 595 | " | " | $Ar^1$-74 | $Ar^1$-74 |
| 596 | " | " | " | $Ar^1$-132 |
| 597 | " | " | " | $Ar^1$-134 |
| 598 | " | " | " | $Ar^1$-136 |
| 599 | " | " | " | $Ar^1$-137 |
| 600 | " | " | " | $Ar^1$-165 |
| 601 | " | " | " | $Ar^1$-200 |
| 602 | " | " | " | $Ar^1$-201 |
| 603 | " | " | $Ar^1$-132 | $Ar^1$-132 |
| 604 | " | " | " | $Ar^1$-134 |
| 605 | " | " | " | $Ar^1$-136 |
| 606 | " | " | " | $Ar^1$-137 |
| 607 | " | " | " | $Ar^1$-165 |
| 608 | " | " | " | $Ar^1$-200 |
| 609 | " | " | " | $Ar^1$-201 |
| 610 | " | " | $Ar^1$-134 | $Ar^1$-134 |
| 611 | " | " | " | $Ar^1$-136 |
| 612 | " | " | " | $Ar^1$-137 |
| 613 | " | " | " | $Ar^1$-165 |
| 614 | " | " | " | $Ar^1$-200 |
| 615 | " | " | " | $Ar^1$-201 |
| 616 | " | " | $Ar^1$-136 | $Ar^1$-136 |
| 617 | " | " | " | $Ar^1$-137 |
| 618 | " | " | " | $Ar^1$-165 |
| 619 | " | " | " | $Ar^1$-200 |
| 620 | " | " | " | $Ar^1$-201 |
| 621 | " | " | $Ar^1$-137 | $Ar^1$-137 |
| 622 | " | " | " | $Ar^1$-165 |
| 623 | " | " | " | $Ar^1$-200 |
| 624 | " | " | " | $Ar^1$-201 |
| 625 | " | " | $Ar^1$-165 | $Ar^1$-165 |
| 626 | " | " | " | $Ar^1$-200 |
| 627 | " | " | " | $Ar^1$-201 |
| 628 | " | " | " | $Ar^1$-200 |
| 629 | " | " | " | $Ar^1$-201 |
| 630 | " | " | $Ar^1$-201 | $Ar^1$-201 |
| 631 | " | $Ar^1$-2 | $Ar^1$-1 | $Ar^1$-1 |
| 632 | " | " | " | $Ar^1$-74 |
| 633 | " | " | " | $Ar^1$-132 |
| 634 | " | " | " | $Ar^1$-134 |
| 635 | " | " | " | $Ar^1$-136 |
| 636 | " | " | " | $Ar^1$-137 |
| 637 | " | " | " | $Ar^1$-165 |
| 638 | " | " | " | $Ar^1$-200 |
| 639 | " | " | " | $Ar^1$-201 |
| 640 | " | " | $Ar^1$-74 | $Ar^1$-74 |
| 641 | " | " | " | $Ar^1$-132 |
| 642 | " | " | " | $Ar^1$-134 |
| 643 | " | " | " | $Ar^1$-136 |
| 644 | " | " | " | $Ar^1$-137 |
| 645 | " | " | " | $Ar^1$-165 |
| 646 | " | " | " | $Ar^1$-200 |
| 647 | " | " | " | $Ar^1$-201 |
| 648 | " | " | $Ar^1$-132 | $Ar^1$-132 |
| 649 | " | " | " | $Ar^1$-134 |
| 650 | " | " | " | $Ar^1$-136 |
| 651 | " | " | " | $Ar^1$-137 |
| 652 | " | " | " | $Ar^1$-165 |
| 653 | " | " | " | $Ar^1$-200 |
| 654 | " | " | " | $Ar^1$-201 |
| 655 | " | " | $Ar^1$-134 | $Ar^1$-134 |
| 656 | " | " | " | $Ar^1$-136 |
| 657 | " | " | " | $Ar^1$-137 |
| 658 | " | " | " | $Ar^1$-165 |
| 659 | " | " | " | $Ar^1$-200 |
| 660 | " | " | " | $Ar^1$-201 |
| 661 | " | " | $Ar^1$-136 | $Ar^1$-136 |
| 662 | " | " | " | $Ar^1$-137 |
| 663 | " | " | " | $Ar^1$-165 |
| 664 | " | " | " | $Ar^1$-200 |
| 665 | " | " | " | $Ar^1$-201 |
| 666 | " | " | $Ar^1$-137 | $Ar^1$-137 |

-continued

| | Base skeleton | $L^1$ or k = 0 | $Ar^1$ | $Ar^1$ |
|---|---|---|---|---|
| 667 | " | " | " | $Ar^1$-165 |
| 668 | " | " | " | $Ar^1$-200 |
| 669 | " | " | " | $Ar^1$-201 |
| 670 | " | " | $Ar^1$-165 | $Ar^1$-165 |
| 671 | " | " | " | $Ar^1$-200 |
| 672 | " | " | " | $Ar^1$-201 |
| 673 | " | " | $Ar^1$-200 | $Ar^1$-200 |
| 674 | " | " | " | $Ar^1$-201 |
| 675 | " | " | $Ar^1$-201 | $Ar^1$-201 |
| 676 | " | $Ar^1$-3 | $Ar^1$-1 | $Ar^1$-1 |
| 677 | " | " | " | $Ar^1$-74 |
| 678 | " | " | " | $Ar^1$-132 |
| 679 | " | " | " | $Ar^1$-134 |
| 680 | " | " | " | $Ar^1$-136 |
| 681 | " | " | " | $Ar^1$-137 |
| 682 | " | " | " | $Ar^1$-165 |
| 683 | " | " | " | $Ar^1$-200 |
| 684 | " | " | " | $Ar^1$-201 |
| 685 | " | " | $Ar^1$-74 | $Ar^1$-74 |
| 686 | " | " | " | $Ar^1$-132 |
| 687 | " | " | " | $Ar^1$-134 |
| 688 | " | " | " | $Ar^1$-136 |
| 689 | " | " | " | $Ar^1$-137 |
| 690 | " | " | " | $Ar^1$-165 |
| 691 | " | " | " | $Ar^1$-200 |
| 692 | " | " | " | $Ar^1$-201 |
| 693 | " | " | $Ar^1$-132 | $Ar^1$-132 |
| 694 | " | " | " | $Ar^1$-134 |
| 695 | " | " | " | $Ar^1$-136 |
| 696 | " | " | " | $Ar^1$-137 |
| 697 | " | " | " | $Ar^1$-165 |
| 698 | " | " | " | $Ar^1$-200 |
| 699 | " | " | " | $Ar^1$-201 |
| 700 | " | " | $Ar^1$-134 | $Ar^1$-134 |
| 701 | " | " | " | $Ar^1$-136 |
| 702 | " | " | " | $Ar^1$-137 |
| 703 | " | " | " | $Ar^1$-165 |
| 704 | " | " | " | $Ar^1$-200 |
| 705 | " | " | " | $Ar^1$-201 |
| 706 | " | " | $Ar^1$-136 | $Ar^1$-136 |
| 707 | " | " | " | $Ar^1$-137 |
| 708 | " | " | " | $Ar^1$-165 |
| 709 | " | " | " | $Ar^1$-200 |
| 710 | " | " | " | $Ar^1$-201 |
| 711 | " | " | $Ar^1$-137 | $Ar^1$-137 |
| 712 | " | " | " | $Ar^1$-165 |
| 713 | " | " | " | $Ar^1$-200 |
| 714 | " | " | " | $Ar^1$-201 |
| 715 | " | " | $Ar^1$-165 | $Ar^1$-165 |
| 716 | " | " | " | $Ar^1$-200 |
| 717 | " | " | " | $Ar^1$-201 |
| 718 | " | " | $Ar^1$-200 | $Ar^1$-200 |
| 719 | " | " | " | $Ar^1$-201 |
| 720 | " | " | $Ar^1$-201 | $Ar^1$-201 |
| 721 | I-1-2-S | k = 0 | $Ar^1$-1 | $Ar^1$-1 |
| 722 | " | " | " | $Ar^1$-74 |
| 723 | " | " | " | $Ar^1$-132 |
| 724 | " | " | " | $Ar^1$-134 |
| 725 | " | " | " | $Ar^1$-136 |
| 726 | " | " | " | $Ar^1$-137 |
| 727 | " | " | " | $Ar^1$-165 |
| 728 | " | " | " | $Ar^1$-200 |
| 729 | " | " | " | $Ar^1$-201 |
| 730 | " | " | $Ar^1$-74 | $Ar^1$-74 |
| 731 | " | " | " | $Ar^1$-132 |
| 732 | " | " | " | $Ar^1$-134 |
| 733 | " | " | " | $Ar^1$-136 |
| 734 | " | " | " | $Ar^1$-137 |
| 735 | " | " | " | $Ar^1$-165 |
| 736 | " | " | " | $Ar^1$-200 |
| 737 | " | " | " | $Ar^1$-201 |
| 738 | " | " | $Ar^1$-132 | $Ar^1$-132 |
| 739 | " | " | " | $Ar^1$-134 |
| 740 | " | " | " | $Ar^1$-136 |
| 741 | " | " | " | $Ar^1$-137 |
| 742 | " | " | " | $Ar^1$-165 |

-continued

| | Base skeleton | $L^1$ or k = 0 | $Ar^1$ | $Ar^1$ |
|---|---|---|---|---|
| 743 | " | " | " | $Ar^1$-200 |
| 744 | " | " | " | $Ar^1$-201 |
| 745 | " | " | $Ar^1$-134 | $Ar^1$-134 |
| 746 | " | " | " | $Ar^1$-136 |
| 747 | " | " | " | $Ar^1$-137 |
| 748 | " | " | " | $Ar^1$-165 |
| 749 | " | " | " | $Ar^1$-200 |
| 750 | " | " | " | $Ar^1$-201 |
| 751 | " | " | $Ar^1$-136 | $Ar^1$-136 |
| 752 | " | " | " | $Ar^1$-137 |
| 753 | " | " | " | $Ar^1$-165 |
| 754 | " | " | " | $Ar^1$-200 |
| 755 | " | " | " | $Ar^1$-201 |
| 756 | " | " | $Ar^1$-137 | $Ar^1$-137 |
| 757 | " | " | " | $Ar^1$-165 |
| 758 | " | " | " | $Ar^1$-200 |
| 759 | " | " | " | $Ar^1$-201 |
| 760 | " | " | " | $Ar^1$-165 |
| 761 | " | " | " | $Ar^1$-200 |
| 762 | " | " | " | $Ar^1$-201 |
| 763 | " | " | $Ar^1$-200 | $Ar^1$-200 |
| 764 | " | " | " | $Ar^1$-201 |
| 765 | " | " | $Ar^1$-201 | $Ar^1$-201 |
| 766 | " | $Ar^1$-1 | $Ar^1$-1 | $Ar^1$-1 |
| 767 | " | " | " | $Ar^1$-74 |
| 768 | " | " | " | $Ar^1$-132 |
| 769 | " | " | " | $Ar^1$-134 |
| 770 | " | " | " | $Ar^1$-136 |
| 771 | " | " | " | $Ar^1$-137 |
| 772 | " | " | " | $Ar^1$-165 |
| 773 | " | " | " | $Ar^1$-200 |
| 774 | " | " | " | $Ar^1$-201 |
| 775 | " | " | $Ar^1$-74 | $Ar^1$-74 |
| 776 | " | " | " | $Ar^1$-132 |
| 777 | " | " | " | $Ar^1$-134 |
| 778 | " | " | " | $Ar^1$-136 |
| 779 | " | " | " | $Ar^1$-137 |
| 780 | " | " | " | $Ar^1$-165 |
| 781 | " | " | " | $Ar^1$-200 |
| 782 | " | " | " | $Ar^1$-201 |
| 783 | " | " | $Ar^1$-132 | $Ar^1$-132 |
| 784 | " | " | " | $Ar^1$-134 |
| 785 | " | " | " | $Ar^1$-136 |
| 786 | " | " | " | $Ar^1$-137 |
| 787 | " | " | " | $Ar^1$-165 |
| 788 | " | " | " | $Ar^1$-200 |
| 789 | " | " | " | $Ar^1$-201 |
| 790 | " | " | $Ar^1$-134 | $Ar^1$-134 |
| 791 | " | " | " | $Ar^1$-136 |
| 792 | " | " | " | $Ar^1$-137 |
| 793 | " | " | " | $Ar^1$-165 |
| 794 | " | " | " | $Ar^1$-200 |
| 795 | " | " | " | $Ar^1$-201 |
| 796 | " | " | $Ar^1$-136 | $Ar^1$-136 |
| 797 | " | " | " | $Ar^1$-137 |
| 798 | " | " | " | $Ar^1$-165 |
| 799 | " | " | " | $Ar^1$-200 |
| 800 | " | " | " | $Ar^1$-201 |
| 801 | " | " | $Ar^1$-137 | $Ar^1$-137 |
| 802 | " | " | " | $Ar^1$-165 |
| 803 | " | " | " | $Ar^1$-200 |
| 804 | " | " | " | $Ar^1$-201 |
| 805 | " | " | $Ar^1$-165 | $Ar^1$-165 |
| 806 | " | " | " | $Ar^1$-200 |
| 807 | " | " | " | $Ar^1$-201 |
| 808 | " | " | $Ar^1$-200 | $Ar^1$-200 |
| 809 | " | " | " | $Ar^1$-201 |
| 810 | " | " | $Ar^1$-201 | $Ar^1$-201 |
| 811 | " | $Ar^1$-2 | $Ar^1$-1 | $Ar^1$-1 |
| 812 | " | " | " | $Ar^1$-74 |
| 813 | " | " | " | $Ar^1$-132 |
| 814 | " | " | " | $Ar^1$-134 |
| 815 | " | " | " | $Ar^1$-136 |
| 816 | " | " | " | $Ar^1$-137 |
| 817 | " | " | " | $Ar^1$-165 |
| 818 | " | " | " | $Ar^1$-200 |

-continued

| | Base skeleton | $L^1$ or k = 0 | $Ar^1$ | $Ar^1$ |
|---|---|---|---|---|
| 819 | " | " | " | $Ar^1$-201 |
| 820 | " | " | $Ar^1$-74 | $Ar^1$-74 |
| 821 | " | " | " | $Ar^1$-132 |
| 822 | " | " | " | $Ar^1$-134 |
| 823 | " | " | " | $Ar^1$-136 |
| 824 | " | " | " | $Ar^1$-137 |
| 825 | " | " | " | $Ar^1$-165 |
| 826 | " | " | " | $Ar^1$-200 |
| 827 | " | " | " | $Ar^1$-201 |
| 828 | " | " | $Ar^1$-132 | $Ar^1$-132 |
| 829 | " | " | " | $Ar^1$-134 |
| 830 | " | " | " | $Ar^1$-136 |
| 831 | " | " | " | $Ar^1$-137 |
| 832 | " | " | " | $Ar^1$-165 |
| 833 | " | " | " | $Ar^1$-200 |
| 834 | " | " | " | $Ar^1$-201 |
| 835 | " | " | $Ar^1$-134 | $Ar^1$-134 |
| 836 | " | " | " | $Ar^1$-136 |
| 837 | " | " | " | $Ar^1$-137 |
| 838 | " | " | " | $Ar^1$-165 |
| 839 | " | " | " | $Ar^1$-200 |
| 840 | " | " | " | $Ar^1$-201 |
| 841 | " | " | $Ar^1$-136 | $Ar^1$-136 |
| 842 | " | " | " | $Ar^1$-137 |
| 843 | " | " | " | $Ar^1$-165 |
| 844 | " | " | " | $Ar^1$-200 |
| 845 | " | " | " | $Ar^1$-201 |
| 846 | " | " | $Ar^1$-137 | $Ar^1$-137 |
| 847 | " | " | " | $Ar^1$-165 |
| 848 | " | " | " | $Ar^1$-200 |
| 849 | " | " | " | $Ar^1$-201 |
| 850 | " | " | $Ar^1$-165 | $Ar^1$-165 |
| 851 | " | " | " | $Ar^1$-200 |
| 852 | " | " | " | $Ar^1$-201 |
| 853 | " | " | $Ar^1$-200 | $Ar^1$-200 |
| 854 | " | " | " | $Ar^1$-201 |
| 855 | " | " | $Ar^1$-201 | $Ar^1$-201 |
| 856 | " | $Ar^1$-3 | $Ar^1$-1 | $Ar^1$-1 |
| 857 | " | " | " | $Ar^1$-74 |
| 858 | " | " | " | $Ar^1$-132 |
| 859 | " | " | " | $Ar^1$-134 |
| 860 | " | " | " | $Ar^1$-136 |
| 861 | " | " | " | $Ar^1$-137 |
| 862 | " | " | " | $Ar^1$-165 |
| 863 | " | " | " | $Ar^1$-200 |
| 864 | " | " | " | $Ar^1$-201 |
| 865 | " | " | $Ar^1$-74 | $Ar^1$-74 |
| 866 | " | " | " | $Ar^1$-132 |
| 867 | " | " | " | $Ar^1$-134 |
| 868 | " | " | " | $Ar^1$-136 |
| 869 | " | " | " | $Ar^1$-137 |
| 870 | " | " | " | $Ar^1$-165 |
| 871 | " | " | " | $Ar^1$-200 |
| 872 | " | " | " | $Ar^1$-201 |
| 873 | " | " | $Ar^1$-132 | $Ar^1$-132 |
| 874 | " | " | " | $Ar^1$-134 |
| 875 | " | " | " | $Ar^1$-136 |
| 876 | " | " | " | $Ar^1$-137 |
| 877 | " | " | " | $Ar^1$-165 |
| 878 | " | " | " | $Ar^1$-200 |
| 879 | " | " | " | $Ar^1$-201 |
| 880 | " | " | $Ar^1$-134 | $Ar^1$-134 |
| 881 | " | " | " | $Ar^1$-136 |
| 882 | " | " | " | $Ar^1$-137 |
| 883 | " | " | " | $Ar^1$-165 |
| 884 | " | " | " | $Ar^1$-200 |
| 885 | " | " | " | $Ar^1$-201 |
| 886 | " | " | $Ar^1$-136 | $Ar^1$-136 |
| 887 | " | " | " | $Ar^1$-137 |
| 888 | " | " | " | $Ar^1$-165 |
| 889 | " | " | " | $Ar^1$-200 |
| 890 | " | " | " | $Ar^1$-201 |
| 891 | " | " | $Ar^1$-137 | $Ar^1$-137 |
| 892 | " | " | " | $Ar^1$-165 |
| 893 | " | " | " | $Ar^1$-200 |
| 894 | " | " | " | $Ar^1$-201 |

-continued

| | Base skeleton | $L^1$ or k = 0 | $Ar^1$ | $Ar^1$ |
|---|---|---|---|---|
| 895 | " | " | $Ar^1$-165 | $Ar^1$-165 |
| 896 | " | " | " | $Ar^1$-200 |
| 897 | " | " | " | $Ar^1$-201 |
| 898 | " | " | $Ar^1$-200 | $Ar^1$-200 |
| 899 | " | " | " | $Ar^1$-201 |
| 900 | " | " | $Ar^1$-201 | $Ar^1$-201 |
| 901 | I-1-4-S | k = 0 | $Ar^1$-1 | $Ar^1$-1 |
| 902 | " | " | " | $Ar^1$-74 |
| 903 | " | " | " | $Ar^1$-132 |
| 904 | " | " | " | $Ar^1$-134 |
| 905 | " | " | " | $Ar^1$-136 |
| 906 | " | " | " | $Ar^1$-137 |
| 907 | " | " | " | $Ar^1$-165 |
| 908 | " | " | " | $Ar^1$-200 |
| 909 | " | " | " | $Ar^1$-201 |
| 910 | " | " | $Ar^1$-74 | $Ar^1$-74 |
| 911 | " | " | " | $Ar^1$-132 |
| 912 | " | " | " | $Ar^1$-134 |
| 913 | " | " | " | $Ar^1$-136 |
| 914 | " | " | " | $Ar^1$-137 |
| 915 | " | " | " | $Ar^1$-165 |
| 916 | " | " | " | $Ar^1$-200 |
| 917 | " | " | " | $Ar^1$-201 |
| 918 | " | " | $Ar^1$-132 | $Ar^1$-132 |
| 919 | " | " | " | $Ar^1$-134 |
| 920 | " | " | " | $Ar^1$-136 |
| 921 | " | " | " | $Ar^1$-137 |
| 922 | " | " | " | $Ar^1$-165 |
| 923 | " | " | " | $Ar^1$-200 |
| 924 | " | " | " | $Ar^1$-201 |
| 925 | " | " | $Ar^1$-134 | $Ar^1$-134 |
| 926 | " | " | " | $Ar^1$-136 |
| 927 | " | " | " | $Ar^1$-137 |
| 928 | " | " | " | $Ar^1$-165 |
| 929 | " | " | " | $Ar^1$-200 |
| 930 | " | " | " | $Ar^1$-201 |
| 931 | " | " | $Ar^1$-136 | $Ar^1$-136 |
| 932 | " | " | " | $Ar^1$-137 |
| 933 | " | " | " | $Ar^1$-165 |
| 934 | " | " | " | $Ar^1$-200 |
| 935 | " | " | " | $Ar^1$-201 |
| 936 | " | " | $Ar^1$-137 | $Ar^1$-137 |
| 937 | " | " | " | $Ar^1$-165 |
| 938 | " | " | " | $Ar^1$-200 |
| 939 | " | " | " | $Ar^1$-201 |
| 940 | " | " | $Ar^1$-165 | $Ar^1$-165 |
| 941 | " | " | " | $Ar^1$-200 |
| 942 | " | " | " | $Ar^1$-201 |
| 943 | " | " | $Ar^1$-200 | $Ar^1$-200 |
| 944 | " | " | " | $Ar^1$-201 |
| 945 | " | " | $Ar^1$-201 | $Ar^1$-201 |
| 946 | " | $Ar^1$-1 | $Ar^1$-1 | $Ar^1$-1 |
| 947 | " | " | " | $Ar^1$-74 |
| 948 | " | " | " | $Ar^1$-132 |
| 949 | " | " | " | $Ar^1$-134 |
| 950 | " | " | " | $Ar^1$-136 |
| 951 | " | " | " | $Ar^1$-137 |
| 952 | " | " | " | $Ar^1$-165 |
| 953 | " | " | " | $Ar^1$-200 |
| 954 | " | " | " | $Ar^1$-201 |
| 955 | " | " | $Ar^1$-74 | $Ar^1$-74 |
| 956 | " | " | " | $Ar^1$-132 |
| 957 | " | " | " | $Ar^1$-134 |
| 958 | " | " | " | $Ar^1$-136 |
| 959 | " | " | " | $Ar^1$-137 |
| 960 | " | " | " | $Ar^1$-165 |
| 961 | " | " | " | $Ar^1$-200 |
| 962 | " | " | " | $Ar^1$-201 |
| 963 | " | " | $Ar^1$-132 | $Ar^1$-132 |
| 964 | " | " | " | $Ar^1$-134 |
| 965 | " | " | " | $Ar^1$-136 |
| 966 | " | " | " | $Ar^1$-137 |
| 967 | " | " | " | $Ar^1$-165 |
| 968 | " | " | " | $Ar^1$-200 |
| 969 | " | " | " | $Ar^1$-201 |
| 970 | " | " | $Ar^1$-134 | $Ar^1$-134 |

-continued

| | Base skeleton | $L^1$ or k = 0 | $Ar^1$ | $Ar^1$ |
|---|---|---|---|---|
| 971 | " | " | " | $Ar^1$-136 |
| 972 | " | " | " | $Ar^1$-137 |
| 973 | " | " | " | $Ar^1$-165 |
| 974 | " | " | " | $Ar^1$-200 |
| 975 | " | " | " | $Ar^1$-201 |
| 976 | " | " | $Ar^1$-136 | $Ar^1$-136 |
| 977 | " | " | " | $Ar^1$-137 |
| 978 | " | " | " | $Ar^1$-165 |
| 979 | " | " | " | $Ar^1$-200 |
| 980 | " | " | " | $Ar^1$-201 |
| 981 | " | " | $Ar^1$-137 | $Ar^1$-137 |
| 982 | " | " | " | $Ar^1$-165 |
| 983 | " | " | " | $Ar^1$-200 |
| 984 | " | " | " | $Ar^1$-201 |
| 985 | " | " | $Ar^1$-165 | $Ar^1$-165 |
| 986 | " | " | " | $Ar^1$-200 |
| 987 | " | " | " | $Ar^1$-201 |
| 988 | " | " | $Ar^1$-200 | $Ar^1$-200 |
| 989 | " | " | " | $Ar^1$-201 |
| 990 | " | " | $Ar^1$-201 | $Ar^1$-201 |
| 991 | " | $Ar^1$-2 | $Ar^1$-1 | $Ar^1$-1 |
| 992 | " | " | " | $Ar^1$-74 |
| 993 | " | " | " | $Ar^1$-132 |
| 994 | " | " | " | $Ar^1$-134 |
| 995 | " | " | " | $Ar^1$-136 |
| 996 | " | " | " | $Ar^1$-137 |
| 997 | " | " | " | $Ar^1$-165 |
| 998 | " | " | " | $Ar^1$-200 |
| 999 | " | " | " | $Ar^1$-201 |
| 1000 | " | " | $Ar^1$-74 | $Ar^1$-74 |
| 1001 | " | " | " | $Ar^1$-132 |
| 1002 | " | " | " | $Ar^1$-134 |
| 1003 | " | " | " | $Ar^1$-136 |
| 1004 | " | " | " | $Ar^1$-137 |
| 1005 | " | " | " | $Ar^1$-165 |
| 1006 | " | " | " | $Ar^1$-200 |
| 1007 | " | " | " | $Ar^1$-201 |
| 1008 | " | " | $Ar^1$-132 | $Ar^1$-132 |
| 1009 | " | " | " | $Ar^1$-134 |
| 1010 | " | " | " | $Ar^1$-136 |
| 1011 | " | " | " | $Ar^1$-137 |
| 1012 | " | " | " | $Ar^1$-165 |
| 1013 | " | " | " | $Ar^1$-200 |
| 1014 | " | " | " | $Ar^1$-201 |
| 1015 | " | " | $Ar^1$-134 | $Ar^1$-134 |
| 1016 | " | " | " | $Ar^1$-136 |
| 1017 | " | " | " | $Ar^1$-137 |
| 1018 | " | " | " | $Ar^1$-165 |
| 1019 | " | " | " | $Ar^1$-200 |
| 1020 | " | " | " | $Ar^1$-201 |
| 1021 | " | " | $Ar^1$-136 | $Ar^1$-136 |
| 1022 | " | " | " | $Ar^1$-137 |
| 1023 | " | " | " | $Ar^1$-165 |
| 1024 | " | " | " | $Ar^1$-200 |
| 1025 | " | " | " | $Ar^1$-201 |
| 1026 | " | " | $Ar^1$-137 | $Ar^1$-137 |
| 1027 | " | " | " | $Ar^1$-165 |
| 1028 | " | " | " | $Ar^1$-200 |
| 1029 | " | " | " | $Ar^1$-201 |
| 1030 | " | " | $Ar^1$-165 | $Ar^1$-165 |
| 1031 | " | " | " | $Ar^1$-200 |
| 1032 | " | " | " | $Ar^1$-201 |
| 1033 | " | " | $Ar^1$-200 | $Ar^1$-200 |
| 1034 | " | " | " | $Ar^1$-201 |
| 1035 | " | " | $Ar^1$-201 | $Ar^1$-201 |
| 1036 | " | $Ar^1$-3 | $Ar^1$-1 | $Ar^1$-1 |
| 1037 | " | " | " | $Ar^1$-74 |
| 1038 | " | " | " | $Ar^1$-132 |
| 1039 | " | " | " | $Ar^1$-134 |
| 1040 | " | " | " | $Ar^1$-136 |
| 1041 | " | " | " | $Ar^1$-137 |
| 1042 | " | " | " | $Ar^1$-165 |
| 1043 | " | " | " | $Ar^1$-200 |
| 1044 | " | " | " | $Ar^1$-201 |
| 1045 | " | " | $Ar^1$-74 | $Ar^1$-74 |
| 1046 | " | " | " | $Ar^1$-132 |

-continued

| | Base skeleton | $L^1$ or k = 0 | $Ar^1$ | $Ar^1$ |
|---|---|---|---|---|
| 1047 | " | " | " | $Ar^1$-134 |
| 1048 | " | " | " | $Ar^1$-136 |
| 1049 | " | " | " | $Ar^1$-137 |
| 1050 | " | " | " | $Ar^1$-165 |
| 1051 | " | " | " | $Ar^1$-200 |
| 1052 | " | " | " | $Ar^1$-201 |
| 1053 | " | " | $Ar^1$-132 | $Ar^1$-132 |
| 1054 | " | " | " | $Ar^1$-134 |
| 1055 | " | " | " | $Ar^1$-136 |
| 1056 | " | " | " | $Ar^1$-137 |
| 1057 | " | " | " | $Ar^1$-165 |
| 1058 | " | " | " | $Ar^1$-200 |
| 1059 | " | " | " | $Ar^1$-201 |
| 1060 | " | " | $Ar^1$-134 | $Ar^1$-134 |
| 1061 | " | " | " | $Ar^1$-136 |
| 1062 | " | " | " | $Ar^1$-137 |
| 1063 | " | " | " | $Ar^1$-165 |
| 1064 | " | " | " | $Ar^1$-200 |
| 1065 | " | " | " | $Ar^1$-201 |
| 1066 | " | " | $Ar^1$-136 | $Ar^1$-136 |
| 1067 | " | " | " | $Ar^1$-137 |
| 1068 | " | " | " | $Ar^1$-165 |
| 1069 | " | " | " | $Ar^1$-200 |
| 1070 | " | " | " | $Ar^1$-201 |
| 1071 | " | " | $Ar^1$-137 | $Ar^1$-137 |
| 1072 | " | " | " | $Ar^1$-165 |
| 1073 | " | " | " | $Ar^1$-200 |
| 1074 | " | " | " | $Ar^1$-201 |
| 1075 | " | " | $Ar^1$-165 | $Ar^1$-165 |
| 1076 | " | " | " | $Ar^1$-200 |
| 1077 | " | " | " | $Ar^1$-201 |
| 1078 | " | " | $Ar^1$-200 | $Ar^1$-200 |
| 1079 | " | " | " | $Ar^1$-201 |
| 1080 | " | " | $Ar^1$-201 | $Ar^1$-201 |
| 1081 | I-1-5-S | k = 0 | $Ar^1$-1 | $Ar^1$-1 |
| 1082 | " | " | " | $Ar^1$-74 |
| 1083 | " | " | " | $Ar^1$-132 |
| 1084 | " | " | " | $Ar^1$-134 |
| 1085 | " | " | " | $Ar^1$-136 |
| 1086 | " | " | " | $Ar^1$-137 |
| 1087 | " | " | " | $Ar^1$-165 |
| 1088 | " | " | " | $Ar^1$-200 |
| 1089 | " | " | " | $Ar^1$-201 |
| 1090 | " | " | $Ar^1$-74 | $Ar^1$-74 |
| 1091 | " | " | " | $Ar^1$-132 |
| 1092 | " | " | " | $Ar^1$-134 |
| 1093 | " | " | " | $Ar^1$-136 |
| 1094 | " | " | " | $Ar^1$-137 |
| 1095 | " | " | " | $Ar^1$-165 |
| 1096 | " | " | " | $Ar^1$-200 |
| 1097 | " | " | " | $Ar^1$-201 |
| 1098 | " | " | $Ar^1$-132 | $Ar^1$-132 |
| 1099 | " | " | " | $Ar^1$-134 |
| 1100 | " | " | " | $Ar^1$-136 |
| 1101 | " | " | " | $Ar^1$-137 |
| 1102 | " | " | " | $Ar^1$-165 |
| 1103 | " | " | " | $Ar^1$-200 |
| 1104 | " | " | " | $Ar^1$-201 |
| 1105 | " | " | $Ar^1$-134 | $Ar^1$-134 |
| 1106 | " | " | " | $Ar^1$-136 |
| 1107 | " | " | " | $Ar^1$-137 |
| 1108 | " | " | " | $Ar^1$-165 |
| 1109 | " | " | " | $Ar^1$-200 |
| 1110 | " | " | " | $Ar^1$-201 |
| 1111 | " | " | $Ar^1$-136 | $Ar^1$-136 |
| 1112 | " | " | " | $Ar^1$-137 |
| 1113 | " | " | " | $Ar^1$-165 |
| 1114 | " | " | " | $Ar^1$-200 |
| 1115 | " | " | " | $Ar^1$-201 |
| 1116 | " | " | $Ar^1$-137 | $Ar^1$-137 |
| 1117 | " | " | " | $Ar^1$-165 |
| 1118 | " | " | " | $Ar^1$-200 |
| 1119 | " | " | " | $Ar^1$-201 |
| 1120 | " | " | $Ar^1$-165 | $Ar^1$-165 |
| 1121 | " | " | " | $Ar^1$-200 |
| 1122 | " | " | " | $Ar^1$-201 |

-continued

| | Base skeleton | $L^1$ or k = 0 | $Ar^1$ | $Ar^1$ |
|---|---|---|---|---|
| 1123 | " | " | $Ar^1$-200 | $Ar^1$-200 |
| 1124 | " | " | " | $Ar^1$-201 |
| 1125 | " | " | $Ar^1$-201 | $Ar^1$-201 |
| 1126 | " | $Ar^1$-1 | $Ar^1$-1 | $Ar^1$-1 |
| 1127 | " | " | " | $Ar^1$-74 |
| 1128 | " | " | " | $Ar^1$-132 |
| 1129 | " | " | " | $Ar^1$-134 |
| 1130 | " | " | " | $Ar^1$-136 |
| 1131 | " | " | " | $Ar^1$-137 |
| 1132 | " | " | " | $Ar^1$-165 |
| 1133 | " | " | " | $Ar^1$-200 |
| 1134 | " | " | " | $Ar^1$-201 |
| 1135 | " | " | $Ar^1$-74 | $Ar^1$-74 |
| 1136 | " | " | " | $Ar^1$-132 |
| 1137 | " | " | " | $Ar^1$-134 |
| 1138 | " | " | " | $Ar^1$-136 |
| 1139 | " | " | " | $Ar^1$-137 |
| 1140 | " | " | " | $Ar^1$-165 |
| 1141 | " | " | " | $Ar^1$-200 |
| 1142 | " | " | " | $Ar^1$-201 |
| 1143 | " | " | $Ar^1$-132 | $Ar^1$-132 |
| 1144 | " | " | " | $Ar^1$-134 |
| 1145 | " | " | " | $Ar^1$-136 |
| 1146 | " | " | " | $Ar^1$-137 |
| 1147 | " | " | " | $Ar^1$-165 |
| 1148 | " | " | " | $Ar^1$-200 |
| 1149 | " | " | " | $Ar^1$-201 |
| 1150 | " | " | $Ar^1$-134 | $Ar^1$-134 |
| 1151 | " | " | " | $Ar^1$-136 |
| 1152 | " | " | " | $Ar^1$-137 |
| 1153 | " | " | " | $Ar^1$-165 |
| 1154 | " | " | " | $Ar^1$-200 |
| 1155 | " | " | " | $Ar^1$-201 |
| 1156 | " | " | $Ar^1$-136 | $Ar^1$-136 |
| 1157 | " | " | " | $Ar^1$-137 |
| 1158 | " | " | " | $Ar^1$-165 |
| 1159 | " | " | " | $Ar^1$-200 |
| 1160 | " | " | " | $Ar^1$-201 |
| 1161 | " | " | $Ar^1$-137 | $Ar^1$-137 |
| 1162 | " | " | " | $Ar^1$-165 |
| 1163 | " | " | " | $Ar^1$-200 |
| 1164 | " | " | " | $Ar^1$-201 |
| 1165 | " | " | $Ar^1$-165 | $Ar^1$-165 |
| 1166 | " | " | " | $Ar^1$-200 |
| 1167 | " | " | " | $Ar^1$-201 |
| 1168 | " | " | " | $Ar^1$-200 |
| 1169 | " | " | " | $Ar^1$-201 |
| 1170 | " | " | $Ar^1$-201 | $Ar^1$-201 |
| 1171 | " | $Ar^1$-2 | $Ar^1$-1 | $Ar^1$-1 |
| 1172 | " | " | " | $Ar^1$-74 |
| 1173 | " | " | " | $Ar^1$-132 |
| 1174 | " | " | " | $Ar^1$-134 |
| 1175 | " | " | " | $Ar^1$-136 |
| 1176 | " | " | " | $Ar^1$-137 |
| 1177 | " | " | " | $Ar^1$-165 |
| 1178 | " | " | " | $Ar^1$-200 |
| 1179 | " | " | " | $Ar^1$-201 |
| 1180 | " | " | $Ar^1$-74 | $Ar^1$-74 |
| 1181 | " | " | " | $Ar^1$-132 |
| 1182 | " | " | " | $Ar^1$-134 |
| 1183 | " | " | " | $Ar^1$-136 |
| 1184 | " | " | " | $Ar^1$-137 |
| 1185 | " | " | " | $Ar^1$-165 |
| 1186 | " | " | " | $Ar^1$-200 |
| 1187 | " | " | " | $Ar^1$-201 |
| 1188 | " | " | $Ar^1$-132 | $Ar^1$-132 |
| 1189 | " | " | " | $Ar^1$-134 |
| 1190 | " | " | " | $Ar^1$-136 |
| 1191 | " | " | " | $Ar^1$-137 |
| 1192 | " | " | " | $Ar^1$-165 |
| 1193 | " | " | " | $Ar^1$-200 |
| 1194 | " | " | " | $Ar^1$-201 |
| 1195 | " | " | $Ar^1$-134 | $Ar^1$-134 |
| 1196 | " | " | " | $Ar^1$-136 |
| 1197 | " | " | " | $Ar^1$-137 |
| 1198 | " | " | " | $Ar^1$-165 |

-continued

| | Base skeleton | $L^1$ or k = 0 | $Ar^1$ | $Ar^1$ |
|---|---|---|---|---|
| 1199 | " | " | " | $Ar^1$-200 |
| 1200 | " | " | " | $Ar^1$-201 |
| 1201 | " | " | $Ar^1$-136 | $Ar^1$-136 |
| 1202 | " | " | " | $Ar^1$-137 |
| 1203 | " | " | " | $Ar^1$-165 |
| 1204 | " | " | " | $Ar^1$-200 |
| 1205 | " | " | " | $Ar^1$-201 |
| 1206 | " | " | $Ar^1$-137 | $Ar^1$-137 |
| 1207 | " | " | " | $Ar^1$-165 |
| 1208 | " | " | " | $Ar^1$-200 |
| 1209 | " | " | " | $Ar^1$-201 |
| 1210 | " | " | $Ar^1$-165 | $Ar^1$-165 |
| 1211 | " | " | " | $Ar^1$-200 |
| 1212 | " | " | " | $Ar^1$-201 |
| 1213 | " | " | " | $Ar^1$-200 |
| 1214 | " | " | " | $Ar^1$-201 |
| 1215 | " | " | $Ar^1$-201 | $Ar^1$-201 |
| 1216 | " | $Ar^1$-3 | $Ar^1$-1 | $Ar^1$-1 |
| 1217 | " | " | " | $Ar^1$-74 |
| 1218 | " | " | " | $Ar^1$-132 |
| 1219 | " | " | " | $Ar^1$-134 |
| 1220 | " | " | " | $Ar^1$-136 |
| 1221 | " | " | " | $Ar^1$-137 |
| 1222 | " | " | " | $Ar^1$-165 |
| 1223 | " | " | " | $Ar^1$-200 |
| 1224 | " | " | " | $Ar^1$-201 |
| 1225 | " | " | $Ar^1$-74 | $Ar^1$-74 |
| 1226 | " | " | " | $Ar^1$-132 |
| 1227 | " | " | " | $Ar^1$-134 |
| 1228 | " | " | " | $Ar^1$-136 |
| 1229 | " | " | " | $Ar^1$-137 |
| 1230 | " | " | " | $Ar^1$-165 |
| 1231 | " | " | " | $Ar^1$-200 |
| 1232 | " | " | " | $Ar^1$-201 |
| 1233 | " | " | $Ar^1$-132 | $Ar^1$-132 |
| 1234 | " | " | " | $Ar^1$-134 |
| 1235 | " | " | " | $Ar^1$-136 |
| 1236 | " | " | " | $Ar^1$-137 |
| 1237 | " | " | " | $Ar^1$-165 |
| 1238 | " | " | " | $Ar^1$-200 |
| 1239 | " | " | " | $Ar^1$-201 |
| 1240 | " | " | $Ar^1$-134 | $Ar^1$-134 |
| 1241 | " | " | " | $Ar^1$-136 |
| 1242 | " | " | " | $Ar^1$-137 |
| 1243 | " | " | " | $Ar^1$-165 |
| 1244 | " | " | " | $Ar^1$-200 |
| 1245 | " | " | " | $Ar^1$-201 |
| 1246 | " | " | $Ar^1$-136 | $Ar^1$-136 |
| 1247 | " | " | " | $Ar^1$-137 |
| 1248 | " | " | " | $Ar^1$-165 |
| 1249 | " | " | " | $Ar^1$-200 |
| 1250 | " | " | " | $Ar^1$-201 |
| 1251 | " | " | $Ar^1$-137 | $Ar^1$-137 |
| 1252 | " | " | " | $Ar^1$-165 |
| 1253 | " | " | " | $Ar^1$-200 |
| 1254 | " | " | " | $Ar^1$-201 |
| 1255 | " | " | $Ar^1$-165 | $Ar^1$-165 |
| 1256 | " | " | " | $Ar^1$-200 |
| 1257 | " | " | " | $Ar^1$-201 |
| 1258 | " | " | " | $Ar^1$-200 |
| 1259 | " | " | " | $Ar^1$-201 |
| 1260 | " | " | $Ar^1$-201 | $Ar^1$-201 |
| 1261 | I-1-7-O | k = 0 | $Ar^1$-1 | $Ar^1$-1 |
| 1262 | " | " | " | $Ar^1$-74 |
| 1263 | " | " | " | $Ar^1$-132 |
| 1264 | " | " | " | $Ar^1$-134 |
| 1265 | " | " | " | $Ar^1$-136 |
| 1266 | " | " | " | $Ar^1$-137 |
| 1267 | " | " | " | $Ar^1$-165 |
| 1268 | " | " | " | $Ar^1$-200 |
| 1269 | " | " | " | $Ar^1$-201 |
| 1270 | " | " | $Ar^1$-74 | $Ar^1$-74 |
| 1271 | " | " | " | $Ar^1$-132 |
| 1272 | " | " | " | $Ar^1$-134 |
| 1273 | " | " | " | $Ar^1$-136 |
| 1274 | " | " | " | $Ar^1$-137 |

-continued

| | Base skeleton | L$^1$ or k = 0 | Ar$^1$ | Ar$^1$ |
|---|---|---|---|---|
| 1275 | " | " | " | Ar$^1$-165 |
| 1276 | " | " | " | Ar$^1$-200 |
| 1277 | " | " | " | Ar$^1$-201 |
| 1278 | " | " | Ar$^1$-132 | Ar$^1$-132 |
| 1279 | " | " | " | Ar$^1$-134 |
| 1280 | " | " | " | Ar$^1$-136 |
| 1281 | " | " | " | Ar$^1$-137 |
| 1282 | " | " | " | Ar$^1$-165 |
| 1283 | " | " | " | Ar$^1$-200 |
| 1284 | " | " | " | Ar$^1$-201 |
| 1285 | " | " | Ar$^1$-134 | Ar$^1$-134 |
| 1286 | " | " | " | Ar$^1$-136 |
| 1287 | " | " | " | Ar$^1$-137 |
| 1288 | " | " | " | Ar$^1$-165 |
| 1289 | " | " | " | Ar$^1$-200 |
| 1290 | " | " | " | Ar$^1$-201 |
| 1291 | " | " | Ar$^1$-136 | Ar$^1$-136 |
| 1292 | " | " | " | Ar$^1$-137 |
| 1293 | " | " | " | Ar$^1$-165 |
| 1294 | " | " | " | Ar$^1$-200 |
| 1295 | " | " | " | Ar$^1$-201 |
| 1296 | " | " | Ar$^1$-137 | Ar$^1$-137 |
| 1297 | " | " | " | Ar$^1$-165 |
| 1298 | " | " | " | Ar$^1$-200 |
| 1299 | " | " | " | Ar$^1$-201 |
| 1300 | " | " | Ar$^1$-165 | Ar$^1$-165 |
| 1301 | " | " | " | Ar$^1$-200 |
| 1302 | " | " | " | Ar$^1$-201 |
| 1303 | " | " | Ar$^1$-200 | Ar$^1$-200 |
| 1304 | " | " | " | Ar$^1$-201 |
| 1305 | " | " | Ar$^1$-201 | Ar$^1$-201 |
| 1306 | " | Ar$^1$-1 | Ar$^1$-1 | Ar$^1$-1 |
| 1307 | " | " | " | Ar$^1$-74 |
| 1308 | " | " | " | Ar$^1$-132 |
| 1309 | " | " | " | Ar$^1$-134 |
| 1310 | " | " | " | Ar$^1$-136 |
| 1311 | " | " | " | Ar$^1$-137 |
| 1312 | " | " | " | Ar$^1$-165 |
| 1313 | " | " | " | Ar$^1$-200 |
| 1314 | " | " | " | Ar$^1$-201 |
| 1315 | " | " | Ar$^1$-74 | Ar$^1$-74 |
| 1316 | " | " | " | Ar$^1$-132 |
| 1317 | " | " | " | Ar$^1$-134 |
| 1318 | " | " | " | Ar$^1$-136 |
| 1319 | " | " | " | Ar$^1$-137 |
| 1320 | " | " | " | Ar$^1$-165 |
| 1321 | " | " | " | Ar$^1$-200 |
| 1322 | " | " | " | Ar$^1$-201 |
| 1323 | " | " | Ar$^1$-132 | Ar$^1$-132 |
| 1324 | " | " | " | Ar$^1$-134 |
| 1325 | " | " | " | Ar$^1$-136 |
| 1326 | " | " | " | Ar$^1$-137 |
| 1327 | " | " | " | Ar$^1$-165 |
| 1328 | " | " | " | Ar$^1$-200 |
| 1329 | " | " | " | Ar$^1$-201 |
| 1330 | " | " | Ar$^1$-134 | Ar$^1$-134 |
| 1331 | " | " | " | Ar$^1$-136 |
| 1332 | " | " | " | Ar$^1$-137 |
| 1333 | " | " | " | Ar$^1$-165 |
| 1334 | " | " | " | Ar$^1$-200 |
| 1335 | " | " | " | Ar$^1$-201 |
| 1336 | " | " | Ar$^1$-136 | Ar$^1$-136 |
| 1337 | " | " | " | Ar$^1$-137 |
| 1338 | " | " | " | Ar$^1$-165 |
| 1339 | " | " | " | Ar$^1$-200 |
| 1340 | " | " | " | Ar$^1$-201 |
| 1341 | " | " | Ar$^1$-137 | Ar$^1$-137 |
| 1342 | " | " | " | Ar$^1$-165 |
| 1343 | " | " | " | Ar$^1$-200 |
| 1344 | " | " | " | Ar$^1$-201 |
| 1345 | " | " | Ar$^1$-165 | Ar$^1$-165 |
| 1346 | " | " | " | Ar$^1$-200 |
| 1347 | " | " | " | Ar$^1$-201 |
| 1348 | " | " | Ar$^1$-200 | Ar$^1$-200 |
| 1349 | " | " | " | Ar$^1$-201 |
| 1350 | " | " | Ar$^1$-201 | Ar$^1$-201 |

-continued

| | Base skeleton | L$^1$ or k = 0 | Ar$^1$ | Ar$^1$ |
|---|---|---|---|---|
| 1351 | " | Ar$^1$-2 | Ar$^1$-1 | Ar$^1$-1 |
| 1352 | " | " | " | Ar$^1$-74 |
| 1353 | " | " | " | Ar$^1$-132 |
| 1354 | " | " | " | Ar$^1$-134 |
| 1355 | " | " | " | Ar$^1$-136 |
| 1356 | " | " | " | Ar$^1$-137 |
| 1357 | " | " | " | Ar$^1$-165 |
| 1358 | " | " | " | Ar$^1$-200 |
| 1359 | " | " | " | Ar$^1$-201 |
| 1360 | " | " | Ar$^1$-74 | Ar$^1$-74 |
| 1361 | " | " | " | Ar$^1$-132 |
| 1362 | " | " | " | Ar$^1$-134 |
| 1363 | " | " | " | Ar$^1$-136 |
| 1364 | " | " | " | Ar$^1$-137 |
| 1365 | " | " | " | Ar$^1$-165 |
| 1366 | " | " | " | Ar$^1$-200 |
| 1367 | " | " | " | Ar$^1$-201 |
| 1368 | " | " | Ar$^1$-132 | Ar$^1$-132 |
| 1369 | " | " | " | Ar$^1$-134 |
| 1370 | " | " | " | Ar$^1$-136 |
| 1371 | " | " | " | Ar$^1$-137 |
| 1372 | " | " | " | Ar$^1$-165 |
| 1373 | " | " | " | Ar$^1$-200 |
| 1374 | " | " | " | Ar$^1$-201 |
| 1375 | " | " | Ar$^1$-134 | Ar$^1$-134 |
| 1376 | " | " | " | Ar$^1$-136 |
| 1377 | " | " | " | Ar$^1$-137 |
| 1378 | " | " | " | Ar$^1$-165 |
| 1379 | " | " | " | Ar$^1$-200 |
| 1380 | " | " | " | Ar$^1$-201 |
| 1381 | " | " | Ar$^1$-136 | Ar$^1$-136 |
| 1382 | " | " | " | Ar$^1$-137 |
| 1383 | " | " | " | Ar$^1$-165 |
| 1384 | " | " | " | Ar$^1$-200 |
| 1385 | " | " | " | Ar$^1$-201 |
| 1386 | " | " | Ar$^1$-137 | Ar$^1$-137 |
| 1387 | " | " | " | Ar$^1$-165 |
| 1388 | " | " | " | Ar$^1$-200 |
| 1389 | " | " | " | Ar$^1$-201 |
| 1390 | " | " | Ar$^1$-165 | Ar$^1$-165 |
| 1391 | " | " | " | Ar$^1$-200 |
| 1392 | " | " | " | Ar$^1$-201 |
| 1393 | " | " | Ar$^1$-200 | Ar$^1$-200 |
| 1394 | " | " | " | Ar$^1$-201 |
| 1395 | " | " | Ar$^1$-201 | Ar$^1$-201 |
| 1396 | " | Ar$^1$-3 | Ar$^1$-1 | Ar$^1$-1 |
| 1397 | " | " | " | Ar$^1$-74 |
| 1398 | " | " | " | Ar$^1$-132 |
| 1399 | " | " | " | Ar$^1$-134 |
| 1400 | " | " | " | Ar$^1$-136 |
| 1401 | " | " | " | Ar$^1$-137 |
| 1402 | " | " | " | Ar$^1$-165 |
| 1403 | " | " | " | Ar$^1$-200 |
| 1404 | " | " | " | Ar$^1$-201 |
| 1405 | " | " | Ar$^1$-74 | Ar$^1$-74 |
| 1406 | " | " | " | Ar$^1$-132 |
| 1407 | " | " | " | Ar$^1$-134 |
| 1408 | " | " | " | Ar$^1$-136 |
| 1409 | " | " | " | Ar$^1$-137 |
| 1410 | " | " | " | Ar$^1$-165 |
| 1411 | " | " | " | Ar$^1$-200 |
| 1412 | " | " | " | Ar$^1$-201 |
| 1413 | " | " | Ar$^1$-132 | Ar$^1$-132 |
| 1414 | " | " | " | Ar$^1$-134 |
| 1415 | " | " | " | Ar$^1$-136 |
| 1416 | " | " | " | Ar$^1$-137 |
| 1417 | " | " | " | Ar$^1$-165 |
| 1418 | " | " | " | Ar$^1$-200 |
| 1419 | " | " | " | Ar$^1$-201 |
| 1420 | " | " | Ar$^1$-134 | Ar$^1$-134 |
| 1421 | " | " | " | Ar$^1$-136 |
| 1422 | " | " | " | Ar$^1$-137 |
| 1423 | " | " | " | Ar$^1$-165 |
| 1424 | " | " | " | Ar$^1$-200 |
| 1425 | " | " | " | Ar$^1$-201 |
| 1426 | " | " | Ar$^1$-136 | Ar$^1$-136 |

-continued

| | Base skeleton | $L^1$ or k = 0 | $Ar^1$ | $Ar^1$ |
|---|---|---|---|---|
| 1427 | " | " | " | $Ar^1$-137 |
| 1428 | " | " | " | $Ar^1$-165 |
| 1429 | " | " | " | $Ar^1$-200 |
| 1430 | " | " | " | $Ar^1$-201 |
| 1431 | " | " | $Ar^1$-137 | $Ar^1$-137 |
| 1432 | " | " | " | $Ar^1$-165 |
| 1433 | " | " | " | $Ar^1$-200 |
| 1434 | " | " | " | $Ar^1$-201 |
| 1435 | " | " | $Ar^1$-165 | $Ar^1$-165 |
| 1436 | " | " | " | $Ar^1$-200 |
| 1437 | " | " | " | $Ar^1$-201 |
| 1438 | " | " | $Ar^1$-200 | $Ar^1$-200 |
| 1439 | " | " | " | $Ar^1$-201 |
| 1440 | " | " | $Ar^1$-201 | $Ar^1$-201 |

The base skeletons specified in the table, which are also generally particularly preferred embodiments of compounds of the formula (I), are as follows:

Formula (I-1-2-O)

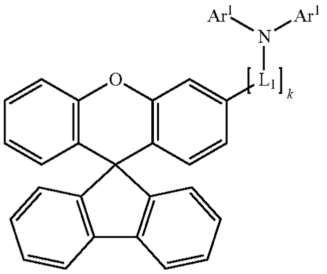

Formula (I-1-2-S)

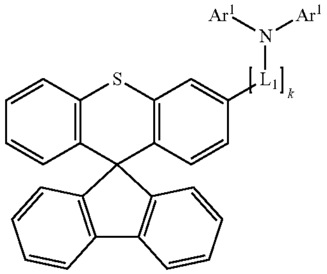

Formula (I-1-4-O)

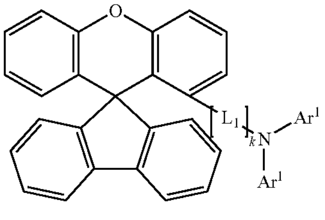

Formula (I-1-4-S)

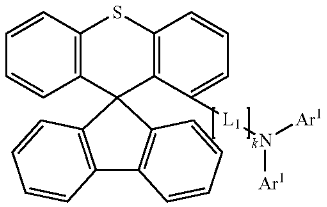

-continued

Formula (I-1-5-O)

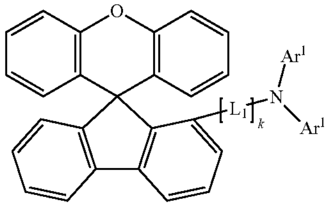

Formula (I-1-5-S)

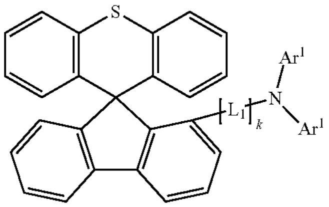

Formula (I-1-7-O)

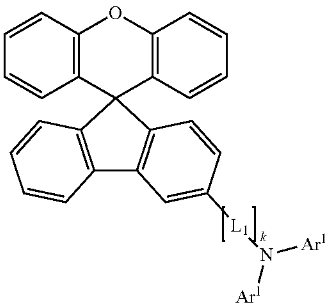

Formula (I-1-7-S)

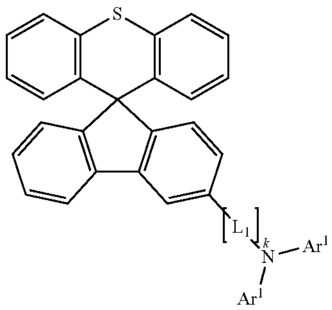

Preferred compounds of the formula (I) are additionally shown in the following table:

-continued
1
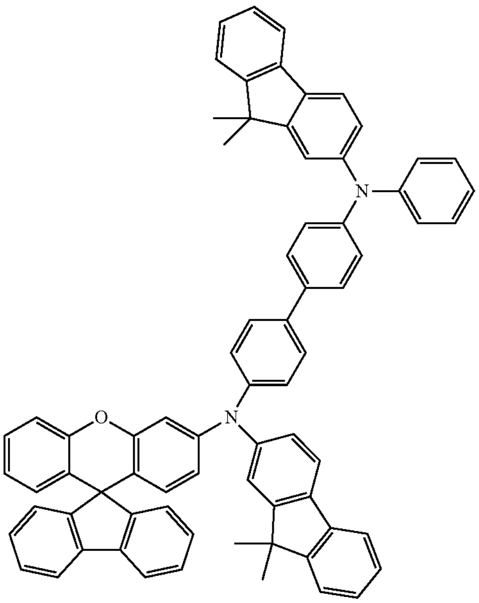 [SMILES: CC1(C)c2ccccc2-c2ccc(N(c3ccccc3)c3ccc(-c4ccc(N(c5ccc6c(c5)Oc5ccccc5C65c6ccccc6-c6ccccc65)c5ccc6c(c5)C(C)(C)c5ccccc5-6)cc4)cc3)cc21]
2
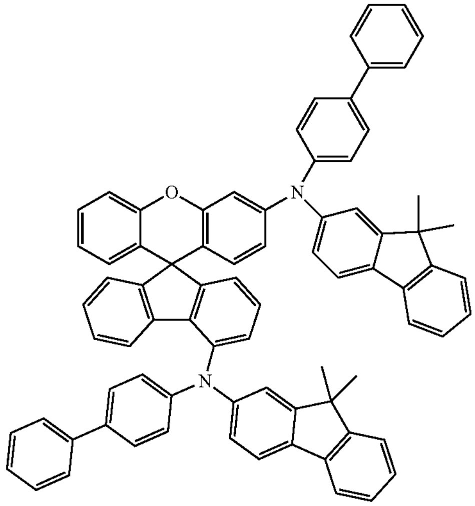 [SMILES: CC1(C)c2ccccc2-c2ccc(N(c3ccc(-c4ccccc4)cc3)c3ccc4c(c3)Oc3ccccc3C43c4ccccc4-c4c(N(c5ccc(-c6ccccc6)cc5)c5ccc6c(c5)C(C)(C)c5ccccc5-6)cccc43)cc21]
3
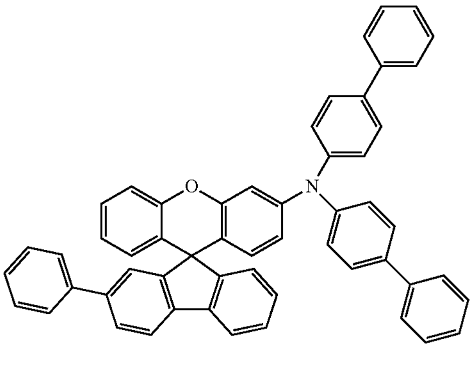 [SMILES: c1ccc(-c2ccc(N(c3ccc(-c4ccccc4)cc3)c3ccc4c(c3)Oc3ccccc3C43c4ccccc4-c4ccc(-c5ccccc5)cc43)cc2)cc1]
4
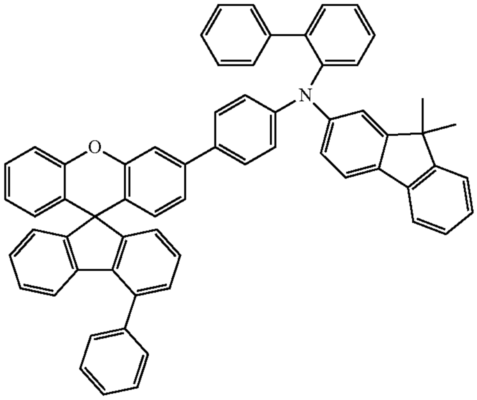 [SMILES: CC1(C)c2ccccc2-c2ccc(N(c3ccc(-c4ccc5c(c4)Oc4ccccc4C54c5ccccc5-c5c(-c6ccccc6)cccc54)cc3)c3ccccc3-c3ccccc3)cc21]
5
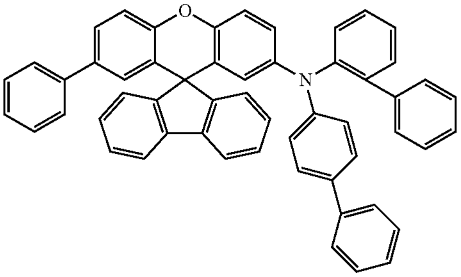 [SMILES: c1ccc(-c2ccc(N(c3ccc4c(c3)C3(c5cc(-c6ccccc6)ccc5O4)c4ccccc4-c4ccccc43)c3ccccc3-c3ccccc3)cc2)cc1]
6
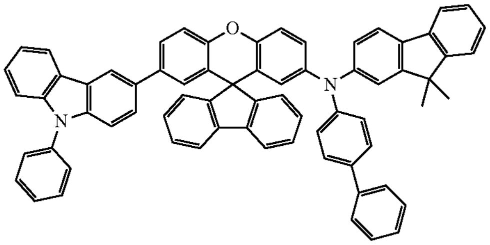 [SMILES: CC1(C)c2ccccc2-c2ccc(N(c3ccc(-c4ccccc4)cc3)c3ccc4c(c3)C3(c5cc(-c6ccc7c(c6)c6ccccc6n7-c6ccccc6)ccc5O4)c4ccccc4-c4ccccc43)cc21]
7
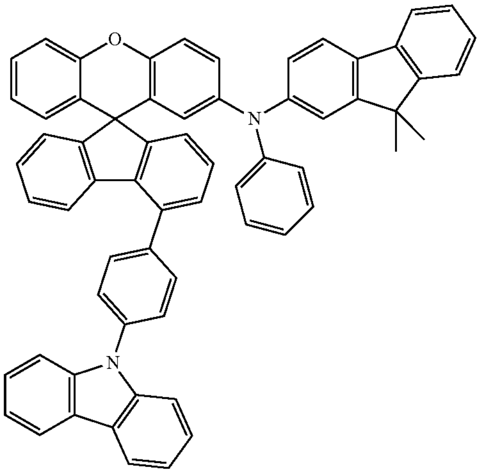 [SMILES: CC1(C)c2ccccc2-c2ccc(N(c3ccccc3)c3ccc4c(c3)C3(c5ccccc5O4)c4ccccc4-c4c(-c5ccc(-n6c7ccccc7c7ccccc76)cc5)cccc43)cc21]

-continued
8
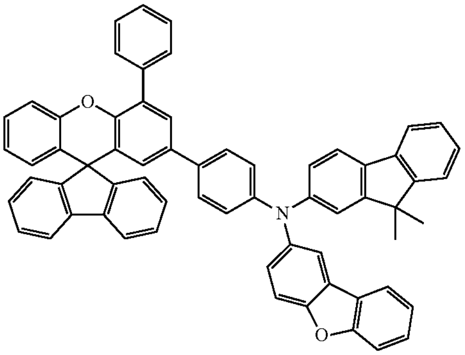 [SMILES: CC1(C)c2ccccc2-c2ccc(N(c3ccc(-c4cc(-c5ccccc5)c5c(c4)C4(c6ccccc6O5)c5ccccc5-c5ccccc54)cc3)c3ccc4oc5ccccc5c4c3)cc21]
9
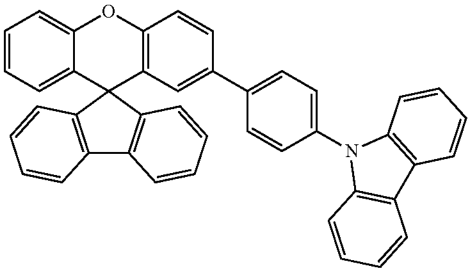 [SMILES: c1ccc2c(c1)Oc1ccc(-c3ccc(-n4c5ccccc5c5ccccc54)cc3)cc1C21c2ccccc2-c2ccccc21]
10
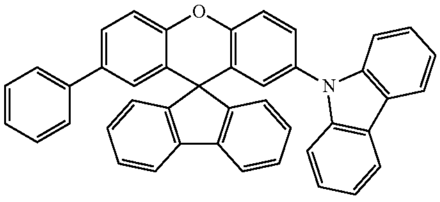 [SMILES: c1ccc(-c2ccc3c(c2)C2(c4cc(-n5c6ccccc6c6ccccc65)ccc4O3)c3ccccc3-c3ccccc32)cc1]
11
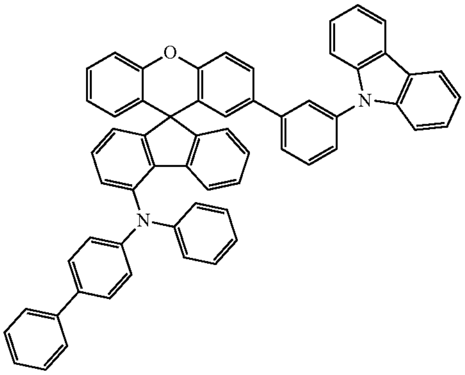 [SMILES: c1ccc(-c2ccc(N(c3ccccc3)c3cccc4c3-c3ccccc3C43c4ccccc4Oc4ccc(-c5cccc(-n6c7ccccc7c7ccccc76)c5)cc43)cc2)cc1]
12
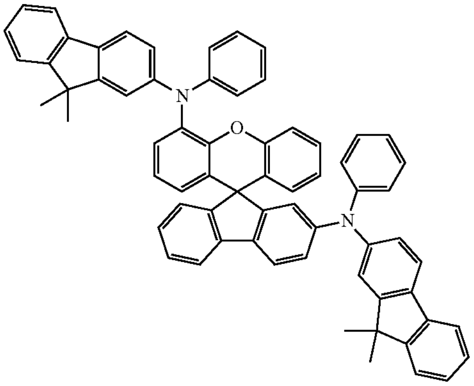 [SMILES: CC1(C)c2ccccc2-c2ccc(N(c3ccccc3)c3ccc4c(c3)C3(c5ccccc5Oc5c(N(c6ccccc6)c6ccc7c(c6)C(C)(C)c6ccccc6-7)cccc53)c3ccccc3-4)cc21]
-continued
13
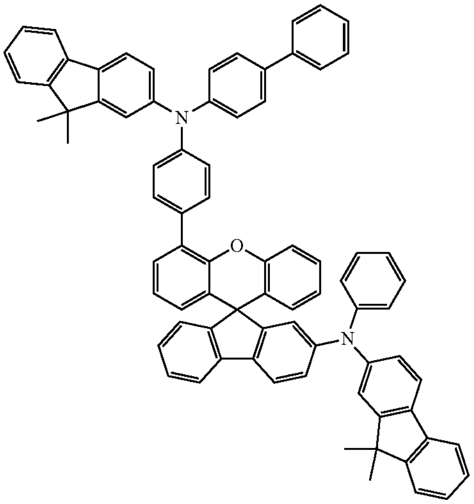 [SMILES: CC1(C)c2ccccc2-c2ccc(N(c3ccc(-c4ccccc4)cc3)c3ccc(-c4cccc5c4Oc4ccccc4C54c5ccccc5-c5ccc(N(c6ccccc6)c6ccc7c(c6)C(C)(C)c6ccccc6-7)cc54)cc3)cc21]
14
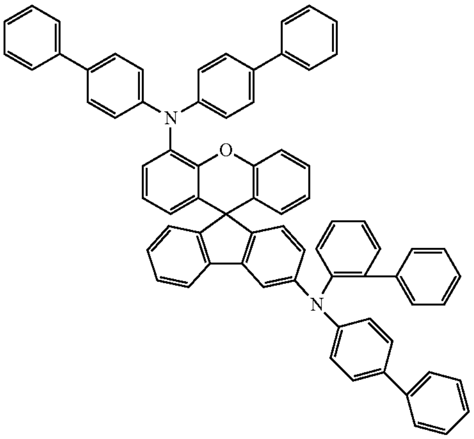 [SMILES: c1ccc(-c2ccc(N(c3ccc4c(c3)-c3ccccc3C43c4ccccc4Oc4c(N(c5ccc(-c6ccccc6)cc5)c5ccc(-c6ccccc6)cc5)cccc43)c3ccccc3-c3ccccc3)cc2)cc1]
15
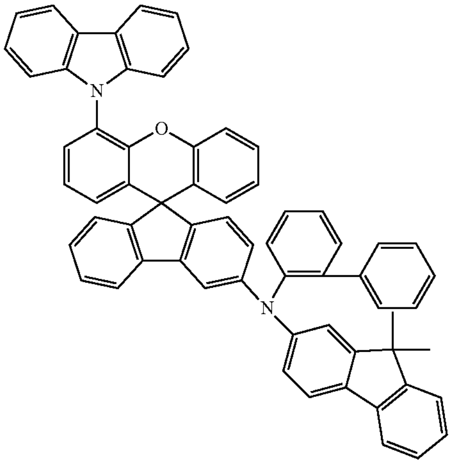 [SMILES: CC1(C)c2ccccc2-c2ccc(N(c3ccc4c(c3)-c3ccccc3C43c4ccccc4Oc4c(-n5c6ccccc6c6ccccc65)cccc43)c3ccccc3-c3ccccc3)cc21]

-continued
16
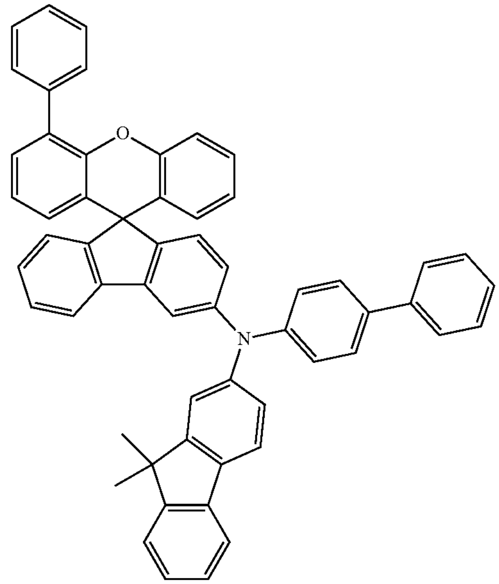 [SMILES: CC1(C)c2ccccc2-c2ccc(N(c3ccc(-c4ccccc4)cc3)c3ccc4c(c3)-c3ccccc3C43c4ccccc4Oc4c(-c5ccccc5)cccc43)cc21]
17
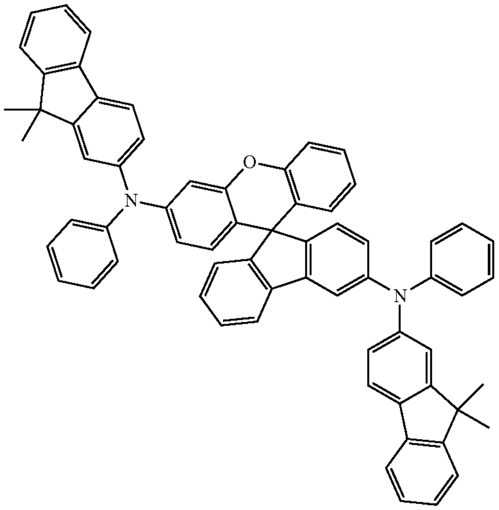 [SMILES: CC1(C)c2ccccc2-c2ccc(N(c3ccccc3)c3ccc4c(c3)Oc3ccccc3C43c4ccccc4-c4cc(N(c5ccccc5)c5ccc6c(c5)C(C)(C)c5ccccc5-6)ccc43)cc21]
18
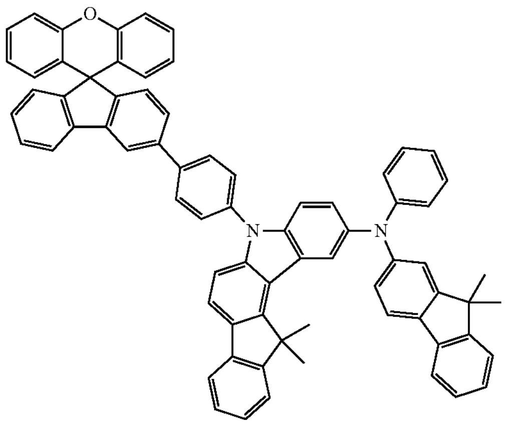 [SMILES: CC1(C)c2ccccc2-c2ccc(N(c3ccccc3)c3ccc4c(c3)c3c5c(ccc3n4-c3ccc(-c4ccc6c(c4)-c4ccccc4C64c6ccccc6Oc6ccccc64)cc3)-c3ccccc3C5(C)C)cc21]
-continued
19
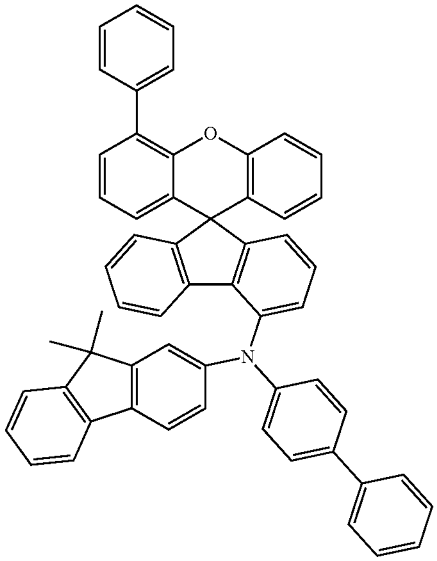 [SMILES: CC1(C)c2ccccc2-c2ccc(N(c3ccc(-c4ccccc4)cc3)c3cccc4c3-c3ccccc3C43c4ccccc4Oc4c(-c5ccccc5)cccc43)cc21]
20
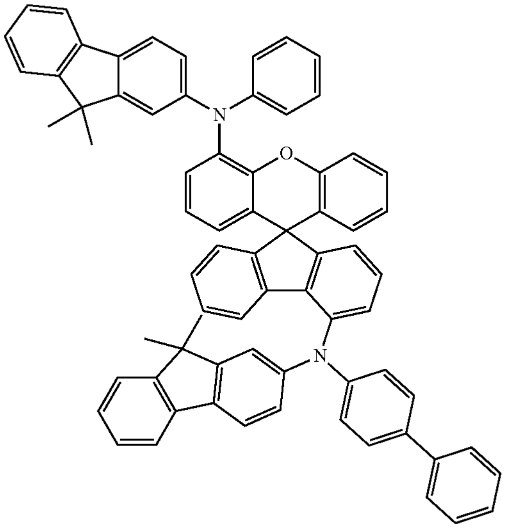 [SMILES: CC1(C)c2ccccc2-c2ccc(N(c3ccccc3)c3cccc4c3Oc3ccccc3C43c4ccccc4-c4c(N(c5ccc(-c6ccccc6)cc5)c5ccc6c(c5)C(C)(C)c5ccccc5-6)cccc43)cc21]
21
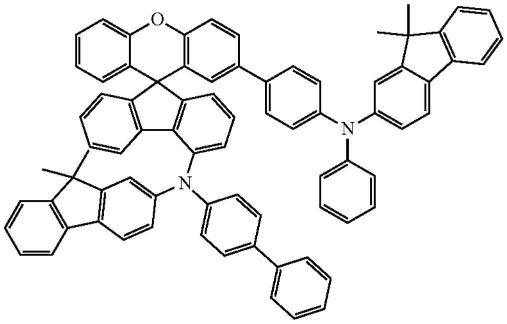 [SMILES: CC1(C)c2ccccc2-c2ccc(N(c3ccccc3)c3ccc(-c4ccc5c(c4)C4(c6ccccc6O5)c5ccccc5-c5c(N(c6ccc(-c7ccccc7)cc6)c6ccc7c(c6)C(C)(C)c6ccccc6-7)cccc54)cc3)cc21]

-continued
22
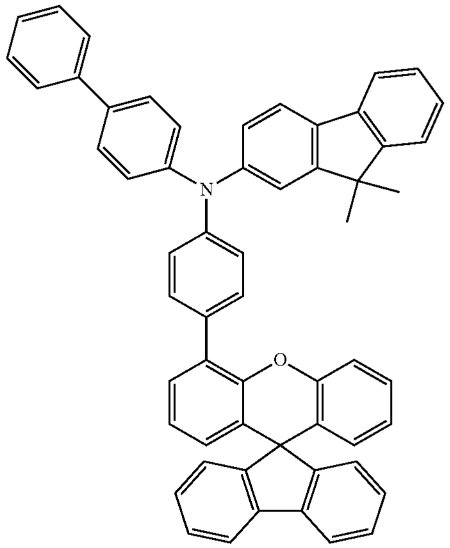 [SMILES: CC1(C)c2ccccc2-c2ccc(N(c3ccc(-c4ccccc4)cc3)c3ccc(-c4cccc5c4Oc4ccccc4C54c5ccccc5-c5ccccc54)cc3)cc21]
23
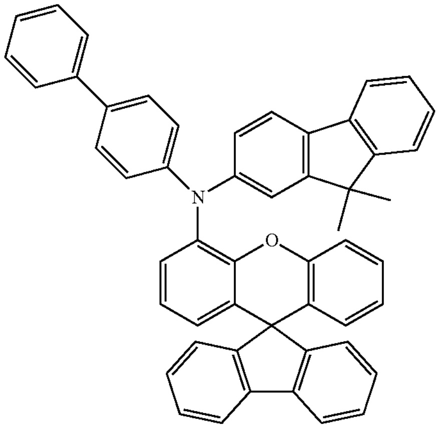 [SMILES: CC1(C)c2ccccc2-c2ccc(N(c3ccc(-c4ccccc4)cc3)c3cccc4c3Oc3ccccc3C43c4ccccc4-c4ccccc43)cc21]
24
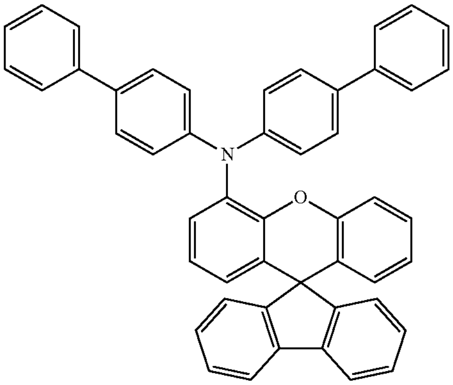 [SMILES: c1ccc(-c2ccc(N(c3ccc(-c4ccccc4)cc3)c3cccc4c3Oc3ccccc3C43c4ccccc4-c4ccccc43)cc2)cc1]
-continued
25
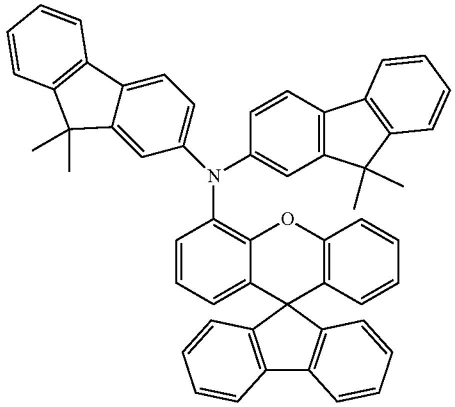 [SMILES: CC1(C)c2ccccc2-c2ccc(N(c3ccc4c(c3)C(C)(C)c3ccccc3-4)c3cccc4c3Oc3ccccc3C43c4ccccc4-c4ccccc43)cc21]
26
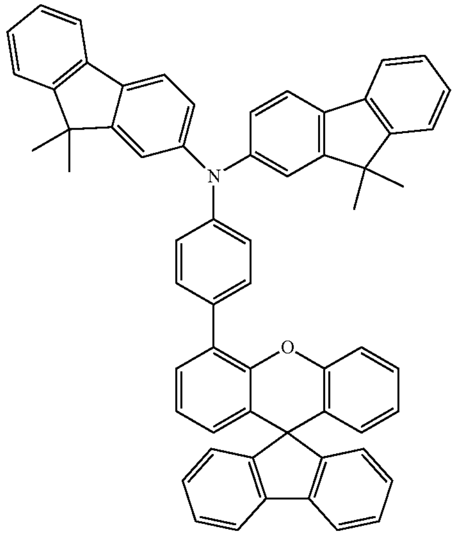 [SMILES: CC1(C)c2ccccc2-c2ccc(N(c3ccc(-c4cccc5c4Oc4ccccc4C54c5ccccc5-c5ccccc54)cc3)c3ccc4c(c3)C(C)(C)c3ccccc3-4)cc21]
27
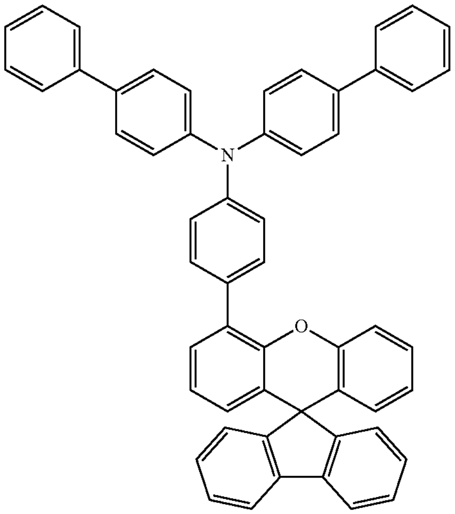 [SMILES: c1ccc(-c2ccc(N(c3ccc(-c4ccccc4)cc3)c3ccc(-c4cccc5c4Oc4ccccc4C54c5ccccc5-c5ccccc54)cc3)cc2)cc1]

28
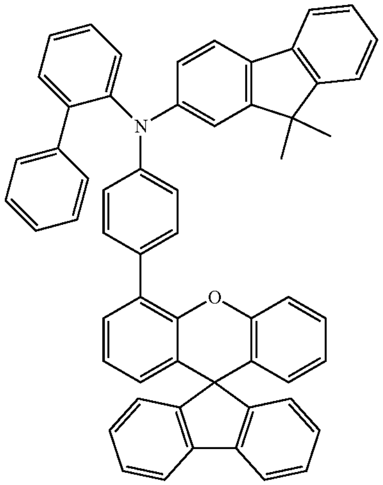 [SMILES: CC1(C)c2ccccc2-c2ccc(N(c3ccc(-c4cccc5c4Oc4ccccc4C54c5ccccc5-c5ccccc54)cc3)c3ccccc3-c3ccccc3)cc21]
29
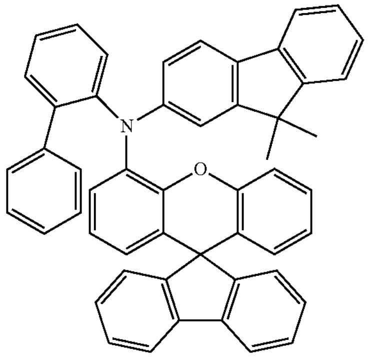 [SMILES: CC1(C)c2ccccc2-c2ccc(N(c3ccccc3-c3ccccc3)c3cccc4c3Oc3ccccc3C43c4ccccc4-c4ccccc43)cc21]
30
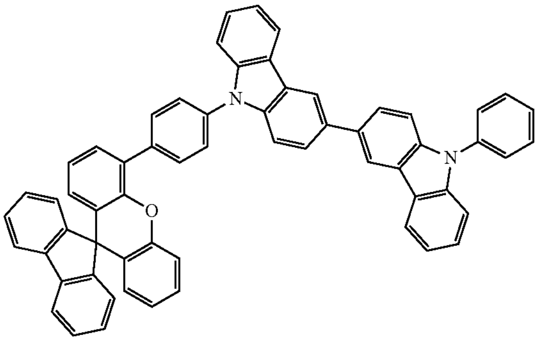 [SMILES: c1ccc(-n2c3ccccc3c3cc(-c4ccc5c(c4)c4ccccc4n5-c4ccc(-c5cccc6c5Oc5ccccc5C65c6ccccc6-c6ccccc65)cc4)ccc32)cc1]
31
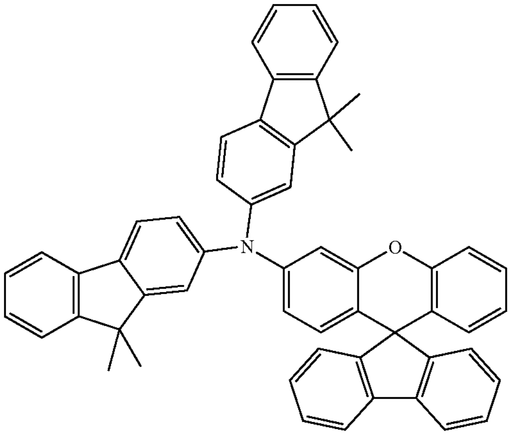 [SMILES: CC1(C)c2ccccc2-c2ccc(N(c3ccc4c(c3)Oc3ccccc3C43c4ccccc4-c4ccccc43)c3ccc4c(c3)C(C)(C)c3ccccc3-4)cc21]
32
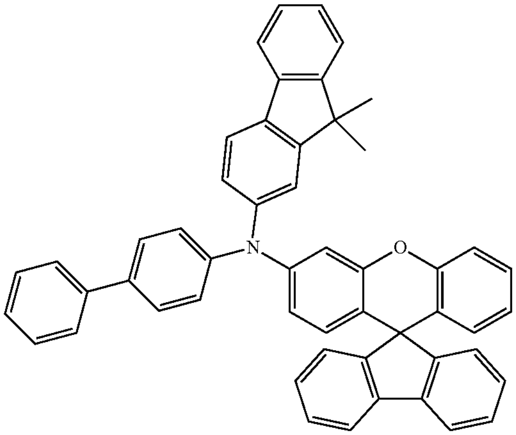 [SMILES: CC1(C)c2ccccc2-c2ccc(N(c3ccc(-c4ccccc4)cc3)c3ccc4c(c3)Oc3ccccc3C43c4ccccc4-c4ccccc43)cc21]
33
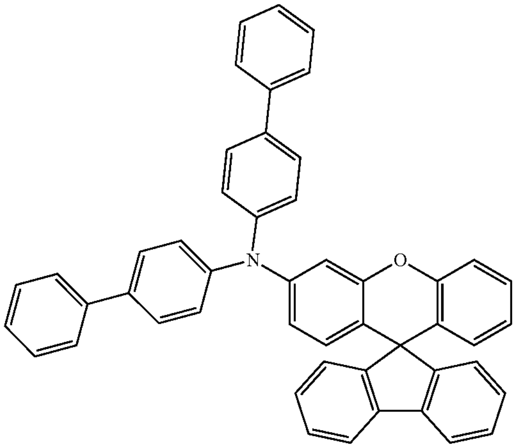 [SMILES: c1ccc(-c2ccc(N(c3ccc(-c4ccccc4)cc3)c3ccc4c(c3)Oc3ccccc3C43c4ccccc4-c4ccccc43)cc2)cc1]
34
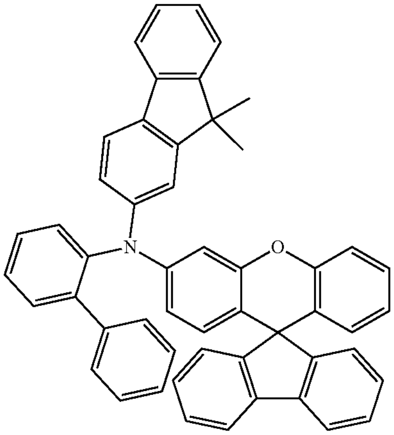 [SMILES: CC1(C)c2ccccc2-c2ccc(N(c3ccc4c(c3)Oc3ccccc3C43c4ccccc4-c4ccccc43)c3ccccc3-c3ccccc3)cc21]

-continued
35
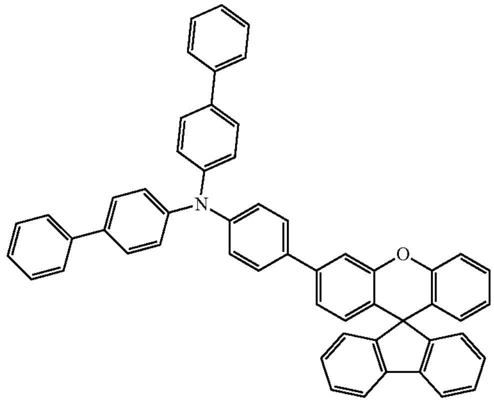 [SMILES: c1ccc(-c2ccc(N(c3ccc(-c4ccccc4)cc3)c3ccc(-c4ccc5c(c4)Oc4ccccc4C54c5ccccc5-c5ccccc54)cc3)cc2)cc1]
36
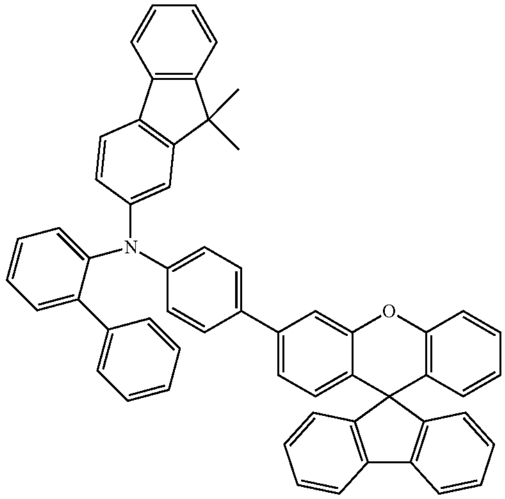 [SMILES: CC1(C)c2ccccc2-c2ccc(N(c3ccc(-c4ccc5c(c4)Oc4ccccc4C54c5ccccc5-c5ccccc54)cc3)c3ccccc3-c3ccccc3)cc21]
37
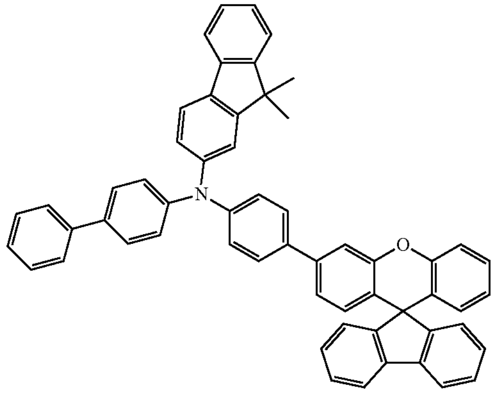 [SMILES: CC1(C)c2ccccc2-c2ccc(N(c3ccc(-c4ccccc4)cc3)c3ccc(-c4ccc5c(c4)Oc4ccccc4C54c5ccccc5-c5ccccc54)cc3)cc21]
-continued
38
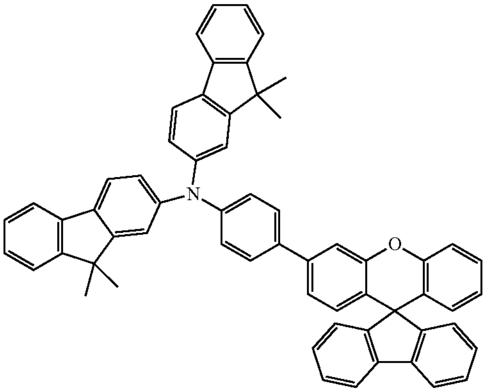 [SMILES: CC1(C)c2ccccc2-c2ccc(N(c3ccc(-c4ccc5c(c4)Oc4ccccc4C54c5ccccc5-c5ccccc54)cc3)c3ccc4c(c3)C(C)(C)c3ccccc3-4)cc21]
39
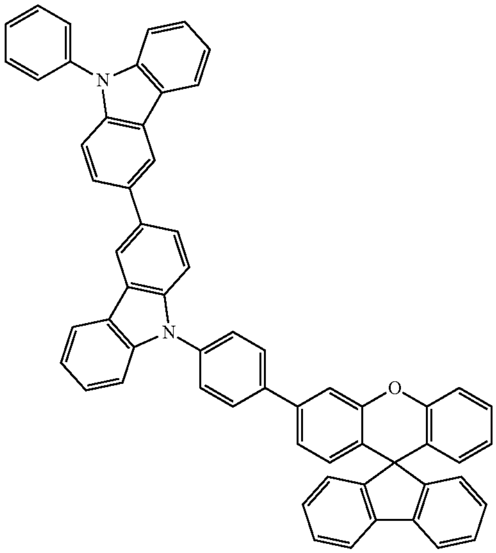 [SMILES: c1ccc(-n2c3ccccc3c3cc(-c4ccc5c(c4)c4ccccc4n5-c4ccc(-c5ccc6c(c5)Oc5ccccc5C65c6ccccc6-c6ccccc65)cc4)ccc32)cc1]
40
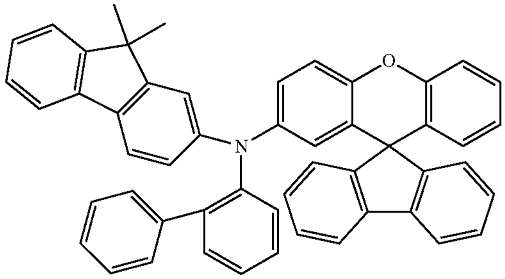 [SMILES: CC1(C)c2ccccc2-c2ccc(N(c3ccc4c(c3)C3(c5ccccc5O4)c4ccccc4-c4ccccc43)c3ccccc3-c3ccccc3)cc21]
41
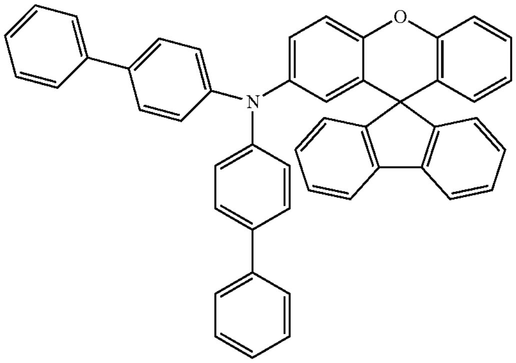 [SMILES: c1ccc(-c2ccc(N(c3ccc(-c4ccccc4)cc3)c3ccc4c(c3)C3(c5ccccc5O4)c4ccccc4-c4ccccc43)cc2)cc1]

-continued
42
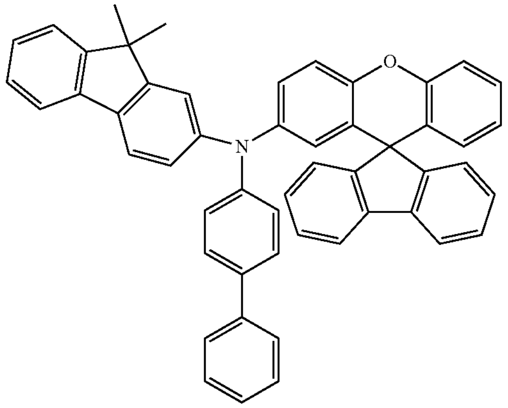 [SMILES: CC1(C)c2ccccc2-c2ccc(N(c3ccc(-c4ccccc4)cc3)c3ccc4c(c3)C3(c5ccccc5O4)c4ccccc4-c4ccccc43)cc21]
43
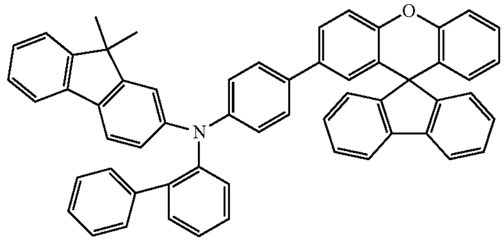 [SMILES: CC1(C)c2ccccc2-c2ccc(N(c3ccc(-c4ccc5c(c4)C4(c6ccccc6O5)c5ccccc5-c5ccccc54)cc3)c3ccccc3-c3ccccc3)cc21]
44
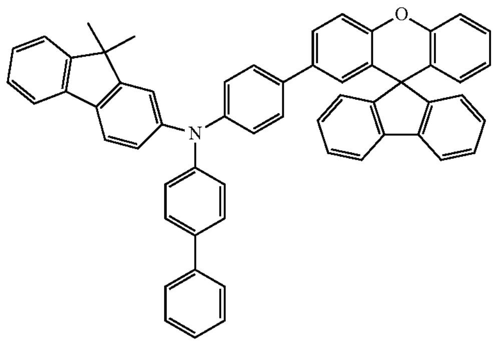 [SMILES: CC1(C)c2ccccc2-c2ccc(N(c3ccc(-c4ccccc4)cc3)c3ccc(-c4ccc5c(c4)C4(c6ccccc6O5)c5ccccc5-c5ccccc54)cc3)cc21]
45
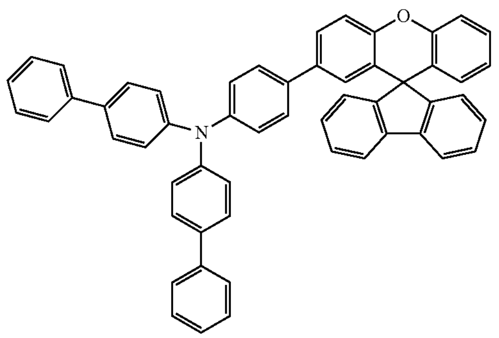 [SMILES: c1ccc(-c2ccc(N(c3ccc(-c4ccccc4)cc3)c3ccc(-c4ccc5c(c4)C4(c6ccccc6O5)c5ccccc5-c5ccccc54)cc3)cc2)cc1]
-continued
46
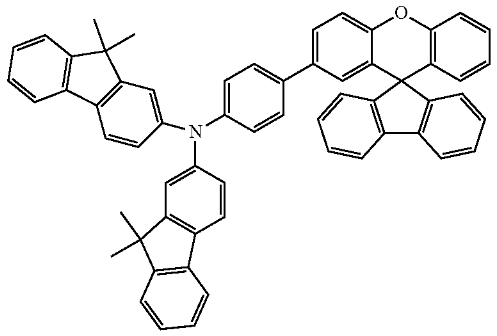 [SMILES: CC1(C)c2ccccc2-c2ccc(N(c3ccc(-c4ccc5c(c4)C4(c6ccccc6O5)c5ccccc5-c5ccccc54)cc3)c3ccc4c(c3)C(C)(C)c3ccccc3-4)cc21]
47
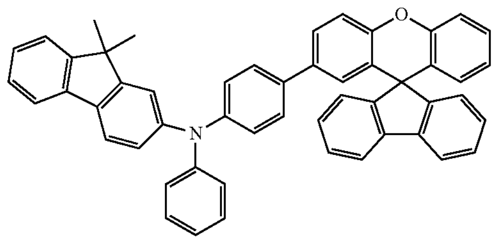 [SMILES: CC1(C)c2ccccc2-c2ccc(N(c3ccccc3)c3ccc(-c4ccc5c(c4)C4(c6ccccc6O5)c5ccccc5-c5ccccc54)cc3)cc21]
48
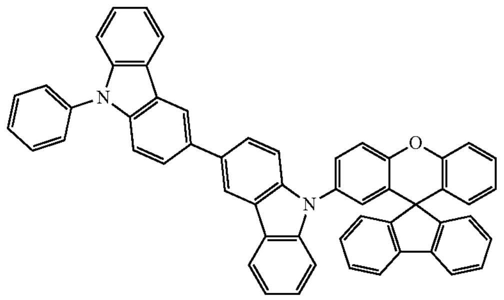 [SMILES: c1ccc(-n2c3ccccc3c3cc(-c4ccc5c(c4)c4ccccc4n5-c4ccc5c(c4)C4(c6ccccc6O5)c5ccccc5-c5ccccc54)ccc32)cc1]
49
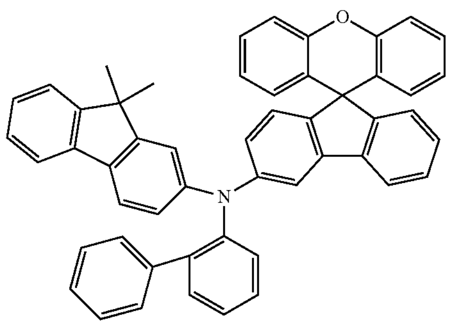
49

-continued
50
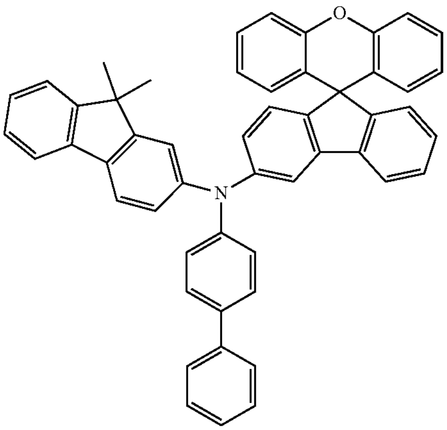 [SMILES: CC1(C)c2ccccc2-c2ccc(N(c3ccc(-c4ccccc4)cc3)c3ccc4c(c3)-c3ccccc3C43c4ccccc4Oc4ccccc43)cc21]
51
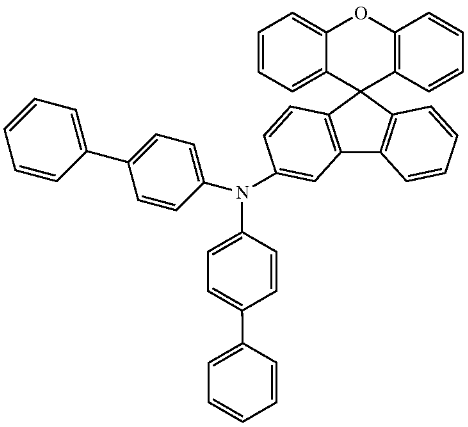 [SMILES: c1ccc(-c2ccc(N(c3ccc(-c4ccccc4)cc3)c3ccc4c(c3)-c3ccccc3C43c4ccccc4Oc4ccccc43)cc2)cc1]
52
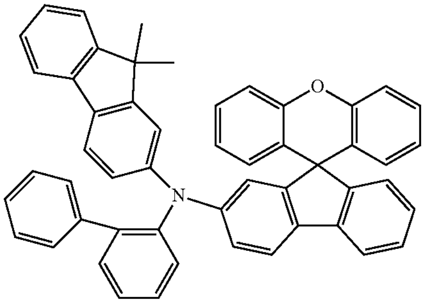 [SMILES: CC1(C)c2ccccc2-c2ccc(N(c3ccc4c(c3)C3(c5ccccc5Oc5ccccc53)c3ccccc3-4)c3ccccc3-c3ccccc3)cc21]
53
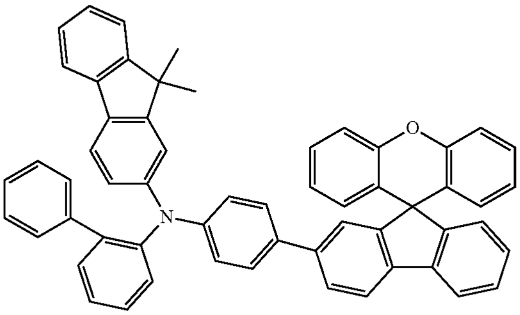 [SMILES: CC1(C)c2ccccc2-c2ccc(N(c3ccc(-c4ccc5c(c4)C4(c6ccccc6Oc6ccccc64)c4ccccc4-5)cc3)c3ccccc3-c3ccccc3)cc21]
-continued
54
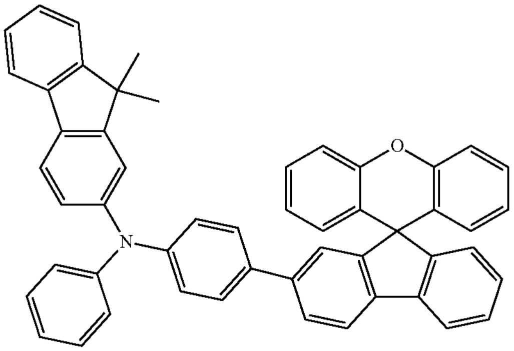 [SMILES: CC1(C)c2ccccc2-c2ccc(N(c3ccccc3)c3ccc(-c4ccc5c(c4)C4(c6ccccc6Oc6ccccc64)c4ccccc4-5)cc3)cc21]
55
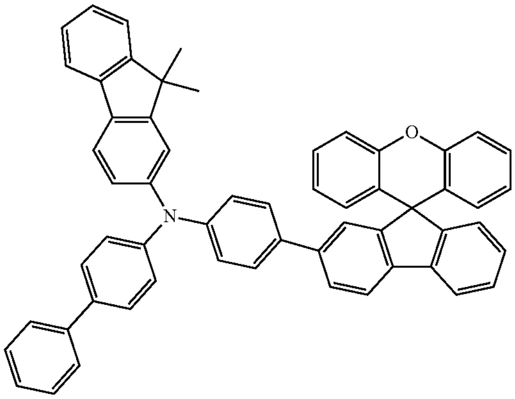 [SMILES: CC1(C)c2ccccc2-c2ccc(N(c3ccc(-c4ccccc4)cc3)c3ccc(-c4ccc5c(c4)C4(c6ccccc6Oc6ccccc64)c4ccccc4-5)cc3)cc21]
56
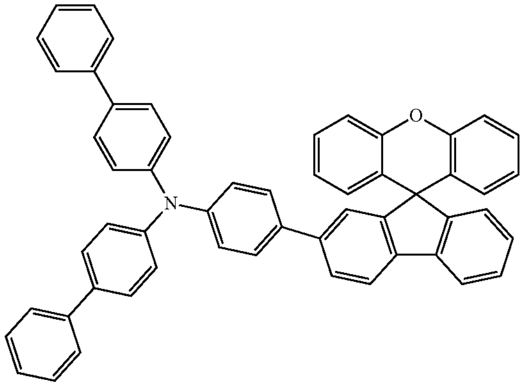 [SMILES: c1ccc(-c2ccc(N(c3ccc(-c4ccccc4)cc3)c3ccc(-c4ccc5c(c4)C4(c6ccccc6Oc6ccccc64)c4ccccc4-5)cc3)cc2)cc1]
57
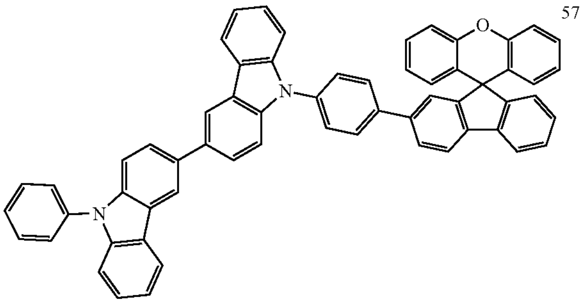

-continued
58
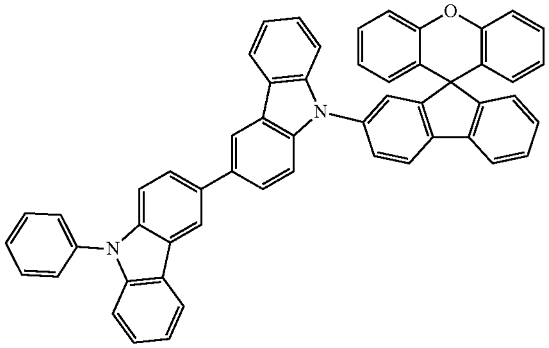 [SMILES: c1ccc(-n2c3ccccc3c3cc(-c4ccc5c(c4)c4ccccc4n5-c4ccc5c(c4)C4(c6ccccc6Oc6ccccc64)c4ccccc4-5)ccc32)cc1]
59
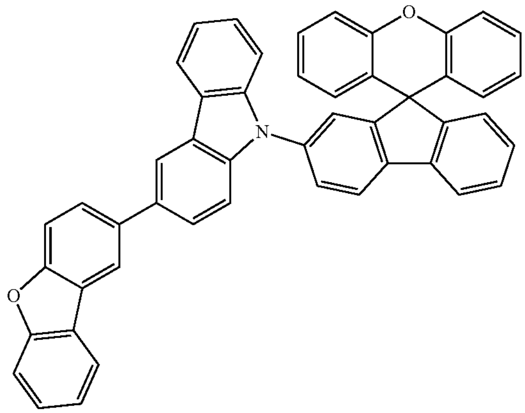 [SMILES: c1ccc2c(c1)Oc1ccccc1C21c2ccccc2-c2ccc(-n3c4ccccc4c4cc(-c5ccc6oc7ccccc7c6c5)ccc43)cc21]
60
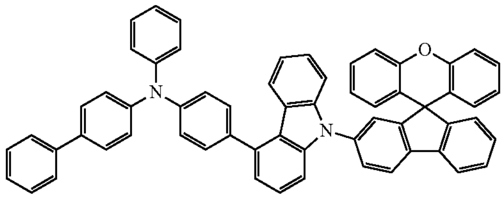 [SMILES: c1ccc(-c2ccc(N(c3ccccc3)c3ccc(-c4cccc5c4c4ccccc4n5-c4ccc5c(c4)C4(c6ccccc6Oc6ccccc64)c4ccccc4-5)cc3)cc2)cc1]
61
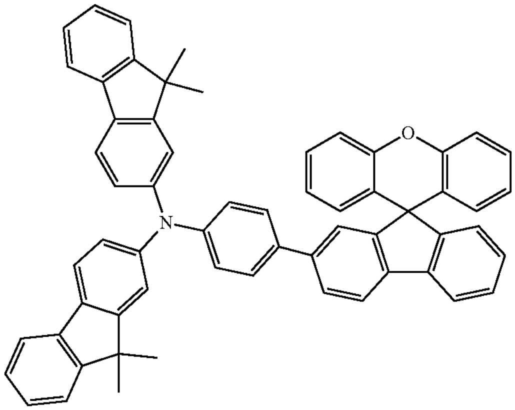 [SMILES: CC1(C)c2ccccc2-c2ccc(N(c3ccc(-c4ccc5c(c4)C4(c6ccccc6Oc6ccccc64)c4ccccc4-5)cc3)c3ccc4c(c3)C(C)(C)c3ccccc3-4)cc21]
-continued
62
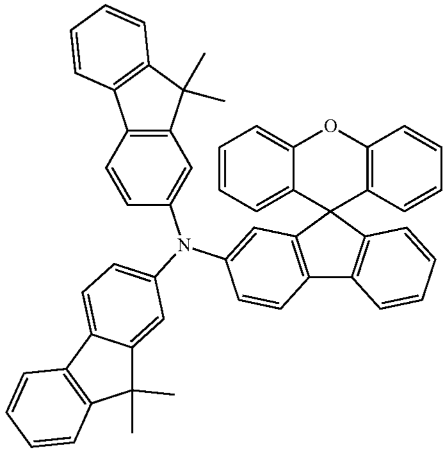 [SMILES: CC1(C)c2ccccc2-c2ccc(N(c3ccc4c(c3)C(C)(C)c3ccccc3-4)c3ccc4c(c3)C3(c5ccccc5Oc5ccccc53)c3ccccc3-4)cc21]
63
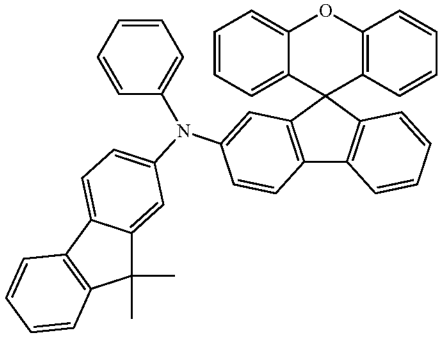 [SMILES: CC1(C)c2ccccc2-c2ccc(N(c3ccccc3)c3ccc4c(c3)C3(c5ccccc5Oc5ccccc53)c3ccccc3-4)cc21]
64
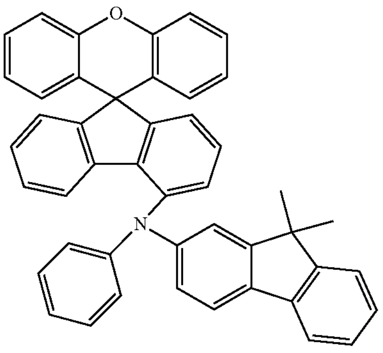 [SMILES: CC1(C)c2ccccc2-c2ccc(N(c3ccccc3)c3cccc4c3-c3ccccc3C43c4ccccc4Oc4ccccc43)cc21]
65
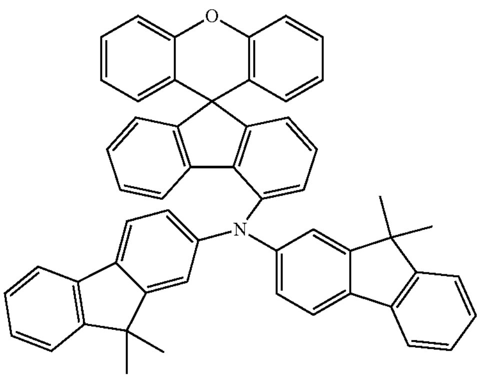 [SMILES: CC1(C)c2ccccc2-c2ccc(N(c3ccc4c(c3)C(C)(C)c3ccccc3-4)c3cccc4c3-c3ccccc3C43c4ccccc4Oc4ccccc43)cc21]

-continued

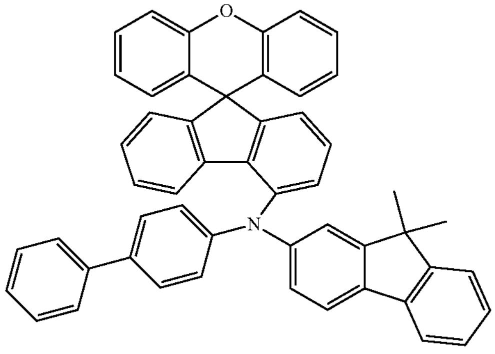 [SMILES: CC1(C)c2ccccc2-c2ccc(N(c3ccc(-c4ccccc4)cc3)c3cccc4c3-c3ccccc3C43c4ccccc4Oc4ccccc43)cc21]

66

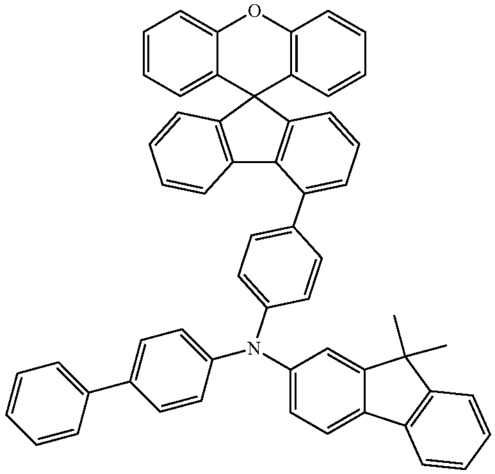 [SMILES: CC1(C)c2ccccc2-c2ccc(N(c3ccc(-c4ccccc4)cc3)c3ccc(-c4cccc5c4-c4ccccc4C54c5ccccc5Oc5ccccc54)cc3)cc21]

67

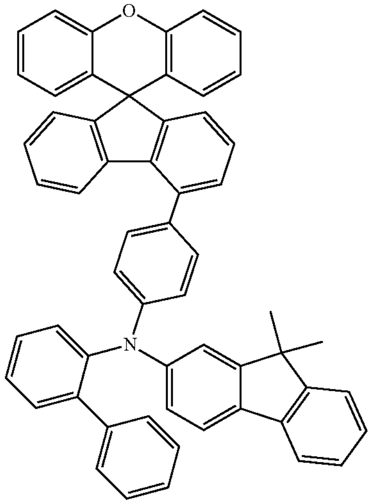 [SMILES: CC1(C)c2ccccc2-c2ccc(N(c3ccc(-c4cccc5c4-c4ccccc4C54c5ccccc5Oc5ccccc54)cc3)c3ccccc3-c3ccccc3)cc21]

68

-continued

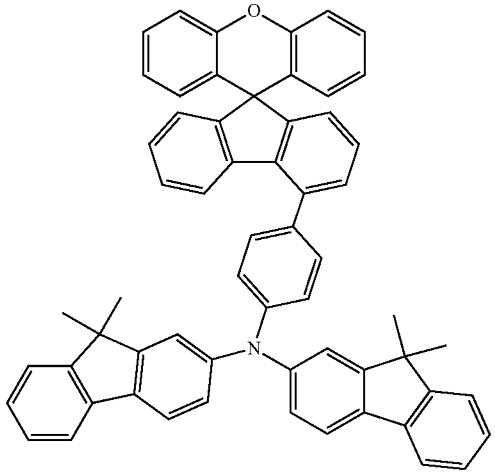 [SMILES: CC1(C)c2ccccc2-c2ccc(N(c3ccc(-c4cccc5c4-c4ccccc4C54c5ccccc5Oc5ccccc54)cc3)c3ccc4c(c3)C(C)(C)c3ccccc3-4)cc21]

69

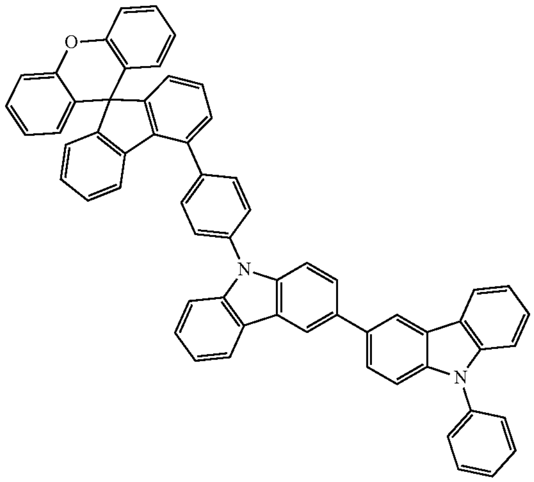 [SMILES: c1ccc(-n2c3ccccc3c3cc(-c4ccc5c(c4)c4ccccc4n5-c4ccc(-c5cccc6c5-c5ccccc5C65c6ccccc6Oc6ccccc65)cc4)ccc32)cc1]

70

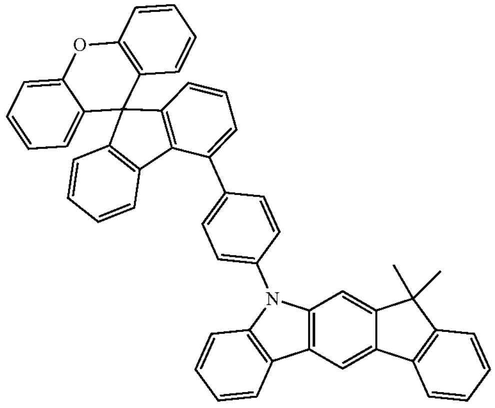 [SMILES: CC1(C)c2ccccc2-c2cc3c4ccccc4n(-c4ccc(-c5cccc6c5-c5ccccc5C65c6ccccc6Oc6ccccc65)cc4)c3cc21]

71

72

For the synthesis of the compounds of the formula (I), it is possible to utilize methods known in the prior art, especially methods disclosed in published specification WO 2014/072017.

The device of the invention is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (0-lasers) and organic electroluminescent devices (OLEDs). It is more preferably an organic electroluminescent device.

In the electronic device of the invention, the compound of the formula (I) is preferably present in a layer arranged adjacent to the anode. This layer preferably comprises a p-dopant. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, 12, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix. Preferably, p-dopants are present in the layer in question in a total proportion of 0.5% to 10% by volume, preferably 0.8% to 8% by volume.

Preferred p-dopants are especially the following compounds:

(D-1)

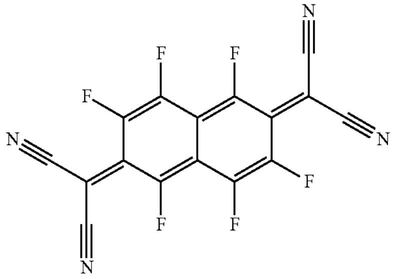

(D-2)

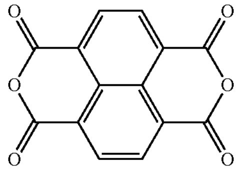

(D-3)

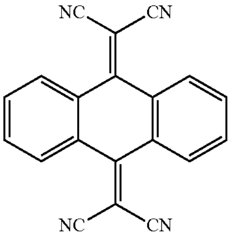

-continued (D-4)

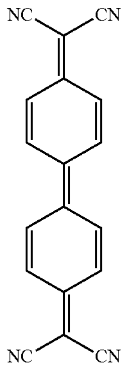

(D-5)

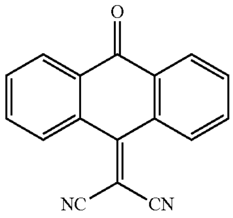

(D-6)

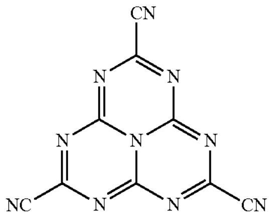

(D-7)

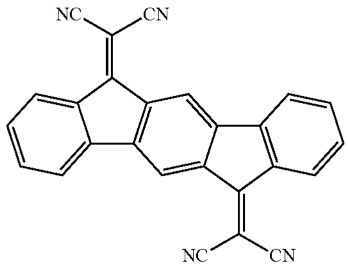

(D-8)

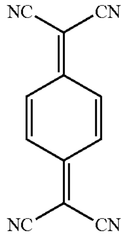

(D-9)

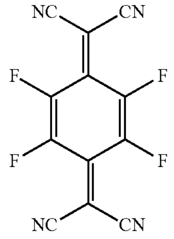

-continued (D-10)

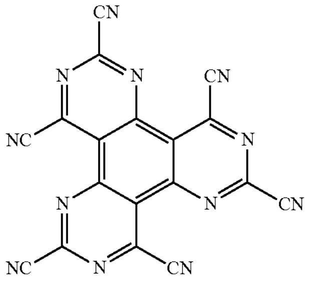

(D-11)

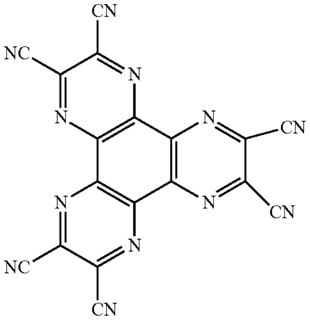

(D-12)

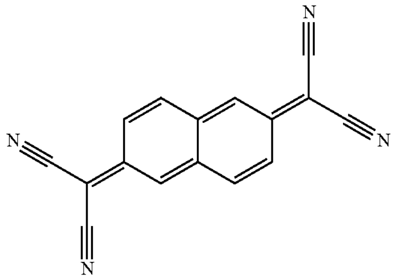

(D-13)

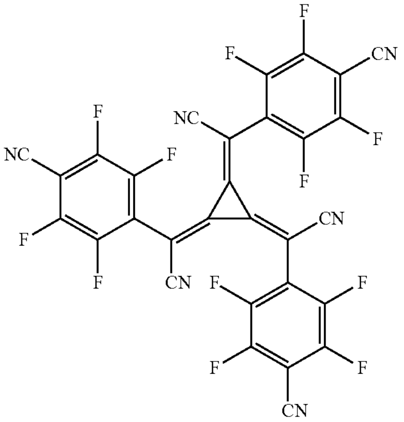

In addition, it is preferable that, as a further feature of the electronic device of the invention, there is at least one further layer that does not include any compound of the formula (I) between the layer comprising the compound of the formula (I) and the emitting layer closest to the anode.

It is preferable that the layer that adjoins the emitting layer closest to the anode on the anode side does not include any compound of the formula (I).

Preferably, the device fulfils both the abovementioned conditions a) and b):

a) the hole-transporting layer directly adjoins the anode; and b) there are at least two further layers arranged between the hole-transporting layer and the emitting layer, and there are no further emitting layers arranged between the emitting layer and the anode.

Preference is given to an electronic device comprising the following layers in the sequence mentioned: anode, hole-transporting layer HTL1, hole-transporting layer HTL2, hole-transporting layer HTL3, emitting layer EML, electron-transporting layer ETL, and cathode, where further layers may be present, where the layer HTL1 adjoins the anode, where the layer HTL3 adjoins the emitting layer, and where the layer HTL1 comprises a compound of the formula (I). Preferably, at the same time, the layer HTL3 does not include any compound of the formula (I).

A particularly preferred embodiment of the device has the following layer sequence between the anode and the emitting layer closest to the anode: anode, hole-transporting layer HTL1 comprising a compound of the formula (I), hole-transporting layer HTL2, hole-transporting layer HTL3 not comprising any compound of the formula (I), emitting layer closest to the anode. In this case, there are preferably no further layers between the anode and the emitting layer closest to the anode. The layer HTL1 here preferably has a thickness of 5 to 50 nm. The layer HTL2 here preferably has a thickness of 5 to 250 nm. The layer HTL3 here preferably has a thickness of 5 to 120 nm.

An alternative particularly preferred embodiment of the device has the following layer sequence between the anode and the emitting layer closest to the anode: anode, hole-transporting layer HTL1 comprising a compound of the formula (I) and a p-dopant, hole-transporting layer HTL2, hole-transporting layer HTL3 not comprising any compound of the formula (I), emitting layer closest to the anode. In this case, there are preferably no further layers between the anode and the emitting layer closest to the anode. The layer HTL1 here preferably has a thickness of 5 to 250 nm. The layer HTL2 here preferably has a thickness of 5 to 250 nm. The layer HTL3 here preferably has a thickness of 5 to 120 nm.

An alternative particularly preferred embodiment of the device has the following layer sequence between the anode and the emitting layer closest to the anode: anode, hole-transporting layer HTL1 comprising a compound of the formula (I) and a p-dopant, hole-transporting layer HTL2a, hole-transporting layer HTL2b comprising a p-dopant, hole-transporting layer HTL3 not comprising any compound of the formula (I), emitting layer closest to the anode. In this case, there are preferably no further layers between the anode and the emitting layer closest to the anode.

The hole-transporting layer that adjoins the emitting layer closest to the anode on the anode side preferably comprises a monoamine compound. A monoamine compound is understood here to mean a compound containing only one amino group. Preferably, this amino group is a diarylamino group. A diarylamino group is understood to mean a group in which there are two groups selected from aryl groups and heteroaryl groups bonded to the amino nitrogen atom.

More preferably, the hole-transporting layer adjoining the emitting layer closest to the anode on the anode side comprises a monoamine compound containing at least one group selected from spirobifluorenyl groups, phenanthrenyl groups, fluorenyl groups, carbazolyl groups, dibenzofuranyl groups and dibenzothiophenyl groups. Among these, particular preference is given to spirobifluorenylmonoamines bearing a diarylamino group at one of positions 1, 3 and 4 on the spirobifluorene base skeleton, especially including the compounds disclosed in published specification WO 2013/120577 on pages 36-51 and 88-122. Very particular preference is given to spirobifluorenylmonoamines bearing a diarylamino group at position 4 on the spirobifluorene base skeleton, especially including the compounds disclosed in published specification WO 2013/120577 on pages 36-51 and 88-122.

It is preferable that the monoamine compound present in the hole-transporting layer that adjoins the emitting layer closest to the anode on the anode side has a HOMO energy level of 5.0 to 5.6 eV, more preferably 5.1 to 5.5 eV. The HOMO energy level is determined here by means of cyclic voltammetry (CV), by the method described at page 28 line 1 to page 29 line 21 of the published specification WO 2011/032624.

The device may, in addition to the layers mentioned, have further layers, especially including layers selected from hole injection layers, hole transport layers, hole blocker layers, electron transport layers, electron injection layers, electron blocker layers, exciton blocker layers, interlayers, charge generation layers and organic or inorganic p/n junctions.

The device preferably comprises only one emitting layer. However, it may also comprise two or more emitting layers. In this case, these multiple emitting layers preferably have multiple emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission.

The emitting layer of the device may be a fluorescent emitting layer, or it may be a phosphorescent emitting layer.

Phosphorescent emitting layers are especially understood to mean layers comprising at least one phosphorescent emitter. The term "phosphorescent emitters" encompasses compounds where the light is emitted through a spin-forbidden transition, for example a transition from an excited triplet state or a state having a higher spin quantum number, for example a quintet state.

Suitable phosphorescent emitters (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitters, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitters.

Preferably, the phosphorescent emitting layer of the device is a green- or red-phosphorescing layer. In addition, the fluorescent emitting layer of the device is preferably a blue-fluorescing layer.

The emitting layers preferably comprise at least one matrix material and at least one emitter.

Especially in the case of phosphorescent emitting layers, it is preferable that the layer in question comprises two or more different matrix materials, preferably two or three and most preferably two (mixed matrix systems). Preferably, in this case, one of the two matrix materials is a material having hole-transporting properties and the other matrix material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1.

There follows a disclosure of the material classes that are used with preference in the functional layers in question in the device.

Preferred phosphorescent emitters for use in the emitting layer can be found in the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable.

Preferred fluorescent emitters are selected from the class of the arylamines. An arylamine or an aromatic amine in the context of this invention is understood here to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9, 10 positions. Aromatic pyreneamines, pyrenediamines, chryseneamines and chrysenediamines are defined analogously, where the diarylamino groups are bonded to the pyrene preferably in the 1 position or 1, 6 positions. Further preferred emitting compounds are indenofluorenamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in WO 2017/036574, the phenoxazines disclosed in WO 2017/028940 and WO 2017/028941, and the fluorene derivatives bonded to furan units or to thiophene units that are disclosed in WO 2016/150544.

Useful matrix materials, preferably for fluorescent emitting layers, include materials of various substance classes. Preferred matrix materials are selected from the classes of the oligoarylenes (e.g. 2,2',7,7-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573.

Preferred matrix materials for phosphorescent emitting compounds are aromatic ketones, aromatic phosphine oxides or aromatic sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Further compounds which are used alongside the compounds of the formula (I), preferably in hole-transporting layers of the OLEDs of the invention, are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051 and WO 2016/102048 and WO 2016/131521, phenanthrenediarylamines, for example according to WO 2015/131976, spirotribenzotropolones, for example according to WO 2016/087017, spirobifluorenes with meta-phenyldiamine groups, for example according to WO 2016/078738, spirobisacridines, for example according to WO 2015/158411, xanthenediarylamines, for example according to WO 2014/072017, and 9,10-dihydroanthracene spiro compounds with diarylamino groups according to WO 2015/086108.

Materials used for the electron transport layer may be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices can be used in displays, as light sources in lighting applications and as light sources in medical and/or cosmetic applications (for example light therapy).

The invention further provides a compound as such that corresponds to a formula (S)

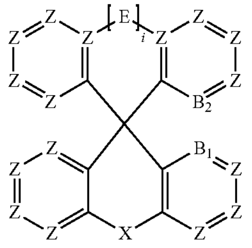

Formula (S)

where an A group has to be bonded to at least one group selected from the $B_1$ and $B_2$ groups, and where the variables that occur are as follows:

$B_1$, $B_2$ are the same or different at each instance and are N or $CR^2$ or C, where a $B_1$ or $B_2$ group is C in the specific case when an A group is bonded to it;

Z is the same or different at each instance and is $CR^2$ or N or C, where a Z group is C in the specific case when an E group is bonded to the Z group in question;

A is an arylamino group optionally substituted by one or more $R^1$ radicals, or a carbazole-containing group optionally substituted by one or more $R^1$ radicals;

E is a single bond;

X is O or S, $R^1$ is the same or different at each instance and is selected from H, D, F, $C(=O)R^3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by $—R^3C=CR^3—$, $—C≡C—$, $Si(R^3)_2$, C=O, $C=NR^3$, —C(=O)O—, $C(=O)NR^3—$, $NR^3$, $P(=O)(R^3)$, —O—, —S—, SO or $SO_2$, $R^2$ is the same or different at each instance and is selected from H, D, F, $C(=O)R^3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by $—R^3C=CR^3—$, $—C≡C—$, $Si(R^3)_2$, C=O, $C=NR^3$, —C(=O)O—, $C(=O)NR^3—$, $NR^3$, $P(=O)(R^3)$, —O—, —S—, SO or $SO_2$;

$R^3$ is the same or different at each instance and is selected from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $—R^4C=CR^4—$, $—C≡C—$, $Si(R^4)_2$, C=O, $C=NR^4$, —C(=O)O—, $C(=O)NR^4—$, $NR^4$, $P(=O)(R^4)$, —O—, —S—, SO or $SO_2$, $R^4$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^4$ radicals may be joined to one another and may form a ring; and where the alkyl, alkoxy, alkenyl and alkynyl groups, aromatic ring systems and heteroaromatic ring systems mentioned may be substituted by F or ON;

i is 0 or 1.

The terms "arylamino group" and "carbazole group" as A group are understood here to mean groups as defined above.

In the compound of the formula (S), X is preferably O.

In addition, i is preferably 1.

In addition, preferably not more than 2 Z groups per ring are N. Further preferably, not more than 4 Z groups per compound of the formula (S), most preferably not more than 2 Z groups per compound of the formula (S), are Z.

More preferably, Z is $CR^2$, where, in the case that an E group is bonded to the Z group in question, this Z group is C.

Preferably, an A group is bonded to exactly one of the two $B_1$ and $B_2$ groups, and no A group is bonded to the other of the two $B_1$ and $B_2$ groups.

With regard to the variables $R^1$ to $R^3$, the preferred embodiments specified above are applicable.

Preferably, the A group is an arylamino group optionally substituted by one or more $R^1$ radicals. The A group as arylamino group is preferably defined as specified above and preferably corresponds to the formula (A) as specified above.

Preferred embodiments of the compound of the formula (S) correspond to the formulae (S-1) and (S-2)

Formul (S-1)

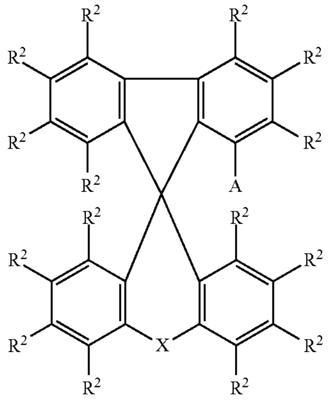

Formula (S-2)

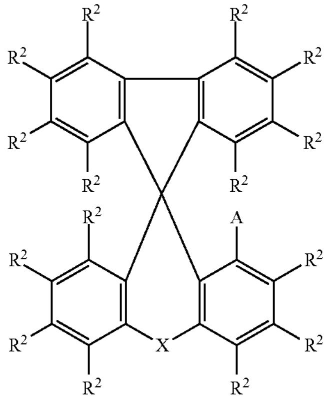

where the variables that occur are as defined above.

Particular preference is given to compounds of the formula (S-1).

A particularly preferred embodiment of the compounds of the formula (S) is that of compounds of the formula (S-1-1)

Formula (S-1-1)

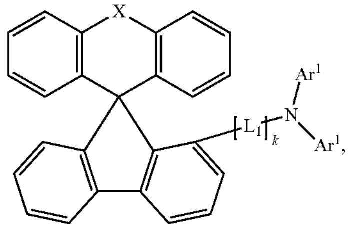

where the compounds may each be substituted on the benzene rings at the positions shown as unsubstituted by $R^2$ radicals, and where the variables that occur as follows:

$L^1$ is the same or different at each instance and is C═O, $Si(R^1)_2$, $PR^1$, P(═O)($R^1$), O, S, SO, $SO_2$, an alkylene group having 1 to 20 carbon atoms or an alkenylene or alkynylene group having 2 to 20 carbon atoms, where one or more $CH_2$ groups in the groups mentioned may be replaced by C═O, C═$NR^1$, C═O—O, C═O—NR', $Si(R^1)_2$, $NR^1$, P(═O)($R^1$), O, S, SO or $SO_2$ and where one or more hydrogen atoms in the abovementioned groups may be replaced by D, F or CN, or an aromatic or heteroaromatic ring system which has 6 to 24 aromatic ring atoms and may be substituted by one or more $R^1$ radicals;

$Ar^1$ is the same or different at each instance and is an aromatic or heteroaromatic ring system which has 6 to 30 aromatic ring atoms and may be substituted by one or more $R^1$ radicals;

k is 0, 1, 2 or 3;

$R^1$, $R^2$, $R^3$ and $R^4$ are as defined above.

Preferably, the compounds of the formula (S-1-1) are unsubstituted on the benzene rings at the positions shown as unsubstituted.

Preferred embodiments of the formula (S) are the compounds listed in the table above under the base skeletons (I-1-5-O) and (I-1-5-S).

Preferred compounds of the formula (S) are depicted below:

Formula (S-1)
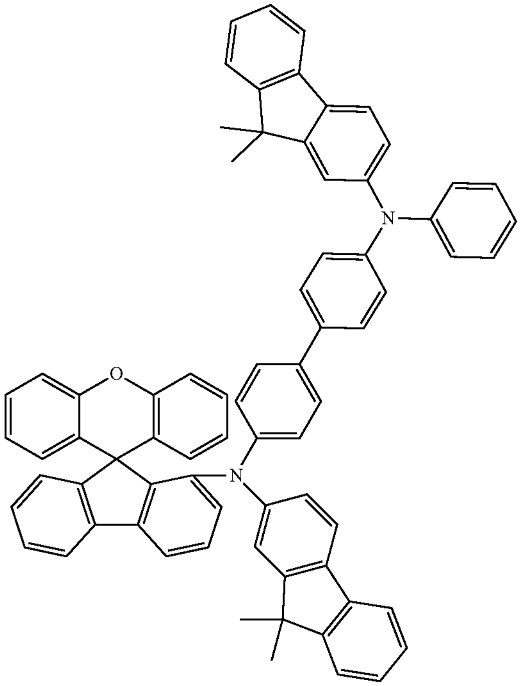
Formula (S-2)
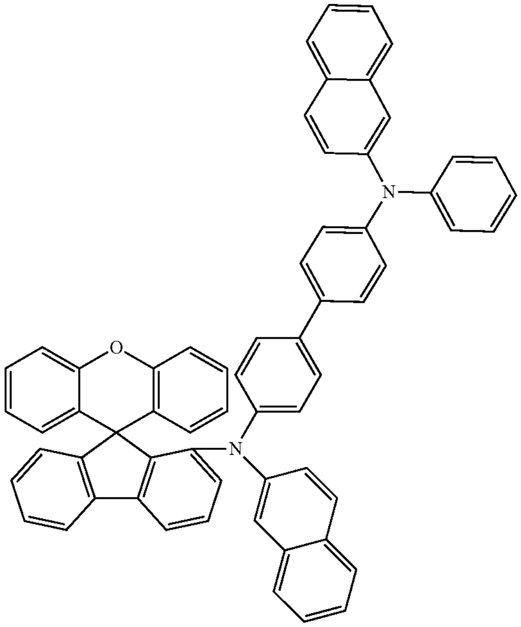
-continued
Formula (S-3)
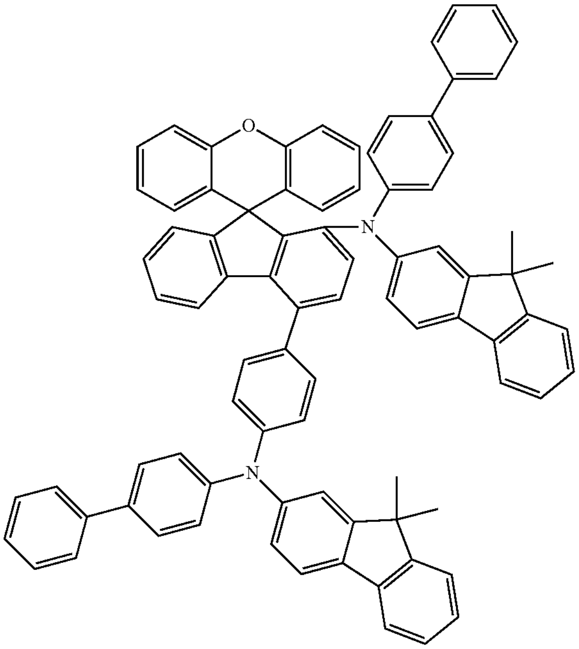
Formula (S-4)
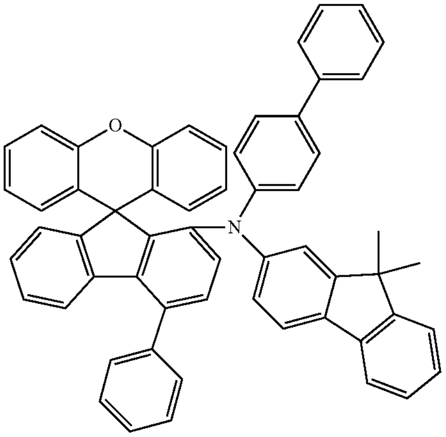
Formula (S-5)
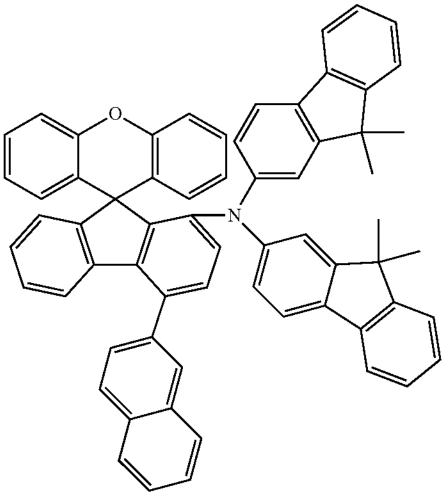

-continued
Formula (S-6)
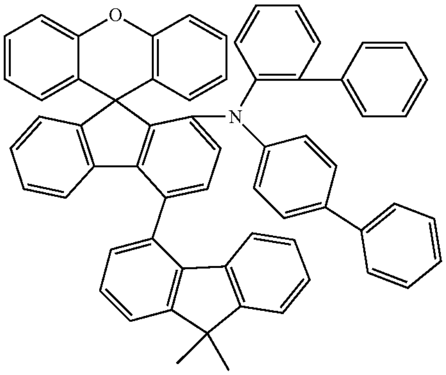
Formula (S-7)
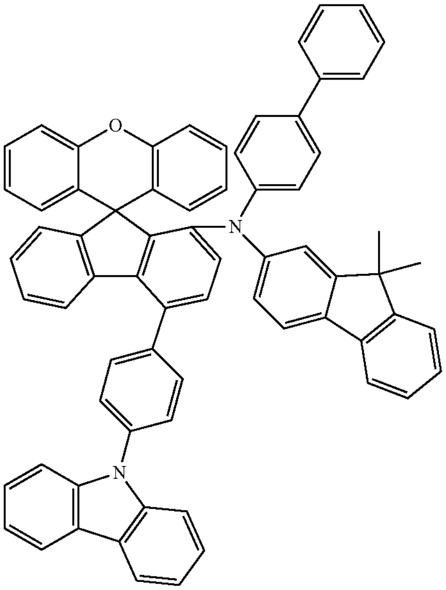
Formula (S-8)
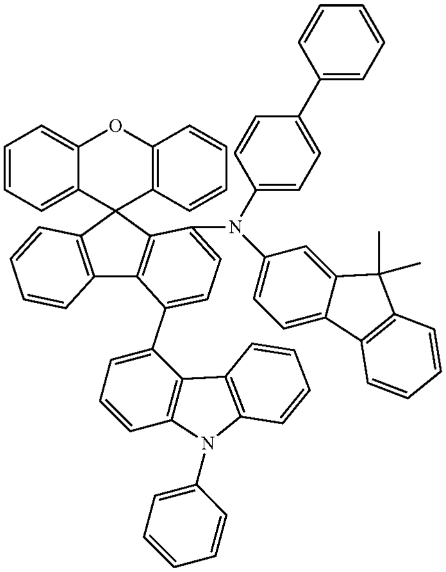
-continued
Formula (S-9)
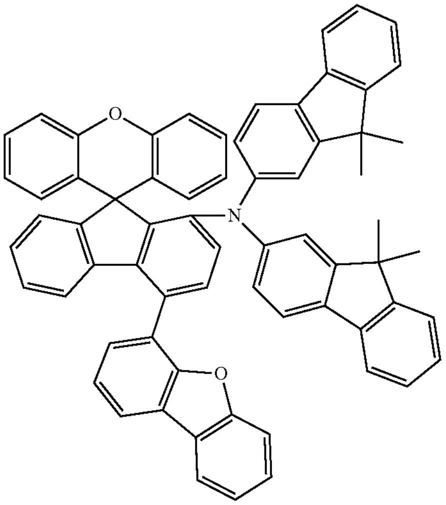
Formula (S-10)
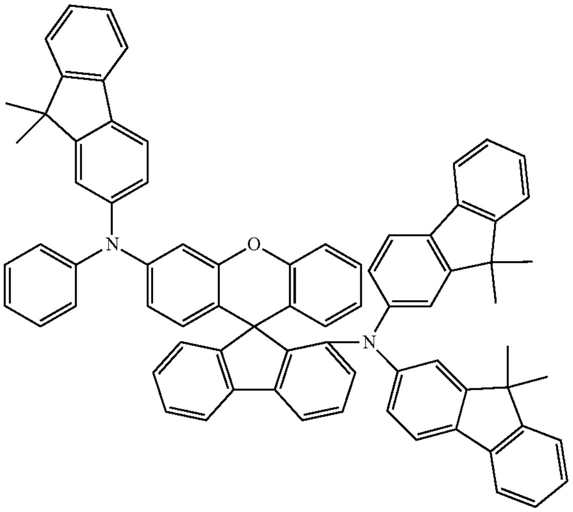
Formula (S-11)
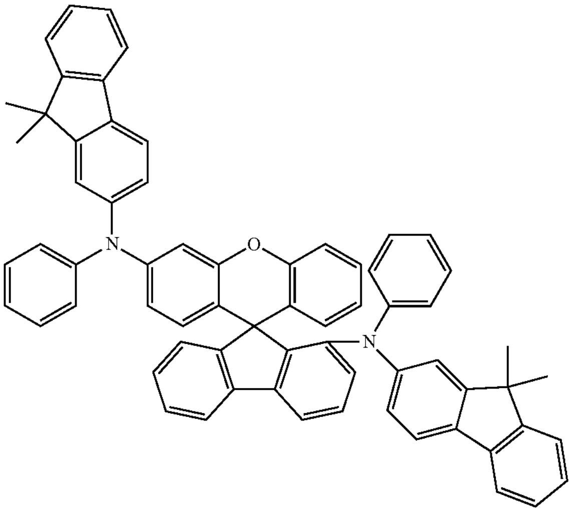

-continued
Formula (S-12)
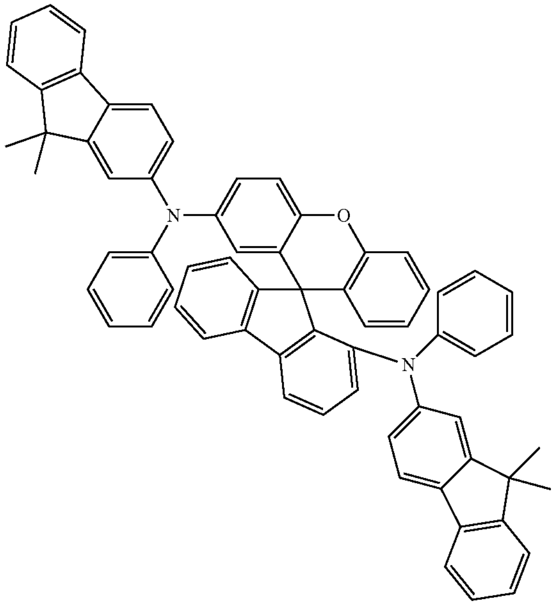
Formula (S-13)
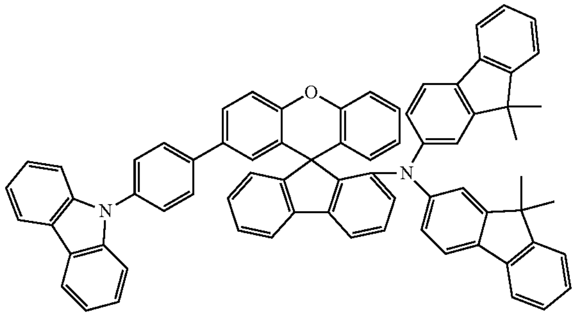
Formula (S-14)
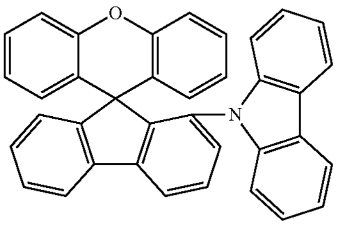
Formula (S-15)
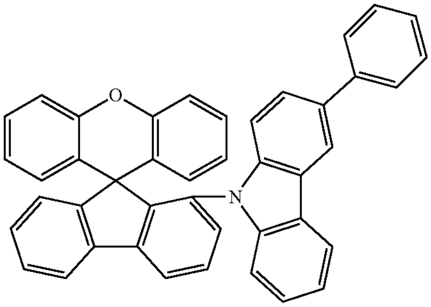
-continued
Formula (S-16)
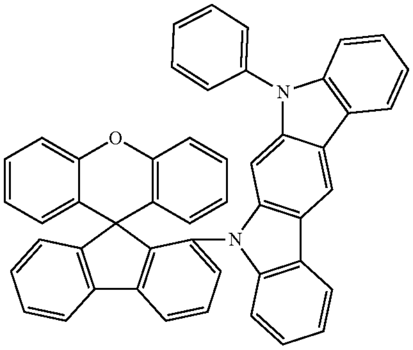
Formula (S-17)
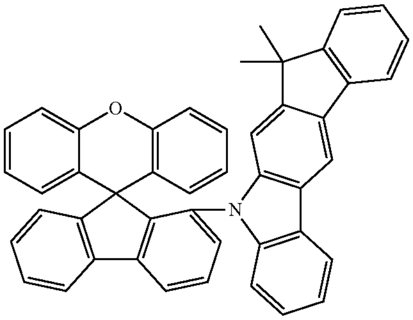
Formula (S-18)
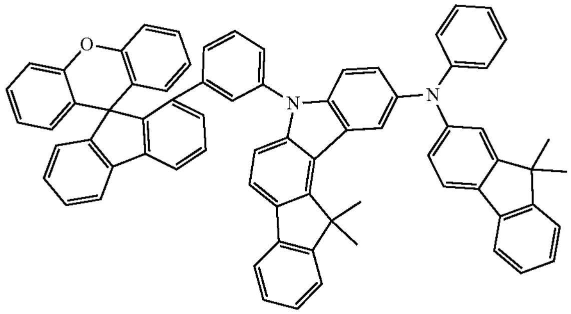
Formula (S-19)
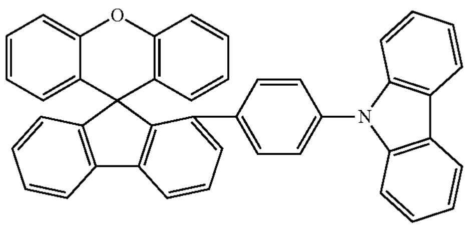
Formula (S-20)
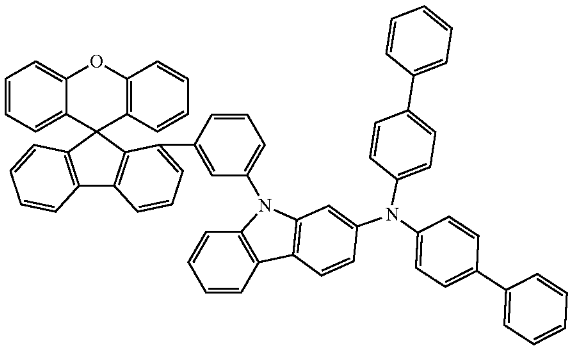

-continued
Formula (S-21)
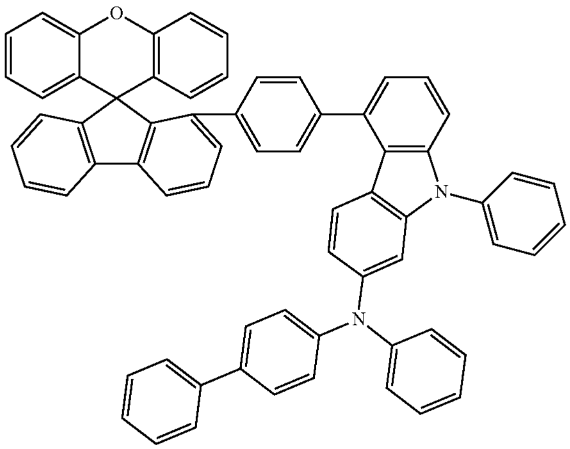
Formula (S-22)
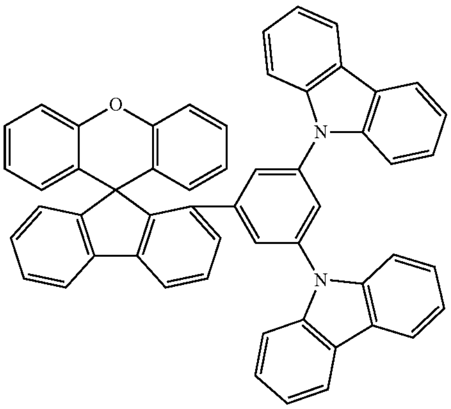
Formula (S-23)
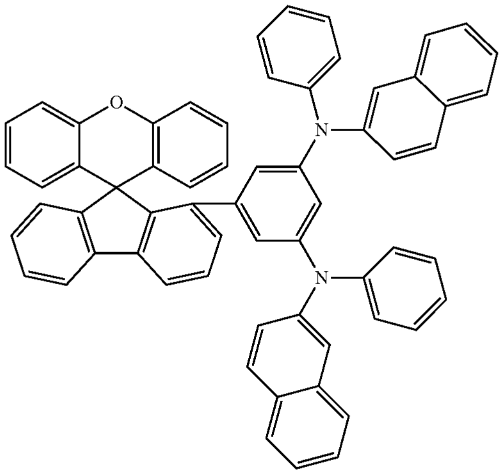
-continued
Formula (S-24)
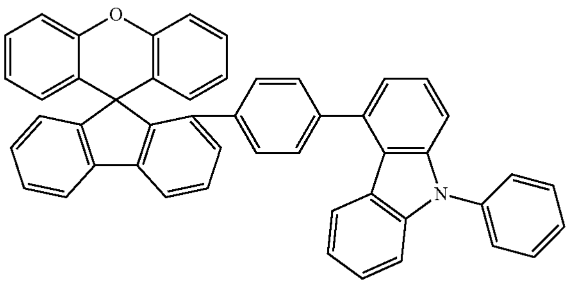
Formula (S-25)
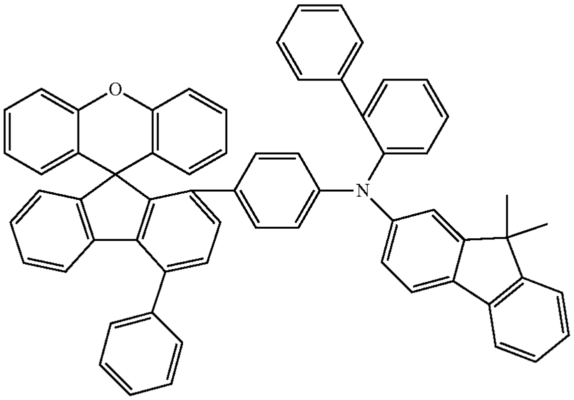
Formula (S-26)
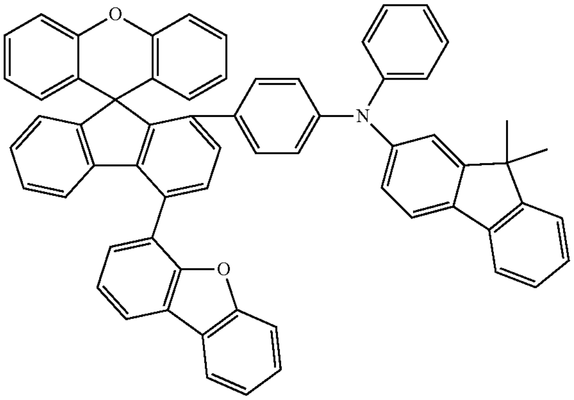
Formula (S-27)
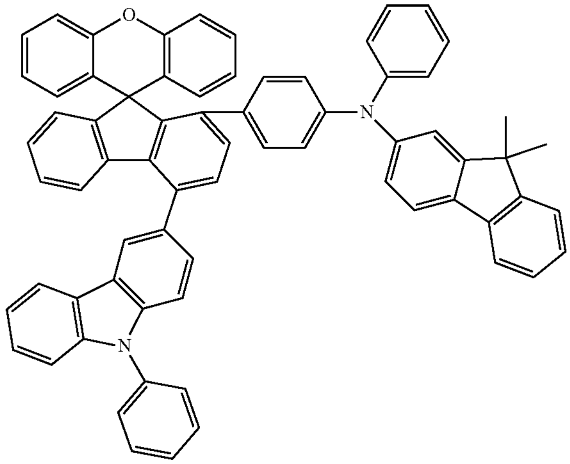

-continued
Formula (S-28)
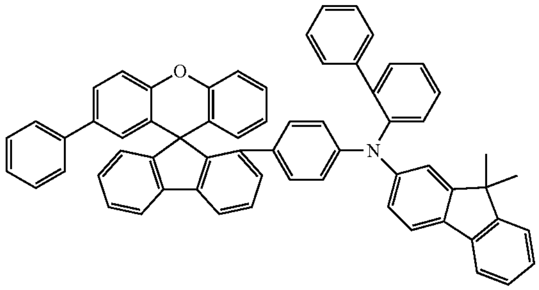
Formula (S-29)
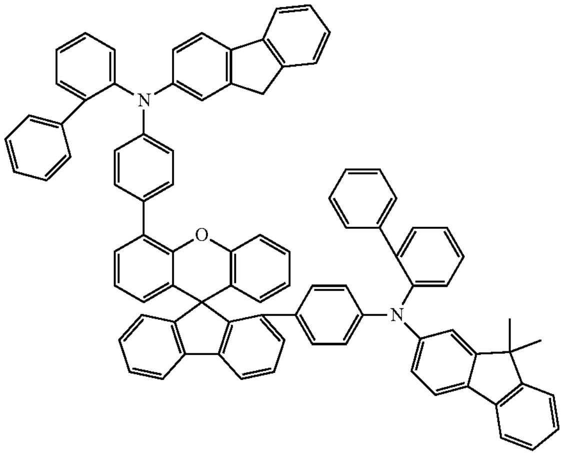
Formula (S-30)
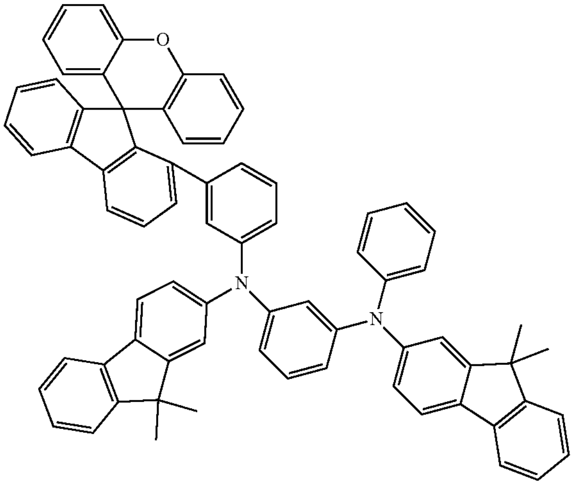
Formula (S-31)
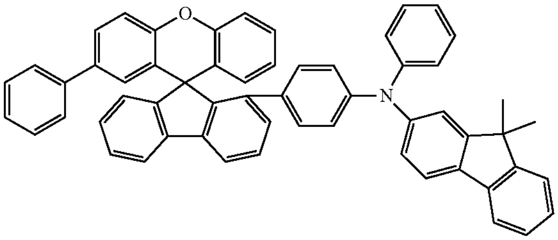
-continued
Formula (S-32)
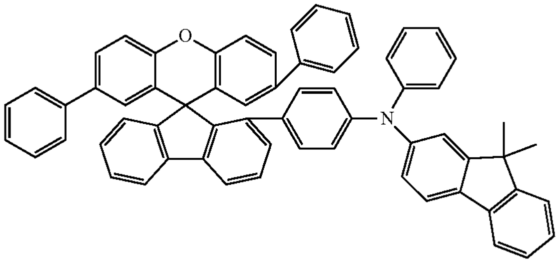
Formula (S-33)
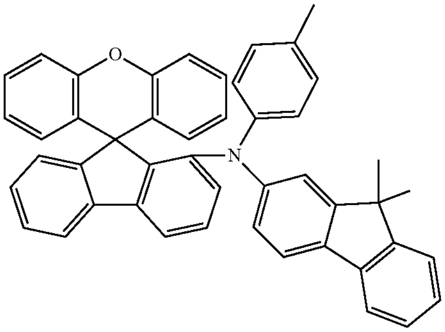
Formula (S-34)
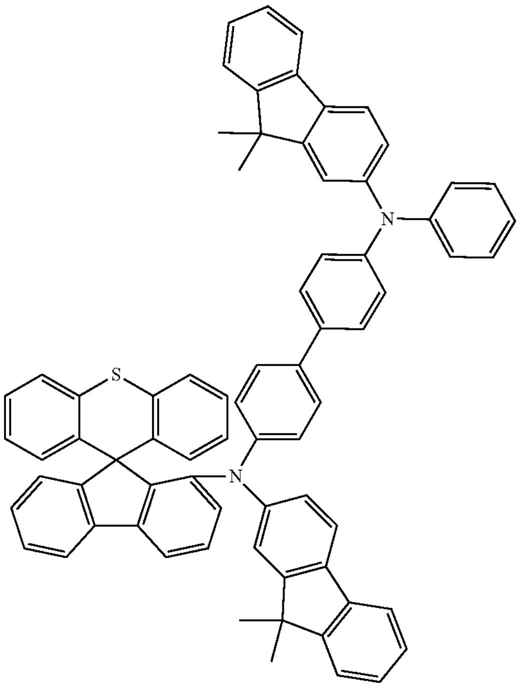

-continued
Formula (S-35)
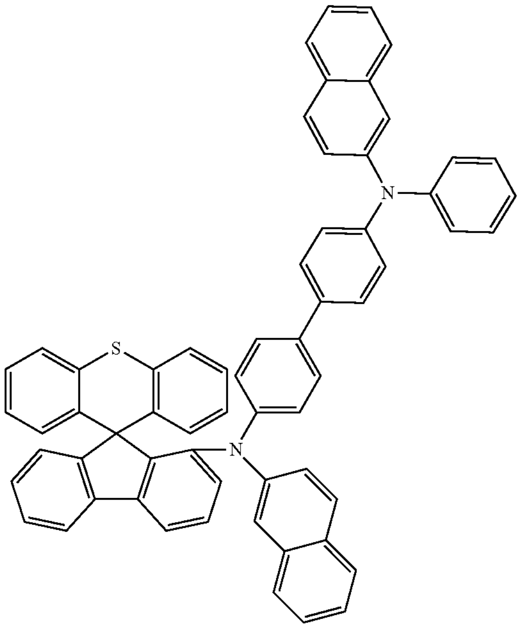
Formula (S-36)
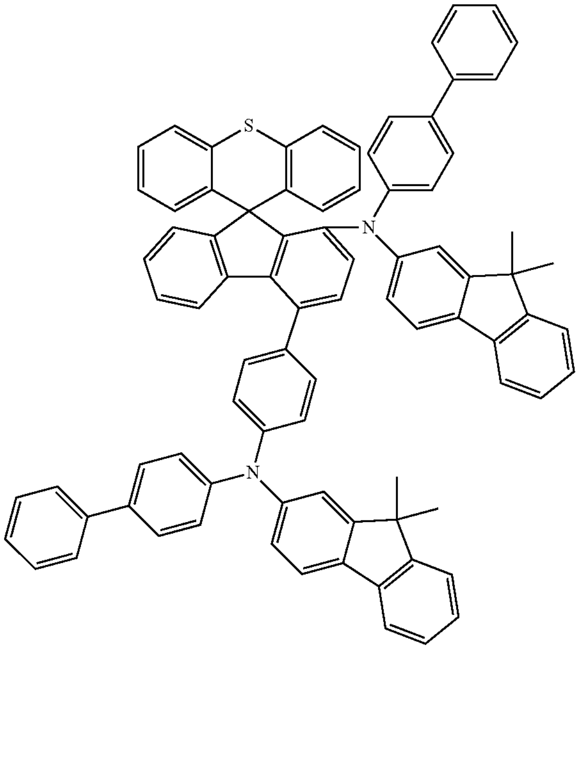
-continued
Formula (S-37)
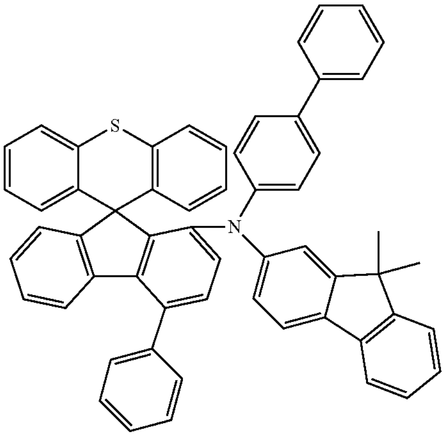
Formula (S-38)
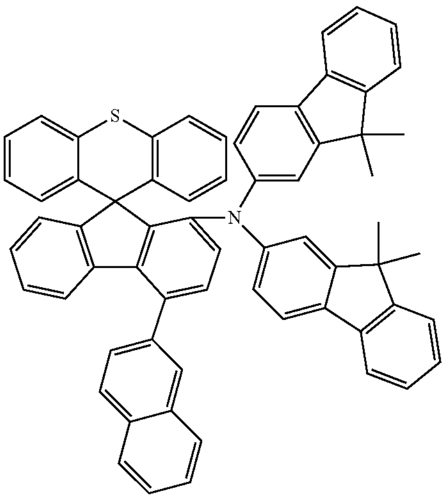
Formula (S-39)
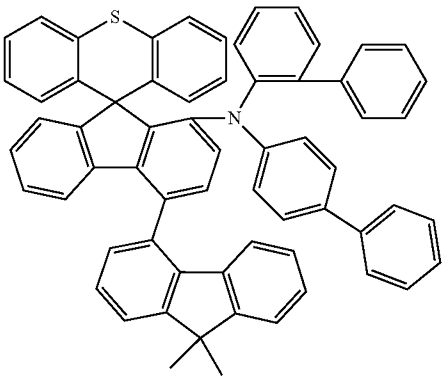

-continued
Formula (S-40)
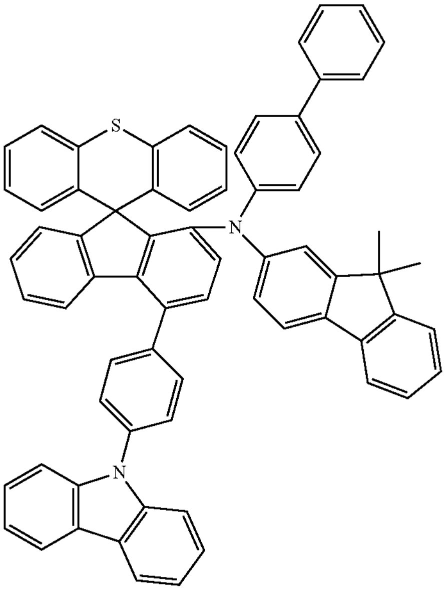
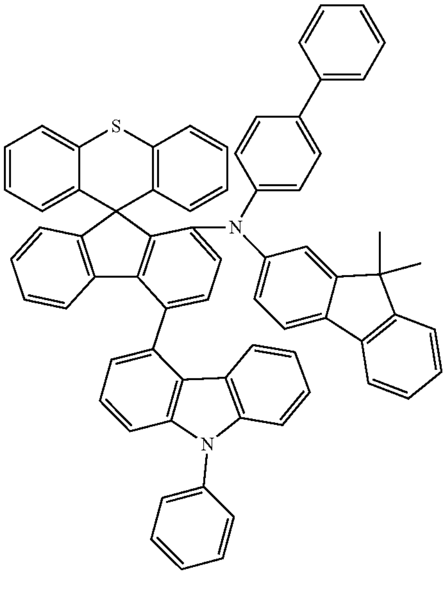
-continued
Formula (S-42)
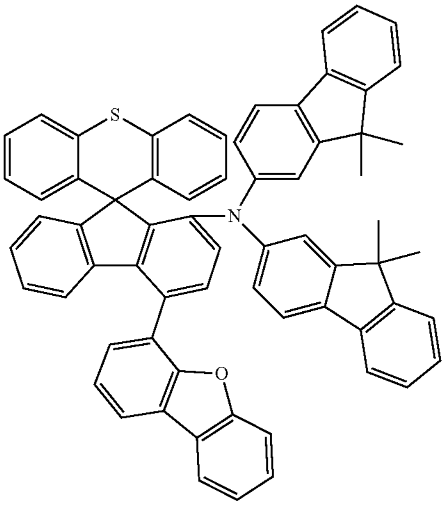
Formula (S-43)
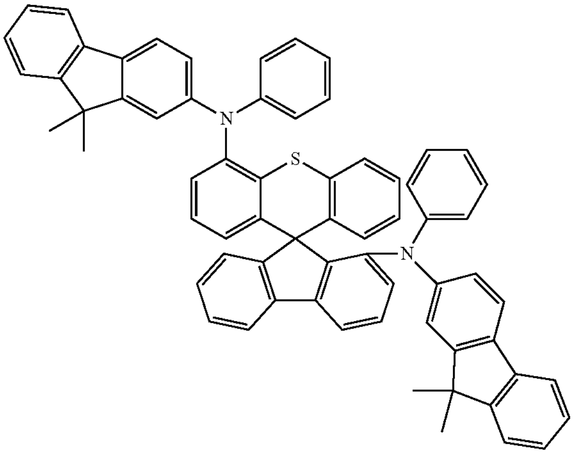
Formula (S-44)
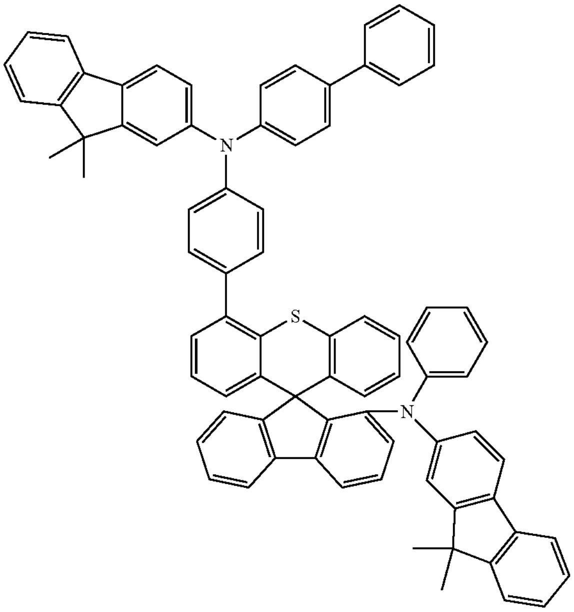

-continued
Formula (S-45)
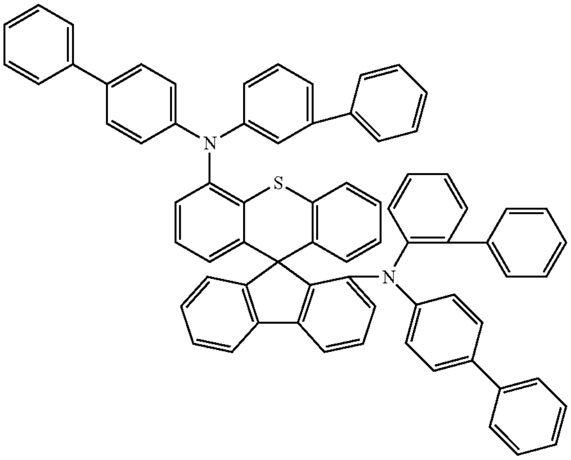
Formula (S-46)
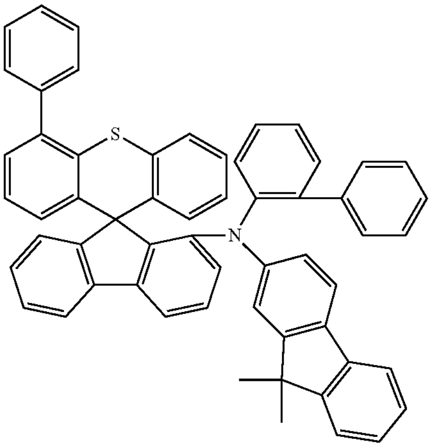
Formula (S-47)
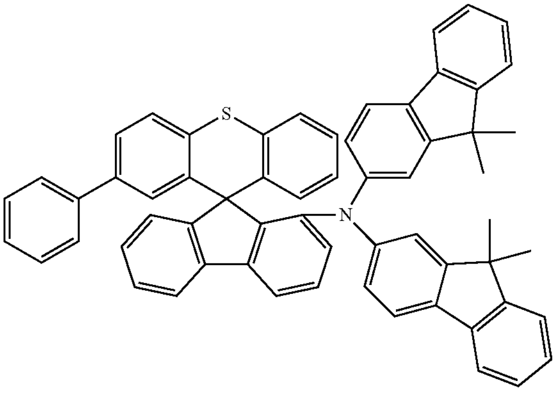
-continued
Formula (S-48)
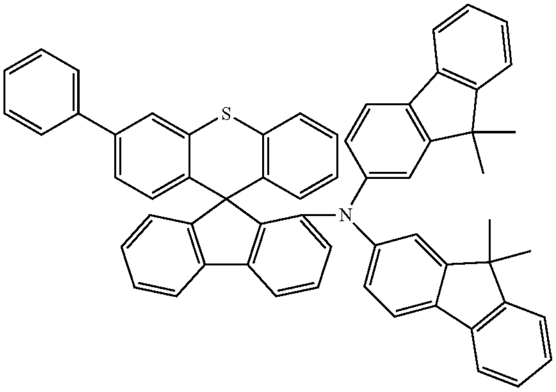
Formula (S-49)
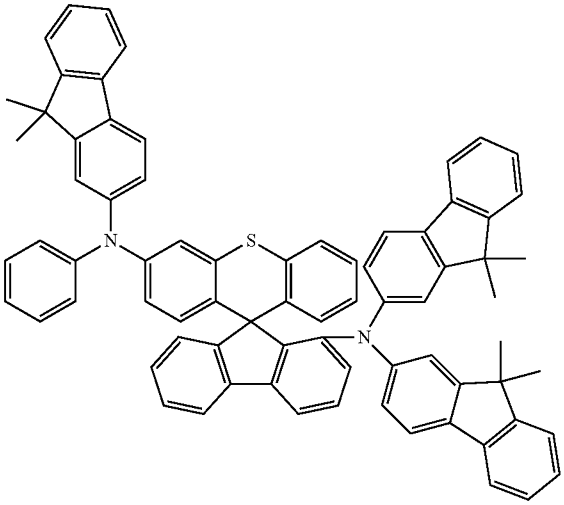
Formula (S-50)
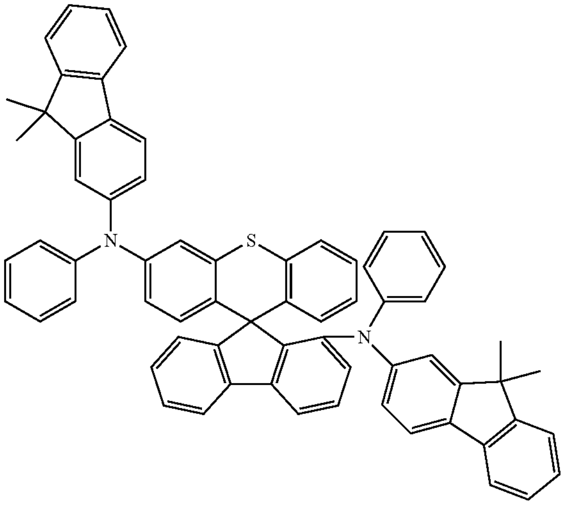

-continued
Formula (S-51)
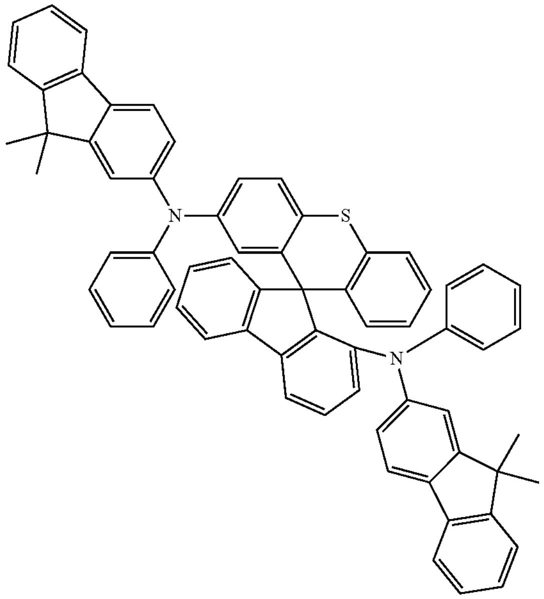
Formula (S-52)
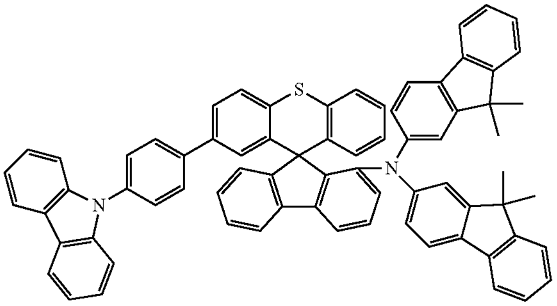
Formula (S-53)
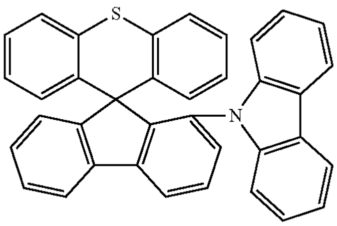
Formula (S-54)
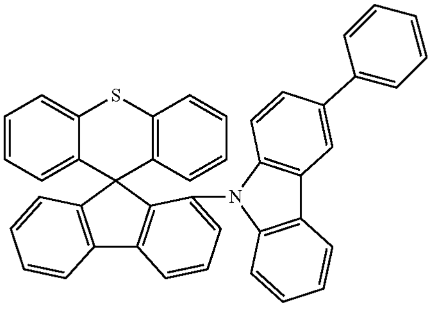
-continued
Formula (S-55)
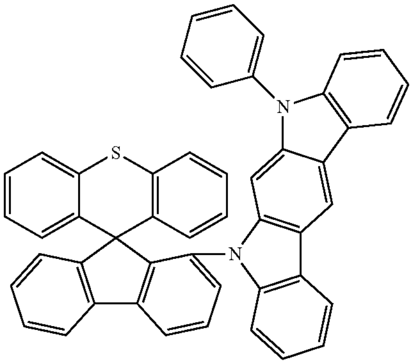
Formula (S-56)
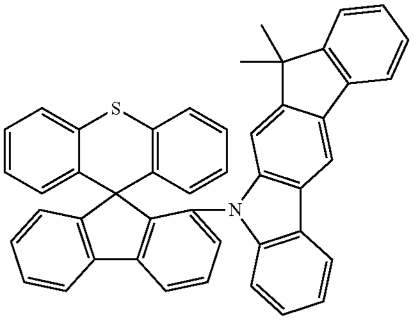
Formula (S-57)
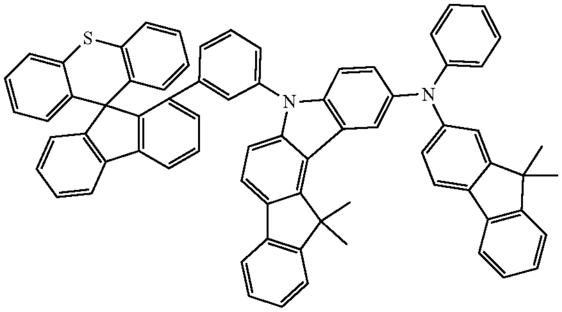
Formula (S-58)
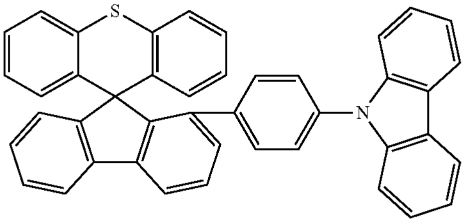

-continued
Formula (S-59)
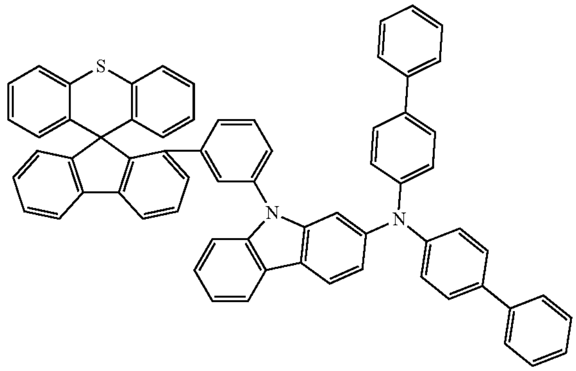
Formula (S-60)
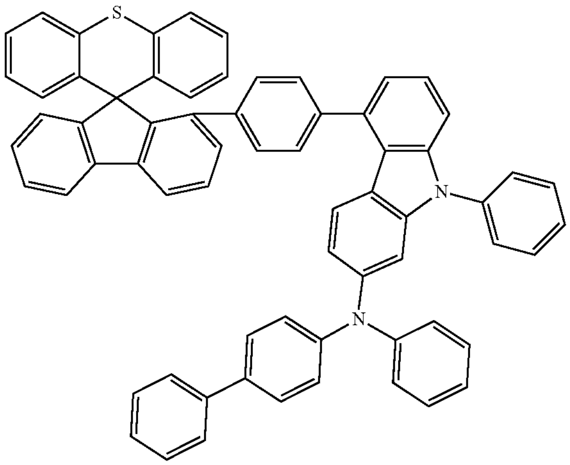
Formula (S-61)
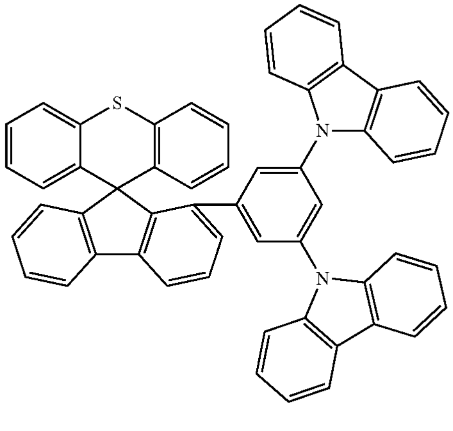
-continued
Formula (S-62)
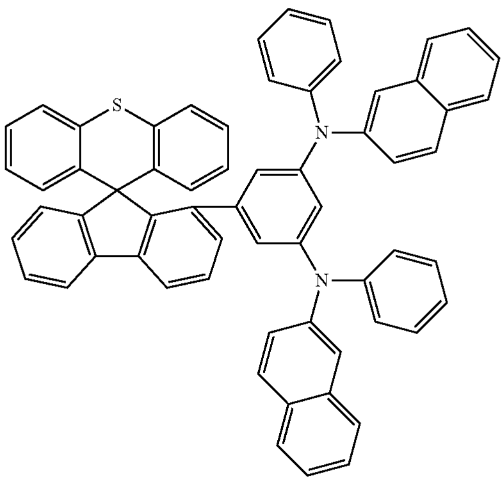
Formula (S-63)
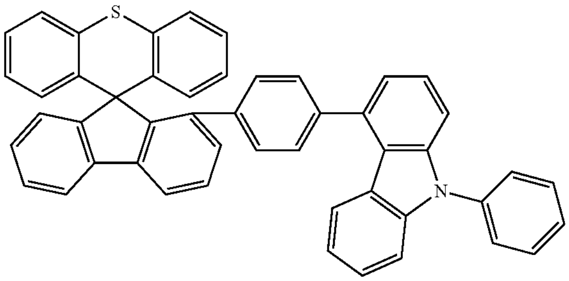
Formula (S-64)
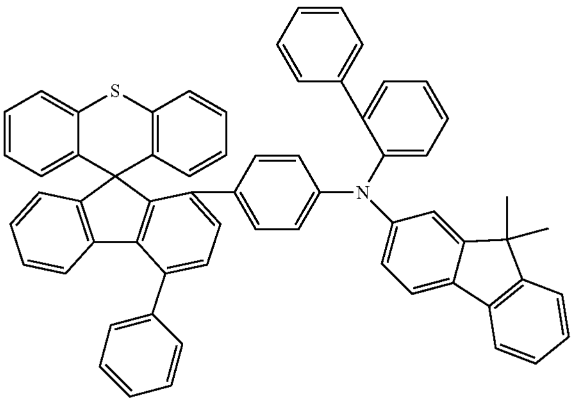
Formula (S-65)
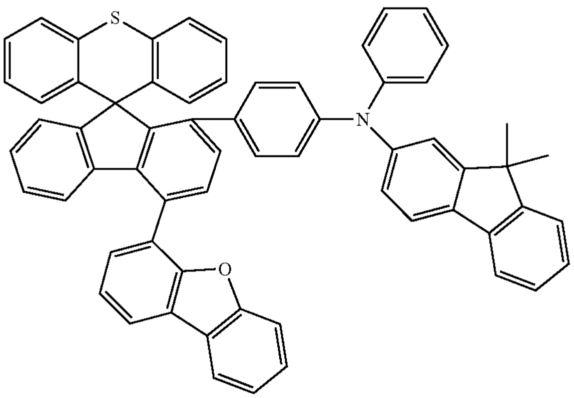

-continued
Formula (S-66)
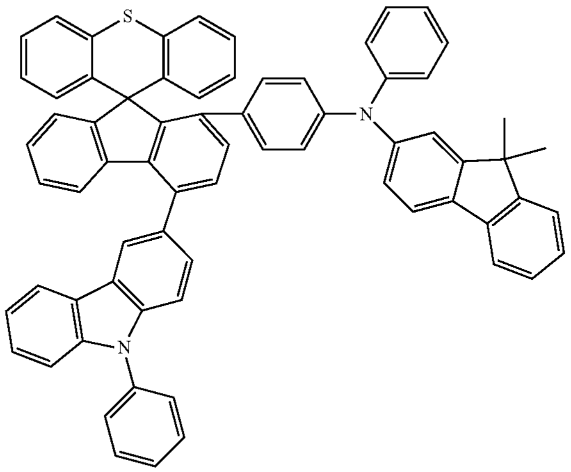
Formula (S-67)
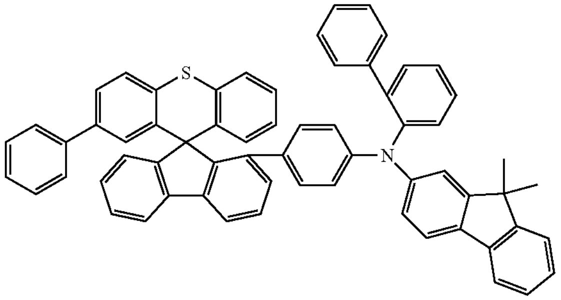
Formula (S-68)
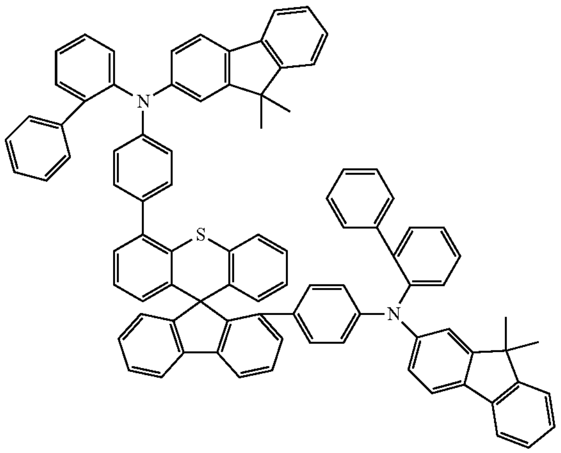
-continued
Formula (S-69)
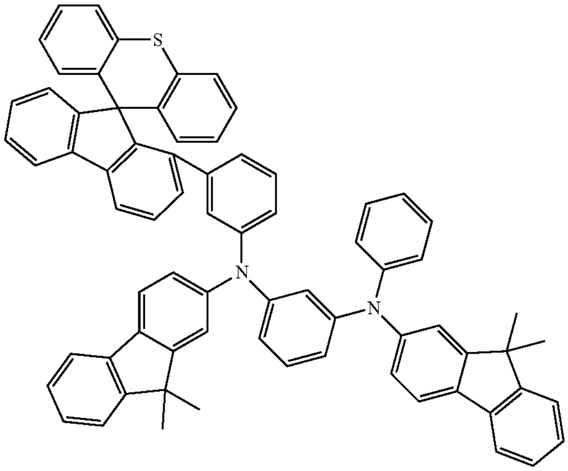
Formula (S-70)
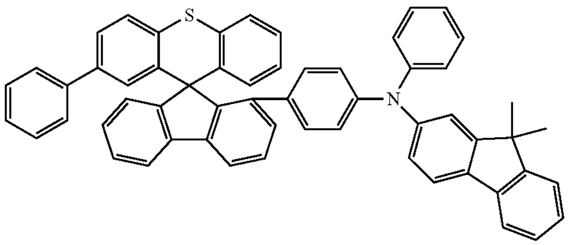
Formula (S-71)
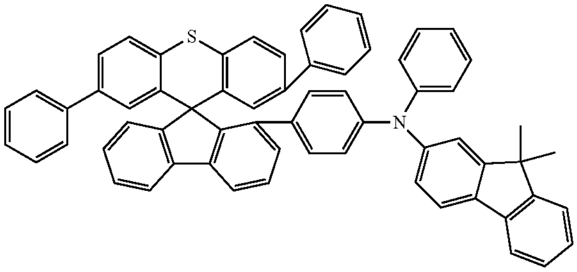
Formula (S-72)
Formula (S-73)
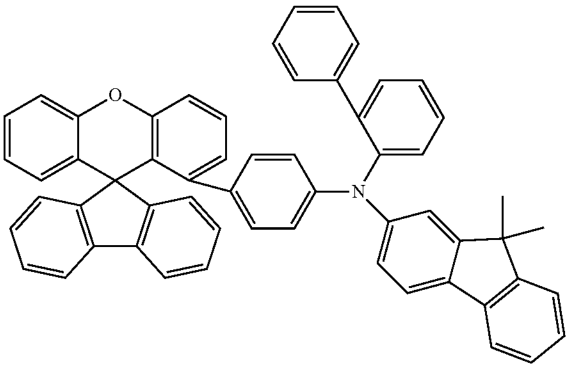

-continued
Formula (S-74)
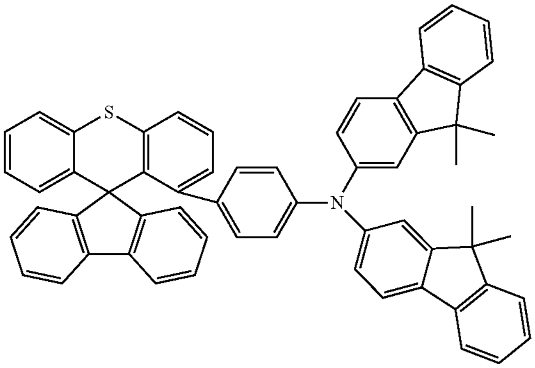
Formula (S-75)
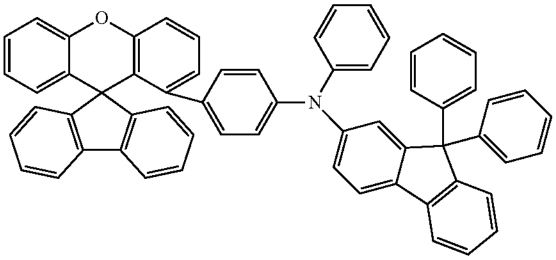
Formula (S-76)
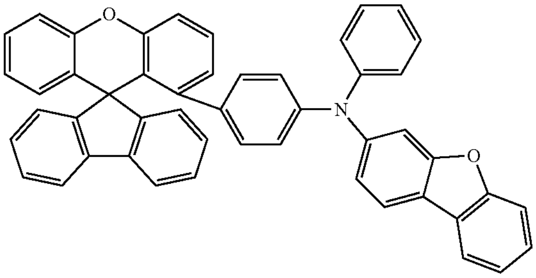
Formula (S-77)
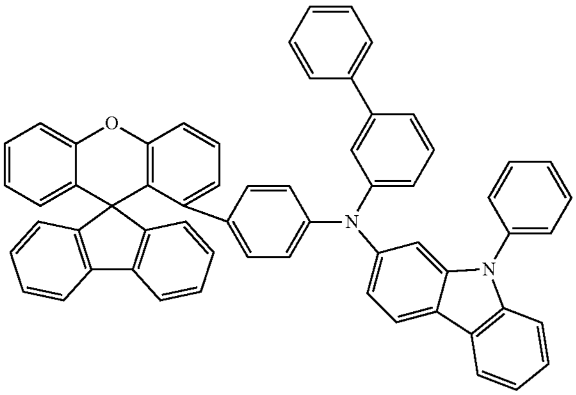
-continued
Formula (S-78)
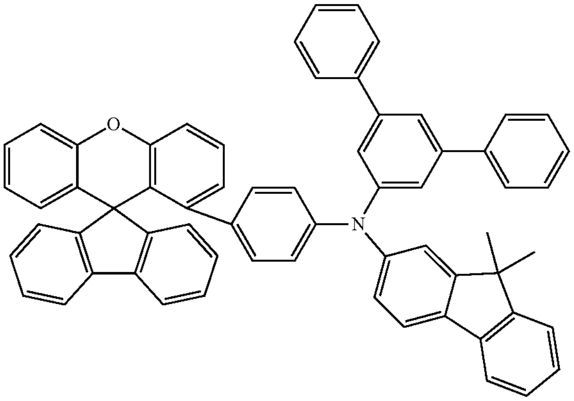
Formula (S-79)
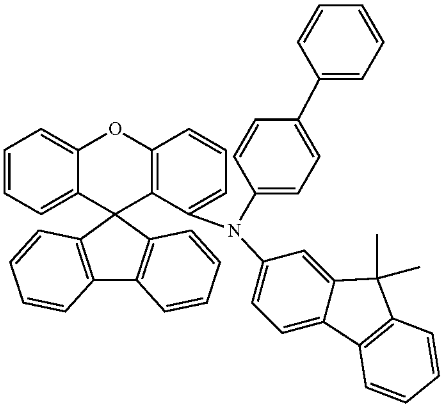
Formula (S-80)
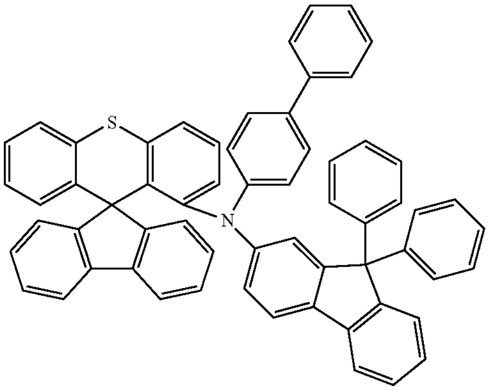

-continued

Formula (S-81)

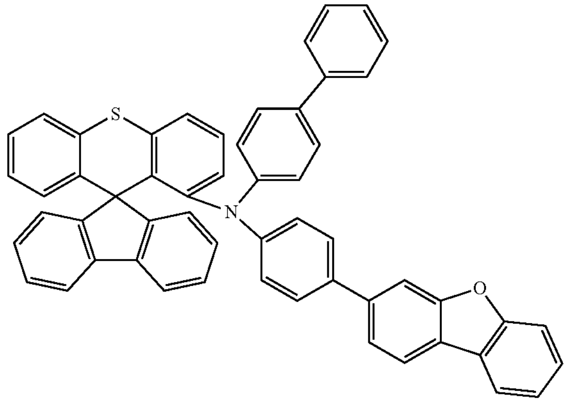

Formula (S-82)

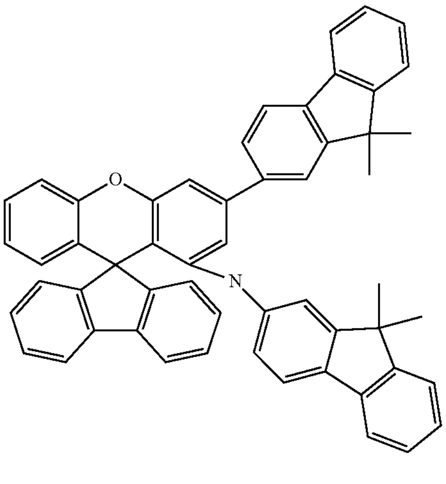

-continued

Formula (S-83)

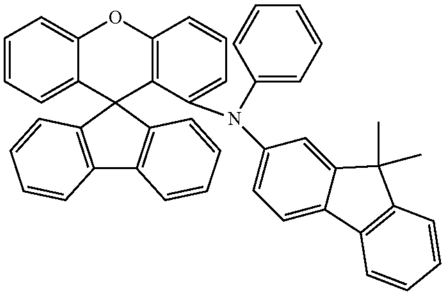

Formula (S-84)

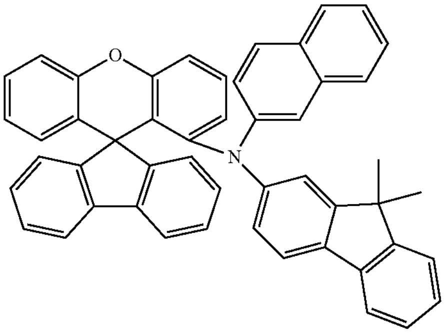

The compounds of the formula (S) can be prepared by means of customary methods of synthetic organic chemistry. Use is made here particularly of Buchwald and Suzuki reactions, nucleophilic addition reactions onto carbonyl groups, and ring-closure reactions by electrophilic aromatic substitution.

A preferred process for preparing compounds of the formula (S) proceeds as follows: First of all, a metallated ether or thioether compound (B in Scheme 1 below) is added onto a ketone C, followed by a ring-closure reaction. Subsequently, an amino group or an aryl group containing an amino group is inserted via a Buchwald or Suzuki reaction. The metallated ether or thioether compound is preferably a lithiated compound or a corresponding Grignard compound.

Scheme 1

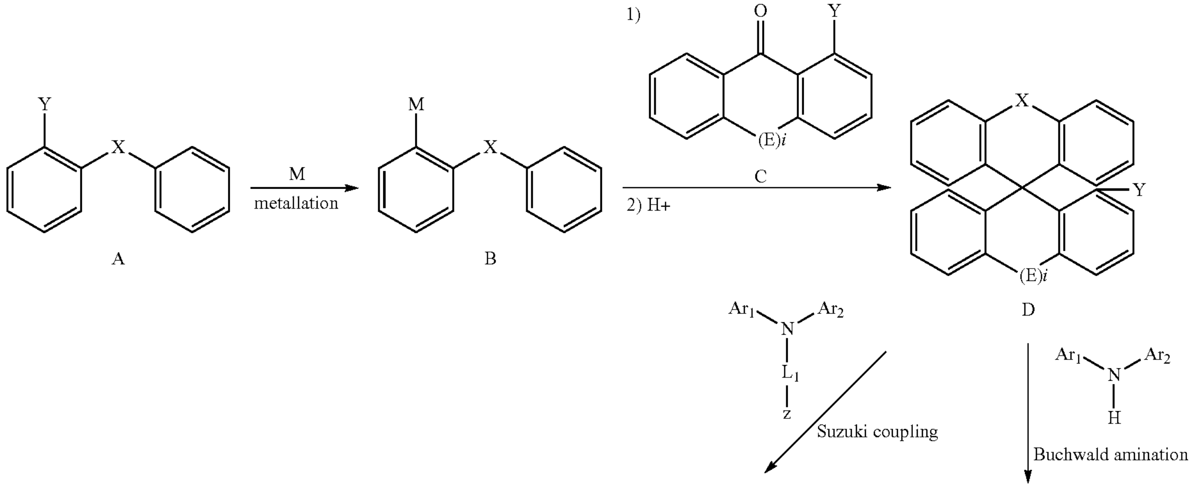

-continued

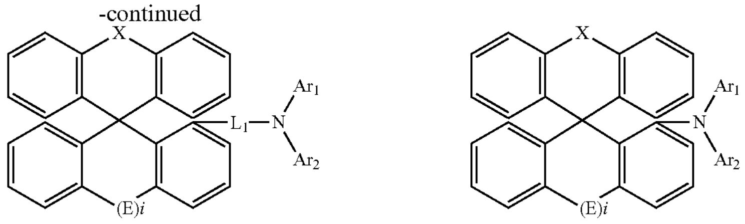

Y, Z = Br, Cl, B(OR)2
X = O, S
E = Single bond
i = 0 or 1

Alternatively, the addition of the metallated ether or thioether group onto the ketone and the ring-closure reaction can also take place after a Suzuki or Buchwald coupling, as shown in Scheme 2.

Scheme 2

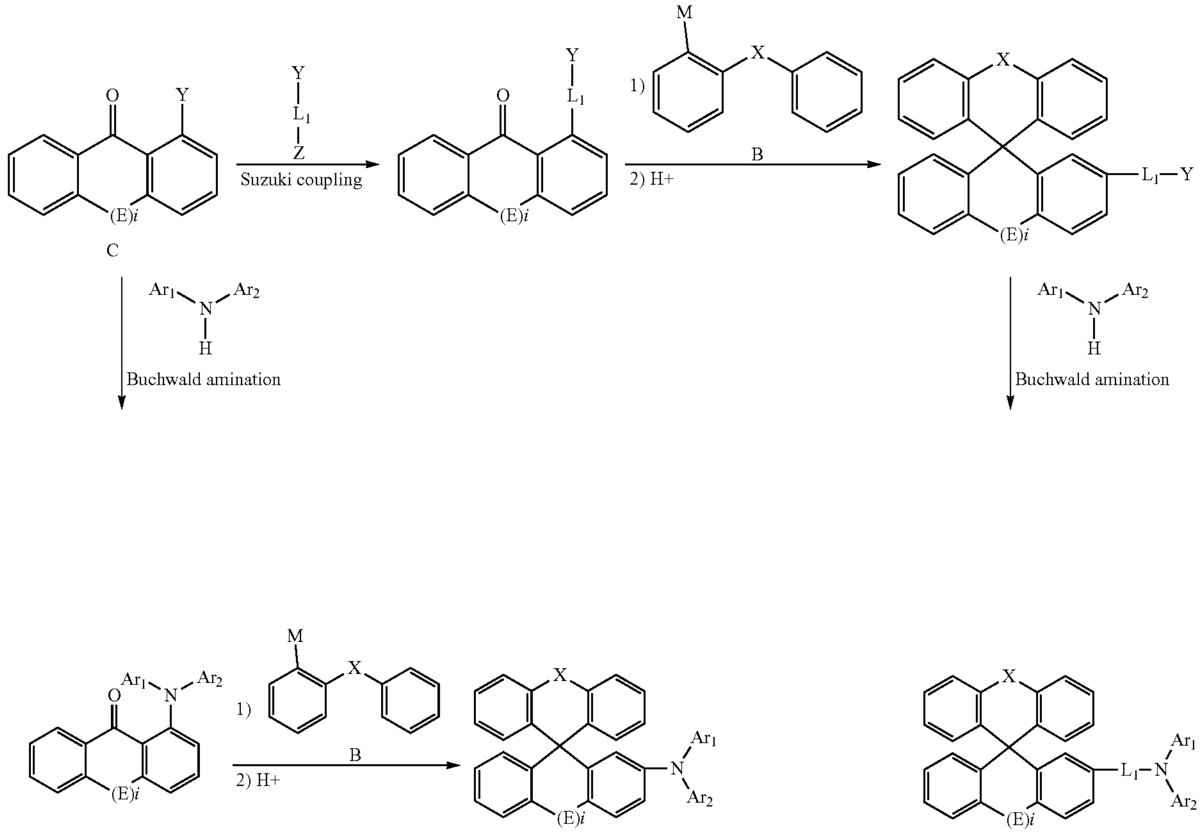

Y, Z = Br, Cl, B(OR)2
X = O, S
E = Single bond
i = 0 or 1

The application thus provides a process for preparing a compound of the formula (S), characterized in that it comprises an addition of a metallated ether or thioether compound onto a diaryl ketone and a subsequent ring-closure reaction. The metallated ether or thioether compound is preferably a metallated diaryl ether or diaryl thioether compound, most preferably a lithiated diaryl ether or diaryl thioether compound or a corresponding Grignard derivative of the diaryl ether or diaryl thioether compound.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (S), wherein the bond(s) to the polymer, oligomer or dendrimer may be localized at any desired positions substituted by $R^1$ or $R^2$ in formula (S). According to the linkage of the compound of formula (S), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (S) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (S) to be joined via a trivalent or higher-valency group, for example via a trivalent or higher-valency aromatic or heteroaromatic group, to give a branched or dendritic oligomer or polymer.

For the repeat units of formula (S) in oligomers, dendrimers and polymers, the same preferences apply as described above for compounds of formula (S).

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (S) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (S) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers. In this regard, the same preferred embodiments as described above for the compounds of the formula (I) are applicable. In addition, the compounds of the formula (S) are also particularly suitable for use in an electron blocker layer of an OLED.

WORKING EXAMPLES

A) Synthesis Examples

Example 1-1

Synthesis of the Inventive Compound 1-1 and Variants

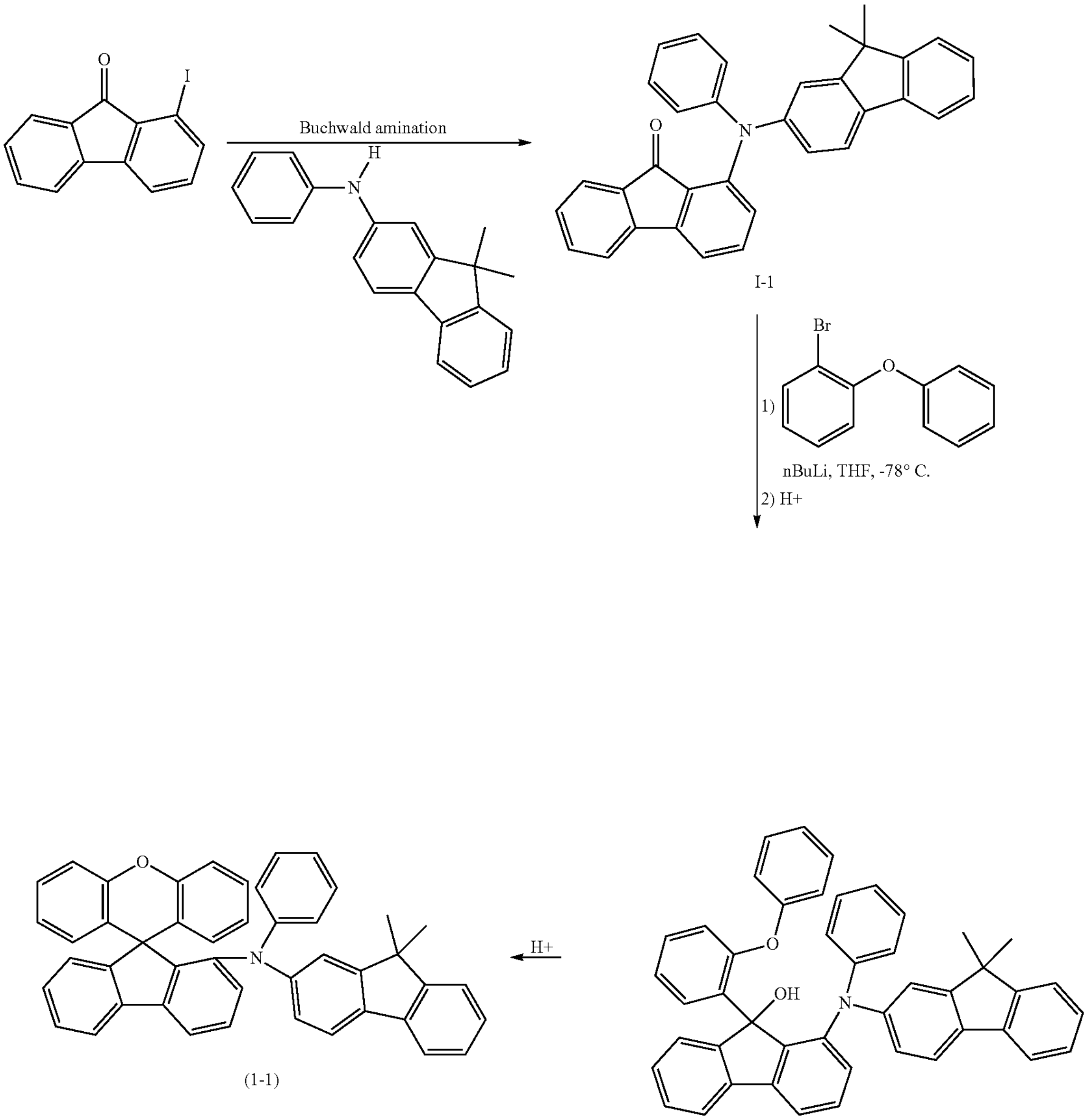

I-1

(1-1)

Intermediate I-1

26.8 g of phenyl(9,9-dimethyl-9H-fluoren-2-yl)amine (87.6 mmol) and 25 g of iodobenzofluorenone (87.6 mmol) are dissolved in 700 ml of toluene. The solution is degassed and saturated with $N_2$. Thereafter, 3.5 ml (3.5 mmol) of a 1 M tri-tert-butylphosphine solution and 0.46 g (1.75 mmol) of palladium(II) acetate are added thereto, and then 16.8 g of sodium tert-butoxide (175 mmol) are added. The reaction mixture is heated to boiling under a protective atmosphere for 5 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 33 g (81% of theory).

The following compounds are prepared in an analogous manner:

| | Reactant 1 | Reactant 2 | Product | Yield |
|---|---|---|---|---|
| I-2 | 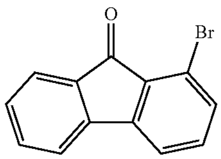 [SMILES: O=C1c2ccccc2-c2cccc(Br)c21] | 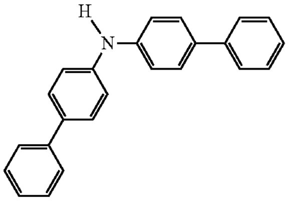 [SMILES: c1ccc(-c2ccc(Nc3ccc(-c4ccccc4)cc3)cc2)cc1] | 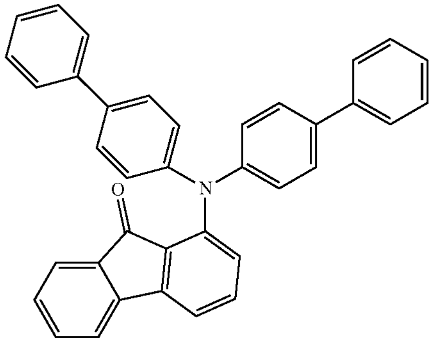 [SMILES: O=C1c2ccccc2-c2cccc(N(c3ccc(-c4ccccc4)cc3)c3ccc(-c4ccccc4)cc3)c21] | 85% |
| I-3 | 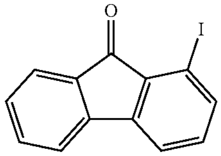 [SMILES: O=C1c2ccccc2-c2cccc(I)c21] | 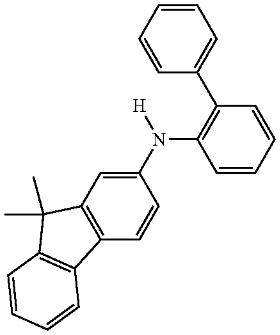 [SMILES: CC1(C)c2ccccc2-c2ccc(Nc3ccccc3-c3ccccc3)cc21] | 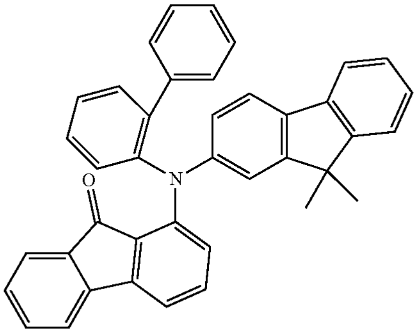 [SMILES: CC1(C)c2ccccc2-c2ccc(N(c3ccccc3-c3ccccc3)c3cccc4c3C(=O)c3ccccc3-4)cc21] | 71% |
| I-4 | 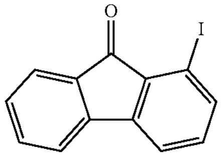 [SMILES: O=C1c2ccccc2-c2cccc(I)c21] | 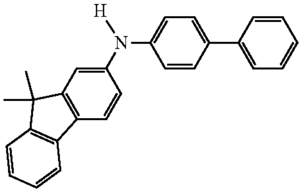 [SMILES: CC1(C)c2ccccc2-c2ccc(Nc3ccc(-c4ccccc4)cc3)cc21] | 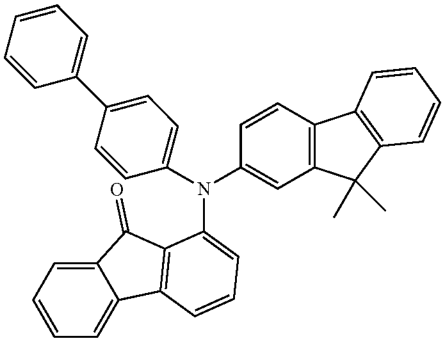 [SMILES: CC1(C)c2ccccc2-c2ccc(N(c3ccc(-c4ccccc4)cc3)c3cccc4c3C(=O)c3ccccc3-4)cc21] | 82% |
| I-5 | 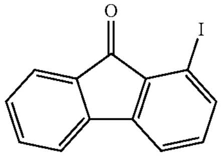 [SMILES: O=C1c2ccccc2-c2cccc(I)c21] | 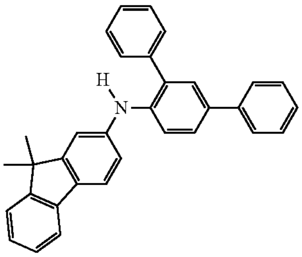 [SMILES: CC1(C)c2ccccc2-c2ccc(Nc3ccc(-c4ccccc4)cc3-c3ccccc3)cc21] | 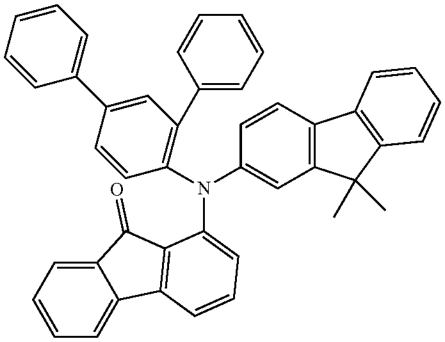 [SMILES: CC1(C)c2ccccc2-c2ccc(N(c3ccc(-c4ccccc4)cc3-c3ccccc3)c3cccc4c3C(=O)c3ccccc3-4)cc21] | 72% |

-continued
| | Reactant 1 | Reactant 2 | Product | Yield |
|---|---|---|---|---|
| I-6 | 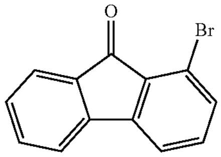 [SMILES: O=C1c2ccccc2-c2cccc(Br)c21] | 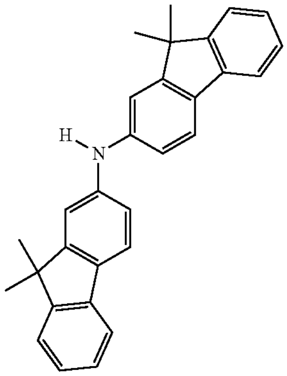 [SMILES: CC1(C)c2ccccc2-c2ccc(Nc3ccc4c(c3)C(C)(C)c3ccccc3-4)cc21] | 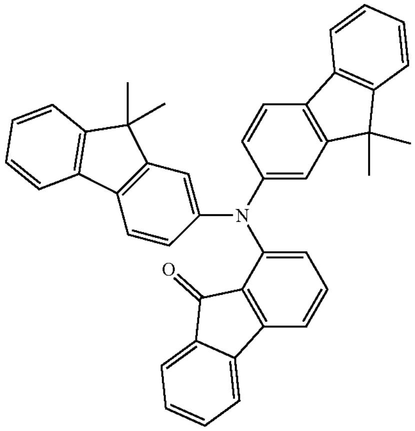 [SMILES: CC1(C)c2ccccc2-c2ccc(N(c3ccc4c(c3)C(C)(C)c3ccccc3-4)c3cccc4c3C(=O)c3ccccc3-4)cc21] | 74% |
| I-7 | 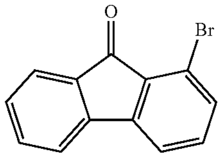 [SMILES: O=C1c2ccccc2-c2cccc(Br)c21] | 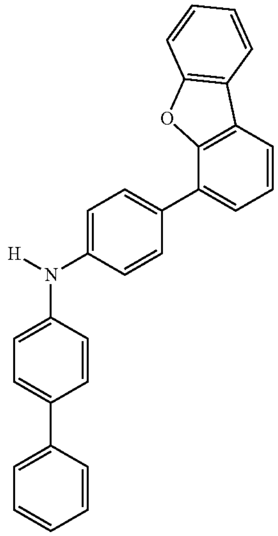 [SMILES: c1ccc(-c2ccc(Nc3ccc(-c4cccc5c4oc4ccccc45)cc3)cc2)cc1] | 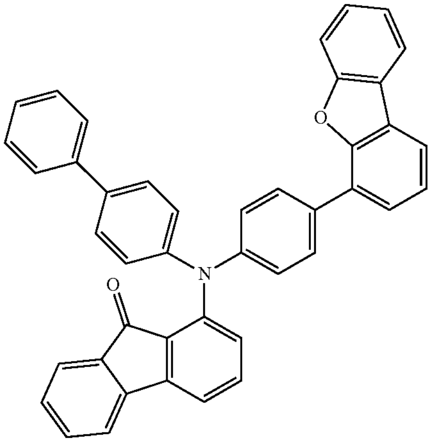 [SMILES: O=C1c2ccccc2-c2cccc(N(c3ccc(-c4ccccc4)cc3)c3ccc(-c4cccc5c4oc4ccccc45)cc3)c21] | 74% |
| I-8 | 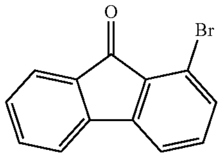 [SMILES: O=C1c2ccccc2-c2cccc(Br)c21] | 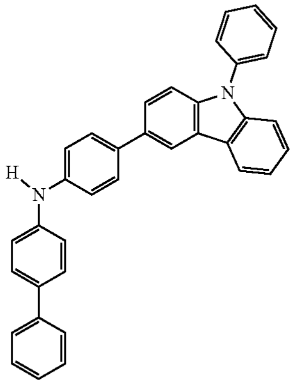 [SMILES: c1ccc(-c2ccc(Nc3ccc(-c4ccc5c(c4)c4ccccc4n5-c4ccccc4)cc3)cc2)cc1] | 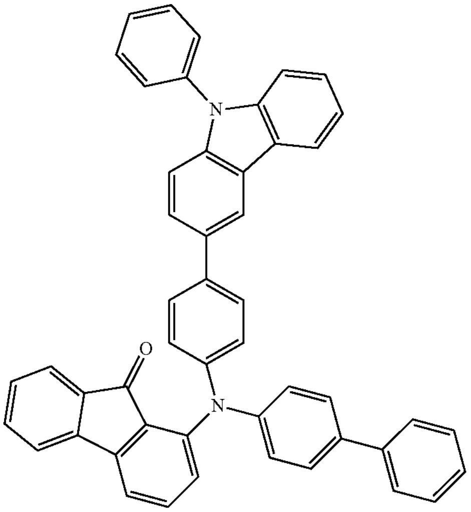 [SMILES: O=C1c2ccccc2-c2cccc(N(c3ccc(-c4ccccc4)cc3)c3ccc(-c4ccc5c(c4)c4ccccc4n5-c4ccccc4)cc3)c21] | 62% |

-continued

| | Reactant 1 | Reactant 2 | Product | Yield |
|---|---|---|---|---|
| I-9 | 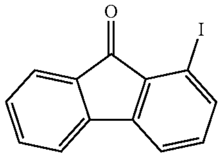 | 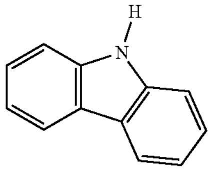 [SMILES: c1ccc2c(c1)[nH]c1ccccc12] | 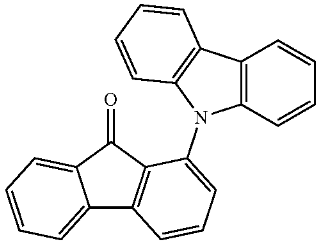 [SMILES: O=C1c2ccccc2-c2cccc(-n3c4ccccc4c4ccccc43)c21] | 35% |
| I-10 | 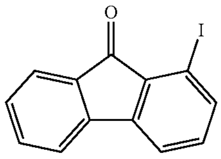 [SMILES: O=C1c2ccccc2-c2cccc(I)c21] | 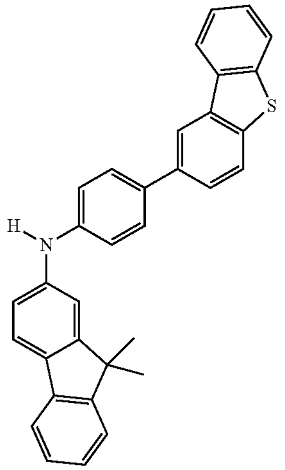 [SMILES: CC1(C)c2ccccc2-c2ccc(Nc3ccc(-c4ccc5sc6ccccc6c5c4)cc3)cc21] | 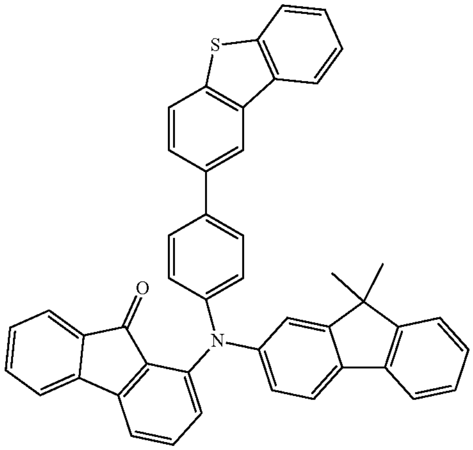 [SMILES: CC1(C)c2ccccc2-c2ccc(N(c3ccc(-c4ccc5sc6ccccc6c5c4)cc3)c3cccc4c3C(=O)c3ccccc3-4)cc21] | 70% |
| I-11 | 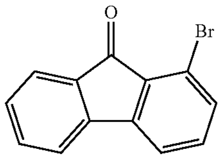 | 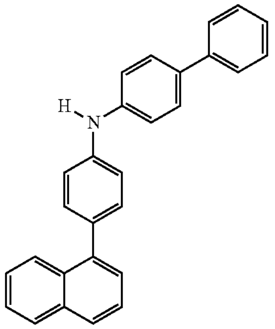 [SMILES: c1ccc(-c2ccc(Nc3ccc(-c4cccc5ccccc45)cc3)cc2)cc1] | 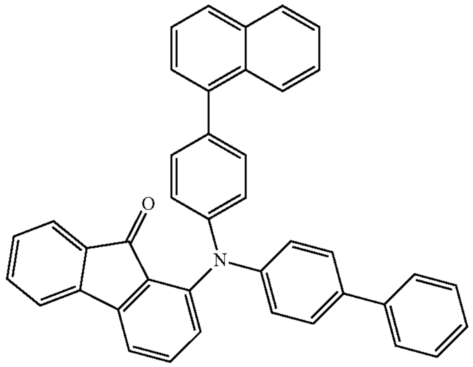 [SMILES: O=C1c2ccccc2-c2cccc(N(c3ccc(-c4ccccc4)cc3)c3ccc(-c4cccc5ccccc45)cc3)c21] | 67% |

Compound 1-1

17.37 g (69.6 mmol) of 1-bromo-2-diphenyl ether are dissolved in a baked-out flask in 300 ml of dried THF. The reaction mixture is cooled to −78° C. At this temperature, 30 ml of a 2.5 M solution of n-BuLi in hexane (69.7 mmol) are slowly added dropwise. The mixture is stirred at −70° C. for a further 1 hour. Subsequently, 30 g of the bromofluorenone derivative (63 mmol) are dissolved in 200 ml of THF and added dropwise at −70° C. After the addition has ended, the reaction mixture is warmed gradually to room temperature, quenched with $NH_4Cl$ and then concentrated on a rotary evaporator. 300 ml of acetic acid are added cautiously to the concentrated solution and then 20 ml of fuming HCl are added. The mixture is heated to 75° C. and kept there for 6 hours. During this time, a white solid precipitates out. The mixture is then cooled to room temperature, and the precipitated solids are filtered off with suction and washed with water and methanol. Yield: 35 g (88%)

The solids are recrystallized from heptane/toluene and finally sublimed under high vacuum.

The following compounds are prepared in an analogous manner:

| | Reactant 1 | Reactant 2 | Product | Yield |
|---|---|---|---|---|
| 1-2 | 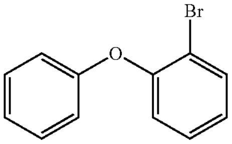 [SMILES: Brc1ccccc1Oc1ccccc1] | 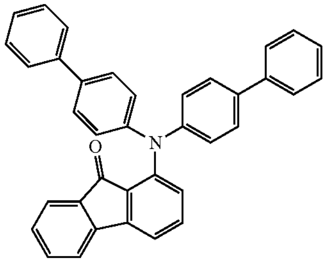 [SMILES: O=C1c2ccccc2-c2cccc(N(c3ccc(-c4ccccc4)cc3)c3ccc(-c4ccccc4)cc3)c21] | 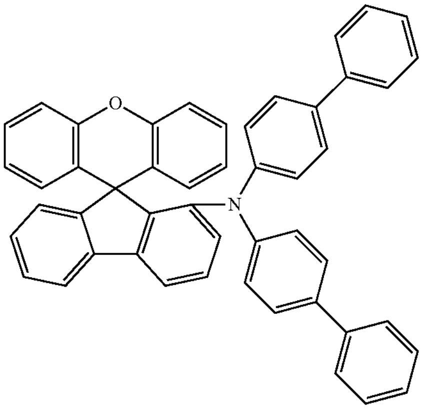 [SMILES: c1ccc(-c2ccc(N(c3ccc(-c4ccccc4)cc3)c3cccc4c3C3(c5ccccc5Oc5ccccc53)c3ccccc3-4)cc2)cc1] | 70% |
| 1-3 | 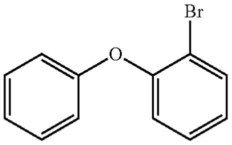 [SMILES: Brc1ccccc1Oc1ccccc1] | 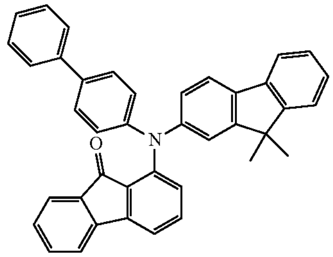 [SMILES: CC1(C)c2ccccc2-c2ccc(N(c3ccc(-c4ccccc4)cc3)c3cccc4c3C(=O)c3ccccc3-4)cc21] | 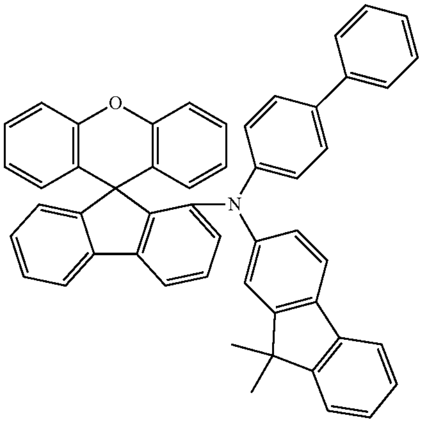 [SMILES: CC1(C)c2ccccc2-c2ccc(N(c3ccc(-c4ccccc4)cc3)c3cccc4c3C3(c5ccccc5Oc5ccccc53)c3ccccc3-4)cc21] | 77% |
| 1-5 | 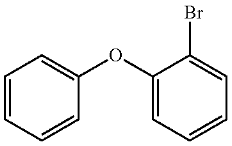 [SMILES: Brc1ccccc1Oc1ccccc1] | 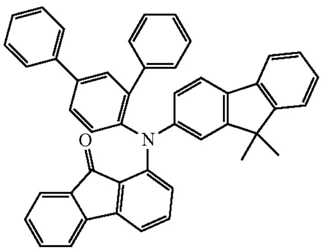 [SMILES: CC1(C)c2ccccc2-c2ccc(N(c3ccc(-c4ccccc4)cc3-c3ccccc3)c3cccc4c3C(=O)c3ccccc3-4)cc21] | 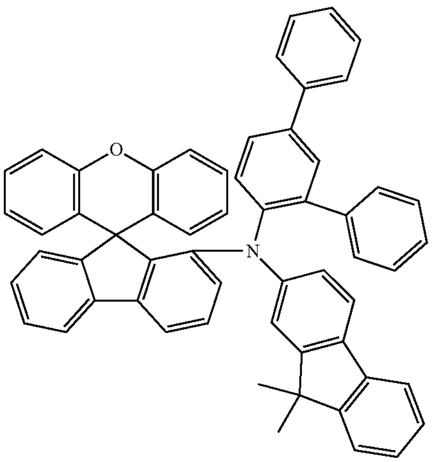 [SMILES: CC1(C)c2ccccc2-c2ccc(N(c3ccc(-c4ccccc4)cc3-c3ccccc3)c3cccc4c3C3(c5ccccc5Oc5ccccc53)c3ccccc3-4)cc21] | 65% |

-continued
| | Reactant 1 | Reactant 2 | Product | Yield |
|---|---|---|---|---|
| 1-6 | 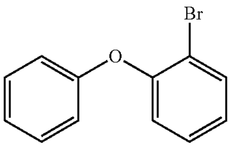 [SMILES: Brc1ccccc1Oc1ccccc1] | 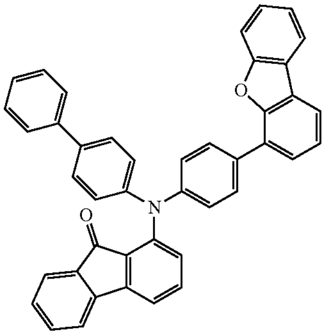 [SMILES: O=C1c2ccccc2-c2cccc(N(c3ccc(-c4ccccc4)cc3)c3ccc(-c4cccc5c4oc4ccccc45)cc3)c21] | 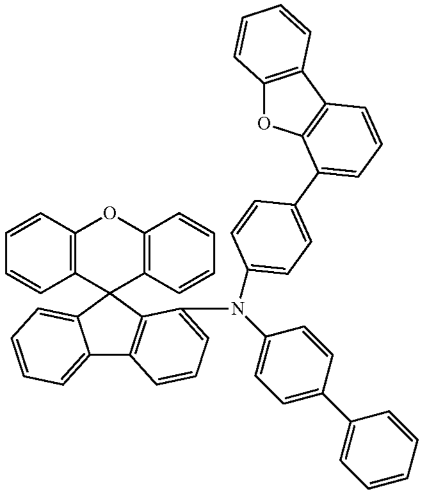 [SMILES: c1ccc(-c2ccc(N(c3ccc(-c4cccc5c4oc4ccccc45)cc3)c3cccc4c3C3(c5ccccc5Oc5ccccc53)c3ccccc3-4)cc2)cc1] | 69% |
| 1-7 | 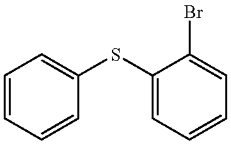 | 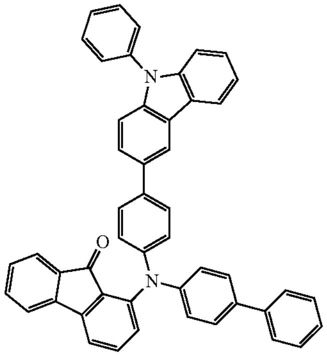 [SMILES: O=C1c2ccccc2-c2cccc(N(c3ccc(-c4ccccc4)cc3)c3ccc(-c4ccc5c(c4)c4ccccc4n5-c4ccccc4)cc3)c21] | 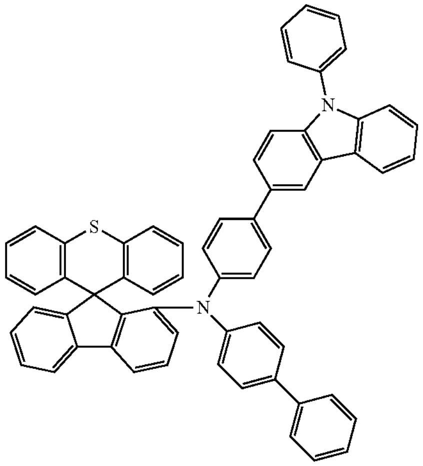 [SMILES: c1ccc(-c2ccc(N(c3ccc(-c4ccc5c(c4)c4ccccc4n5-c4ccccc4)cc3)c3cccc4c3C3(c5ccccc5Sc5ccccc53)c3ccccc3-4)cc2)cc1] | 79% |
| 1-8 | 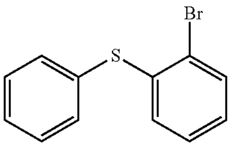 | 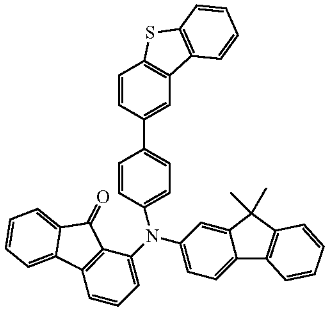 [SMILES: CC1(C)c2ccccc2-c2ccc(N(c3ccc(-c4ccc5sc6ccccc6c5c4)cc3)c3cccc4c3C(=O)c3ccccc3-4)cc21] | 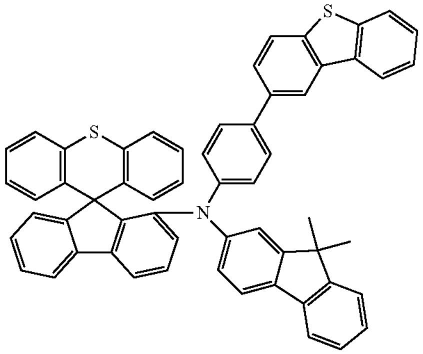 [SMILES: CC1(C)c2ccccc2-c2ccc(N(c3ccc(-c4ccc5sc6ccccc6c5c4)cc3)c3cccc4c3C3(c5ccccc5Sc5ccccc53)c3ccccc3-4)cc21] | 81% |

-continued
| | Reactant 1 | Reactant 2 | Product | Yield |
|---|---|---|---|---|
| 1-9 | 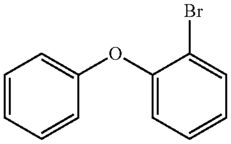 [SMILES: Brc1ccccc1Oc1ccccc1] | 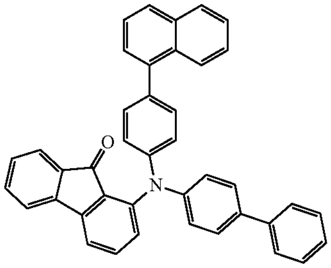 [SMILES: O=C1c2ccccc2-c2cccc(N(c3ccc(-c4ccccc4)cc3)c3ccc(-c4cccc5ccccc45)cc3)c21] | 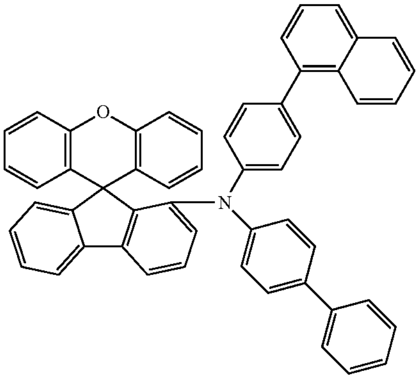 [SMILES: c1ccc(-c2ccc(N(c3ccc(-c4cccc5ccccc45)cc3)c3cccc4c3C3(c5ccccc5Oc5ccccc53)c3ccccc3-4)cc2)cc1] | 80% |
| 1-10 | 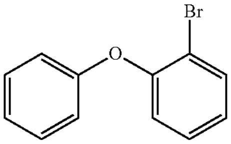 [SMILES: Brc1ccccc1Oc1ccccc1] | 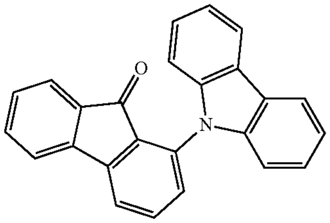 [SMILES: O=C1c2ccccc2-c2cccc(-n3c4ccccc4c4ccccc43)c21] | 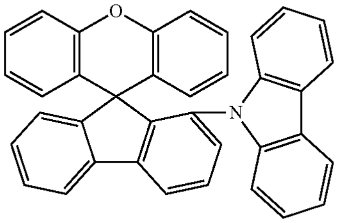 [SMILES: c1ccc2c(c1)Oc1ccccc1C21c2ccccc2-c2cccc(-n3c4ccccc4c4ccccc43)c21] | 40% |
| 1-11 | 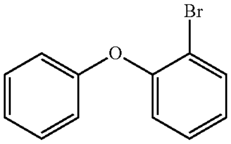 | 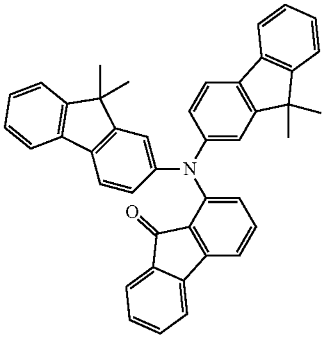 [SMILES: CC1(C)c2ccccc2-c2ccc(N(c3ccc4c(c3)C(C)(C)c3ccccc3-4)c3cccc4c3C(=O)c3ccccc3-4)cc21] | 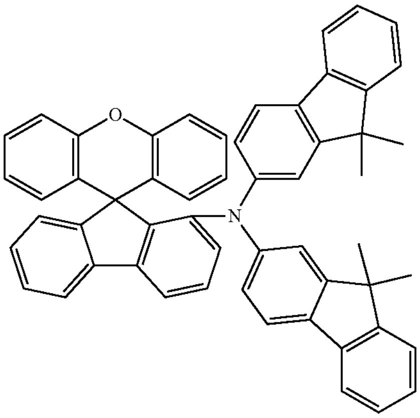 [SMILES: CC1(C)c2ccccc2-c2ccc(N(c3ccc4c(c3)C(C)(C)c3ccccc3-4)c3cccc4c3C3(c5ccccc5Oc5ccccc53)c3ccccc3-4)cc21] | 79% |
Example 2-1
Synthesis of the Inventive Compound 2-1 and Variants
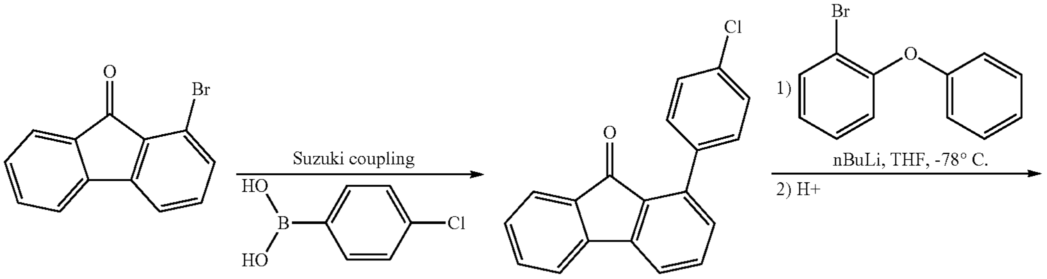
II-1

-continued

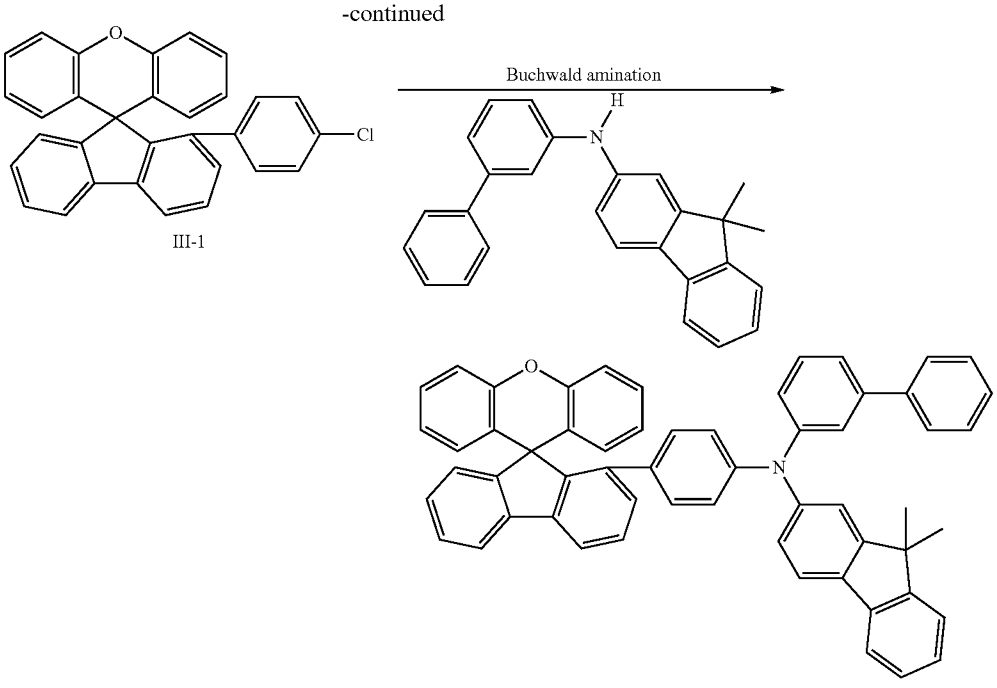

III-1

(2-1)

Intermediate II-1

38 g of 4-chlorophenylboronic acid (243 mmol) and 60 g of 1-bromofluoren-9-one (232 mmol) are suspended in 800 ml of THF. 230 ml of 2 M potassium carbonate solution are slowly added dropwise. The solution is degassed and saturated with $N_2$. Thereafter, 8 g (7 mmol) of $Pd(Ph_3P)_4$ are added. The reaction mixture is heated to boiling under a protective atmosphere for 16 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from MeOH. The yield is 63 g (90% of theory).

The following compounds are prepared in an analogous manner:

| | Reactant 1 | Reactant 2 | Product | Yield |
|---|---|---|---|---|
| II-2 | 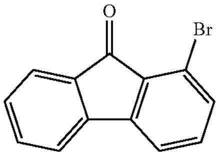 [SMILES: O=C1c2ccccc2-c2cccc(Br)c21] | 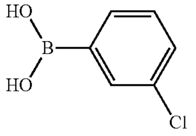 (63503-60-6) | 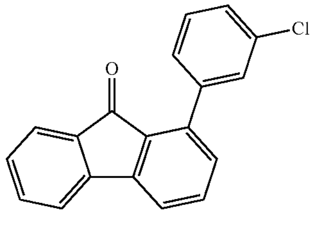 [SMILES: O=C1c2ccccc2-c2cccc(-c3cccc(Cl)c3)c21] | 80% |
| II-3 | 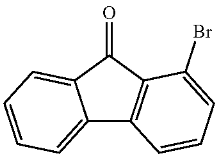 | 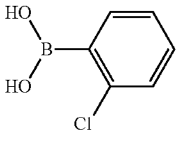 (3900-89-8) | 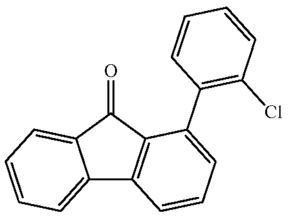 [SMILES: O=C1c2ccccc2-c2cccc(-c3ccccc3Cl)c21] | 88% |

-continued
| | Reactant 1 | Reactant 2 | Product | Yield |
|---|---|---|---|---|
| II-4 | 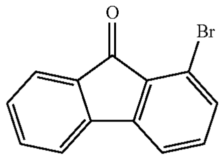 [SMILES: O=C1c2ccccc2-c2cccc(Br)c21] | 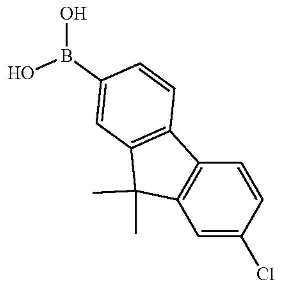 (851119-06-7) | 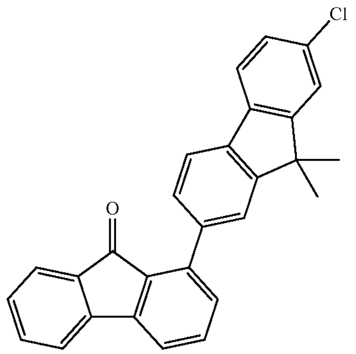 [SMILES: CC1(C)c2cc(Cl)ccc2-c2ccc(-c3cccc4c3C(=O)c3ccccc3-4)cc21] | 82% |
| II-5 | 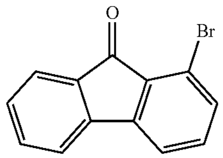 [SMILES: O=C1c2ccccc2-c2cccc(Br)c21] | 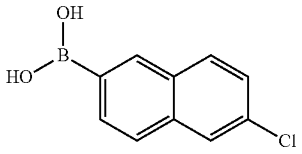 (870822-86-9) | 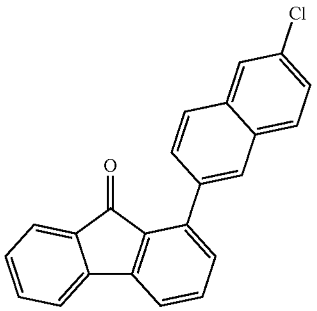 [SMILES: O=C1c2ccccc2-c2cccc(-c3ccc4cc(Cl)ccc4c3)c21] | 89% |
| II-6 | 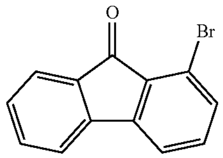 [SMILES: O=C1c2ccccc2-c2cccc(Br)c21] | 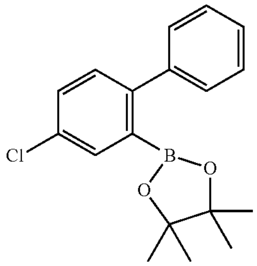 (1399362-31-2) | 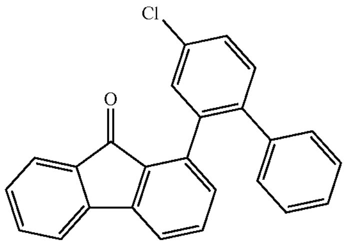 [SMILES: O=C1c2ccccc2-c2cccc(-c3cc(Cl)ccc3-c3ccccc3)c21] | 64% |
| II-7 | 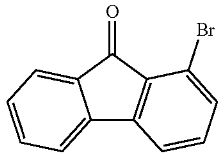 | 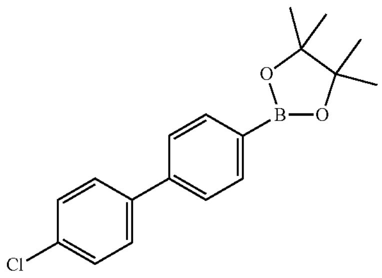 (942589-53-9) | 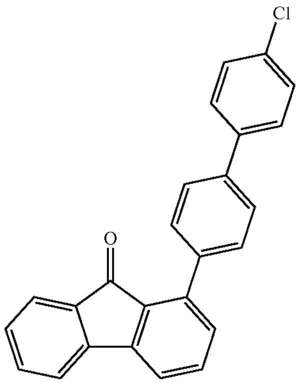 [SMILES: O=C1c2ccccc2-c2cccc(-c3ccc(-c4ccc(Cl)cc4)cc3)c21] | 80% |

-continued

| | Reactant 1 | Reactant 2 | Product | Yield |
|---|---|---|---|---|
| II-8 | 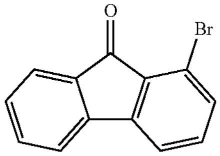 | 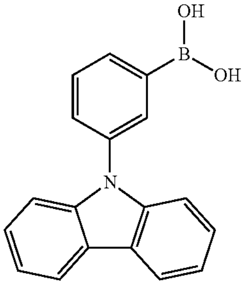 (864377-33-3) | 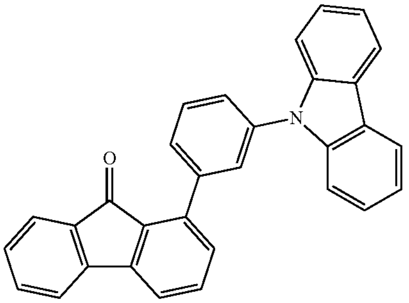 [SMILES: O=C1c2ccccc2-c2cccc(-c3cccc(-n4c5ccccc5c5ccccc54)c3)c21] | 83% |

Intermediate III-1

30 g (120 mmol) of 1-bromo-2-diphenyl ether are dissolved in a baked-out flask in 500 ml of dried THF. The reaction mixture is cooled to −78° C. At this temperature, 480 ml of a 2.5 M solution of n-BuLi in hexane (120 mmol) are slowly added dropwise. The mixture is stirred at −70° C. for a further 1 hour. Subsequently, 33 g of 1-(4-chlorophenyl)fluorenone (114 mmol) are dissolved in 100 ml of THF and added dropwise at −70° C. After the addition has ended, the reaction mixture is warmed gradually to room temperature, quenched with $NH_4Cl$ and then concentrated on a rotary evaporator.

300 ml of acetic acid are added cautiously to the concentrated solution and then 20 ml of fuming HCl are added. The mixture is heated to 75° C. and kept there for 6 hours. During this time, a white solid precipitates out. The mixture is then cooled to room temperature, and the precipitated solids are filtered off with suction and washed with water and methanol. Yield: 38 g (70%).

Finally, the residue is recrystallized.

The following compounds are prepared in an analogous manner:

| | Reactant 1 | Reactant 2 | Product | Yield |
|---|---|---|---|---|
| III-2 | 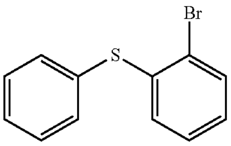 | 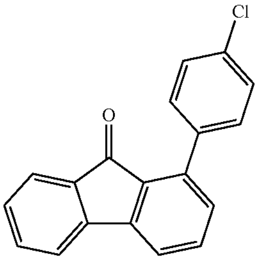 [SMILES: O=C1c2ccccc2-c2cccc(-c3ccc(Cl)cc3)c21] | 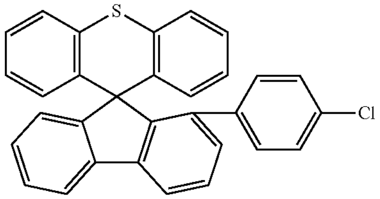 [SMILES: Clc1ccc(-c2cccc3c2C2(c4ccccc4Sc4ccccc42)c2ccccc2-3)cc1] | 70% |
| III-3 | 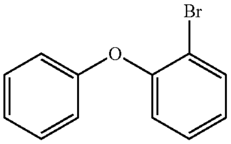 [SMILES: Brc1ccccc1Oc1ccccc1] | 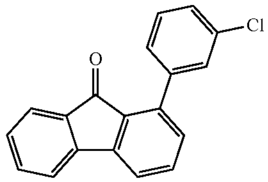 [SMILES: O=C1c2ccccc2-c2cccc(-c3cccc(Cl)c3)c21] | 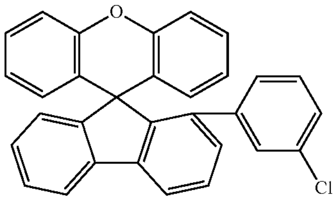 [SMILES: Clc1cccc(-c2cccc3c2C2(c4ccccc4Oc4ccccc42)c2ccccc2-3)c1] | 77% |
| III-4 | 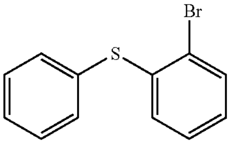 [SMILES: Brc1ccccc1Sc1ccccc1] | 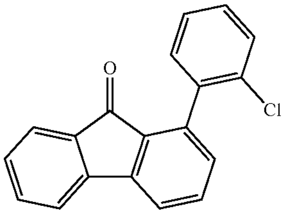 [SMILES: O=C1c2ccccc2-c2cccc(-c3ccccc3Cl)c21] | 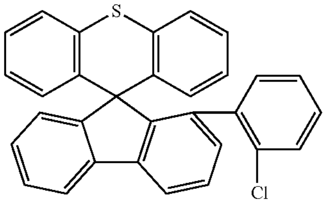 [SMILES: Clc1ccccc1-c1cccc2c1C1(c3ccccc3Sc3ccccc31)c1ccccc1-2] | 67% |

-continued

| | Reactant 1 | Reactant 2 | Product | Yield |
|---|---|---|---|---|
| III-5 | 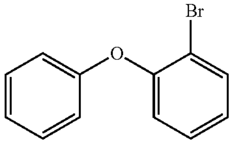 [SMILES: Brc1ccccc1Oc1ccccc1] | 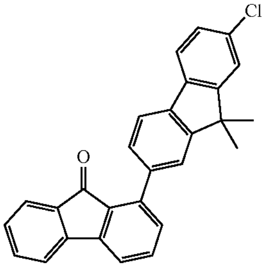 [SMILES: CC1(C)c2cc(Cl)ccc2-c2ccc(-c3cccc4c3C(=O)c3ccccc3-4)cc21] | 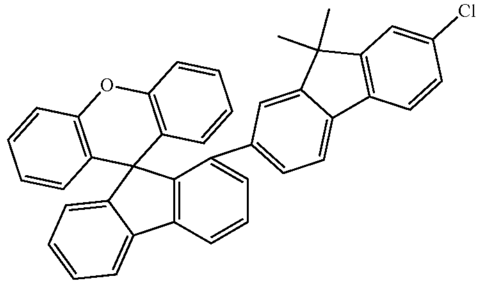 [SMILES: CC1(C)c2cc(Cl)ccc2-c2ccc(-c3cccc4c3C3(c5ccccc5Oc5ccccc53)c3ccccc3-4)cc21] | 65% |
| III-6 | 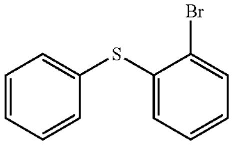 | 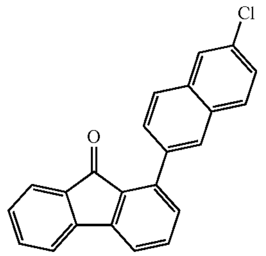 [SMILES: O=C1c2ccccc2-c2cccc(-c3ccc4cc(Cl)ccc4c3)c21] | 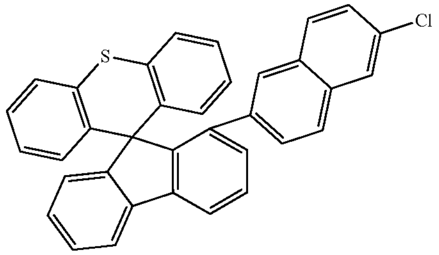 [SMILES: Clc1ccc2cc(-c3cccc4c3C3(c5ccccc5Sc5ccccc53)c3ccccc3-4)ccc2c1] | 73% |
| III-7 | 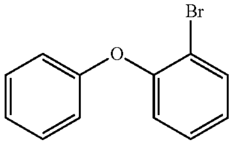 [SMILES: Brc1ccccc1Oc1ccccc1] | 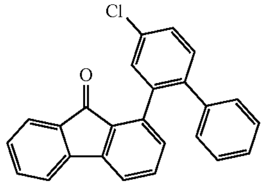 [SMILES: O=C1c2ccccc2-c2cccc(-c3cc(Cl)ccc3-c3ccccc3)c21] | 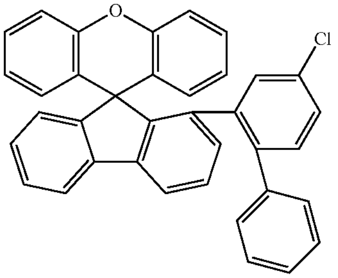 [SMILES: Clc1ccc(-c2ccccc2)c(-c2cccc3c2C2(c4ccccc4Oc4ccccc42)c2ccccc2-3)c1] | 69% |
| III-8 | 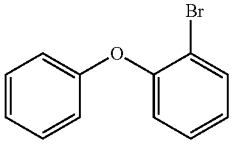 | 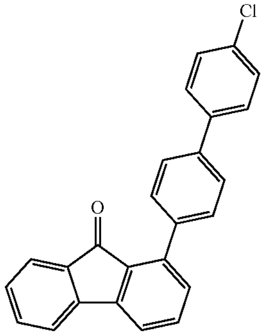 [SMILES: O=C1c2ccccc2-c2cccc(-c3ccc(-c4ccc(Cl)cc4)cc3)c21] | 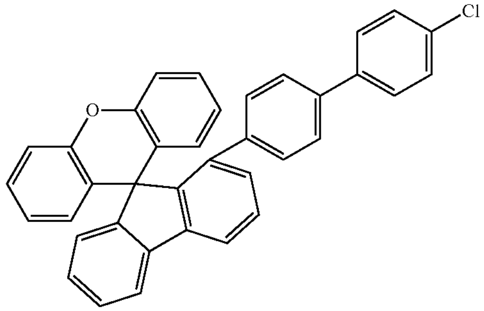 [SMILES: Clc1ccc(-c2ccc(-c3cccc4c3C3(c5ccccc5Oc5ccccc53)c3ccccc3-4)cc2)cc1] | 83% |
| III-9 | 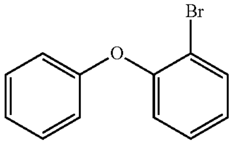 | 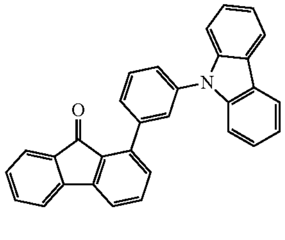 [SMILES: O=C1c2ccccc2-c2cccc(-c3cccc(-n4c5ccccc5c5ccccc54)c3)c21] | 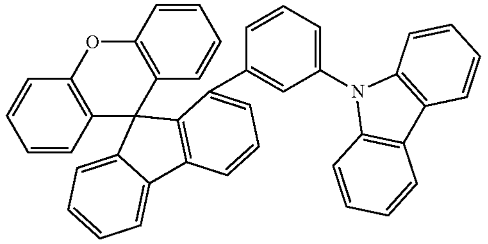 [SMILES: c1cc(-c2cccc3c2C2(c4ccccc4Oc4ccccc42)c2ccccc2-3)cc(-n2c3ccccc3c3ccccc32)c1] | 71% |

Compound 2-1

16.3 g of biphenyl-3-yl(9,9-dimethyl-9H-fluoren-2-yl) amine (45.26 mmol) and 29 g of the chloro derivative III-1 (45.2 mmol) are dissolved in 400 ml of toluene. The solution is degassed and saturated with $N_2$. Thereafter, 740 mg (1.81 mmol) of S-Phos and 830 mg (0.9 mmol) of $Pd_2(dba)_3$ are added thereto, and then 6.5 g of sodium tert-butoxide (67.7 mmol) are added. The reaction mixture is heated to boiling under a protective atmosphere for 5 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 27 g (78% of theory). The solids are recrystallized from heptane/toluene and finally sublimed under high vacuum.

The following compounds are prepared in an analogous manner:

| | Reactant 1 | Reactant 2 | Product | Yield |
|---|---|---|---|---|
| 2-2 | 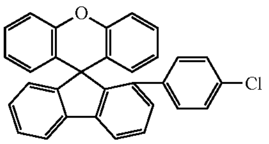 [SMILES: Clc1ccc(-c2cccc3c2C2(c4ccccc4Oc4ccccc42)c2ccccc2-3)cc1] | 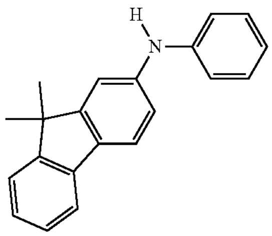 [SMILES: CC1(C)c2ccccc2-c2ccc(Nc3ccccc3)cc21] | 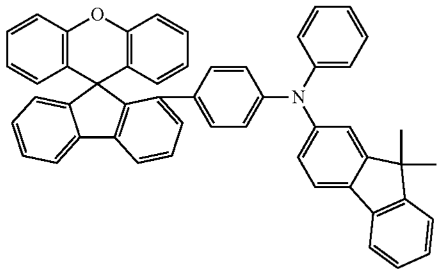 [SMILES: CC1(C)c2ccccc2-c2ccc(N(c3ccccc3)c3ccc(-c4cccc5c4C4(c6ccccc6Oc6ccccc64)c4ccccc4-5)cc3)cc21] | 78% |
| 2-3 | 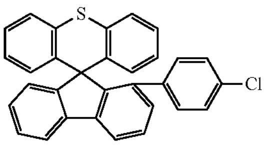 | 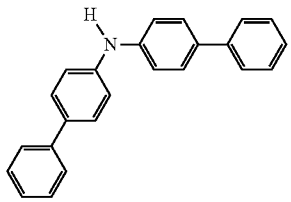 [SMILES: c1ccc(-c2ccc(Nc3ccc(-c4ccccc4)cc3)cc2)cc1] | 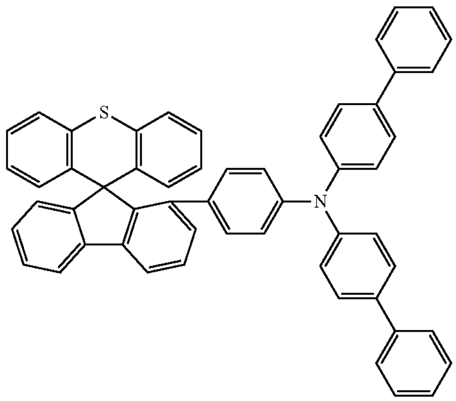 [SMILES: c1ccc(-c2ccc(N(c3ccc(-c4ccccc4)cc3)c3ccc(-c4cccc5c4C4(c6ccccc6Sc6ccccc64)c4ccccc4-5)cc3)cc2)cc1] | 71% |
| 2-4 | 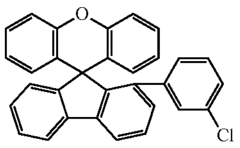 [SMILES: Clc1cccc(-c2cccc3c2C2(c4ccccc4Oc4ccccc42)c2ccccc2-3)c1] | 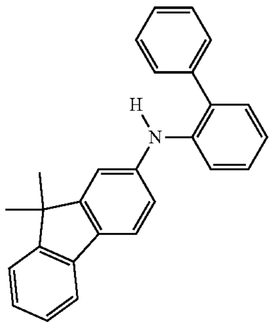 [SMILES: CC1(C)c2ccccc2-c2ccc(Nc3ccccc3-c3ccccc3)cc21] | 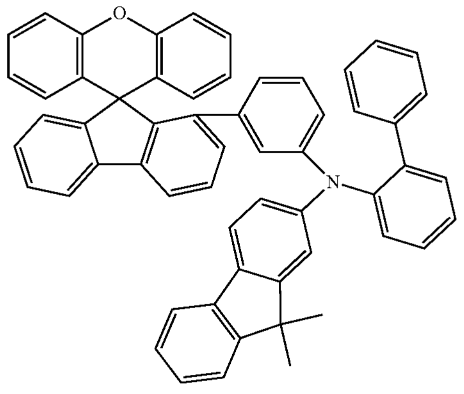 [SMILES: CC1(C)c2ccccc2-c2ccc(N(c3cccc(-c4cccc5c4C4(c6ccccc6Oc6ccccc64)c4ccccc4-5)c3)c3ccccc3-c3ccccc3)cc21] | 82% |
| 2-5 | 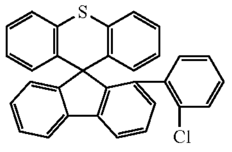 [SMILES: Clc1ccccc1-c1cccc2c1C1(c3ccccc3Sc3ccccc31)c1ccccc1-2] | 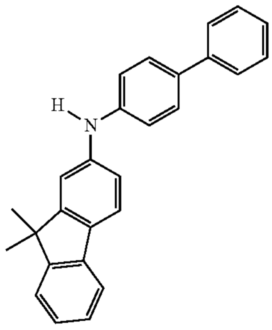 [SMILES: CC1(C)c2ccccc2-c2ccc(Nc3ccc(-c4ccccc4)cc3)cc21] | 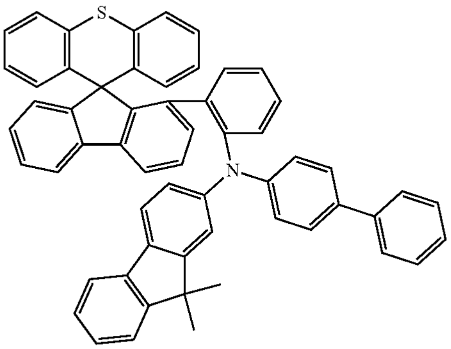 [SMILES: CC1(C)c2ccccc2-c2ccc(N(c3ccc(-c4ccccc4)cc3)c3ccccc3-c3cccc4c3C3(c5ccccc5Sc5ccccc53)c3ccccc3-4)cc21] | 89% |

-continued
| | Reactant 1 | Reactant 2 | Product | Yield |
| --- | --- | --- | --- | --- |
| 2-6 | 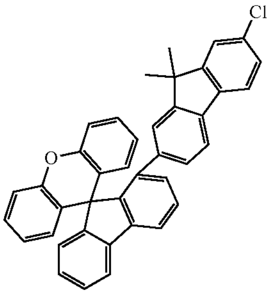 [SMILES: CC1(C)c2cc(Cl)ccc2-c2ccc(-c3cccc4c3C3(c5ccccc5Oc5ccccc53)c3ccccc3-4)cc21] | 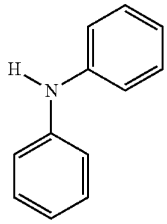 | 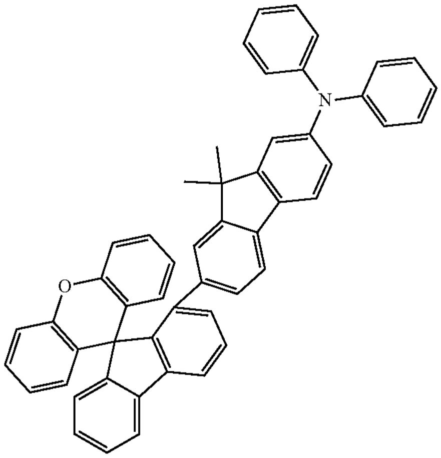 [SMILES: CC1(C)c2cc(-c3cccc4c3C3(c5ccccc5Oc5ccccc53)c3ccccc3-4)ccc2-c2ccc(N(c3ccccc3)c3ccccc3)cc21] | 69% |
| 2-7 | 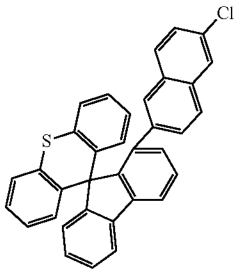 [SMILES: Clc1ccc2cc(-c3cccc4c3C3(c5ccccc5Sc5ccccc53)c3ccccc3-4)ccc2c1] | 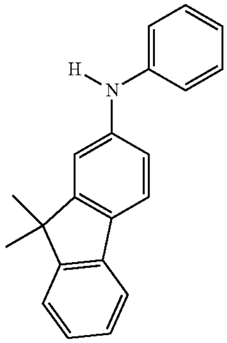 [SMILES: CC1(C)c2ccccc2-c2ccc(Nc3ccccc3)cc21] | 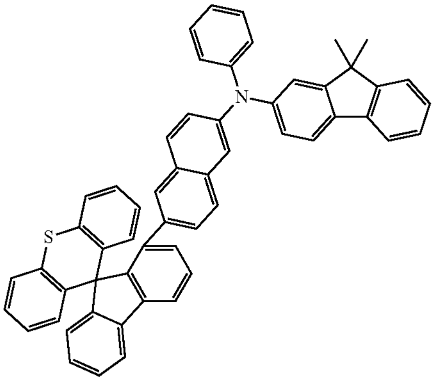 [SMILES: CC1(C)c2ccccc2-c2ccc(N(c3ccccc3)c3ccc4cc(-c5cccc6c5C5(c7ccccc7Sc7ccccc75)c5ccccc5-6)ccc4c3)cc21] | 88% |
| 2-8 | 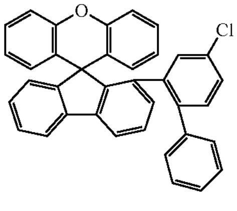 [SMILES: Clc1ccc(-c2ccccc2)c(-c2cccc3c2C2(c4ccccc4Oc4ccccc42)c2ccccc2-3)c1] | 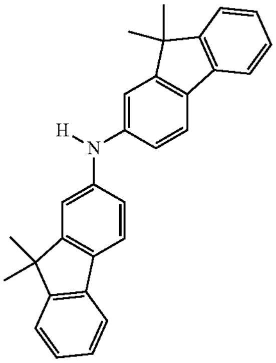 [SMILES: CC1(C)c2ccccc2-c2ccc(Nc3ccc4c(c3)C(C)(C)c3ccccc3-4)cc21] | 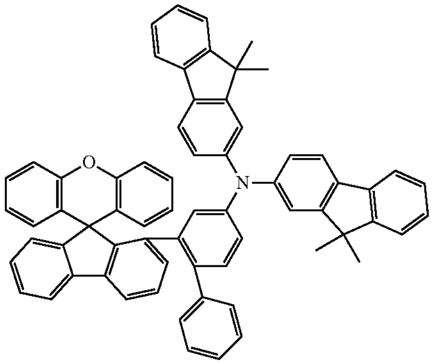 [SMILES: CC1(C)c2ccccc2-c2ccc(N(c3ccc(-c4ccccc4)c(-c4cccc5c4C4(c6ccccc6Oc6ccccc64)c4ccccc4-5)c3)c3ccc4c(c3)C(C)(C)c3ccccc3-4)cc21] | 85% |

-continued

| | Reactant 1 | Reactant 2 | Product | Yield |
|---|---|---|---|---|
| 2-9 | 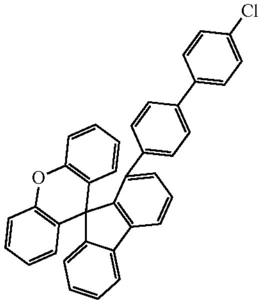 [SMILES: Clc1ccc(-c2ccc(-c3cccc4c3C3(c5ccccc5Oc5ccccc53)c3ccccc3-4)cc2)cc1] | 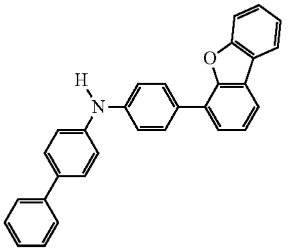 [SMILES: c1ccc(-c2ccc(Nc3ccc(-c4cccc5c4oc4ccccc45)cc3)cc2)cc1] | 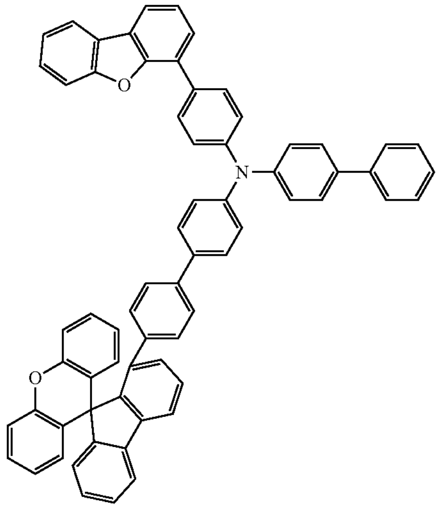 [SMILES: c1ccc(-c2ccc(N(c3ccc(-c4ccc(-c5cccc6c5C5(c7ccccc7Oc7ccccc75)c5ccccc5-6)cc4)cc3)c3ccc(-c4cccc5c4oc4ccccc45)cc3)cc2)cc1] | 75% |
| 2-10 | 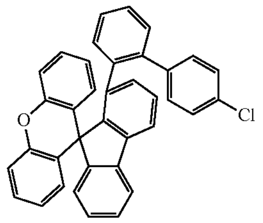 [SMILES: Clc1ccc(-c2ccccc2-c2cccc3c2C2(c4ccccc4Oc4ccccc42)c2ccccc2-3)cc1] | 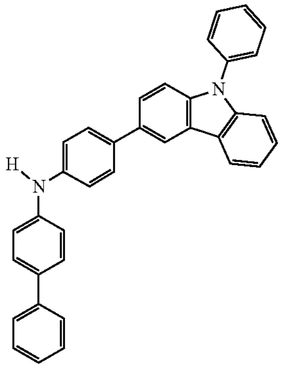 [SMILES: c1ccc(-c2ccc(Nc3ccc(-c4ccc5c(c4)c4ccccc4n5-c4ccccc4)cc3)cc2)cc1] | 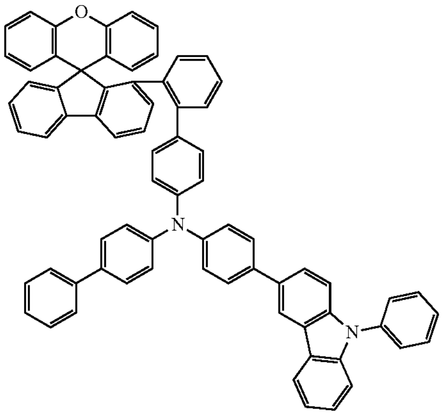 [SMILES: c1ccc(-c2ccc(N(c3ccc(-c4ccc5c(c4)c4ccccc4n5-c4ccccc4)cc3)c3ccc(-c4ccccc4-c4cccc5c4C4(c6ccccc6Oc6ccccc64)c4ccccc4-5)cc3)cc2)cc1] | 75% |

B) Use Examples

OLED devices according to the present application and comparative devices are produced in order to show the technical effects of the OLED devices of the invention. The OLEDs are produced according to the general method described in the working examples of published specification WO 2004/058911, unless stated otherwise below.

The OLEDs produced have glass plaques coated with structured ITO (indium tin oxide) in a thickness of 50 nm as substrates. The layers that follow the substrate, the thickness thereof and the substances of which they consist are listed separately for each example device in one of the tables which follow. The counterelectrode applied as the last layer is an aluminium layer in a thickness of 100 nm.

All materials are applied by thermal gas phase deposition in a vacuum chamber. In the examples, the emission layer always consists of at least one matrix material and an emitting compound as dopant. The latter is added to the matrix material(s) by coevaporation. An expression "SMB: SEB (5%)" means here that the material SMB is present in the layer in a proportion of 95% by volume, and the material SEB is present in the layer in a proportion of 5% by volume. Not just the emission layer but also other layers may analogously consist of a mixture of two or more materials.

The OLEDs are characterized by standard methods. For this purpose, the electroluminescence spectra, the external quantum efficiency (EQE, measured in %) as a function of luminance, calculated from current-voltage-luminance characteristics (IUL characteristics) assuming Lambertian emission characteristics, and the lifetime are determined. In that case, the expression "EQE @ 40 $mA/cm^2$" means, for example, the external quantum efficiency at an operating luminance of 40 $mA/cm^2$. The lifetime is measured at 20 $mA/cm^2$ for green-emitting devices, and at 60 $mA/cm^2$ for blue-emitting devices. Assuming an exponential drop in the OLEDs, the LT80 values for the lifetime are then approximated with an acceleration factor of 1.8 to the lifetime at 1000 $cd/m^2$. LT80 @ 1000 $cd/m^2$ is then the approximated lifetime by which the OLED has dropped from a starting luminance of 1000 $cd/m^2$ to a luminance of 800 $cd/m^2$.

The chemical structures of the materials that are used in the examples are given in Table A. The synthesis of the spiroxantheneamines is effected as in the preceding Synthesis Examples section, or it can be effected as in the prior art, for example as disclosed in WO 2014/072017.

TABLE A
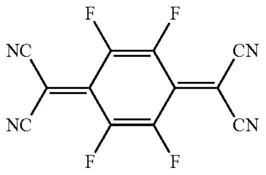 [SMILES: N#CC(C#N)=c1c(F)c(F)c(=C(C#N)C#N)c(F)c1F]
F4TCNQ
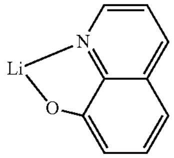
LiQ
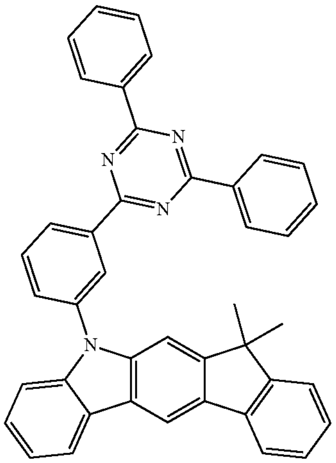 [SMILES: CC1(C)c2ccccc2-c2cc3c4ccccc4n(-c4cccc(-c5nc(-c6ccccc6)nc(-c6ccccc6)n5)c4)c3cc21]
H1
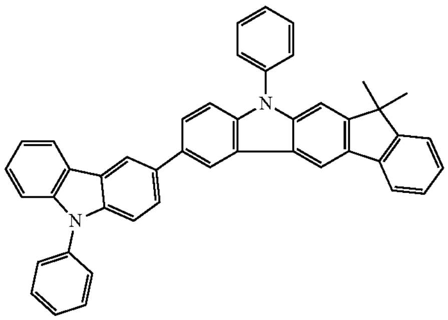 [SMILES: CC1(C)c2ccccc2-c2cc3c4cc(-c5ccc6c(c5)c5ccccc5n6-c5ccccc5)ccc4n(-c4ccccc4)c3cc21]
H2
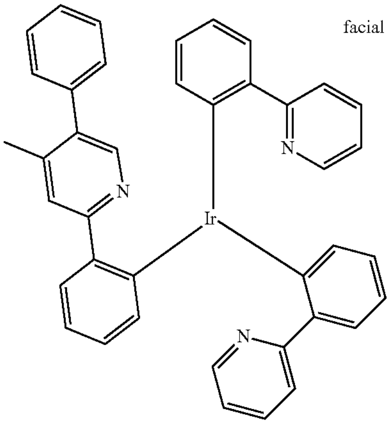
TEG TABLE A-continued
ETM
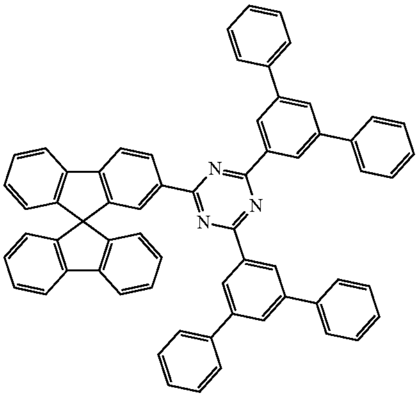 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
SMB
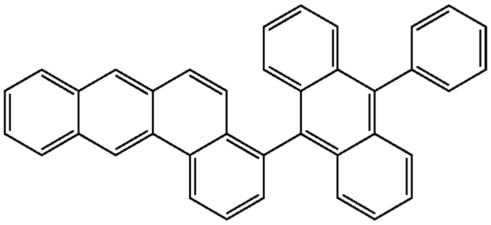 [SMILES: c1ccc(-c2c3ccccc3c(-c3cccc4c3ccc3cc5ccccc5cc34)c3ccccc23)cc1]
SEB
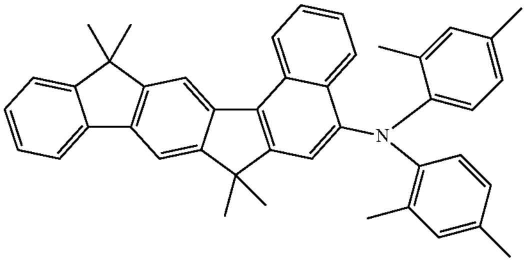 [SMILES: Cc1ccc(N(c2ccc(C)cc2C)c2cc3c(c4ccccc24)-c2cc4c(cc2C3(C)C)-c2ccccc2C4(C)C)c(C)c1]
HTMV1 = HIM
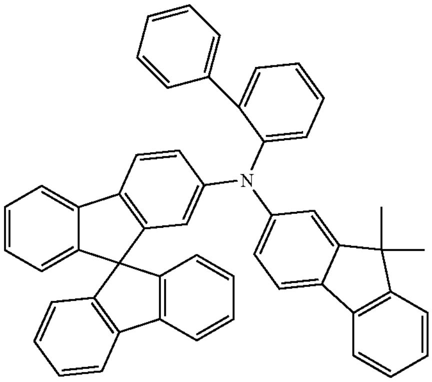 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

TABLE A-continued
HTMC2
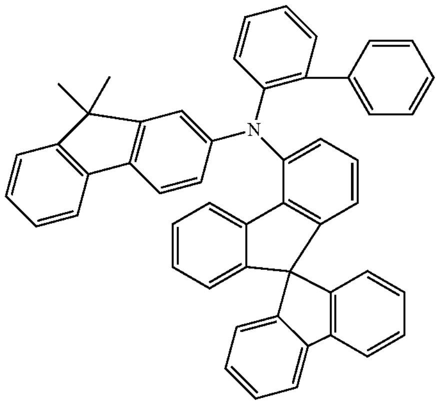 [SMILES: CC1(C)c2ccccc2-c2ccc(N(c3ccccc3-c3ccccc3)c3cccc4c3-c3ccccc3C43c4ccccc4-c4ccccc43)cc21]
HTM1
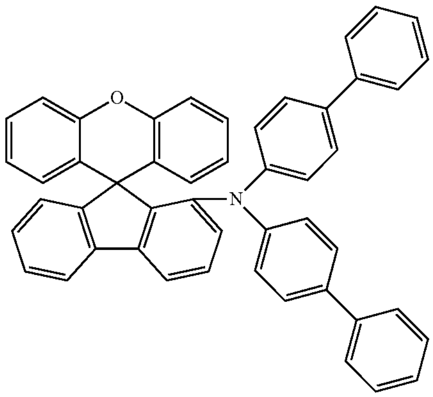 [SMILES: c1ccc(-c2ccc(N(c3ccc(-c4ccccc4)cc3)c3cccc4c3C3(c5ccccc5Oc5ccccc53)c3ccccc3-4)cc2)cc1]
HTM2
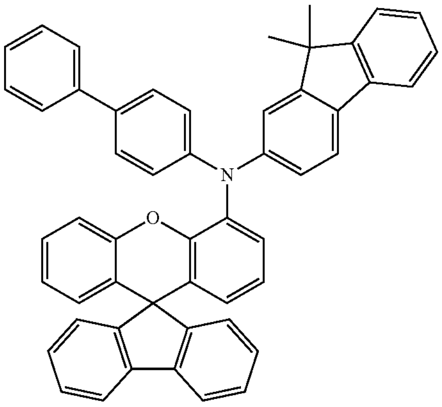 [SMILES: CC1(C)c2ccccc2-c2ccc(N(c3ccc(-c4ccccc4)cc3)c3cccc4c3Oc3ccccc3C43c4ccccc4-c4ccccc43)cc21]

TABLE A-continued
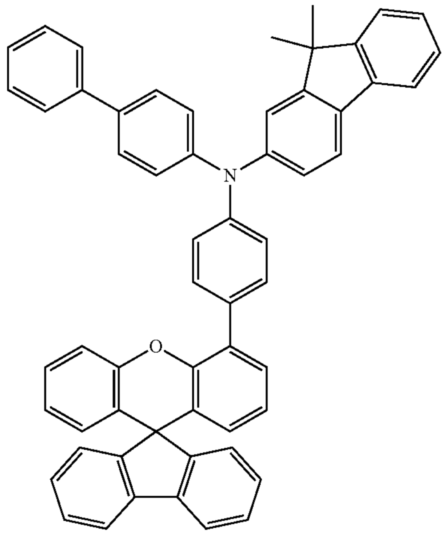 [SMILES: CC1(C)c2ccccc2-c2ccc(N(c3ccc(-c4ccccc4)cc3)c3ccc(-c4cccc5c4Oc4ccccc4C54c5ccccc5-c5ccccc54)cc3)cc21]
HTM4
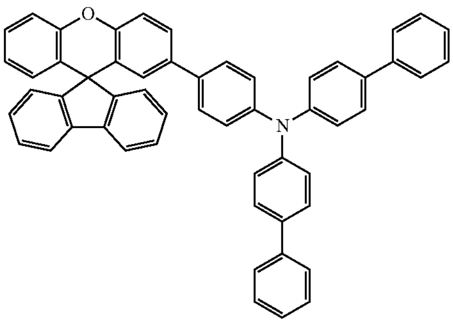 [SMILES: c1ccc(-c2ccc(N(c3ccc(-c4ccccc4)cc3)c3ccc(-c4ccc5c(c4)C4(c6ccccc6O5)c5ccccc5-c5ccccc54)cc3)cc2)cc1]
HTM5
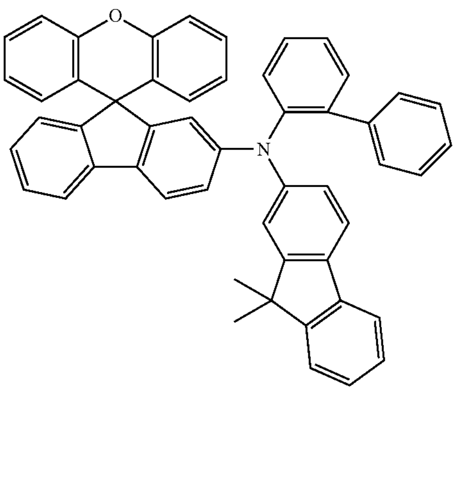 [SMILES: CC1(C)c2ccccc2-c2ccc(N(c3ccc4c(c3)C3(c5ccccc5Oc5ccccc53)c3ccccc3-4)c3ccccc3-c3ccccc3)cc21]
HTM6

TABLE A-continued
HTM7
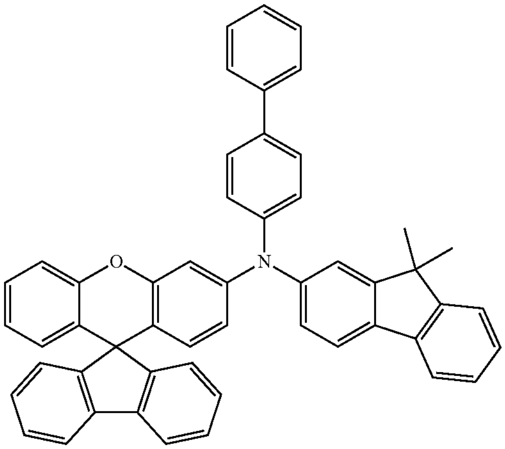 [SMILES: CC1(C)c2ccccc2-c2ccc(N(c3ccc(-c4ccccc4)cc3)c3ccc4c(c3)Oc3ccccc3C43c4ccccc4-c4ccccc43)cc21]
HTM8
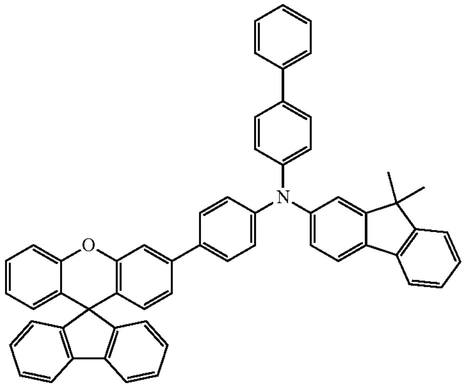 [SMILES: CC1(C)c2ccccc2-c2ccc(N(c3ccc(-c4ccccc4)cc3)c3ccc(-c4ccc5c(c4)Oc4ccccc4C54c5ccccc5-c5ccccc54)cc3)cc21]
HTM9
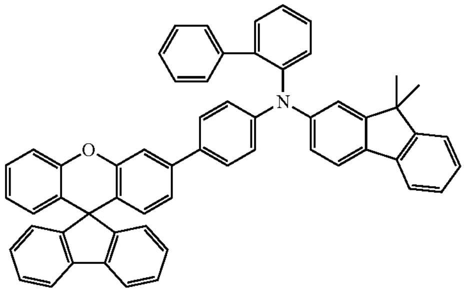 [SMILES: CC1(C)c2ccccc2-c2ccc(N(c3ccc(-c4ccc5c(c4)Oc4ccccc4C54c5ccccc5-c5ccccc54)cc3)c3ccccc3-c3ccccc3)cc21]
HTM13
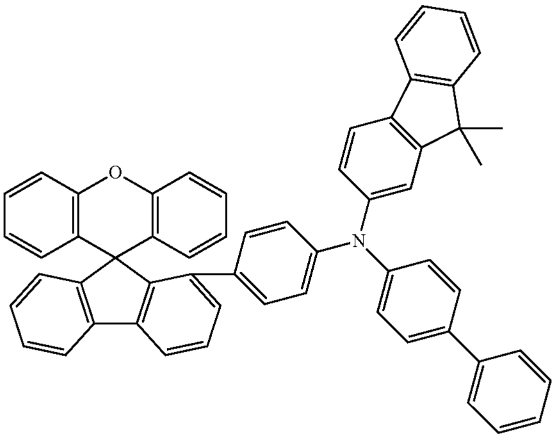 [SMILES: CC1(C)c2ccccc2-c2ccc(N(c3ccc(-c4ccccc4)cc3)c3ccc(-c4cccc5c4C4(c6ccccc6Oc6ccccc64)c4ccccc4-5)cc3)cc21]

TABLE A-continued

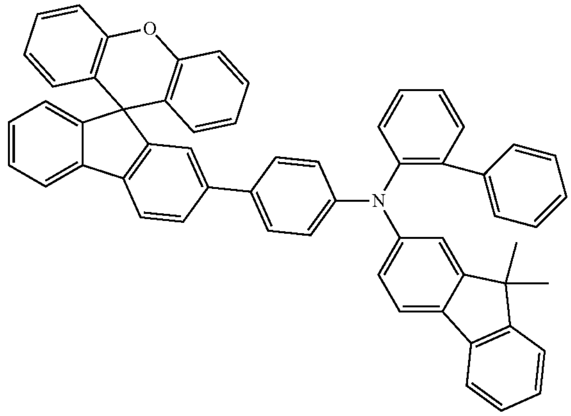 [SMILES: CC1(C)c2ccccc2-c2ccc(N(c3ccc(-c4ccc5c(c4)C4(c6ccccc6Oc6ccccc64)c4ccccc4-5)cc3)c3ccccc3-c3ccccc3)cc21]

HTM14

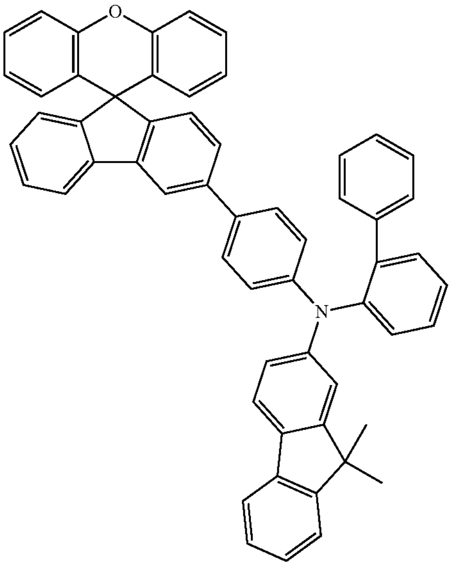 [SMILES: CC1(C)c2ccccc2-c2ccc(N(c3ccc(-c4ccc5c(c4)-c4ccccc4C54c5ccccc5Oc5ccccc54)cc3)c3ccccc3-c3ccccc3)cc21]

HTM15

1) Use of Spiroxantheneamines as HTL and HIL Materials

The following OLEDs C3 (comparative example) and I3, I5, I7, I9, I10, I14, I15 and I16 (inventive examples) are produced.

C3 as a comparative example comprises the compound HIM (a spirobifluorene derivative) as HTL and HIL material. The abovementioned use examples I3, I5, I7, I9, I10, I14, I15 and I16 comprise the materials HTM2, HTM4, HTM5, HTM6, HTM7, HTM8, HTM9, HTM13, HTM14 and HTM15 as HTL and HIL materials. Otherwise, the construction thereof is identical to that of C3 (Table 1).

For all the devices of the invention, a significant rise in lifetime is observed compared to example C3 (Table 2).

This shows the excellent suitability of the spiroxantheneamines as HIL and HTL materials, compared to the HTL/HIL material HIM according to the prior art.

TABLE 1

Structure of the OLEDs

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| C3 | HIM: F4TCNQ(5%) 20 nm | HIM 180 nm | HTMC2 10 nm | SMB: SEB(5%) 20 nm | ETM: LiQ(50%) 30 nm | LiQ 1 nm |
| I3 | HTM2: F4TCNQ(5%) 20 nm | HTM2 180 nm | HTMC2 10 nm | SMB: SEB(5%) 20 nm | ETM: LiQ(50%) 30 nm | LiQ 1 nm |
| I5 | HTM4: F4TCNQ(5%) 20 nm | HTM4 180 nm | HTMC2 10 nm | SMB: SEB(5%) 20 nm | ETM: LiQ(50%) 30 nm | LiQ 1 nm |
| I7 | HTM6: F4TCNQ(5%) 20 nm | HTM6 180 nm | HTMC2 10 nm | SMB: SEB(5%) 20 nm | ETM: LiQ(50%) 30 nm | LiQ 1 nm |

TABLE 1-continued

| Structure of the OLEDs | | | | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| I9 | HTM8: F4TCNQ(5%) 20 nm | HTM8 180 nm | HTMC2 10 nm | SMB: SEB(5%) 20 nm | ETM: LiQ(50%) 30 nm | LiQ 1 nm |
| I10 | HTM9: F4TCNQ(5%) 20 nm | HTM9 180 nm | HTMC2 10 nm | SMB: SEB(5%) 20 nm | ETM: LiQ(50%) 30 nm | LiQ 1 nm |
| I14 | HTM5: F4TCNQ(5%) 20 nm | HTM13 180 nm | HTMC2 10 nm | SMB: SEB(5%) 20 nm | ETM: LiQ(50%) 30 nm | LiQ 1 nm |
| I15 | HTM6: F4TCNQ(5%) 20 nm | HTM14 180 nm | HTMC2 10 nm | SMB: SEB(5%) 20 nm | ETM: LiQ(50%) 30 nm | LiQ 1 nm |
| I16 | HTM7: F4TCNQ(5%) 20 nm | HTM15 180 nm | HTMC2 10 nm | SMB: SEB(5%) 20 nm | ETM: LiQ(50%) 30 nm | LiQ 1 nm |

TABLE 2

| Data of the OLEDs | | |
|---|---|---|
| Ex. | U @ 10 mA/cm$^2$ [V] | LT80 @ 1000 cd/m$^2$ [h] |
| C3 | 3.8 | 4790 |
| I3 | 4.4 | 6800 |
| I5 | 4.3 | 4960 |
| I7 | 3.8 | 5610 |
| I9 | 4.3 | 5180 |
| I10 | 4.2 | 7390 |
| I14 | 3.9 | 5500 |

TABLE 2-continued

| Data of the OLEDs | | |
|---|---|---|
| Ex. | U @ 10 mA/cm$^2$ [V] | LT80 @ 1000 cd/m$^2$ [h] |
| I15 | 3.8 | 6600 |
| I16 | 4.0 | 7400 |

A comparison between OLEDs that differ merely by the fact that the spiroxantheneamines are present in the EBL rather than in the HTL/HIL is shown in Tables 3 and 4 below.

Table 3 shows the construction of the comparative OLEDs.

Table 4 shows the results of the direct comparisons with respect to one another. One line lists the data to be compared with one another in each case. In all cases, if the spiroxanthenes are present in the HIL/HTL, significantly higher lifetimes are obtained (examples on the right-hand side of Table 4).

This shows the advantages that are obtained through the use of the spiroxantheneamine compounds in the HIL and the HTL of OLEDs.

TABLE 3

| Structure of the OLEDs | | | | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| I17 | HIM: F4TCNQ(5%) 20 nm | HIM 180 nm | HTM2 10 nm | SMB: SEB(5%) 20 nm | ETM: LiQ(50%) 30 nm | LiQ 1 nm |
| I19 | HIM: F4TCNQ(5%) 20 nm | HIM 180 nm | HTM4 10 nm | SMB: SEB(5%) 20 nm | ETM: LiQ(50%) 30 nm | LiQ 1 nm |
| I21 | HIM: F4TCNQ(5%) 20 nm | HIM 180 nm | HTM6 10 nm | SMB: SEB(5%) 20 nm | ETM: LiQ(50%) 30 nm | LiQ 1 nm |
| I23 | HIM: F4TCNQ(5%) 20 nm | HIM 180 nm | HTM8 10 nm | SMB: SEB(5%) 20 nm | ETM: LiQ(50%) 30 nm | LiQ 1 nm |
| I24 | HIM: F4TCNQ(5%) 20 nm | HIM 180 nm | HTM9 10 nm | SMB: SEB(5%) 20 nm | ETM: LiQ(50%) 30 nm | LiQ 1 nm |

TABLE 4

| Data of the OLEDs | | | | | |
|---|---|---|---|---|---|
| Ex. | U @ 10 mA/cm$^2$ [V] | LT80 @ 1000 cd/m$^2$ [h] | LT80 @ 1000 cd/m$^2$ [h] | U @ 10 mA/cm$^2$ [V] | Ex. |
| I17 | 3.9 | 3082 | 6800 | 4.4 | E3 |
| I19 | 3.8 | 2278 | 4960 | 4.3 | E5 |
| I21 | 3.9 | 2464 | 5610 | 3.8 | E7 |

TABLE 4-continued

| Data of the OLEDs | | | | | |
|---|---|---|---|---|---|
| Ex. | U @ 10 mA/cm$^2$ [V] | LT80 @ 1000 cd/m$^2$ [h] | LT80 @ 1000 cd/m$^2$ [h] | U @ 10 mA/cm$^2$ [V] | Ex. |
| I23 | 3.7 | 3881 | 5180 | 4.3 | E9 |
| I24 | 3.7 | 4126 | 7390 | 4.2 | E10 |

2) Use of Spiroxanthenes Substituted by an Amino Group in the 1 Position as EBL Materials The following OLEDs C1, C2, I1 and I2 are produced (for construction see Table 5).

C1 and C2 are comparative examples that use a 4-spirobifluoreneamine (HTMC2) as EBL material. C1 differs from C2 in that a different spirobifluoreneamine is used as HIL and HTL material (HTMC1 in C1, and HTMC2 in C2).

I1 is a direct comparison with C1. In I1, the spiroxantheneamine HTM1 is used as EBL material in place of the spirobifluoreneamine HTMC2. I2 is a direct comparison with C2. In I2, the spiroxantheneamine HTM1 is used as EBL material in place of the spirobifluoreneamine HTMC2.

Both for I1 and for I2, a significant relative rise in lifetime (LT80) is observed compared to examples C1 and C2. In parallel, there is an improvement in the efficiency of the OLEDs (Table 6).

This shows the technical effect which is achieved with 1-spiroxantheneamines, especially when used as EBL materials.

TABLE 5

| Structure of the OLEDs | | | | | | | |
|---|---|---|---|---|---|---|---|
| Ex. | HIL Thickness/ nm | HTL Thickness/ nm | EBL Thickness/ nm | EML Thickness/ nm | HBL Thickness/ nm | ETL Thickness/ nm | EIL Thickness/ nm |
| C1 | HTMC1: F4TCNQ(5%) 20 nm | HTMC1 220 nm | HTMC2 10 nm | H1:H2(29%): TEG(12%) 30 nm | ETM 10 nm | ETM: LiQ(50%) 30 nm | LiQ 1 nm |
| I1 | HTMC1: F4TCNQ(5%) 20 nm | HTMC1 220 nm | HTM1 10 nm | H1:H2(29%): TEG(12%) 30 nm | ETM 10 nm | ETM: LiQ(50%) 30 nm | LiQ 1 nm |
| C2 | HTMC2: F4TCNQ(5%) 20 nm | HTMC2 220 nm | HTMC2 10 nm | H1:H2(29%): TEG(12%) 30 nm | ETM 10 nm | ETM: LiQ(50%) 30 nm | LiQ 1 nm |
| I2 | HTMC2: F4TCNQ(5%) 20 nm | HTMC2 220 nm | HTM1 10 nm | H1:H2(29%): TEG(12%) 30 nm | ETM 10 nm | ETM: LiQ(50%) 30 nm | LiQ 1 nm |

TABLE 6

| Data of the OLEDs | | | |
|---|---|---|---|
| Ex. | U @ 2 mA/cm$^2$ [V] | EQE @ 2 mA/cm$^2$ % | LT80 @ 1000 cd/m$^2$ [h] |
| C1 | 3.1 | 17.4 | 53400 |
| I1 | 3.3 | 18.0 | 69900 |
| C2 | 3.2 | 17.7 | 69000 |
| I2 | 3.5 | 17.9 | 76400 |

The invention claimed is:

1. A compound of a formula (I-1-3)

Formula (I-1-3)

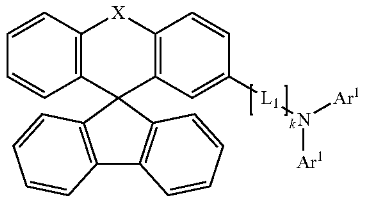

which may be substituted on the benzene rings at the positions shown as unsubstituted by $R^2$ radicals, and where:

both of the two $Ar^1$ are selected, differently, from the formulae $Ar^1$-59 to $Ar^1$-62, $Ar^1$-59

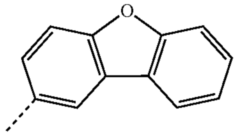

Ar1-60

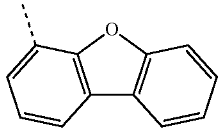

-continued $Ar^1$-61

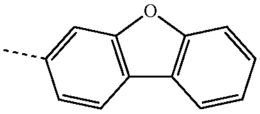

$Ar^1$-62

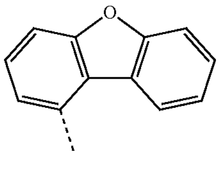

-continued

Ar1-63

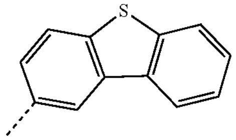

each of which is substituted by $R^1$ radicals;

X is O or S;

$R^1$ is the same or different at each instance and is selected from H, N $(R^3)_2$;

$R^2$ H;

$R^3$ is the same or different at each instance and is selected from H, F, CN, straight-chain alkyl groups having 1 to 20 carbon atoms, and branched or cyclic alkyl groups having 3 to 20 carbon atoms, where the alkyl groups mentioned may each be substituted by one or more $R^4$ radicals;

$R^4$ is the same or different at each instance and is selected from H, D, F, and CN;

k is 0.

2. The compound according to claim 1, characterized in that X is O.

3. An electronic device, selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices OLEDs), characterized in that it comprises the compound according to claim 1.

4. An organic electroluminescent device comprises the compound according to claim 1.

5. The compound according to claim 1, wherein $R^1$ in $Ar^1$-59 to $Ar^1$-62 is H.

6. A compound of a formula (I-1-3)

Formula (I-1-3)

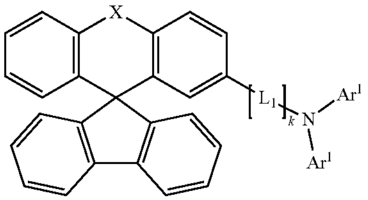

which may be substituted on the benzene rings at the positions shown as unsubstituted by $R^2$ radicals, and where:

one of the two $Ar^1$ is $Ar^1$-62, and the other one of the two $Ar^1$ is $Ar^1$-132;

Ar1-62

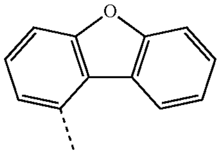

Ar1-132

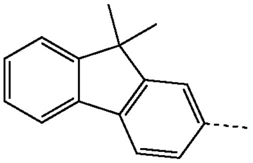

each of which is substituted by $R^1$ radicals;

X is O or S;

$R^1$ is H;

$R^2$ is H;

k is 0.

* * * * *